(12) United States Patent
Momose et al.

(10) Patent No.: US 7,179,823 B1
(45) Date of Patent: Feb. 20, 2007

(54) 5-MEMBERED N-HETEROCYCLIC COMPOUNDS WITH HYPOGLYCEMIC AND HYPOLIPIDEMIC ACTIVITY

(75) Inventors: Yu Momose, Takarazuka (JP); Tsuyoshi Maekawa, Nara (JP); Hiroyuki Odaka, Kobe (JP); Hiroyuki Kimura, Sakai (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 652 days.

(21) Appl. No.: 10/129,702

(22) PCT Filed: Nov. 9, 2000

(86) PCT No.: PCT/JP00/07877

§ 371 (c)(1),
(2), (4) Date: May 9, 2002

(87) PCT Pub. No.: WO01/38325

PCT Pub. Date: May 31, 2001

(30) Foreign Application Priority Data

Nov. 10, 1999 (JP) .................................. 11-320317
Dec. 10, 1999 (JP) .................................. 11-352237

(51) Int. Cl.
C07D 263/32 (2006.01)
C07D 277/24 (2006.01)
C07D 401/04 (2006.01)
A61K 31/422 (2006.01)
A61K 31/4439 (2006.01)

(52) U.S. Cl. .............. 514/341; 514/365; 514/374; 546/276.1; 548/205; 548/236

(58) Field of Classification Search ........... 548/340.1; 514/397, 341; 546/275.4
See application file for complete search history.

(56) References Cited

U.S. PATENT DOCUMENTS

| 4,775,687 A | 10/1988 | Meguro et al. | 514/369 |
| 4,918,073 A | 4/1990 | Ruger et al. | 514/255 |
| 5,475,016 A * | 12/1995 | Hanko et al. | 514/397 |
| 6,548,529 B1 | 4/2003 | Robl et al. | 514/406 |

FOREIGN PATENT DOCUMENTS

| AU | 715785 | 2/2000 |
| EP | 0 629 624 | 12/1994 |
| EP | 1 052 238 | 11/2000 |
| FR | 2707641 | * 1/1995 |
| JP | 10-72434 | 3/1998 |
| WO | 99/38829 | 8/1999 |
| WO | 99/58510 | 11/1999 |

OTHER PUBLICATIONS

Ca 139: 190635.*
Ca 140:128610.*
Caplus 120:217671.*
PubMed ID: 116:03645.*
Embase 2004016455.*
PubMed 11224652.*
Caplus 121:131033.*
PubMed ID: 15455705.*
Hcaplus 128:204878, "Preparation of pyrazinobenzothiazine derivatives and analogs for the treatment of inflammation and autoimmune diseases", Kaneko et. al., WO 9806720.*
Dodey et al., STN International, CAPLUS Database, Columbus, OH, Accession No. 1995:543545 (2004).*
Hanko et al., STN International, CAPLUS Database, Columbus, OH, Accession No. 1994:217671 (2004).*

* cited by examiner

Primary Examiner—Joseph K. McKane
Assistant Examiner—Andrew B. Freistein
(74) Attorney, Agent, or Firm—Wenderoth, Lind & Ponack, L.L.P.

(57) ABSTRACT

A compound of formula (I) F wherein $R^1$ represents a hydrocarbon group which may be substituted or a heterocyclic group which may be substituted; x represents a bond, an oxygen atom, a sulfur atom, or a group of the formula: —CO—, —CS—, —$CR^4(OR^5)$— or —$NR^6$— wherein each of $R^4$ and $R^6$ represents a hydrogen atom or a hydrocarbon group which may be stubstituted, $R^5$ represents a hydrogen atom or a protective group for a hydroxyl group; m represents an integer of 0 to 3; Y represents an oxygen atom, a sulfur atom, or a group of the formula: —SO—, —$SO_2$—, —$NR_7$—, —$CONR_7$— or —$NR^7CO$— wherein $R^7$ represents a hydrogen atom or a hydrocarbon group which may be substituted; ring A represents an aromatic ring which may further have 1 to 3 substituents; n represents an integer of 1 to 8; ring B represents a nitrogen-containing 5-membered hetero ring which may further be substituted by an alkyl group.

17 Claims, No Drawings

SEQUENCE LISTING

<160> NUMBER OF SEQ ID NOS: 8

<210> SEQ ID NO 1
<211> LENGTH: 33
<212> TYPE: DNA
<213> ORGANISM: Artificial Sequence

```
<220> FEATURE:
<223> OTHER INFORMATION: Description of Artificial Sequence: DNA PRIMER

<400> SEQUENCE: 1
gtgggtaccg aaatgaccat ggttgacaca gag                                33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: DNA PRIMER

<400> SEQUENCE: 2
ggggtcgacc aggactctct gctagtacaa gtc                                33

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: DNA PRIMER

<400> SEQUENCE: 3
ttagaattcg acatggacac caaacatttc ctg                                33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: DNA PRIMER

<400> SEQUENCE: 4
cccctcgagc taagtcattt ggtgcggcgc ctc                                33

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: DNA PRIMER

<400> SEQUENCE: 5
tcgacagggg accaggacaa aggtcacgtt cgggag                             36

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: DNA PRIMER

<400> SEQUENCE: 6
tcgactcccg aacgtgacct ttgtcctggt cccctg                             36

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: DNA PRIMER

<400> SEQUENCE: 7
cccagatctc cccagcgtct tgtcattg                                      28
```

```
<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: DNA PRIMER

<400> SEQUENCE: 8
tcaccatggt caagctttta agcgggtc                                            28
```

5-MEMBERED N-HETEROCYCLIC COMPOUNDS WITH HYPOGLYCEMIC AND HYPOLIPIDEMIC ACTIVITY

This application is a 371 of PCT/JP00/07877 filed Nov. 9, 2000.

TECHNICAL FIELD

The present invention relates to a novel nitrogen containing 5-membered heterocyclic compound having an excellent hypoglycemic action and hypolipidemic action, which is useful as an agent for preventing or treating diabetes mellitus, hyperlipidemia, impaired glucose tolerance, inflammatory diseases, arteriosclerosis, etc.

The present invention also relates to an agent for preventing or treating diabetes mellitus, hyperlipidemia or impaired glucose tolerance, which comprises a nitrogen containing 5-membered heterocyclic compound.

The present invention further relates to a retinoid-related receptor function regulating agent or an insulin resistance improving agent, which comprises a nitrogen containing 5-membered heterocyclic compound.

BACKGROUND ART

JP-A 10-72434 discloses a 2,4-substituted aniline derivative of the formula:

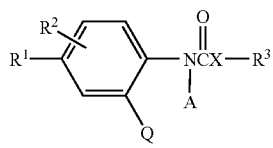

wherein $R^1$ represents alkyl, haloalkyl, alkoxy, or the like; $R^2$ represents hydrogen atom, alkyl, haloalkyl, or the like; $R^3$ represents alkyl, cycloalkyl, alkenyl, or the like; X represents oxygen, sulfur, $NR^5$ or a single bond; Q represents an azole or the like, and a herbicide comprising it.

However, said derivative is not reported to possess hypoglycemic action and hypolipidemic action.

Peroxisome proliferator-activated receptor gamma (PPARγ), a member of the intranuclear hormone receptor superfamily, which is typically exemplified by steroid hormone receptors and thyroid hormone receptors, plays an important role as a master regulator in the differentiation of adipose cells with its expression induced in the very early stage of adipose cell differentiation. PPARγ forms a dimer with the retinoid X receptor (RXR) by binding to a ligand, and binds to a responsive site of the target gene in the nucleus to directly control (activate) transcription efficiency. In recent years, the possibility that 15-deoxy-$\Delta^{12.14}$ prostaglandin $J_2$, a metabolite of prostaglandin $D_2$, serves as an endogenous ligand for PPARγ, has been suggested, and it has been shown that a class of insulin resistance enhancers, typically exemplified by thiazolidinedione derivatives, possess ligand activity for PPARγ, and that its potency is proportional to its hypoglycemic action or adipose cell differentiation-promoting action [Cell, vol. 83, p. 803 (1995): the Journal of Biological Chemistry, vol. 270, p. 12953 (1995); Journal of Medicinal Chemistry, vol. 39, p. 655 (1996)]. Furthermore, in recent years, it has been shown that 1) PPAR γ is expressed in cultured cells of human liposarcoma origin, whose proliferation is ceased by the addition of a PPARγ ligand [Proceedings of the National Academy of Sciences of the United States of America, vol. 94, p. 237 (1997)], 2) nonsteroidal anti-inflammatory drugs, typically exemplified by indomethacin and fenoprofen, have PPARγ ligand activity [the Journal of Biological Chemistry, vol. 272, p. 3406 (1997)], 3) PPARγ is expressed at high levels in activated macrophages, with the transcription of a gene involved in inflammation inhibited by the addition of a ligand therefor [Nature, vol. 391, p. 79 (1998)], and 4) PPARγ ligands suppress the production of inflammatory cytokines (TNFα, IL-1β, IL-6) by monocytes [Nature, vol. 391, p. 82 (1998)].

There is a demand for development of a novel compound useful as an agent for preventing or treating diabetes mellitus, hyperlipidemia, impaired glucose tolerance, inflammatory diseases, arteriosclerosis etc., and having pharmaceutically excellent properties such as low side effects, etc.

DISCLOSURE OF INVENTION

The present invention relates to (1) a compound of the formula:

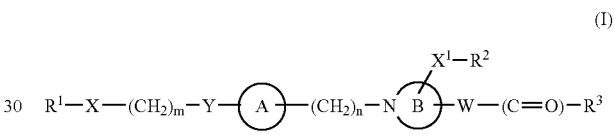

wherein $R^1$ represents a hydrocarbon group which may be substituted or a heterocyclic group which may be substituted;

X represents a bond, an oxygen atom, a sulfur atom, or a group of the formula: —CO—, —CS—, —$CR^4(OR^5)$— or —$NR^6$— wherein each of $R^4$ and $R^6$ represents a hydrogen atom or a hydrocarbon group which may be substituted, $R^5$ represents a hydrogen atom or a protective group for a hydroxyl group;

m represents an integer of 0 to 3;

Y represents an oxygen atom, a sulfur atom, or a group of the formula: —SO—, —$SO_2$—, —$NR^7$—, —$CONR^7$— or —$NR^7CO$— wherein $R^7$ represents a hydrogen atom or a hydrocarbon group which may be substituted;

ring A represents an aromatic ring which may further have 1 to 3 substituents;

n represents an integer of 1 to 8;

ring B represents a nitrogen-containing 5-membered hetero ring which may further be substituted by an alkyl group;

$X^1$ represents a bond, an oxygen atom, a sulfur atom, or a group of the formula: —SO—, —$SO_2$—, —O—$SO_2$— or —$NR^{16}$— wherein $R^{16}$ represents a hydrogen atom or a hydrocarbon group which may be substituted;

$R^2$ represents a hydrogen atom, a hydrocarbon group which may be substituted or a heterocyclic group which may be substituted;

W represents a bond or a divalent hydrocarbon residue having 1 to 20 carbon atoms;

$R^3$ represents a group of the formula: —$OR^8$ ($R^8$ represents a hydrogen atom or a hydrocarbon group which may be substituted) or —$NR^9R^{10}$ (each of $R^9$ and $R^{10}$, whether identical or not, represents a hydrogen atom, a hydrocarbon group which may be substituted, a heterocyclic group which may be substituted, or an acyl group which may be substituted; $R^9$ and $R^{10}$ may bind together to form a ring);

provided that $R^1$ is a heterocyclic group which may be substituted or $R^2$ is an aromatic hydrocarbon group which may be substituted or a heterocyclic group which may be substituted, when ring A is a benzene ring which may be substituted, and Y is an oxygen atom, a sulfur atom, —NH— or —CONH—; or a salt thereof;

(2) a compound according to the above (1), wherein $X^1$ is a bond and ring B is a nitrogen-containing 5-membered heterocyclic ring;

(3) a compound according to the above (1), wherein $R^1$ is a heterocyclic group which may be substituted or a cyclic hydrocarbon group which may be substituted;

(4) a compound according to the above (1), wherein $R^1$ is a heterocyclic group which may be substituted;

(5) a compound according to the above (1), wherein X is a bond;

(6) a compound according to the above (1), wherein m is 1 or 2;

(7) a compound according to the above (1), wherein Y is an oxygen atom;

(8) a compound according to the above (1), wherein ring A is a benzene ring or pyridine ring, each of which may further have 1 to 3 substituents;

(9) a compound according to the above (1), wherein n is an integer of 1 to 3;

(10) a compound according to the above (1), wherein $X^1$ is a bond or an oxygen atom;

(11) a compound according to the above (1), wherein W is a divalent hydrocarbon residue having 1 to 8 carbon atoms;

(12) a compound according to the above (1), wherein $R^3$ is a group of the formula: —$OR^8$ ($R^8$ represents a hydrogen atom or a hydrocarbon group which may be substituted);

(13) a compound according to the above (1), which is
3-[3-ethoxy-1-[4-(2-phenyl-4-thiazolylmethoxy)benzyl]-1H-pyrazol-4-yl]propionic acid,
3-[3-ethoxy-1-[4-(2-phenyl-4-oxazolylmethoxy)benzyl]-1H-pyrazol-4-yl]propionic acid,
3-[3-ethoxy-1-[4-[3-methyl-1-(2-pyridyl)-1H-pyrazol-4-ylmethoxy]benzyl]-1H-pyrazol-4-yl]propionic acid,
3-[1-[4-(5-methyl-2-phenyl-4-oxazolylmethoxy)benzyl]-3-(2-thienyl)-1H-pyrazol-4-yl]propionic acid,
3-[1-[4-(2-phenyl-4-thiazolylmethoxy)benzyl]-3-(2-thienyl)-1H-pyrazol-4-yl]propionic acid, or
3-[1-[4-(2-phenyl-4-oxazolylmethoxy)benzyl]-3-(2-thienyl)-1H-pyrazol-4-yl]propionic acid;

(14) a prodrug of a compound as defined in the above (1);

(15) a pharmaceutical composition comprising a compound of the formula:

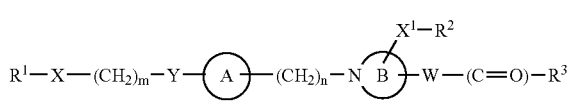

(II)

wherein $R^1$ represents a hydrocarbon group which may be substituted or a heterocyclic group which may be substituted;

X represents a bond, an oxygen atom, a sulfur atom, or a group of the formula: —CO—, —CS—, —$CR^4(OR^5)$— or —$NR^6$— wherein each of $R^4$ and $R^6$ represents a hydrogen atom or a hydrocarbon group which may be substituted, $R^5$ represents a hydrogen atom or a protective group for a hydroxyl group;

m represents an integer of 0 to 3;

Y represents an oxygen atom, a sulfur atom, or a group of the formula: —SO—, —$SO_2$—, —$NR^7$—, —$CONR^7$— or —$NR^7CO$— wherein $R^7$ represents a hydrogen atom or a hydrocarbon group which may be substituted;

ring A represents an aromatic ring which may further have 1 to 3 substituents;

n represents an integer of 1 to 8;

ring B represents a nitrogen-containing 5-membered hetero ring which may further be substituted by an alkyl group;

$X^1$ represents a bond, an oxygen atom, a sulfur atom, or a group of the formula: —SO—, —$SO_2$—, —$SO_2$— or —$NR^{16}$—wherein $R^{16}$ represents a hydrogen atom or a hydrocarbon group which may be substituted;

$R^2$ represents a hydrogen atom, a hydrocarbon group which may be substituted or a heterocyclic group which may be substituted;

W represents a bond or a divalent hydrocarbon residue having 1 to 20 carbon atoms;

$R^3$ represents a group of the formula: —$OR^8$ ($R^8$ represents a hydrogen atom or a hydrocarbon group which may be substituted) or —$NR^9R^{10}$ (each of $R^9$ and $R^{10}$, whether identical or not, represents a hydrogen atom, a hydrocarbon group which may be substituted, a heterocyclic group which may be substituted, or an acyl group which may be substituted; $R^9$ and $R^{10}$ may bind together to form a ring); or a salt thereof or a prodrug thereof;

(16) a composition according to the above (15), wherein $X^1$ is a bond and ring B is a nitrogen-containing 5-membered heterocyclic ring;

(17) an agent for preventing or treating diabetes mellitus comprising a compound of the formula (II) or a salt thereof or a prodrug thereof;

(18) an agent for preventing or treating hyperlipidemia comprising a compound of the formula (II) or a salt thereof or a prodrug thereof;

(19) an agent for preventing or treating impaired glucose tolerance comprising a compound of the formula (II) or a salt thereof or a prodrug thereof;

(20) a retinoid-related receptor function regulating agent comprising a compound of the formula (II) or a salt thereof or a prodrug thereof;

(21) an agent according to the above (20), which is a ligand for peroxisome proliferator-activated receptors;

(22) an agent according to the above (20), which is a ligand for retinoid X receptors;

(23) an insulin resistance improving agent comprising a compound of the formula (II) or a salt thereof or a prodrug thereof;

(24) a method for preventing or treating diabetes mellitus in a mammal in need thereof, which comprises administering to said mammal an effective amount of a compound of the formula (II) or a salt thereof or a prodrug thereof;

(25) a method for preventing or treating hyperlipidemia in a mammal in need thereof, which comprises administering to said mammal an effective amount of a compound of the formula (II) or a salt thereof or a prodrug thereof;

(26) a method for preventing or treating impaired glucose tolerance in a mammal in need thereof, which comprises administering to said mammal an effective amount of a compound of the formula (II) or a salt thereof or a prodrug thereof;

(27) a method for regulating a retinoid-related receptor function in a mammal in need thereof, which comprises administering to said mammal an effective amount of a compound of the formula (II) or a salt thereof or a prodrug thereof;

(28) use of a compound of the formula (II) or a salt thereof or a prodrug thereof, for the manufacture of a pharmaceutical preparation for preventing or treating diabetes mellitus;

(29) use of a compound of the formula (II) or a salt thereof or a prodrug thereof, for the manufacture of a pharmaceutical preparation for preventing or treating, hyperlipidemia;

(30) use of a compound of the formula (II) or a salt thereof or a prodrug thereof, for the manufacture of a pharmaceutical preparation for preventing or treating impaired glucose tolerance; and

(31) use of a compound of the formula (II) or a salt thereof or a prodrug thereof, for the manufacture of an agent for regulating a retinoid-related receptor function.

(1) Definition of $R^1$ (1-1) Definition of the "Hydrocarbon Group" in $R^1$

The hydrocarbon group in the "hydrocarbon group which may be substituted" for $R^1$ in the formulae (I) and (II) is exemplified by aliphatic hydrocarbon groups, alicyclic hydrocarbon groups, alicyclic-aliphatic hydrocarbon groups, aromatic-aliphatic hydrocarbon groups, and aromatic hydrocarbon groups. The number of carbon atoms in these hydrocarbon groups is preferably 1 to 14.

The aliphatic hydrocarbon groups are preferably aliphatic hydrocarbon groups having 1 to 8 carbon atoms. Examples of the aliphatic hydrocarbon groups include saturated aliphatic hydrocarbon groups having 1 to 8 carbon atoms (e.g., alkyl groups), such as methyl, ethyl, propyl, isopropyl, butyl, isobutyl, sec.-butyl, t.-butyl, pentyl, isopentyl, neopentyl, hexyl, isohexyl, heptyl, and octyl; and unsaturated aliphatic hydrocarbon groups having 2 to 8 carbon atoms (e.g., alkenyl groups having 2 to 8 carbon atoms, alkadienyl groups having 4 to 8 carbon atoms, alkenylalkynyl groups having 2 to 8 carbon atoms, alkadiynyl groups having 4 to 8 carbon atoms), such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, and 1-octynyl.

The alicyclic hydrocarbon groups are preferably alicyclic hydrocarbon groups having 3 to 7 carbon atoms. Examples of the alicyclic hydrocarbon groups include saturated alicyclic hydrocarbon groups having 3 to 7 carbon atoms (e.g., cycloalkyl groups), such as cyclopropyl, cyclobutyl, cyclopentyl, cyclohexyl, and cycloheptyl; and unsaturated alicyclic hydrocarbon groups having 5 to 7 carbon atoms (e.g., cycloalkenyl groups, cycloalkadienyl groups), such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, and 2,4-cycloheptadienyl.

The alicyclic-aliphatic hydrocarbon groups are exemplified by those resulting from binding of the aforementioned alicyclic hydrocarbon groups and aliphatic hydrocarbon groups (e.g., cycloalkyl-alkyl groups, cycloalkenyl-alkyl groups), with preference given to alicyclic-aliphatic hydrocarbon groups having 4 to 9 carbon atoms. Examples of the alicyclic-aliphatic hydrocarbon groups include cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, and cycloheptylethyl.

The aromatic-aliphatic hydrocarbon groups are preferably aromatic-aliphatic hydrocarbon groups having 7 to 13 carbon atoms (e.g., aralkyl groups having 7 to 13 carbon atoms, arylalkenyl groups having 8 to 13 carbon atoms). Examples of the aromatic-aliphatic hydrocarbon groups include phenylalkyls having 7 to 9 carbon atoms, such as benzyl, phenethyl, 1-phenylethyl, 1-phenylpropyl, 2-phenylpropyl, and 3-phenylpropyl; naphthylalkyls having 11 to 13 carbon atoms, such as α-naphthylmethyl, α-naphthylethyl, β-naphthylmethyl, and β-naphthylethyl; phenylalkenyls having 8 to 10 carbon atoms, such as styryl; and naphthylalkenyls having 12 to 13 carbon atoms, such as 2-(2-naphthylvinyl).

The aromatic hydrocarbon groups are preferably aromatic hydrocarbon groups having 6 to 14 carbon atoms (e.g., aryl groups). Examples of the aromatic hydrocarbon groups include phenyl, naphthyl, anthryl, phenanthryl, acenaphthylenyl, and biphenylyl, with preference given to phenyl, 1-naphthyl, 2-naphthyl, etc.

Of the aforementioned hydrocarbon groups, cyclic hydrocarbon groups such as alicyclic hydrocarbon groups and aromatic hydrocarbon groups are preferred. The hydrocarbon groups are more preferably aromatic hydrocarbon groups having 6 to 14 carbon atoms, with preference given to phenyl, naphthyl etc.

(1-2) Definition of the "Heterocyclic Group" in $R^1$

The heterocyclic group in the "heterocyclic group which may be substituted" for $R^1$ in the formulae (I) and (II) is exemplified by 5- to 7-membered monocyclic heterocyclic groups containing 1 to 4 hetero atoms selected from oxygen atoms, sulfur atoms and nitrogen atoms, in addition to carbon atoms, as ring constituent atoms, or condensed heterocyclic groups. Examples of the condensed heterocyclic groups include groups resulting from condensation of these 5- to 7-membered monocyclic heterocyclic groups with a 6-membered ring containing 1 to 2 nitrogen atoms, benzene rings or a 5-membered ring containing 1 sulfur atom.

Specifically, examples of the heterocyclic groups include aromatic heterocyclic groups such as 2-furyl, 3-furyl, 2-thienyl, 3-thienyl, 2-pyriyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 1-pyrrolyl, 2-pyrrolyl, 3-pyrrolyl, 1-imidazolyl, 2-imidazolyl, 4-imidazolyl, 5-imidazolyl, 1-pyrazolyl, 3-pyrazolyl, 4-pyrazolyl, isoxazolyl, isothiazolyl, 2-thiazolyl, 4-thiazolyl, 5-thiazolyl, 2-oxazolyl, 4-oxazolyl, 5-oxazolyl, 1,2,4-oxadiazol-3-yl, 1,2,4-oxadiazol-5-yl, 1,3,4-oxadiazol-2-yl, 1,3,4-thiadiazol-2-yl, 1,2,4-triazol-1-yl, 1,2,4-triazol-3-yl, 1,2,3-triazol-1-yl, 1,2,3-triazol-2-yl, 1,2,3-triazol-4-yl, tetrazol-1-yl, tetrazol-5-yl, 2-quinolyl, 3-quinolyl, 4-quinolyl, 2-quinazolyl, 4-quinazolyl, 2-quinoxalyl, 2-benzoxazolyl, 2-benzothiazolyl, benzimidazol-1-yl, benzimidazol-2-yl, indol-1-yl, indol-3-yl, 1H-indazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin-2-yl, 1H-imidazo[4,5-b]pyrazin-2-yl and benztriazol-1-yl; and non-aromatic heterocyclic groups such as 1-pyrrolidinyl, piperidino, morpholino, thiomorpholino, 1-piperazinyl, hexamethyleneimin-1-yl, oxazolidin-3-yl, thiazolidin-3-yl, imidazolidin-3-yl, 2-oxoimidazolidin-1-yl, 2,4-dioxoimidazolidin-3-yl, 2,4-dioxooxazolidin-3-yl, 2,4-dioxothiazolidin-3-yl, 1-oxo-phthalazin-2-yl and 2-oxo-2,3-dihydro-4H-1,4-benzothiazin-4-yl.

The heterocyclic groups are preferably aromatic heterocyclic groups, and more preferably 5- or 6-membered aromatic heterocyclic groups which may be condensed with a benzene ring (preferably furyl, thienyl, pyridyl, pyrimidinyl, pyrazinyl, pyrazolyl, oxazolyl, thiazolyl, triazolyl, oxadiazolyl). Especially preferred are furyl, thienyl, pyridyl, pyrimidinyl, pyrazinyl, pyrazolyl, oxazolyl, thiazolyl, oxadiazolyl, benzoxazolyl, benzothiazolyl, quinolyl, etc.

(1-3) Definition of the "Substituent" in $R^1$

Each of the hydrocarbon group and heterocyclic group for $R^1$ in the formulae (I) and (II) may have 1 to 5, preferably 1 to 3, substituents at substitutable positions. Examples of the substituents include "halogen atoms", "nitro groups", "aliphatic hydrocarbon groups which may be substituted", "alicyclic hydrocarbon groups which may be substituted", "aromatic hydrocarbon groups which may be substituted", "aromatic heterocyclic groups which may be substituted", "non-aromatic heterocyclic groups which may be substituted", "acyl groups which may be substituted", "amino group which may be substituted", "hydroxy group which may be substituted", "thiol group which may be substituted", and "carboxyl group which may be esterified or amidated".

Examples of the "halogen atoms" include fluorine, chlorine, bromine and iodine, with preference given to fluorine and chlorine.

The aliphatic hydrocarbon groups in "aliphatic hydrocarbon groups which may be substituted" are exemplified by straight-chain or branched aliphatic hydrocarbon groups having 1 to 15 carbon atoms, such as alkyl groups, alkenyl groups, and alkinyl groups.

Preferred examples of the alkyl groups include alkyl groups having 1 to 10 carbon atoms, such as methyl, ethyl, propyl, isopropyl, butyl, isobutyl, sec.-butyl, t.-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, and decyl.

Preferred examples of the alkenyl groups include alkenyl groups having 2 to 10 carbon atoms, such as ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, and 1-octenyl.

Preferred examples of the alkynyl groups include alkynyl groups having 2 to 10 carbon atoms, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, and 1-octynyl.

Examples of the substituents in "aliphatic hydrocarbon groups which may be substituted" include cycloalkyl groups having 3 to 10 carbon atoms, aryl groups having 6 to 14 carbon atoms (e.g., phenyl, naphthyl), aromatic heterocyclic groups (e.g., thienyl, furyl, pyridyl, oxazolyl, thiazolyl), non-aromatic heterocyclic groups (e.g., tetrahydrofuryl, morpholino, thiomorpholino, piperidino, pyrrolidinyl, piperazinyl), aralkyl groups having 7 to 9 carbon atoms, amino group, amino group mono- or di-substituted by alkyl groups having 1 to 4 carbon atoms or acyl groups having 2 to 8 carbon atoms (e.g., alkanoyl groups), amidino group, acyl groups having 2 to 8 carbon atoms (e.g., alkanoyl groups), carbamoyl group, carbamoyl group mono- or di-substituted by alkyl groups having 1 to 4 carbon atoms, sulfamoyl group, sulfamoyl group mono- or di-substituted by alkyl groups having 1 to 4 carbon atoms, carboxyl group, alkoxycarbonyl groups having 2 to 8 carbon atoms, hydroxy group, alkoxy groups having 1 to 6 carbon atoms which may be substituted by 1 to 3 halogen atoms (e.g., fluorine, chlorine, bromine, iodine), alkenyloxy groups having 2 to 5 carbon atoms which may be substituted by 1 to 3 halogen atoms (e.g., fluorine, chlorine, bromine, iodine), cycloalkyloxy groups having 3 to 7 carbon atoms, aralkyloxy groups having 7 to 9 carbon atoms, aryloxy groups having 6 to 14 carbon atoms (e.g., phenyloxy, naphthyloxy), thiol group, alkylthio groups having 1 to 6 carbon atoms which may be substituted by 1 to 3 halogen atoms (e.g., fluorine, chlorine, bromine, iodine), aralkylthio groups having 7 to 9 carbon atoms, arylthio groups having 6 to 14 carbon atoms (e.g., phenylthio, naphthylthio), sulfo group, cyano group, azide group, nitro group, nitroso group, and halogen atoms (e.g., fluorine, chlorine, bromine, iodine). The number of the substituents is, for example, 1 to 3.

The alicyclic hydrocarbon groups in "alicyclic hydrocarbon groups which may be substituted" are exemplified by saturated or unsaturated alicyclic hydrocarbon groups having 3 to 12 carbon atoms, such as cycloalkyl groups, cycloalkenyl groups, and cycloalkadinenyl groups.

Preferred examples of the cycloalkyl groups include cycloalkyl groups having 3 to 10 carbon atoms, such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, and bicyclo[4.3.1]decyl.

Preferred examples of the cycloalkenyl groups include cycloalkenyl groups having 3 to 10 carbon atoms, such as 2-cyclopenten-1-yl, 3-cyclopenten-1-yl, 2-cyclohexen-1-yl, and 3-cyclohexen-1-yl.

Preferred examples of the cycloalkadienyl groups include cycloalkadienyl groups having 4 to 10 carbon atoms, such as 2,4-cyclopentadien-1-yl, 2,4-cyclohexadien-1-yl, and 2,5-cyclohexadien-1-yl.

Preferred examples of the aromatic hydrocarbon groups in "aromatic hydrocarbon groups which may be substituted" include aromatic hydrocarbon groups having 6 to 14 carbon atoms (e.g., aryl groups), such as phenyl, naphthyl, anthryl, phenanthryl, acenaphthylenyl, and biphenylyl, with preference given to phenyl, 1-naphthyl, 2-naphthyl etc.

Preferred examples of the aromatic heterocyclic groups in "aromatic heterocyclic groups which may be substituted" include 5- to 7-membered aromatic monocyclic heterocyclic groups containing 1 to 4 hetero atoms selected from oxygen atoms, sulfur atoms and nitrogen atoms, in addition to carbon atoms, as ring constituent atoms, such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thaidiazolyl, 1,2,4-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl, and triazinyl; and bicyclic or tricyclic aromatic condensed heterocyclic groups having 3 to 13 carbon atoms and containing 1 to 5 hetero atoms selected from oxygen atoms, sulfur atoms and nitrogen atoms, in addition to carbon atoms, as ring constituent atoms, such as benzofuranyl, isobenzofuranyl, benzo[b]thienyl, indolyl, isoindolyl, 1H-indazolyl, benzimidazolyl, benzoxazolyl, benzothiazolyl, 1H-benzotriazolyl, quinolyl, isoquinolyl, cinnolyl, quinazolyl, quinoxalinyl, phthalazinyl, naphthylidinyl, purinyl, pteridinyl, carbazolyl, α-carbonylyl, β-carbonylyl, γ-carbonylyl, acridinyl, phenoxazinyl, phenothiazinyl, phenazinyl, phenoxathiinyl, thianthrenyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, and 1,2,4-triazolo[4,3-b]pyridazinyl.

Preferred examples of the non-aromatic heterocyclic groups in "non-aromatic heterocyclic groups which may be substituted" include non-aromatic heterocyclic groups having 2 to 10 carbon atoms and containing 1 to 3 hetero atoms selected from oxygen atoms, sulfur atoms and nitrogen atoms, in addition to carbon atoms, as ring constituent atoms, such as oxylanyl, azetidinyl, oxetanyl, thietanyl, pyrrolidinyl, tetrahydrofuryl, tetrahydropyranyl, morpholinyl, thiomorpholinyl, piperazinyl, pyrrolidinyl, piperidino, morpholino, and thiomorpholino.

Examples of the substituents in the aforementioned "alicyclic hydrocarbon groups which may be substituted", "aromatic hydrocarbon groups which may be substituted", "aromatic heterocyclic groups which may be substituted" and "non-aromatic heterocyclic groups which may be substituted" include alkyl groups having 1 to 6 carbon atoms which may be substituted by 1 to 3 halogen atoms (e.g., fluorine, chlorine, bromine, iodine), alkenyl groups having 2 to 6 carbon atoms which may be substituted by 1 to 3 halogen atoms (e.g., fluorine, chlorine, bromine, iodine), cycloalkyl groups having 3 to 10 carbon atoms, aryl groups having 6 to 14 carbon atoms (e.g., phenyl, naphthyl), aromatic heterocyclic groups (e.g., thienyl, furyl, pyridyl, oxazolyl, thiazolyl), non-aromatic heterocyclic groups (e.g., tetrahydrofuryl, morpholino, thiomorpholino, piperidino, pyrrolidinyl, piperazinyl), aralkyl groups having 7 to 9 carbon atoms, amino group, amino group mono- or di-substituted by alkyl groups having 1 to 4 carbon atoms or acyl groups having 2 to 8 carbon atoms (e.g., alkanoyl groups), amidino group, acyl groups having 2 to 8 carbon atoms (e.g., alkanoyl groups), carbamoyl group, carbamoyl groups mono- or di-substituted by alkyl groups having 1 to 4 carbon atoms, sulfamoyl group, sulfamoyl group mono- or di-substituted by alkyl groups having 1 to 4 carbon atoms, carboxyl group, alkoxycarbonyl groups having 2 to 8 carbon atoms, hydroxy group, alkoxy groups having 1 to 6 carbon atoms which may be substituted by 1 to 3 halogen atoms (e.g., fluorine, chlorine, bromine, iodine), alkenyloxy groups having 2 to 5 carbon atoms which may be substituted by 1 to 3 halogen atoms (e.g., fluorine, chlorine, bromine, iodine), cycloalkyloxy groups having 3 to 7 carbon atoms, aralkyloxy groups having 7 to 9 carbon atoms, aryloxy groups having 6 to 14 carbon atoms (e.g., phenyloxy, naphthyloxy), thiol group, alkylthio groups having 1 to 6 carbon atoms which may be substituted by 1 to 3 halogen atoms (e.g., fluorine, chlorine, bromine, iodine), aralkylthio groups having 7 to 9 carbon atoms, arylthio groups having 6 to 14 carbon atoms (e.g., phenylthio, naphthylthio), sulfo group, cyano group, azide group, nitro group, nitroso group, and halogen atoms (e.g., fluorine, chlorine, bromine, iodine). The number of the substituents is, for example, 1 to 3.

The acyl groups in "acyl groups which may be substituted" are exemplified by acyl groups having 1 to 13 carbon atoms, specifically formyl and groups of the formulae: —$COR^{11}$, —$SO_2R^{11}$, —$SOR^{11}$ or —$PO_3R^{11}R^{12}$ wherein each of $R^{11}$ and $R^{12}$, whether identical or not, represents a hydrocarbon group or an aromatic heterocyclic group.

The hydrocarbon group for $R^{11}$ or $R^{12}$ is exemplified by the hydrocarbon groups mentioned to exemplify $R^1$ above. Especially preferred are alkyl groups having 1 to 10 carbon atoms, cycloalkyl groups having 3 to 10 carbon atoms, alkenyl groups having 2 to 10 carbon atoms, cycloalkenyl groups having 3 to 10 carbon atoms, and aryl groups having 6 to 12 carbon atoms.

The aromatic heterocyclic group for $R^{11}$ or $R^{12}$ is exemplified by the aromatic heterocyclic groups mentioned to exemplify $R^1$ above. Especially preferred are thienyl, furyl, pyridyl, etc.

Preferred examples of the acyl groups include acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, and isonicotinoyl.

Said acyl group may have 1 to 3 substituents at substitutable positions. Examples of such substituents include $C_{1-6}$ alkyl groups which may be substituted by 1 to 3 halogen atoms (e.g., fluorine, chlorine, iodine), $C_{1-6}$ alkoxy groups which may be substituted by 1 to 3 halogen atoms (e.g., fluorine, chlorine, bromine, iodine), halogen atoms (e.g., fluorine, chlorine, bromine, iodine), nitro, hydroxy, and amino.

"Amino group which may be substituted" is exemplified by an amino group which may be mono- or di-substituted by alkyl groups having 1 to 10 carbon atoms, cycloalkyl groups having 3 to 10 carbon atoms, alkenyl groups having 2 to 10 carbon atoms, cycloalkenyl groups having 3 to 10 carbon atoms, acyl groups having 1 to 13 carbon atoms or aryl groups having 6 to 12 carbon atoms.

Here, the acyl groups are exemplified by the same acyl groups as those mentioned above, and are preferably alkanoyl groups having 2 to 10 carbon atoms, arylcarbonyl groups having 7 to 13 carbon atoms, etc.

Examples of the substituted amino groups include methylamino, dimethylamino, ethylamino, diethylamino, propylamino, dibutylamino, diallylamino, cyclohexylamino, acetylamino, propionylamino, benzoylamino, phenylamino, and N-methyl-N-phenylamino.

"Hydroxy group which may be substituted" is exemplified by hydroxy group which may be substituted by alkyl groups having 1 to 10 carbon atoms, alkenyl groups having 2 to 10 carbon atoms, aralkyls having 7 to 10 carbon atoms, acyl groups having 1 to 13 carbon atoms or aryl groups having 6 to 12 carbon atoms, each of which groups may be substituted.

Examples of the substituents which may be possessed by these "alkyl groups having 1 to 10 carbon atoms", "alkenyl groups having 2 to 10 carbon atoms", "aralkyl groups having 7 to 10 carbon atoms", "acyl groups having 1 to 13 carbon atoms" and "aryl groups having 6 to 12 carbon atoms" include halogen atoms (e.g., fluorine, chlorine, bromine, iodine), $C_{1-6}$ alkoxy groups which may be substituted by 1 to 3 halogen atoms (e.g., fluorine, chlorine, bromine, iodine), hydroxy, nitro, and amino. The number of the substituents is, for example, 1 to 2.

Examples of the substituted hydroxy group include alkoxy groups, alkenyloxy groups, aralkyloxy groups, acyloxy groups, and aryloxy groups, each of which groups may be substituted.

Preferred examples of the alkoxy groups include alkoxy groups having 1 to 10 carbon atoms, such as methoxy, ethoxy, propoxy, isopropoxy, butoxy, isobutoxy, sec.-butoxy, t.-butoxy, pentyloxy, isopentyloxy, neopentyloxy, hexyloxy, heptyloxy, nonyloxy, cyclobutoxy, cyclopentyloxy, and cyclohexyloxy.

Preferred examples of the alkenyloxy groups include alkenyloxy groups having 2 to 10 carbon atoms, such as allyloxy, crotyloxy, 2-pentenyloxy, 3-hexenyloxy, 2-cyclopentenyloxy, and 2-cyclohexenyloxy.

Preferred examples of the aralkyloxy groups include aralkyloxy groups having 7 to 10 carbon atoms, such as phenyl-$C_{1-4}$ alkyloxys (e.g., benzyloxy, phenethyloxy).

Preferred examples of the acyloxy groups include acyloxy groups having 2 to 13 carbon atoms, with greater preference given to alkanoyloxys having 2 to 4 carbon atoms (e.g., acetyloxy, propionyloxy, butyryloxy, isobutyryloxy).

Preferred examples of the aryloxy groups include aryloxy groups having 6 to 14 carbon atoms, such as phenoxy and naphthyloxy.

The aforementioned alkoxy groups, alkenyloxy groups, aralkyloxy groups, acyloxy groups and aryloxy groups may have 1 to 2 substituents at substitutable positions. Examples of such substituents include halogen atoms (e.g., fluorine, chlorine, bromine, iodine), $C_{1-6}$ alkoxy groups which may be substituted by 1 to 3 halogen atoms (e.g., fluorine, chlorine, bromine, iodine), hydroxy, nitro, and amino. For example, examples of the substituted aryloxy groups include 4-chlorophenoxy and 2-methoxyphenoxy.

Thiol group which may be substituted is exemplified by thiol group which may be substituted by alkyls having 1 to 10 carbon atoms, cycloalkyls having 3 to 10 carbon atoms, aralkyls having 7 to 10 carbon atoms, acyls having 2 to 13 carbon atoms, aryls having 6 to 14 carbon atoms, heteroaryls, etc.

Examples of the substituted thiol groups include alkylthios, cycloalkylthios, aralkylthios, acylthios, arylthios, and heteroarylthios.

Preferred examples of the alkylthio groups include alkylthio groups having 1 to 10 carbon atoms, such as methylthio, ethylthio, propylthio, isopropylthio, butylthio, isobutylthio, sec.-butylthio, t.-butylthio, pentylthio, isopentylthio, neopentylthio, hexylthio, heptylthio, and nonylthio.

Preferred examples of the cycloalkylthio groups include cycloalkylthio groups having 3 to 10 carbon atoms, such as cyclobutylthio, cyclopentylthio, and cyclohexylthio.

Preferred examples of the aralkylthio groups include aralkylthio groups having 7 to 10 carbon atoms, such as phenyl-$C_{1-4}$ alkylthios (e.g., benzylthio, phenethylthio).

Preferred examples of the acylthio groups include acylthio groups having 2 to 13 carbon atoms, with greater preference given to alkanoylthio groups having 2 to 4 carbon atoms (e.g., acetylthio, propionylthio, butyrylthio, isobutyrylthio).

Preferred examples of the arylthio groups include arylthio groups having 6 to 14 carbon atoms, such as phenylthio and naphthylthio.

Preferred examples of the heteroarylthio groups include 2-pyridylthio, 3-pyridylthio, 2-imidazolylthio, and 1,2,4-triazol-5-ylthio.

Esterified carboxyl groups in the carboxyl groups which may be esterified are exemplified by alkoxycarbonyl groups having 2 to 5 carbon atoms (e.g., methoxycarbonyl, ethoxycarbonyl, propoxycarbonyl, butoxycarbonyl), aralkyloxycarbonyl groups having 8 to 10 carbon atoms (e.g., benzyloxycarbonyl), and aryloxycarbonyl groups having 7 to 15 carbon atoms (e.g., phenoxycarbonyl, p-tolyloxycarbonyl) which may be substituted by 1 or 2 alkyl groups having 1 to 3 carbon atoms.

Amidated carboxyl groups in the carboxyl groups which may be amidated are exemplified by groups of the formula: —CON($R^{13}$)($R^{14}$) wherein each of $R^{13}$ and $R^{14}$, whether identical or not, represents a hydrogen atom, a hydrocarbon group which may be substituted or a heterocyclic group which may be substituted.

Here, the hydrocarbon group in the "hydrocarbon group which may be substituted" for $R^{13}$ and $R^{14}$ is exemplified by the aliphatic hydrocarbon groups, alicyclic hydrocarbon groups and aromatic hydrocarbon groups mentioned to exemplify the hydrocarbon group in the "hydrocarbon group which may be substituted" for $R^1$. In addition, the heterocyclic group in the "heterocyclic group which may be substituted" for $R^{13}$ and $R^{14}$ is exemplified by the heterocyclic groups mentioned to exemplify the heterocyclic group in the "heterocyclic group which may be substituted" for $R^1$. These hydrocarbon groups and heterocyclic groups may have 1 to 3 substituents at substitutable positions. Examples of such substituents include halogen atoms (e.g., fluorine, chlorine, bromine, iodine), $C_{1-6}$ alkyl groups which may be substituted by 1 to 3 halogen atoms (e.g., fluorine, chlorine, bromine, iodine), $C_{1-6}$ alkoxy groups which may be substituted by 1 to 3 halogen atoms (e.g., fluorine, chlorine, bromine, iodine), nitro, hydroxy, and amino.

The substituents in the hydrocarbon group and heterocyclic group for $R^1$ in the formulae (I) and (II) are preferably:

1) alkyl groups having 1 to 10 (preferably 1 to 4) carbon atoms which may have 1 to 3 substituents selected from the group consisting of alkoxy groups having 1 to 6 carbon atoms which may be substituted by 1 to 3 halogen atoms (e.g., fluorine, chlorine, bromine, iodine), halogen atoms (e.g., fluorine, chlorine, bromine, iodine), nitro, hydroxy, and amino;

2) cycloalkyl groups having 3 to 10 (preferably 3 to 7) carbon atoms which may have 1 to 3 substituents selected from the group consisting of alkyl groups having 1 to 6 carbon atoms which may be substituted by 1 to 3 halogen atoms (e.g., fluorine, chlorine, bromine, iodine), alkoxy groups having 1 to 6 carbon atoms which may be substituted by 1 to 3 halogen atoms (e.g., fluorine, chlorine, bromine, iodine), halogen atoms (e.g., fluorine, chlorine, bromine, iodine), nitro, hydroxy, and amino;

3) aromatic heterocyclic groups (preferably furyl, thienyl, pyridyl, pyrazinyl, etc.) which may have 1 to 3 substituents selected from the group consisting of alkyl groups having 1 to 6 carbon atoms which may be substituted by 1 to 3 halogen atoms (e.g., fluorine, chlorine, bromine, iodine), alkoxy groups having 1 to 6 carbon atoms which may be substituted by 1 to 3 halogen atoms (e.g., fluorine, chlorine, bromine, iodine), halogen atoms (e.g., fluorine, chlorine, bromine, iodine), nitro, hydroxy, and amino;

4) aryl groups having 6 to 14 carbon atoms (preferably phenyl, naphthyl, etc.) which may have 1 to 3 substituents selected from the group consisting of alkyl groups having 1 to 6 carbon atoms which may be substituted by 1 to 3 halogen atoms (e.g., fluorine, chlorine, bromine, iodine), alkoxy groups having 1 to 6 carbon atoms which may be substituted by 1 to 3 halogen atoms (e.g., fluorine, chlorine, bromine, iodine), halogen atoms (e.g., fluorine, chlorine, bromine, iodine), nitro, hydroxy, and amino; etc. The number of the substituents is, for example, 1 to 3, preferably 1 or 2.

The substituents are preferably alkyl groups having 1 to 4 carbon atoms, furyl, thienyl, phenyl, naphthyl etc.

(1-4) Preferred Examples of $R^1$

In the formulae (I) and (II), $R^1$ is preferably a heterocyclic group which may be substituted or a cyclic hydrocarbon group which may be substituted. $R^1$ is more preferably a heterocyclic group which may be substituted. Here, the heterocyclic group is preferably a 5- or 6-membered aromatic heterocyclic group (preferably furyl, thienyl, pyridyl, pyrimidinyl, pyrazinyl, oxazolyl, thiazolyl, triazolyl, oxadiazolyl, pyrazolyl) which may be condensed with a benzene ring. Especially preferred are furyl, thienyl, pyridyl, pyrimidinyl, pyrazinyl, oxazolyl, thiazolyl, oxadiazolyl, benzoxazolyl, benzothiazolyl, quinolyl, pyrazolyl, etc.

Preferred examples of the substituents which may be possessed by the aforementioned heterocyclic group or cyclic hydrocarbon group include 1) furyl, thienyl, pyridyl, pyrazinyl, phenyl or naphthyl, each of which may have 1 to 3 substituents selected from the group consisting of alkyl groups having 1 to 6 carbon atoms which may be substituted by 1 to 3 halogen atoms (e.g., fluorine, chlorine, bromine, iodine), alkoxy groups having 1 to 6 carbon atoms which may be substituted by 1 to 3 halogen atoms (e.g., fluorine, chlorine, bromine, iodine), halogen atoms (e.g., fluorine, chlorine, bromine, iodine), nitro, hydroxy, and amino;

2) alkyl groups having 1 to 4 carbon atoms or cycloalkyl groups having 3 to 7 carbon atoms, each of which may have 1 to 3 substituents selected from the group consisting of alkoxy groups having 1 to 6 carbon atoms which may be substituted by 1 to 3 halogen atoms (e.g., fluorine, chlorine, bromine, iodine), halogen atoms (e.g., fluorine, chlorine, bromine, iodine), nitro, hydroxy, and amino. The number of the substituents is, for example, 1 or 2.

$R^1$ is especially preferably pyridyl, oxazolyl, thiazolyl, triazolyl or pyrazolyl, each of which may have 1 to 2 substituents selected from the group consisting of alkyl groups having 1 to 3 carbon atoms, cycloalkyl groups having 3 to 7 carbon atoms, furyl, thienyl, pyridyl, phenyl and naphthyl.

(2) Definition of X

In the formulae (I) and (II), X represents a bond, an oxygen atom, a sulfur atom, or a group of the formula: —CO—, —CS—, —CR$^4$(OR$^5$)— or —NR$^6$— wherein each of $R^4$ and $R^6$ represents a hydrogen atom or a hydrocarbon group which may be substituted, $R^5$ represents a hydrogen atom or a protective group for a hydroxyl group; and is preferably a bond, —CR$^4$(OR$^5$)— or —NR$^6$— wherein the symbols have the same meanings as above, more preferably a bond or —NR$^6$— wherein the symbol has the same meaning as above. X is especially preferably a bond.

Here, the "hydrocarbon groups which may be substituted" for $R^4$ and $R^6$ is exemplified by the "hydrocarbon groups which may be substituted" mentioned to exemplify $R^1$ above. Said "hydrocarbon groups which may be substituted" are preferably alkyl groups having 1 to 4 carbon atoms which may be substituted, such as methyl, ethyl, propyl, isopropyl, butyl, isobutyl, sec.-butyl, and t.-butyl. Said alkyl groups may have 1 to 3 substituents at substitutable positions. Examples of such substituents include halogen atoms (e.g., fluorine, chlorine, bromine, iodine), alkoxy groups having 1 to 4 carbon atoms (e.g., methoxy, ethoxy, propoxy, isopropoxy, butoxy, isobutoxy, sec.-butoxy, t.-butoxy), hydroxy, nitro, amino, and acyl groups having 1 to 4 carbon atoms (e.g., alkanoyl groups having 1 to 4 carbon atoms, such as formyl, acetyl and propionyl).

$R^4$ and $R^6$ are preferably hydrogen atom or alkyl groups having 1 to 4 carbon atoms.

Examples of the protective groups for a hydroxyl group for $R^5$ include $C_{1-6}$ alkyls (e.g., methyl, ethyl, propyl, isopropyl, butyl, tert-butyl), phenyl, trityl, $C_{7-10}$ aralkyls (e.g., benzyl), formyl, $C_{1-6}$ alkyl-carbonyls (e.g., acetyl, propionyl), benzoyl, $C_{7-10}$ aralkyl-carbonyls (e.g., benzylcarbonyl), 2-tetrahydropyranyl, 2-tetrahydrofuranyl, silyls (e.g., trimethylsilyl, triethylsilyl, dimethylphenylsilyl, tert-butyldimethylsilyl, tert-butyldiethylsilyl), and $C_{2-6}$ alkenyls (e.g., 1-allyl). These groups may be substituted by 1 to 3 halogen atoms (e.g., fluorine, chlorine, bromine, iodine), $C_{1-6}$ alkyls (e.g., methyl, ethyl, propyl), $C_{1-6}$ alkoxy (e.g., methoxy, ethoxy, propoxy), nitro, or the like.

(3) Definitions of m and Y

In the formulae (I) and (II), m represents an integer of 0 to 3, preferably an integer of 1 to 3, and more preferably 1 or 2.

In the formulae (I) and (II), Y represents an oxygen atom, a sulfur atom, or a group of the formula: —SO—, —SO$_2$—, —NR$^7$—, —CONR$^7$— or —NR$^7$CO— wherein $R^7$ represents a hydrogen atom or a hydrocarbon group which may be substituted, and is preferably an oxygen atom, a sulfur atom, —NR$^7$— or —NR$^7$CO— wherein the symbol has the same meaning as above.

Here, "hydrocarbon groups which may be substituted" for $R^7$ is exemplified by the "hydrocarbon groups which may be substituted" mentioned to exemplify $R^4$ and $R^6$ above. $R^7$ is preferably a hydrogen atom. Y is especially preferably an oxygen atom.

(4) Definition of Ring A

In the formulae (I) and (II), the "aromatic ring" in the "aromatic ring which may further have 1 to 3 substituents" for ring A is exemplified by benzene ring, condensed aromatic hydrocarbon rings, 5- or 6-membered aromatic hetero rings, and condensed aromatic hetero rings.

Here, examples of the "condensed aromatic hydrocarbon rings" include condensed aromatic hydrocarbon rings having 9 to 14 carbon atoms. Specifically, there may be mentioned naphthalene, indene, fluorene, anthracene, etc.

Examples of the "5- or 6-membered aromatic hetero rings" include 5- or 6-membered aromatic hetero rings containing 1 to 3 hetero atoms selected from nitrogen atom, sulfur atom and oxygen atom, in addition to carbon atoms. Specifically, there may be mentioned thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, furazane etc.

Examples of the "condensed aromatic hetero rings" include 9- to 14-membered (preferably 9- or 10-membered) condensed aromatic hetero rings containing 1 to 4 hetero atoms selected from nitrogen atom, sulfur atom, and oxygen atom, in addition to carbon atoms. Specifically, there may be mentioned benzofuran, benzothiophene, benzimidazole, benzoxazole, benzothiazole, benzisothiazole, naphtho[2,3-b]thiophene, isoquinoline, quinoline, indole, quinoxaline, phenanthridine, phenothiazine, phenoxazine, phthalazine, naphthyridine, quinazoline, cinnoline, carbazole, β-carboline, acridine, phenazine, phthalimide, etc.

The "aromatic ring" is preferably benzene ring, a condensed aromatic hydrocarbon ring having 9 to 14 carbon atoms (preferably naphthalene, etc.), a 5- or 6-membered aromatic hetero ring (preferably, pyridine, isoxazole, etc.), or the like.

Examples of the "substituents" in the "aromatic ring which may further have 1 to 3 substituents" for ring A include aliphatic hydrocarbon groups (preferably alkyl groups) which may be substituted, hydroxy group which may be substituted, halogen atoms, acyl groups which may be substituted, nitro group, and amino group which may be substituted. All of these substituents are those mentioned to exemplify the substituents in $R^1$. Said substituents are preferably alkyl groups having 1 to 4 carbon atoms, hydroxy group, alkoxy groups having 1 to 4 carbon atoms, aralkyloxy groups having 7 to 10 carbon atoms (preferably benzyloxy), or halogen atoms.

Ring A is preferably "benzene ring or pyridine ring, each of which may further have 1 to 3 substituents", more preferably benzene ring or pyridine ring, each of which may further have 1 to 3 substituents selected from the group consisting of alkyl groups having 1 to 4 carbon atoms, hydroxy group, alkoxy groups having 1 to 4 carbon atoms, aralkyloxy groups having 7 to 10 carbon atoms, and halogen atoms. Ring A is especially preferably benzene ring.

(5) Definition of n

In the formulae (I) and (II), n represents an integer of 1 to 8, preferably an integer of 1 to 3.

(6) Definition of Ring B

In the formulae (I) and (II), the "nitrogen-containing 5-membered hetero ring" in the "nitrogen-containing 5-membered hetero ring which may further be substituted by an alkyl group" for ring B is exemplified by 5-membered hetero rings which contain at least 1 nitrogen atom, in addition to carbon atoms, as ring constituent atoms, and which may further contain 1 to 3 hetero atoms selected from oxygen atom, sulfur atom and nitrogen atom.

Preferred examples of the nitrogen-containing 5-membered hetero rings include 5-membered aromatic hetero rings such as pyrrole, pyrazole, imidazole, thiazole, isothiazole, oxazole, isoxazole, 1,2,4-triazole, 1,2,3-triazole, 1,2,3-oxadiazole, 1,2,4-oxadiazole, 1,3,4-oxadiazole, furazane, 1,2,3-thiadiazole, 1,2,4-thiadiazole, 1,3,4-thiadiazole, and tetrazole; and 5-membered non-aromatic hetero rings such as pyrrolidine, imidazolidine, and pyrazolidine. The nitrogen-containing 5-membered hetero rings are preferably 5-membered aromatic hetero rings which contain at least 1 nitrogen atom, in addition to carbon atoms, as ring constituent atoms, and which may further contain 1 hetero atom selected from oxygen atom, sulfur atom and nitrogen atom, such as pyrrole, pyrazole, imidazole, thiazole, isothiazole, oxazole, and isoxazole. Especially preferred are pyrrole, pyrazole, imidazole, etc.

The "alkyl group" in the "nitrogen-containing 5-membered hetero ring which may further be substituted by an alkyl group" is exemplified by alkyl groups having 1 to 4 carbon atoms. Specifically, there may be mentioned methyl, ethyl, propyl, butyl, isobutyl, sec-butyl, t-butyl etc., with preference given to methyl and ethyl.

Ring B is preferably pyrrole, pyrazole or imidazole, each of which may further be substituted by an alkyl group having 1 to 4 carbon atoms. Ring B is especially preferably pyrazole.

(7) Definition of $X^1$

In the formulae (I) and (II), $X^1$ represents a bond, an oxygen atom, a sulfur atom, or a group of the formula: —SO—, —$SO_2$—, —O—$SO_2$— or —$NR^{16}$— wherein $R^{16}$ represents a hydrogen atom or a hydrocarbon group which may be substituted.

Here, the "hydrocarbon group which may be substituted" for $R^{16}$ is exemplified by the "hydrocarbon groups which may be substituted" mentioned to exemplify $R^4$ and $R^6$ above.

$X^1$ is preferably a bond or an oxygen atom.

(8) Definition of $R^2$

In the formulae (I) and (II), the "hydrocarbon group which may be substituted" and "heterocyclic group which may be substituted" for $R^2$ is respectively exemplified by the "hydrocarbon groups which may be substituted" and "heterocyclic groups which may be substituted" mentioned to exemplify $R^1$.

(8-1) Cases Where $X^1$ in the Formulae (I) and (II) is a Bond

The hydrocarbon group in the "hydrocarbon group which may be substituted" for $R^2$ is preferably an aliphatic hydrocarbon group having 1 to 8 carbon atoms (preferably an alkyl group) or an aromatic hydrocarbon group having 6 to 14 carbon atoms, and more preferably an aromatic hydrocarbon group having 6 to 14 carbon atoms (e.g., phenyl, naphthyl).

The heterocyclic group in the "heterocyclic group which may be substituted" for $R^2$ is preferably a 5- or 6-membered aromatic heterocyclic group (e.g., furyl, thienyl, pyridyl).

The substituents in the aforementioned "hydrocarbon group which may be substituted" and "heterocyclic group which may be substituted" are preferably 1) halogen atoms (e.g., fluorine, chlorine, bromine, iodine), 2) alkyl groups having 1 to 4 carbon atoms (e.g., methyl, trifluoromethyl, propyl, isopropyl) which may be substituted by 1 to 3 halogen atoms (e.g., fluorine, chlorine, bromine, iodine), 3) alkoxy groups having 1 to 4 carbon atoms (e.g., methoxy, trifluoromethoxy) which may be substituted by 1 to 3 halogen atoms (e.g., fluorine, chlorine, bromine, iodine), 4) aralkyloxy groups having 7 to 10 carbon atoms (e.g., benzyloxy), 5) aryloxy groups having 6 to 14 carbon atoms (e.g., phenoxy), 6) aromatic heterocyclic groups (e.g., furyl, thienyl), or the like. The number of the substituents is, for example, 1 to 3.

$R^2$ is preferably 1) aromatic hydrocarbon groups having 6 to 14 carbon atoms (e.g., phenyl, naphthyl) which may be substituted, or 2) 5- or 6-membered aromatic heterocyclic groups (e.g., furyl, thienyl, pyridyl) which may be substituted.

$R^2$ is more preferably 1) aromatic hydrocarbon groups having 6 to 14 carbon atoms (e.g., phenyl, naphthyl), or 2) 5- or 6-membered aromatic heterocyclic groups (e.g., furyl, thienyl, pyridyl). Especially preferred are phenyl, furyl, thienyl, etc.

(8-2) Cases where $X^1$ in the formulae (I) and (II) is an oxygen atom, a sulfur atom, or a group of the formula: —SO—, —$SO_2$—, —O—$SO_2$— or —$NR^{16}$— wherein the symbol has the same meaning as above.

The hydrocarbon group in the "hydrocarbon group which may be substituted" for $R^2$ is preferably an aliphatic hydrocarbon group having 1 to 8 carbon atoms (preferably an alkyl group (e.g., methyl, ethyl, propyl, isopropyl)), an aromatic-aliphatic hydrocarbon group having 7 to 13 carbon atoms (preferably an aralkyl group (e.g., benzyl)), an aromatic hydrocarbon group having 6 to 14 carbon atoms (e.g., phenyl, naphthyl).

The heterocyclic group in the "heterocyclic group which may be substituted" for $R^2$ is preferably a 5- or 6-membered aromatic heterocyclic group (e.g., furyl, thienyl, pyridyl).

The substituents in the aforementioned "hydrocarbon group which may be substituted" and "heterocyclic group which may be substituted" are preferably 1) halogen atoms (e.g., fluorine, chlorine, bromine, iodine), 2) alkyl groups having 1 to 4 carbon atoms (e.g., methyl, ethyl, trifluoromethyl) which may be substituted by 1 to 3 halogen atoms (e.g., fluorine, chlorine, bromine, iodine), 3) aralkyloxy groups having 7 to 10 carbon atoms (e.g., benzyloxy), 4) [5- or 6-membered aromatic heterocyclic groups (e.g., pyridyl, oxazolyl, thiazolyl, triazolyl) which may have 1 or 2 substituents selected from alkyl groups having 1 to 3 carbon atoms, cycloalkyl groups having 3 to 7 carbon atoms (e.g., cyclohexyl), furyl, thienyl, phenyl and naphthyl]-alkoxy groups having 1 to 6 carbon atoms (e.g., methoxy, ethoxy), 5) aromatic heterocyclic groups (e.g., furyl, thienyl, pyridyl), 6) aryloxy groups having 6 to 14 carbon atoms (e.g., phenoxy), 7) alkoxy groups having 1 to 4 carbon atoms (e.g., methoxy, ethoxy, trifluoromethoxy) which may be substituted by 1 to 3 halogen atoms (e.g., fluorine, chlorine, bromine, iodine), or the like. The number of the substituents is, for example, 1 to 3.

$R^2$ is preferably an aliphatic hydrocarbon group having 1 to 8 carbon atoms (preferably an alkyl group (e.g., methyl, ethyl, propyl, isopropyl)) which may be substituted, an aromatic-aliphatic hydrocarbon group having 7 to 13 carbon atoms (preferably an aralkyl group (e.g., benzyl)) which may be substituted, or a heterocyclic group (preferably a 5- or 6-membered aromatic heterocyclic group (e.g., furyl, thienyl, pyridyl)) which may be substituted.

$R^2$ is more preferably an aliphatic hydrocarbon group having 1 to 8 carbon atoms (preferably an alkyl group (e.g., methyl, ethyl, propyl, isopropyl)) or an aromatic-aliphatic hydrocarbon group having 7 to 13 carbon atoms (preferably an aralkyl group (e.g., benzyl)).

(9) Definition of W

In the formulae (I) and (II), the "divalent hydrocarbon residue having 1 to 20 carbon atoms" for W is exemplified by "divalent non-cyclic hydrocarbon residues", "divalent cyclic hydrocarbon residues", and divalent groups obtained by combining 1 or more "divalent non-cyclic hydrocarbon residues" and 1 or more "divalent cyclic hydrocarbon residues".

Here, examples of the "divalent non-cyclic hydrocarbon residues" include alkylenes having 1 to 20 carbon atoms, alkenylenes having 2 to 20 carbon atoms, and alkynylenes having 2 to 20 carbon atoms.

Examples of the "divalent cyclic hydrocarbon residues" include divalent groups obtained by removing two optionally selected hydrogen atoms from cycloalkanes having 5 to 20 carbon atoms, cycloalkenes having 5 to 20 carbon atoms, or aromatic hydrocarbons having 6 to 20 carbon atoms (e.g., benzene, naphthalene, indene, anthracene). Specifically, there may be mentioned 1,2-cyclopentylene, 1,3-cyclopentylene, 1,2-cyclohexylene, 1,3-cyclohexylene, 1,4-cyclohexylene, 1,2-cycloheptylene, 1,3-cycloheptylene, 1,4-cycloheptylene, 3-cyclohexen-1,4-ylene, 3-cyclohexen-1,2-ylene, 2,5-cyclohexadien-1,4-ylene, 1,2-phenylene, 1,3-phenylene, 1,4-phenylene, 1,4-naphthylene, 1,6-naphthylene, 2,6-naphthylene, 2,7-naphthylene, 1,5-indenylene, 2,5-indenylene, etc.

The compounds wherein W in the formulae (I) and (II) is a divalent hydrocarbon residue having 1 to 20 carbon atoms possess more potent hypoglycemic and hypolipidemic actions than those wherein W is a bond. It is therefore preferable that W be a divalent hydrocarbon residue having 1 to 20 carbon atoms. W is more preferably a "divalent hydrocarbon residue having 1 to 8 carbon atoms", with preference given to:

(1) $C_{1-8}$ alkylenes (e.g., $—CH_2—$, $—(CH_2)_2—$, $—(CH_2)_3—$, $—(CH_2)_4—$, $—(CH_2)_5—$, $—(CH_2)_6—$, $—(CH_2)_7—$, $—(CH_2)_8—$, $—CH(CH_3)—$, $—C(CH_3)_2—$, $—(CH(CH_3))_2—$, $—(CH_2)_2C(CH_3)_2—$, $—(CH_2)_3C(CH_3)_2—$);

(2) $C_{2-8}$ alkenylenes (e.g., $—CH=CH—$, $—CH_2—CH=CH—$, $—C(CH_3)_2—CH=CH—$, $—CH_2—CH=CH—CH_2—$, $—CH_2—CH_2—CH=CH—$, $—CH=CH—CH=$, $—CH=CH—CH_2—CH_2—CH_2—$); or (3) $C_{2-8}$ alkynylenes (e.g., $—C≡C—$, $—CH_2—C≡C—$, $—CH_2—C≡C—CH_2—CH_2—$).

W is especially preferably $—CH_2—$, $—(CH_2)_2—$, $—(CH_2)_3—$, $—(CH_2)_4—$, $—CH=CH—$, or the like.

(10) Definition of $R^3$

In the formulae (I) and (II), $R^3$ is a group of the formula: $—OR^8$ ($R^8$ represents a hydrogen atom or a hydrocarbon group which may be substituted) or $—NR^9R^{10}$ (each of $R^9$ and $R^{10}$, whether identical or not, represents a hydrogen atom, a hydrocarbon group which may be substituted, a heterocyclic group which may be substituted, or an acyl group which may be substituted; $R^9$ and $R^{10}$ may bind together to form a ring).

The "hydrocarbon group which may be substituted" for $R^8$ is exemplified by the "hydrocarbon groups which may be substituted" mentioned to exemplify $R^1$.

Said "hydrocarbon group which may be substituted" is preferably an "alkyl group having 1 to 4 carbon atoms", an "aryl group having 6 to 10 carbon atoms which may have 1 to 3 substituents selected from alkyl groups having 1 to 4 carbon atoms and halogen atoms (e.g., fluorine, chlorine, bromine, iodine)", or the like. Here, examples of the "alkyl group having 1 to 4 carbon atoms" include methyl, ethyl, propyl, butyl, isobutyl, sec-butyl, t-butyl etc., with preference given to methyl and ethyl. As a "halogen atom", chlorine is preferred. Examples of the "aryl group having 6 to 10 carbon atoms" include phenyl and naphthyl, with preference given to phenyl.

The "hydrocarbon group which may be substituted" and "heterocyclic group which may be substituted" for $R^9$ and $R^{10}$ are exemplified by the "hydrocarbon group which may be substituted" and "heterocyclic group which may be substituted" respectively mentioned to exemplify $R^1$.

The "acyl group which may be substituted" for $R^9$ and $R^{10}$ is exemplified by the "acyl group which may be substituted" mentioned to exemplify a substituent in $R^1$.

Examples of the ring formed by $R^9$ and $R^{10}$ bound together include 5- to 7-membered cyclic amino groups, preferably 1-pyrrolidinyl, 1-piperidinyl, 1-hexamethyleneiminyl, 4-morpholino, 4-thiomorpholino, etc.

$R^9$ and $R^{10}$ are preferably a hydrogen atom or an alkyl group having 1 to 4 carbon atoms (e.g., methyl, ethyl).

$R^3$ is preferably a group of the formula: $—OR^8$ (the symbol has the same meaning as above), and $R^8$ is preferably a hydrogen atom or an alkyl group having 1 to 4 carbon atoms (e.g., methyl, ethyl).

(11) Preferable Compounds

Preferred examples of compounds of the formula (I) and (II) include the compounds below.

(A) Compounds in which $R^1$ is a 5- or 6-membered aromatic heterocyclic group (preferably furyl, thienyl, pyridyl, pyrimidinyl, pyrazinyl, oxazolyl, thiazolyl, triazolyl, oxadiazolyl, pyrazolyl) which may be condensed with a benzene ring, and which may have 1 or 2 substituents selected from 1) furyl, thienyl, pyridyl, pyrazinyl, phenyl or naphthyl, each of which may have 1 to 3 substituents selected from the group consisting of alkyl groups having 1 to 6 carbon atoms which may be substituted by 1 to 3 halogen atoms (e.g., fluorine, chlorine, bromine, iodine), alkoxy groups having 1 to 6 carbon atoms which may be substituted by 1 to 3 halogen atoms (e.g., fluorine, chlorine, bromine, iodine), halogen atoms (e.g., fluorine, chlorine, bromine, iodine), nitro, hydroxy, and amino; and 2) alkyl groups having 1 to 4 carbon atoms or cycloalkyl groups having 3 to 7 carbon atoms, each of which may have 1 to 3 substituents selected from the group consisting of alkoxy groups having 1 to 6 carbon atoms which may be substituted by 1 to 3 halogen atoms (e.g., fluorine, chlorine, bromine, iodine), halogen atoms (e.g., fluorine, chlorine, bromine, iodine), nitro, hydroxy, and amino;

X is a bond or —$NR^6$— wherein $R^6$ is a hydrogen atom or an alkyl group having 1 to 4 carbon atoms;

m is 1 or 2;

Y is an oxygen atom, a sulfur atom, —NH— or —NHCO—;

ring A is benzene ring, a condensed aromatic hydrocarbon ring having 9 to 14 carbon atoms (preferably naphthalene, etc.) or a 5- or 6-membered aromatic hetero ring (preferably pyridine, isoxazole, etc.), each of which ring may further have 1 to 3 substituents selected from the group consisting of alkyl groups having 1 to 4 carbon atoms, hydroxy group, alkoxy groups having 1 to 4 carbon atoms, aralkyloxy groups having 7 to 10 carbon atoms and halogen atoms;

n is an integer of 1 to 3;

ring B is a "5-membered aromatic hetero ring which contains at least 1 nitrogen atom, in addition to carbon atoms, as ring constituent atoms, and which may further contain 1 hetero atom selected from oxygen atom, sulfur atom and nitrogen atom" (e.g., pyrrole, pyrazole, imidazole, thiazole, isothiazole, oxazole, isoxazole) which may further be substituted by an alkyl group having 1 to 4 carbon atoms;

$X^1$ is a bond;

$R^2$ is an aliphatic hydrocarbon group having 1 to 8 carbon atoms (preferably an alkyl group), an aromatic hydrocarbon group having 6 to 14 carbon atoms (e.g., phenyl, naphthyl) or a 5- or 6-membered aromatic heterocyclic group (e.g., furyl, thienyl, pyridyl), each of which may be substituted by 1 to 3 substituents selected from the group consisting of 1) halogen atoms (e.g., fluorine, chlorine, bromine, iodine), 2) alkyl groups having 1 to 4 carbon atoms (e.g., methyl, trifluoromethyl, propyl, isopropyl) which may be substituted by 1 to 3 halogen atoms (e.g., fluorine, chlorine, bromine, iodine), 3) alkoxy groups having 1 to 4 carbon atoms (e.g., methoxy, trifluoromethoxy) which may be substituted by 1 to 3 halogen atoms (e.g., fluorine, chlorine, bromine, iodine), 4) aralkyloxy groups having 7 to 10 carbon atoms (e.g., benzyloxy), 5) aryloxy groups having 6 to 14 carbon atoms (e.g., phenoxy) and 6) aromatic heterocyclic groups (e.g., furyl, thienyl);

W is a $C_{1-8}$ alkylene, a $C_{2-8}$ alkenylene or a $C_{2-8}$ alkynylene;

$R^3$ is —$OR^8$ ($R^8$ is a hydrogen atom, an "alkyl group having 1 to 4 carbon atoms" or an "aryl group having 6 to 10 carbon atoms which may have 1 to 3 substituents selected from alkyl groups having 1 to 4 carbon atoms and halogen atoms (e.g., fluorine, chlorine, bromine, iodine)") or —$NR^9R^{10}$ (each of $R^9$ and $R^{10}$, whether identical or not, is a hydrogen atom or an alkyl group having 1 to 4 carbon atoms).

(B) Compounds in which $R^1$ is a 5- or 6-membered aromatic heterocyclic group (preferably furyl, thienyl, pyridyl, pyrimidinyl, pyrazinyl, oxazolyl, thiazolyl, triazolyl, oxadiazolyl, pyrazolyl) which may be condensed with a benzene ring, and which may have 1 or 2 substituents selected from 1) furyl, thienyl, pyridyl, pyrazinyl, phenyl or naphthyl, each of which may have 1 to 3 substituents selected from the group consisting of alkyl groups having 1 to 6 carbon atoms which may be substituted by 1 to 3 halogen atoms (e.g., fluorine, chlorine, bromine, iodine), alkoxy groups having 1 to 6 carbon atoms which may be substituted by 1 to 3 halogen atoms (e.g., fluorine, chlorine, bromine, iodine), halogen atoms (e.g., fluorine, chlorine, bromine, iodine), nitro, hydroxy, and amino; and 2) alkyl groups having 1 to 4 carbon atoms or cycloalkyl groups having 3 to 7 carbon atoms, each of which may have 1 to 3 substituents selected from the group consisting of alkoxy groups having 1 to 6 carbon atoms which may be substituted by 1 to 3 halogen atoms (e.g., fluorine, chlorine, bromine, iodine), halogen atoms (e.g., fluorine, chlorine, bromine, iodine), nitro, hydroxy, and amino;

X is a bond or —$NR^6$— wherein $R^6$ is a hydrogen atom or an alkyl group having 1 to 4 carbon atoms;

m is 1 or 2;

Y is an oxygen atom, a sulfur atom, —NH— or —NHCO—;

ring A is benzene ring, a condensed aromatic hydrocarbon ring having 9 to 14 carbon atoms (preferably naphthalene, etc.) or a 5- or 6-membered aromatic hetero ring (preferably pyridine, isoxazole, etc.), each of which ring may further have 1 to 3 substituents selected from the group consisting of alkyl groups having 1 to 4 carbon atoms, hydroxy group, alkoxy groups having 1 to 4 carbon atoms, aralkyloxy groups having 7 to 10 carbon atoms and halogen atoms;

n is an integer of 1 to 3;

ring B is a "5-membered aromatic hetero ring which contains at least 1 nitrogen atom, in addition to carbon atoms, as ring constituent atoms, and which may further contain 1 hetero atom selected from oxygen atom, sulfur atom and nitrogen atom" (e.g., pyrrole, pyrazole, imidazole, thiazole, isothiazole, oxazole, isoxazole) which may further be substituted by an alkyl group having 1 to 4 carbon atoms;

$X^1$ is a bond;

$R^2$ is an aliphatic hydrocarbon group having 1 to 8 carbon atoms (preferably an alkyl group (e.g., methyl, ethyl, propyl, isopropyl)), an aromatic-aliphatic hydrocarbon group having 7 to 13 carbon atoms (preferably an aralkyl group (e.g., benzyl)) or a 5- or 6-membered aromatic heterocyclic group (e.g., furyl, thienyl, pyridyl), each of which may be substituted by 1 to 3 substituents selected from the group consisting of 1) halogen atoms (e.g., fluorine, chlorine, bromine, iodine), 2) alkyl groups having 1 to 4 carbon atoms (e.g., methyl, ethyl, trifluoromethyl) which may be substituted by 1 to 3 halogenatoms (e.g., fluorine, chlorine, bromine, iodine), 3) aralkyloxy groups having 7 to 10 carbon atoms (e.g., benzyloxy), 4) [5- or 6-membered aromatic heterocyclic groups (e.g., pyridyl, oxazolyl, thiazolyl, triazolyl) which may have 1 or 2 substituents selected from alkyl groups having 1 to 3 carbon atoms, cycloalkyl groups having 3 to 7 carbon atoms (e.g., cyclohexyl), furyl, thienyl, phenyl and naphthyl]-alkoxy groups having 1 to 6 carbon atoms (e.g., methoxy, ethoxy), 5) aromatic heterocyclic groups (e.g., furyl, thienyl, pyridyl), 6) aryloxy groups having 6 to 14 carbon atoms (e.g., phenoxy) and 7) alkoxy groups having 1 to 4 carbon atoms (e.g., methoxy, ethoxy, trifluoromethoxy) which may be substituted by 1 to 3 halogen atoms (e.g., fluorine, chlorine, bromine, iodine);

W is a $C_{1-8}$ alkylene, a $C_{2-8}$ alkenylene or a $C_{2-8}$ alkynylene;

$R^3$ is —$OR^8$ ($R^8$ is a hydrogen atom, an "alkyl group having 1 to 4 carbon atoms" or an "aryl group having 6 to 10 carbon atoms which may have 1 to 3 substituents selected from alkyl groups having 1 to 4 carbon atoms and halogen atoms (e.g., fluorine, chlorine, bromine, iodine)") or —$NR^9R^{10}$ (each of $R^9$ and $R^{10}$, whether identical or not, is a hydrogen atom or an alkyl group having 1 to 4 carbon atoms).

(12) Salts

The salt of a compound of the formula (I) or (II) (hereinafter also referred to as Compound (I) or (II), respectively) is preferably a pharmacologically acceptable salt, and is exemplified by salts with inorganic bases, salts with organic bases, salts with inorganic acids, salts with organic acids, and salts with basic or acidic amino acids.

Preferred examples of the salts with inorganic bases include alkali metal salts such as sodium salts and potassium salts; alkaline earth metal salts such as calcium salts and magnesium salts; and aluminum salts and ammonium salts.

Preferred examples of the salts with organic bases include salts with trimethylamine, triethylamine, pyridine, picoline, ethanolamine, diethanolamine, triethanolamine, dicyclohexylamine, N,N-dibenzylethylenediamine, etc.

Preferred examples of the salts with inorganic acids include salts with hydrochloric acid, hydrobromic acid, nitric acid, sulfuric acid, phosphoric acid, etc.

Preferred examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

Preferred examples of the salts with basic amino acids include salts with arginine, lysine, ornithine, etc.

Examples of preferred salts with acidic amino acids include salts with aspartic acid, glutamic acid, etc.

Of the aforementioned salts, sodium salts, potassium salts, hydrochlorides, etc. are preferred.

(13) Prodrugs Etc.

A prodrug of Compound (II) refers to a compound capable of being converted to Compound (II) by reactions of an enzyme, gastric juice, or the like, under physiological conditions in vivo, specifically a compound capable of being converted to Compound (II) upon enzymatic oxidation, reduction, hydrolysis, or the like, or a compound capable of being converted to Compound (II) upon hydrolysis or the like by gastric juice or the like. Examples of the prodrugs of Compound (II) include compounds derived by acylation, alkylation or phosphorylation of the amino group of Compound (II) (e.g., compounds derived by eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation of the amino group of Compound (II)); compounds derived by acylation, alkylation, phosphorylation or boration of the hydroxyl group of Compound (II) (e.g., compounds derived by acetylation, palmitoylation, propanoylation, pivaloylation, succinylation, fumarylation, alanylation or dimethylaminomethylcarbonylation of the hydroxyl group of Compound (II)); and compounds derived by esterification or amidation of the carboxyl group of Compound (II) (e.g., compounds derived by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methylamidation of the carboxyl group of Compound (II)). These compounds can be produced from Compound (II) by per se known methods.

The prodrug of Compound (II) may be one capable of being converted to Compound (II) under physiological conditions, as described in "Iyakuhin No Kaihatsu (Development of Drugs)", vol. 7, Molecular Designing, published by Hirokawa Shoten, 1990, pages 163–198.

Prodrugs of Compound (I) are exemplified by the same prodrugs as those of Compound (II).

In addition, Compound (I) and Compound (II) may be labeled with an isotope (e.g., $^3H$, $^{14}C$, $^{35}S$, $^{125}I$).

Furthermore, Compound (I) and Compound (II) may be anhydrides or hydrates.

(14) Formulations

Compounds (I) and (II) and salts thereof (hereinafter also referred to as "compound of the present invention") are of low toxicity and can be used as an agent for preventing or treating the various diseases mentioned below in mammals (e.g., humans, mice, rats, rabbits, dogs, cats, bovines, horses, swine, monkeys), as such or in the form of pharmaceutical compositions prepared by admixing with a pharmacologically acceptable carrier, etc.

Here, the pharmacologically acceptable carriers are exemplified by various organic or inorganic carrier substances in common use as materials for pharmaceutical preparations, and they are formulated as excipients, lubricants, binders, and disintegrants for solid preparations; and as solvents, solubilizers, suspending agents, isotonizing agents, buffers, soothing agents, etc. for liquid preparations. In addition, other additives for pharmaceutical preparations, such as antiseptics, antioxidants, coloring agents, and sweetening agents, may also be used as necessary.

Preferred examples of the excipients include lactose, saccharose, D-mannitol, D-sorbitol, starch, gelatinized starch, dextrin, crystalline cellulose, low-substituted hydroxypropylcellulose, carboxymethylcellulose sodium, gum arabic, dextrin, pullulan, light silicic anhydride, synthetic aluminum silicate, and magnesium metasilicate aluminate.

Preferred examples of the lubricants include magnesium stearate, calcium stearate, talc, and colloidal silica.

Preferred examples of the binders include gelatinized starch, sucrose, gelatin, gum arabic, methylcellulose, carboxymethylcellulose, carboxymethylcellulose sodium, crystalline cellulose, saccharose, D-mannitol, trehalose, dextrin, pullulan, hydroxypropylcellulose, hydroxypropylmethylcellulose, and polyvinylpyrrolidone.

Preferred examples of the disintegrants include lactose, saccharose, starch, carboxymethylcellulose, carboxymethylcellulose calcium, croscarmellose sodium, carboxymethyl starch sodium, light silicic anhydride, and low-substituted hydroxypropylcellulose.

Preferred examples of the solvents include water for injection, physiological saline, Ringer's solution, alcohol, propylene glycol, polyethylene glycol, sesame oil, corn oil, olive oil, and cottonseed oil.

Preferred examples of the solubilizers include polyethylene glycol, propylene glycol, D-mannitol, trehalose, benzyl benzoate, ethanol, trisaminomethane, cholesterol, triethanolamine, sodium carbonate, sodium citrate, sodium salicylate, and sodium acetate.

Preferred examples of the suspending agents include surfactants such as stearyltriethanolamine, sodium lauryl sulfate, laurylaminopropionic acid, lecithin, benzalkonium chloride, benzethonium chloride, and monostearic glycerol; hydrophilic polymers such as polyvinyl alcohol, polyvinylpyrrolidone, carboxymethylcellulose sodium, methylcellulose, hydroxymethylcellulose, hydroxyethylcellulose, and hydroxypropylcellulose; and polysorbates and polyoxyethylene-hardened castor oil.

Preferred examples of the isotonizing agents include sodium chloride, glycerol, D-mannitol, D-sorbitol, and glucose.

Preferred examples of the buffers include buffer solutions of phosphates, acetates, carbonates, citrates etc.

Preferred examples of the soothing agents include benzyl alcohol.

Preferred examples of the antiseptics include p-oxybenzoic acid esters, chlorobutanol, benzyl alcohol, phenethyl alcohol, dehydroacetic acid, and sorbic acid.

Preferred examples of the antioxidants include sulfites and ascorbates.

Preferred examples of the coloring agents include food colors such as water-soluble tar colors for food (e.g., Food Color Red Nos. 2 and 3, Food Color Yellow Nos. 4 and 5, Food Color Blue Nos. 1 and 2), water-insoluble lake colors (e.g., aluminum salts of the aforementioned water-soluble tar colors for food), and natural colors (e.g., β-carotene, chlorophyll, red oxide).

Preferred examples of the sweetening agents include saccharin sodium, dipotassium glycyrrhetinate, aspartame, and stevia.

(15) Dosage Forms

Examples of the dosage forms of the pharmaceutical composition include oral preparations such as tablets, capsules (including soft capsules and microcapsules), granules, powders, syrups, emulsions, and suspensions; and non-oral preparations such as injections (e.g., subcutaneous injections, intravenous injections, intramuscular injections, intraperitoneal injections), external preparations (e.g., preparations for nasal administration, dermal preparations, ointments), suppositories (e.g., rectal suppositories, vaginal suppositories), pellets, drip infusions, and sustained-release preparations. These preparations can each be orally or non-orally safely administered.

The pharmaceutical composition can be prepared by conventional methods in the fields of pharmaceutical manufacturing techniques, for example, methods described in the Japanese Pharmacopoeia. Specific production methods for such preparations are hereinafter described in detail.

An oral preparation, for instance, is produced by adding to the active ingredient an excipient (e.g., lactose, saccharose, starch, D-mannitol), a disintegrant (e.g., carboxymethylcellulose calcium), a binder (e.g., gelatinized starch, gum arabic, carboxymethylcellulose, hydroxypropylcellulose, polyvinylpyrrolidone) or a lubricant (e.g., talc, magnesium stearate, polyethyleneglycol 6000), compression molding the obtained mixture, then, if necessary coating by a per se known method using a coating base for the purpose of taste masking, enteric coating or sustained release.

Examples of the coating base include a sugar coating base, a water-soluble film coating base, an enteric film coating base, a sustained-release film coating base.

As the sugar coating base saccharose is employed. Further, one or two or more species selected from talc, precipitated calcium carbonate, gelatin, gum arabic, pullulan, carnauba wax and the like may be used in combination.

Examples of the water-soluble film coating base include cellulose polymers such as hydroxypropylcellulose, hydroxypropylmethylcellulose, hydroxyethylcellulose, methylhydroxyethylcellulose; synthetic polymers such as polyvinylacetal diethylaminoacetate, aminoalkyl methacrylate copolymer E [Eudragit E (trademark), Rhom Pharma] and polyvinylpyrrolidone; polysaccharides such as pullulan.

Examples of the enteric film coating base include cellulose polymers such as hydroxypropylmethylcellulose phthalate, hydroxypropylmethylcellulose acetate succinate, carboxymethylethylcellulose, cellulose acetate phthalate; acrylic acid polymers such as methacrylic acid copolymer L [Eudragit L (trademark), Rhom Pharma], methacrylic acid copolymer LD [Eudragit L-30D55 (trademark), Rhom Pharma], methacrylic acid copolymer S [Eudragit S (trademark), Rhom Pharma]; natural products such as shellac and the like.

Examples of the sustained-release film coating base include cellulose polymers such as ethylcellulose; acrylic acid polymers such as aminoalkyl methacrylate copolymer RS [Eudragit RS (trademark), Rhom Pharma] and an ethyl acrylate-methyl methacrylate copolymer suspension [Eudragit NE (trademark), Rhom Pharma].

Two or more of the above coating bases may be used in admixture in an appropriate ratio. On the occasion of coating, a shading agent such as titanium oxide, red ferric oxide may be used.

Injections are produced by dissolving, suspending or emulsifying the active ingredient in an aqueous solvent (e.g. distilled water, physiological saline, Ringer's solution) or an oleaginous solvent (e.g. vegetable oils such as olive oil, sesame oil, cotton seed oil, corn oil; propylene glycol), together with a dispersant (e.g. polysorbate 80, polyoxyethylene-hardened castor oil 60), polyethylene glycol, carboxymethylcellulose, sodium alginate), a preservative (e.g. methylparaben, propylparaben, benzyl alcohol, chlorobutanol, phenol), an isotonizing agent (e.g. sodium chloride, glycerol, D-mannitol, D-sorbitol, glucose) and the like. If desirable, additives such as a solubilizer (e.g. sodium salicylate, sodium acetate), a stabilizer (e.g. human serum albumin), a soothing agent (e.g. benzyl alcohol), may be used.

(16) Agents

The compound of the present invention can be used as an insulin resistance improving agent, an insulin sensitivity enhancing agent, a retinoid-related receptor function regulating agent, a ligand for peroxisome proliferator-activated receptors, and a ligand for retinoid X receptor, etc. The term "function regulating agent" used here stands for both an agonist and an antagonist. The function regulating agent may be a partial agonist or a partial antagonist.

The compound of the present invention has a hypoglycemic action, a hypolipidemic action, a hypoinsulinemic action, an insulin resistance improving action, an insulin sensitivity enhancing action, and a retinoid-related receptor function regulating action. The term "retinoid-related receptor" used here is classified as nuclear receptors, and is a DNA-binding transcription factor whose ligand is a signal molecule such as oil-soluble vitamins, etc., and may be any of a monomer receptor, a homodimer receptor and a heterodimer receptor.

Here, examples of the monomer receptor include retinoid O receptor (hereinafter, also abbreviated as ROR) a (GenBank Accession No. L14611), RORβ (GenBank Accession No. L14160), RORγ (GenBank Accession No. U16997); Rev-erb α (GenBank Accession No. M24898), Rev-erb β

(GenBank Accession No. L31785); ERRα (GenBank Accession No. X51416), ERRβ (GenBank Accession No. X51417); Ftz-FIα (GenBank Accession No. S65876), Ftz-FIβ (GenBank Accession No. M81385); TIx (GenBank Accession No. S77482); GCNF (GenBank Accession No. U14666).

Examples of the homodimer receptor include homodimers formed by retinoid X receptor (hereinafter, also abbreviated as RX R) α (GenBank Accession No. X52733), RXRβ (GenBank Accession No. M84820), RXRγ (GenBank Accession No. U38480); COUPα (GenBank Accession No. X12795), COUPβ (GenBank Accession No. M64497), COUPγ (GenBank Accession No. X12794); TR2α (GenBank Accession No. M29960), TR2β (GenBank Accession No. L27586); or HNF4α (GenBank Accession No. X76930), HNF4γ (GenBank Accession No. Z49826), etc.

Examples of the heterodimer receptor include heterodimers which are formed by the above-mentioned retinoid X receptor (RXRα, RXRβ or RXTγ) and one receptor selected from retinoid A receptor (hereinafter, also abbreviated as RAR) α (GenBank Accession No. X00614), RARβ (GenBank Accession No. Y00291), RARγ (GenBank Accession No. M24857); thyroid hormone receptor (hereinafter, also abbreviated as TR) α (GenBank Accession No. M24748), TRβ (GenBank Accession No. M26747); vitamin D receptor (VDR) (GenBank Accession No. J03258): peroxisome proliferator-activated receptor (hereinafter, also abbreviated as PPAR) α (GenBank Accession No. L02932), PPARβ (PPAR δ) (GenBank Accession No. U10375), PPAR γ (GenBank Accession No. L40904); LXRα (GenBank Accession No. U22662), LXRβ (GenBank Accession No. U14534); FXR (GenBank Accession No. U18374); MB67 (GenBank Accession No. L29263); ONR (GenBank Accession No. X75163); and NURα (GenBank Accession No. L13740), NURβ (GenBank Accession No. X75918) and NURγ (GenBank Accession No. U12767).

The compound of the present invention has an excellent ligand activity particularly to retinoid X receptors (RXRα, RXRβ, RXRγ) and to peroxisome proliferator-activated receptors (PPARα, PPARβ (PPARδ), PPARγ) among the above-mentioned retinoid-related receptors.

Further, the compound of the present invention has an excellent ligand activity to peroxisome proliferator-activated receptors in heterodimer receptors formed from a retinoid X receptor and a peroxisome proliferator-activated receptor, and preferably in heterodimer receptors formed from RXRα and PPARγ.

Accordingly, the retinoid-related receptor ligand of the present invention can be used advantageously as a ligand for peroxisome proliferator-activated receptors or a ligand for retinoid X receptors.

Of the compound of the present invention, especially one having a divalent hydrocarbon residue having 1 to 20 carbon atoms (especially alkylene such as methylene) for W can be used preferably as a PPARγ agonist or a PPARγ partial agonist.

While, of the compound of the present invention, especially one having a bond for W can be used preferably as a PPARγ antagonist or a PPARγ partial antagonist.

(17) Target Diseases

The compound of the present invention and the pharmaceutical composition of the present invention can be used as, for example, an agent for preventing or treating diabetes (e.g., type 1 diabetes mellitus, type 2 diabetes mellitus, gestational diabetes mellitus); an agent for preventing or treating hyperlipidemia (e.g., hypertriglycemia, hypercholesterolemia, hypo-high-density-lipoproteinemia, postprandial hyperlipemia); an agent for enhancing insulin sensitivity; an agent for improving insulin resistance; an agent for preventing or treating impaired glucose tolerance (IGT); and an agent for preventing progress from impaired glucose tolerance to diabetes mellitus.

Regarding diagnostic criteria of diabetes mellitus, new diagnostic criteria were reported by the Japan Diabetes Society in 1998.

According to this report, diabetes mellitus is a condition wherein the fasting blood glucose level (glucose concentration in venous plasma) is not less than 126 mg/dl, the 2-hour value (glucose concentration in venous plasma) of the 75 g oral glucose tolerance test (75 g OGTT) is not less than 200 mg/dl, or the non-fasting blood glucose level (glucose concentration in venous plasma) is not less than 200 mg/dl. In addition, a condition which does not fall within the scope of the above definition of diabetes mellitus, and which is not a "condition wherein the fasting blood glucose level (glucose concentration in venous plasma) is less than 110 mg/dl or the 2-hour value (glucose concentration in venous plasma) of the 75 g oral glucose tolerance test (75 g OGTT) is less than 140 mg/dl" (normal type), is called the "borderline type".

In addition, regarding diagnostic criteria for diabetes mellitus, new diagnostic criteria were reported by ADA (American Diabetic Association) in 1997 and by WHO in 1998.

According to these reports, diabetes mellitus is a condition wherein the fasting blood glucose level (glucose concentration in venous plasma) is not less than 126 mg/dl, and the 2-hour value (glucose concentration in venous plasma) of the 75 g oral glucose tolerance test is not less than 200 mg/dl.

In addition, according to the above reports, impaired glucose tolerance is a condition wherein the fasting blood glucose level (glucose concentration in venous plasma) is less than 126 mg/dl, and the 2-hour value (glucose concentration in venous plasma) of the 75 g oral glucose tolerance test is not less than 140 mg/dl and less than 200 mg/dl. Furthermore, according to the ADA report, a condition wherein the fasting blood glucose level (glucose concentration in venous plasma) is not less than 110 mg/dl and less than 126 mg/dl, is called IFG (impaired fasting glucose). On the other hand, according to the WHO report, a condition of IFG (impaired fasting glucose) as such wherein the 2-hour value (glucose concentration in venous plasma) of the 75 g oral glucose tolerance test is less than 140 mg/dl, is called IFG (impaired fasting glycemia).

The compound of the present invention and the pharmaceutical composition of the present invention can be used as an agent for preventing or treating diabetes mellitus, borderline type, impaired glucose tolerance, IFG (impaired fasting glucose) and IFG (impaired fasting glycemia) as defined by the above new diagnostic criteria. Furthermore, the compound of the present invention and the pharmaceutical composition of the present invention can also be used to prevent the progression of the borderline type, impaired glucose tolerance, IFG (impaired fasting glucose) or IFG (impaired fasting glycemia) to diabetes mellitus.

The compound of the present invention and the pharmaceutical composition of the present invention can be used also as an agent for preventing or treating diabetic complications (e.g., neuropathy, nephropathy, retinopathy, cataract, macroangiopathy, osteopenia, diabetic hyperosmolar coma, infectious diseases (e.g., respiratory infection, urinary tract infection, gastrointestinal tract infection, dermal soft tissue infection, inferior limb infection), diabetic gangrene, xerostomia, lowered sense of hearing, cerebrovascular disease, peripheral circulatory disturbance, etc.), obesity, osteoporosis, cachexia (e.g., carcinomatous cachexia, tuberculous cachexia, diabetic cachexia, hemopathic cachexia, endocrinopathic cachexia, infectious cachexia, cachexia induced by acquired immunodeficiency syndrome), fatty liver, hypertension, polycystic ovary syndrome, renal diseases (e.g., diabetic nephropathy, glomerular nephritis, glomerulosclerosis, nephrotic syndrome, hypertensive nephrosclerosis, terminal renal disorder), muscular dystrophy, myocardiac infarction, angina pectoris, cerebrovascular disease (e.g., cerebral infarction, cerebral apoplexy), insulin resistant syndrome, syndrome X, hyperinsulinemia, hyperinsulinemia-induced sensory disorder, tumor (e.g., leukemia, breast cancer, prostate cancer, skin cancer), irritable intestinum syndrome, acute or chronic diarrhea, inflammatory diseases (e.g., chronic rheumatoid arthritis, spondylitis deformans, osteoarthritis, lumbago, gout, postoperative or traumatic inflammation, remission of swelling, neuralgia, pharyngolaryngitis, cystitis, hepatitis (including steatohepatitis such as non-alcoholic steatohepatitis), pneumonia, pancreatitis, inflammatory colitis, ulcerative colitis), visceral obesity syndrome, etc.

The compound of the present invention and the pharmaceutical composition of the present invention possess a total cholesterol lowering action and enhance a plasma anti-arteriosclerosis index [(HDL cholesterol/total cholesterol)×100], and therefore, can be used as an agent for preventing or treating arteriosclerosis (e.g., atherosclerosis), etc.

Also, the compound of the present invention and the pharmaceutical composition of the present invention can be used for ameliorating bellyache, nausea, vomiting, or dysphoria in epigastrium, each of which is accompanied by gastrointestinal ulcer, acute or chronic gastritis, biliary dyskinesia, or cholecystitis.

Further, the compound of the present invention and the pharmaceutical composition of the present invention can control (enhance or inhibit) appetite and food intake, and therefore, can be used as an agent for treating leanness and cibophobia (the weight increase in administration subjects suffering from leanness or cibophobia) or an agent for treating obesity.

The compound of the present invention and the pharmaceutical composition of the present invention can be also used as an agent for preventing or treating TNF-α mediated inflammatory diseases. The TNF-α mediated inflammatory diseases mean inflammatory diseases which occur in the presence of TNF-α and can be treated by way of a TNF-α inhibitory action. Examples of such inflammatory diseases include diabetic complications (e.g., retinopathy, nephropathy, neuropathy, macroangiopathy), rheumatoid arthritis, spondylitis deformans, osteoarthritis, lumbago, gout, postoperative or traumatic inflammation, remission of swelling, neuralgia, pharyngolaryngitis, cystitis, hepatitis, pneumonia, gastric mucosal injury (including aspirin-induced gastric mucosal injury), etc.

The compound of the present invention and the pharmaceutical composition of the present invention have an apoptosis inhibitory activity, and can be used as an agent for preventing or treating diseases mediated by promotion of apoptosis. Examples of the diseases mediated by promotion of apoptosis include viral diseases (e.g., AIDS, fulminant hepatitis), neurodegenerative diseases (e.g., Alzheimer's disease, Parkinson's disease, amyotropic lateral sclerosis, retinitis pigmentosa, cerebellar degeneration), myelodysplasia (e.g., aplastic anemia), ischemic diseases (e.g., myocardial infarction, cerebral apoplexy), hepatic diseases (e.g., alcoholic hepatitis, hepatitis B, hepatitis C), joint-diseases (e.g., osteoarthritis), atherosclerosis, etc.

The compound of the present invention and the pharmaceutical composition of the present invention can be used for reducing visceral fats, inhibiting accumulation of visceral fats, ameliorating glycometabolism, ameliorating lipidmetabolism, ameliorating insulin resistance, inhibiting production of oxidized LDL, ameliorating lipoprotein metabolism, ameliorating coronary artery metabolism, preventing or treating cardiovascular complications, preventing or treating heart failure complications, lowering blood remnant, preventing or treating anovulation, preventing or treating hirsutism, preventing or treating hyperandrogenism, etc.

The compound of the present invention and the pharmaceutical composition of the present invention can be used for secondary prevention and for inhibition in progress, of the various diseases described above (e.g., cardiovascular events such as myocardial infarction, etc.).

The compound of the present invention and the pharmaceutical composition of the present invention can be used in combination with midazolam, ketoconazole, etc.

Although the doses of the compound of the present invention and the pharmaceutical composition of the present invention vary depending on administration subject, administration route, target disease, clinical condition, etc., it is desirable that the active ingredient, i.e., the compound of the present invention, be administered at a usual dosage per administration of about 0.01 to 100 mg/kg body weight, preferably 0.05 to 10 mg/kg body weight, more preferably 0.1 to 2 mg/kg body weight, 1 to 3 times a day, for oral administration to an adult diabetic patient, for instance.

(18) Concomitant Use of Drugs

The compound of the present invention can be used in combination with a drug such as a therapeutic agent for diabetes mellitus, a therapeutic agent for diabetic complications, an antihyperlipidemic agent, a hypotensive agent, an antiobesity agent, a diuretic agent, a chemotherapeutic agent, an immunotherapeutic agent, a therapeutic agent for osteoporosis, an antidementia agent, an erection dysfunction ameliorating agent, a therapeutic agent for incontinentia or pollakiuria, and the like (hereinafter, abbreviated as a concomitant drug). On such occasions, the timing of administration of the compound of the present invention and that of the concomitant drug is not limited. They may be administered simultaneously or at staggered times to the administration subject. The dose of the concomitant drug can be appropriately selected based on the dose which is clinically employed. The proportion of the compound of the present invention and the concomitant drug can be appropriately selected according to the administration subject, administration route, target disease, clinical condition, combination, and other factors. In cases where the administration subject is human, for instance, the concomitant drug may be used in an amount of 0.01 to 100 parts by weight per part by weight of the compound of the present invention.

Examples of the therapeutic agent for diabetes mellitus include insulin preparations (e.g., animal insulin preparations extracted from the bovine or swine pancreas; human insulin preparations synthesized by a genetic engineering technique using *Escherichia coli* or a yeast), insulin resistance improving agents (e.g., pioglitazone hydrochloride, troglitazone, rosiglitazone or its maleate, GI-262570, JTT-501, MCC-555, YM-440, KRP-297, CS-011, FK-614), α-glucosidase inhibitors (e.g., voglibose, acarbose, miglitol, emiglitate), biguanides (e.g., phenformin, metformin, buformin), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, senaglinide, nateglinide, mitiglinide or its calcium salt hydrate, GLP-1), amyrin agonist (e.g., pramlintide), phosphotyrosine phosphatase inhibitors (e.g., vanadic acid), dipeptidylpeptidase IV inhibitors (e.g., NVP-DPP-278, PT-100, P32/98), β3 agonists (e.g., CL-316243, SR-58611-A, UL-TG-307, SB-226552, AJ-9677, BMS-196085, AZ40140), gluconeogenesis inhibitors (e.g., glycogen phosphorylase inhibitors, glucose-6-phosphatse inhibitors, glucagon antagonists), SGLT (sodium-glucose cotransporter) inhibitors (e.g., T-1095).

Examples of the therapeutic agent for diabetic complications include aldose reductase inhibitors (e.g., tolrestat, epalrestat, zenarestat, zopolrestat, minalrestat, fidarestat, SNK-860, CT-112), neurotrophic factors (e.g., NGF, NT-3, BDNF), PKC inhibitors (e.g., LY-333531), AGE inhibitors (e.g., ALT946, pimagedine, pyratoxathine, N-phenacylthiazolium bromide (ALT766), EXO-226), active oxygen scavengers (e.g. thioctic acid), cerebral vasodilators (e.g., tiapuride, mexiletine).

Examples of the antihyperlipidemic agent include statin compounds which are cholesterol synthesis inhibitors (e.g., cerivastatin, pravastatin, simvastatin, lovastatin, atorvastatin, fluvastatin, itavastatin or their salts (e.g., sodium salt)), squalene synthase inhibitors or fibrate compounds (e.g., bezafibrate, clofibrate, simfibrate, clinofibrate) having a triglyceride lowering action.

Examples of the hypotensive agent include angiotensin converting enzyme inhibitors (e.g., captopril, enalapril, delapril), angiotensin II antagonists (e.g., losartan, candesartan cilexetil, losartan, eprosartan, valsartan, termisartan, irbesartan, tasosartan), calcium antagonist (e.g., manidipine, nifedipine, amlodipine, efonidipine, nicardipine), clonidine.

Examples of the antiobesity agent include antiobesity drugs acting on the central nervous system (e.g. dexfenfluramine, fenfluramine, phentermine, sibutramine, anfepramon, dexamphetamine, mazindol, phenylpropanolamine, clobenzorex), pancreatic lipase inhibitors (e.g. orlistat), β3 agonists (e.g. CL-316243, SR-58611-A, UL-TG-307, SB-226552, AJ-9677, BMS-196085, AZ40140), anorectic peptides (e.g. leptin, CNTF (Ciliary Neurotrophic Factor)), cholecystokinin agonists (e.g. lintitript, FPL-15849).

Examples of the diuretic agent include xanthine derivatives (e.g., theobromine and sodium salicylate, theobromine and calcium salicylate), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlorthalidone, mefruside, indapamide), azosemide, isosorbide, ethacrynic acid, piretanide, bumetanide, furosemide.

Examples of the chemotherapeutic agent include alkylating agents (e.g., cyclophosphamide, ifosamide), metabolic antagonists (e.g., methotrexate, 5-fluorouracil), antitumor antibiotics (e.g., mitomycin, adriamycin), plant-derived antitumor agents (e.g., vincristine, vindesine, Taxol), cisplatin, carboplatin, etoposide. Among these, 5-fluorouracil derivatives such as Furtulon and Neo-Furtulon are preferable.

Examples of the immunotherapeutic agent include microorganism- or bacterium-derived components (e.g., muramyl dipeptide derivatives, Picibanil), immunopotentiator polysaccharides (e.g., lentinan, schizophyllan, krestin), genetically engineered cytokines (e.g., interferons, interleukins (IL)), colony stimulating agents (e.g., granulocyte colony stimulating factor, erythropoietin), etc. Among these, IL-1, IL-2, IL-12 and the like are preferable.

Examples of the therapeutic agent for osteoporosis include alfacalcidol, calcitriol, elcatonin, calcitonin salmon, estriol, ipriflavone, pamidronate disodium, alendronate sodium hydrate, incadronate disodium.

Examples of the antidementia agent include tacrine, donepezil, rivastigmine, galantamine.

Examples of the erection dysfunction ameliorating agent include apomorphine, sildenafil citrate.

Examples of the therapeutic agent for incontinentia or pollakiuria include flavoxate hydrochloride, oxybutynin hydrochloride, propiverine hydrochloride.

Further, agents whose effects of ameliorating cachexia have been confirmed in animal models or clinically, namely cyclooxygenase inhibitors (e.g., indomethacin) (Cancer Research, vol. 49, pp. 5935–5939, 1989), progesterone derivatives (e.g., megestrol acetate) (Journal of Clinical Oncology, vol. 12, pp. 213–225, 1994), glucocorticoids (e.g. dexamethasone), metoclopramide pharmaceuticals, tetrahydrocannabinol pharmaceuticals (the above references are applied to both), fat metabolism ameliorating agents (e.g., eicosapentanoic acid) (British Journal of Cancer, vol. 68, pp. 314–318, 1993), growth hormones, IGF-1, and antibodies to the cachexia-inducing factor TNF-α, LIF, IL-6 or oncostatin M, can also be used in combination with the compound of the present invention.

The concomitant drug is preferably an insulin preparation, an insulin resistance improving agent, an α-glucosidase inhibitor, a biguanide, an insulin secretagogue (preferably sulfonylurea), etc.

The above concomitant drugs can be used as a mixture of two or more species in an appropriate ratio. In the case of using two or more concomitant drugs, preferable combinations include the followings.

1) an insulin resistance improving agent and an insulin preparation;

2) an insulin resistance improving agent and an insulin secretagogue (preferably a sulfonylurea);

3) an insulin resistance improving agent and an α-glucosidase inhibitor;

4) an insulin resistance improving agent and a biguanide;

5) an insulin resistance improving agent, an insulin preparation and a biguanide;

6) an insulin resistance improving agent, an insulin preparation and an insulin secretagogue (preferably a sulfonylurea);

7) an insulin resistance improving agent, an insulin preparation and an α-glucosidase inhibitor;

8) an insulin resistance improving agent, an insulin secretagogue (preferably a sulfonylurea) and a biguanide;

9) an insulin resistance improving agent, an insulin secretagogue (preferably a sulfonylurea) and an α-glucosidase inhibitor; and 10) an insulin resistance improving agent, a biguanide and an α-glucosidase inhibitor.

When the compound or pharmaceutical composition of the present invention are used in combination with a concomitant drug, the amount of each drug can be reduced within a safe range by taking their adverse effects into consideration. Particularly, the dose of an insulin resistance improving agent, an insulin secretagogue (preferably a sulfonylurea) and a biguanide can be reduced as compared with the normal dose. Accordingly, an adverse effect which may be caused by these agents can be safely prevented. In addition, the dose of an agent for diabetic complications, an anti-hyperlipemic agent and a hypotensive agent can be reduced whereby an adverse effect which may be caused by these agents can be effectively prevented.

(19) Production Method

The production method for the compound of the present invention is hereinafter described. Since Compound (I) is included in Compound (II), the production method for Compound (II) is described.

Compound (II) can be produced by a per se known method, e.g., any of Methods A through F, and Method H below, or methods analogous thereto.

[Method A]

$$R^1-X-(CH_2)_m-Y-\!\!\left(\!\!A\!\!\right)\!\!-(CH_2)_n-Z \ +$$

(III)

$$HN\!\!\left(\!\!B\!\!\right)\!\!\overset{X^1-R^2}{-}W-(C\!\!=\!\!O)-R^3 \longrightarrow \text{(II)}$$

(IV)

wherein Z represents a hydroxy group, a halogen atom or a group of the formula: $OSO_2R^{15}$ wherein $R^{15}$ represents an alkyl group having 1 to 4 carbon atoms or an aryl group having 6 to 10 carbon atoms which may be substituted by an alkyl group having 1 to 4 carbon atoms; the other symbols have the same meanings as above.

Here, the alkyl group having 1 to 4 carbon atoms in the "alkyl group having 1 to 4 carbon atoms" and "aryl group having 6 to 10 carbon atoms which may be substituted by an alkyl group having 1 to 4 carbon atoms" for $R^{15}$ is exemplified by methyl, ethyl, propyl, isopropyl, butyl, isobutyl, sec.-butyl, and t.-butyl, with preference given to methyl.

The aryl group having 6 to 10 carbon atoms in the "aryl group having 6 to 10 carbon atoms which may be substituted by an alkyl group having 1 to 4 carbon atoms" for $R^{15}$ is exemplified by phenyl and naphthyl, with preference given to phenyl.

In this method, Compound (II) is produced by a reaction of Compound (III) and Compound (IV).

When Z is a hydroxy group, this reaction is carried out by a per se known method, e.g., the method described in Synthesis, page 1 (1981), or a method analogous thereto. Namely, this reaction is normally carried out in the presence of an organic phosphorus compound and an electrophilic agent in a solvent which does not interfere with the reaction.

Examples of the organic phosphorus compound include triphenylphosphine and tributylphosphine.

Examples of the electrophilic agent include diethyl azodicarboxylate, diisopropyl azodicarboxylate, and azodicarbonylpiperazine.

The amount of the organic phosphorus compound and electrophilic agent used is preferably about 1 to about 5 mole equivalents relative to Compound (IV).

Examples of the solvent which does not interfere with the reaction include ethers such as diethyl ether, tetrahydrofuran, and dioxane; halogenated hydrocarbons such as chloroform and dichloromethane; aromatic hydrocarbons such as benzene, toluene, and xylene; amides such as N,N-dimethylformamide; and sulfoxides such as dimethyl sulfoxide. These solvents may be used in mixture in appropriate ratios.

The reaction temperature is normally about −50 to about 150° C., preferably about −10 to about 100° C.

The reaction time is normally about 0.5 to about 20 hours.

When Z is a halogen atom or a group of the formula: $OSO_2R^{15}$, this reaction is carried out by a conventional method in the presence of a base in a solvent which does not interfere with the reaction.

Examples of the base include alkali metal salts such as potassium hydroxide, sodium hydroxide, sodium hydrogen carbonate, and potassium carbonate; amines such as pyridine, triethylamine, N,N-dimethylaniline, and 1,8-diazobicyclo[5.4.0]undec-7-ene; metal hydrides such as potassium hydride and sodium hydride; and alkali metal alkoxides such as sodium methoxide, sodium ethoxide, and potassium t.-butoxide.

The amount of these bases used is preferably about 1 to about 5 mole equivalents relative to Compound (IV).

Examples of the solvent which does not interfere with the reaction include aromatic hydrocarbons such as benzene, toluene, and xylene; ethers such as tetrahydrofuran, dioxane, and diethyl ether; ketones such as acetone and 2-butanone; halogenated hydrocarbons such as chloroform and dichloromethane; amides such as N,N-dimethylformamide; and sulfoxides such as dimethyl sulfoxide. These solvents may be used in mixture in appropriate ratios.

The reaction temperature is normally about −50 to about 150° C., preferably about −10 to about 100° C.

The reaction time is normally about 0.5 to about 20 hours.

Compound (II) thus obtained may be isolated and purified by known means of separation and purification such as concentration, concentration under reduced pressure, solvent extraction, crystallization, recrystallization, redissolution and chromatography.

Compound (III) and Compound (IV), which are used as the starting compounds in Method A above, are known compounds. Compound (III) wherein Z is a hydroxy group, for example, is described in EP-A 710659. In addition, Compound (III) is described in EP-A 629624 (JP-A 7(1995)-53555), WO 98/03505, etc. Furthermore, Compound (III) can also be produced by methods analogous to those described in these patent publications.

On the other hand, Compound (IV) is described in, for example, Journal of Heterocyclic Chemistry, vol. 24, p. 1669 (1987); Journal of Organic Chemistry, vol. 62, p. 2649 (1997); Bioorganic & Medicinal Chemistry Letters, vol. 6, p. 1047 (1996), etc. In addition, Compound (IV) can also be produced by methods analogous to those described in these publications.

A compound of the formula (II) wherein $R^3$ is $OR^8$ and W is —CH=CH— or —(CH$_2$)$_2$— [Compound (II-2) or (II-3), respectively] can also be produced by Method B below.

[Method B]

$$R^1-X-(CH_2)_m-Y-\!\!\left(\!\!A\!\!\right)\!\!-(CH_2)_n-N\!\!\left(\!\!B\!\!\right)\!\!\overset{X^1-R^2}{-}(C\!\!=\!\!O)-OR^8$$

(II-1)

Process 1 ↓

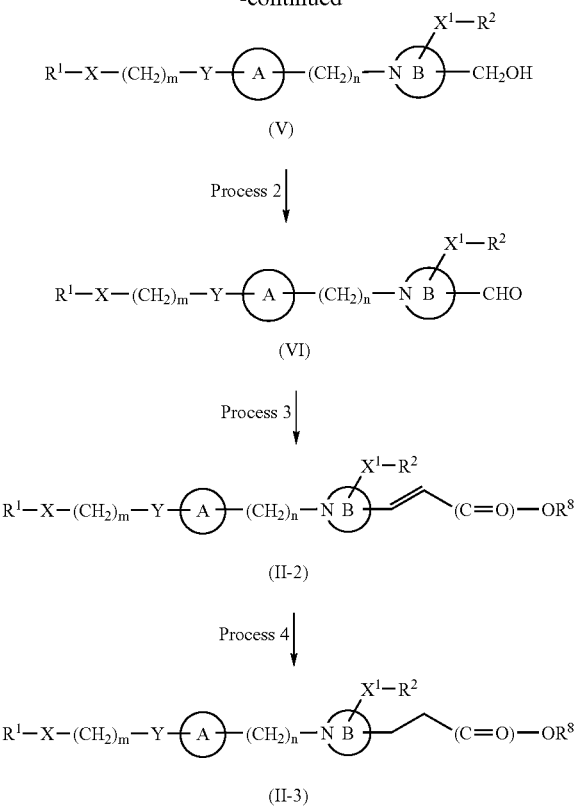

wherein the symbols have the same meanings as above.

(Process 1)

This reaction is carried out by a conventional method in the presence of a reducing agent in a solvent which does not interfere with the reaction.

Examples of the reducing agent include sodium borohydride, lithium borohydride, lithium aluminum hydride, and diisobutyl aluminum hydride.

The amount of the reducing agent used is preferably about 0.5 to about 10 mole equivalents relative to Compound (II-1).

Examples of the solvent which does not interfere with the reaction include aromatic hydrocarbons such as benzene, toluene, and xylene; halogenated hydrocarbons such as chloroform and dichloromethane; ethers such as tetrahydrofuran, dioxane, and diethyl ether; water; and alcohols such as methanol, ethanol, and isopropanol. These solvents may be used in mixture in appropriate ratios.

The reaction temperature is normally about −50 to about 150° C., preferably about −10 to about 100° C.

The reaction time is normally about 0.5 to about 20 hours.

Compound (V) thus obtained may be isolated and purified by known means of separation and purification such as concentration, concentration under reduced pressure, solvent extraction, crystallization, recrystallization, redissolution and chromatography.

Compound (II-1), which is used as the starting compound in Process 1 of Method B above, can be produced by, for example, Method A above. In addition, Compound (II-1) can also be produced by the method described in, for example, Journal of Heterocyclic Chemistry, vol. 24, p. 1669 (1987); Journal of Organic Chemistry, vol. 62, p. 2649 (1997); Bioorganic & Medicinal Chemistry Letters, vol. 6, p. 1047 (1996), etc., or a method analogous thereto.

(Process 2)

This reaction is carried out by a conventional method in the presence of an oxidant in a solvent which does not interfere with the reaction.

Examples of the oxidant include metal oxidants such as manganese dioxide, pyridinium chlorochromate, pyridinium dichromate, and ruthenium oxide.

The amount of the oxidant used is preferably about 1 to about 10 mole equivalents relative to Compound (V).

Examples of the solvent which does not interfere with the reaction include aromatic hydrocarbons such as benzene, toluene, and xylene; ethers such as tetrahydrofuran, dioxane, and diethyl ether; and halogenated hydrocarbons such as chloroform and dichloromethane. These solvents may be used in mixture in appropriate ratios.

The reaction temperature is normally about −50 to about 150° C., preferably about −10 to about 100° C.

The reaction time is normally about 0.5 to about 20 hours.

In addition, Compound (VI) can also be produced by adding a reaction reagent such as sulfur trioxide-pyridine complex or oxalyl chloride to compound (V) in dimethyl sulfoxide or a solvent mixture of dimethyl sulfoxide and a halogenated hydrocarbon such as chloroform or dichloromethane, and reacting it with an organic base such as triethylamine or N-methylmorpholine.

The amount of the reaction reagent is preferably about 1 to about 10 mole equivalents relative to Compound (V).

The amount of the organic base used is preferably about 1 to about 10 mole equivalents relative to Compound (V).

The reaction temperature is normally about −50 to about 150° C., preferably about −10 to about 100° C.

The reaction time is normally about 0.5 to about 20 hours.

Compound (VI) thus obtained may be isolated and purified by known means of separation and purification such as concentration, concentration under reduced pressure, solvent extraction, crystallization, recrystallization, redissolution and chromatography.

(Process 3)

In this reaction, Compound (II-2) is produced by a reaction of an organic phosphorus reagent and Compound (VI).

This reaction is carried out by a conventional method in the presence of a base in a solvent which does not interfere with the reaction.

Examples of the organic phosphorus reagent include methyl dimethylphosphonoacetate, ethyl diethylphosphonoacetate, and ethyl dimethylphosphonoacetate.

The amount of the organic phosphorus reagent used is preferably about 1 to about 10 mole equivalents relative to Compound (VI).

Examples of the base include alkali metal salts such as potassium hydroxide, sodium hydroxide, sodium hydrogen carbonate, and potassium carbonate; amines such as pyridine, triethylamine, N,N-dimethylaniline, and 1,8-diazobicyclo[5.4.0]undec-7-ene; metal hydrides such as potassium hydride and sodium hydride; and alkali metal alkoxides such as sodium methoxide, sodium ethoxide, and potassium t.-butoxide.

The amount of these bases used is preferably about 1 to about 5 mole equivalents relative to Compound (VI).

Examples of the solvent which does not interfere with the reaction include aromatic hydrocarbons such as benzene, toluene, and xylene; ethers such as tetrahydrofuran, dioxane, and diethyl ether; halogenated hydrocarbons such as chloroform and dichloromethane; amides such as N,N-dimethylformamide; and sulfoxides such as dimethyl sulfoxide. These solvents may be used in mixture in appropriate ratios.

The reaction temperature is normally about −50 to about 150° C., preferably about −10 to about 100° C.

The reaction time is normally about 0.5 to about 20 hours.

Compound (II-2) thus obtained may be isolated and purified by known means of separation and purification such as concentration, concentration under reduced pressure, solvent extraction, crystallization, recrystallization, redissolution and chromatography.

(Process 4)

This reaction is carried out by a conventional method under a hydrogen atmosphere or in the presence of a hydrogen source (e.g., formic acid) and a metal catalyst in a solvent which does not interfere with the reaction.

Examples of the metal catalyst include transition metal catalysts such as palladium-carbon, palladium black, platinum oxide, Raney nickel, and Wilkinson's catalyst.

The amount of these transition metal catalysts used is preferably about 0.01 to about 10 mole equivalents relative to Compound (II-2).

Examples of the solvent which does not interfere with the reaction include aromatic hydrocarbons such as benzene, toluene, and xylene; ethers such as tetrahydrofuran, dioxane, and diethyl ether; halogenated hydrocarbons such as chloroform and dichloromethane; amides such as N,N-dimethylformamide; and alcohols such as methanol, ethanol, and isopropanol. These solvents may be used in mixture in appropriate ratios.

The reaction temperature is normally about −50 to about 150° C., preferably about −10 to about 100° C.

-continued

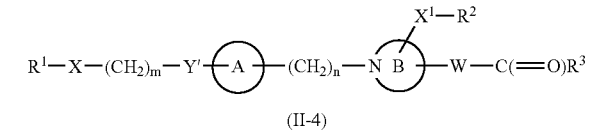

(II-4)

wherein Y' represents an oxygen atom, a sulfur atom or group of the formula: —$NR^7$— wherein $R^7$ has the same meaning as above; the other symbols have the same meaning as above.

In this method, compound (II-4) is produced by the reaction of Compound (VII) and Compound (VIII). This reaction is carried out in the same manner as the reaction of Compound (III) and Compound (IV) in Method A.

Compound (II-4) thus obtained may be isolated and purified by known means of separation and purification such as concentration, concentration under reduced pressure, solvent extraction, crystallization, recrystallization, redissolution and chromatography.

Compound (VII), which is used as the starting compound in Method C above, is a known compound and described in, for example, Chemical and Pharmaceutical Bulletin, vol. 34, p. 2840 (1986); Journal of Medicinal Chemistry, vol. 35, p. 2617 (1992); WO 98/03505, etc. Further, Compound (VII) can be produced by a method analogous to methods described in these publications.

[Method D]

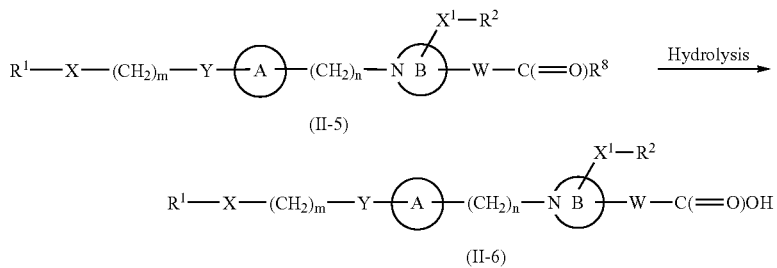

The reaction time is normally about 0.5 to about 20 hours.

Compound (II-3) thus obtained may be isolated and purified by known means of separation and purification such as concentration, concentration under reduced pressure, solvent extraction, crystallization, recrystallization, redissolution and chromatography.

[Method C]

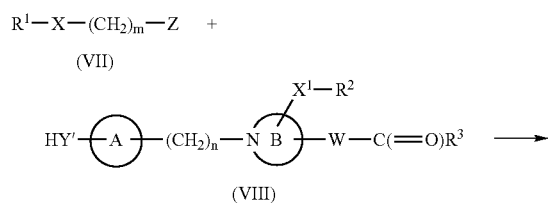

wherein the symbols have the same meanings as above.

In this method, Compound (II-6) is produced by hydrolyzing Compound (II-5).

This hydrolytic reaction is carried out by a conventional method in the presence of an acid or a base in a hydrated solvent.

Examples of the acid include hydrochloric acid, sulfuric acid, acetic acid, and hydrobromic acid.

Examples of the base include alkali metal carbonates such as potassium carbonate and sodium carbonate; alkali metal alkoxides such as sodium methoxide; and alkali metal hydroxides such as potassium hydroxide, sodium hydroxide, and lithium hydroxide.

The amount of the acid or base used is normally in excess to Compound (II-5). Preferably, the amount of the acid used is about 2 to about 50 equivalents relative to Compound (II-5), and the amount of the base used is about 1.2 to about 5 equivalents relative to Compound (II-5).

Examples of the hydrated solvents include solvent mixtures of water and one or more solvents selected from alcohols such as methanol and ethanol; ethers such as tetrahydrofuran, dioxane, and diethyl ether; dimethyl sulfoxide and acetone.

The reaction temperature is normally about −20 to about 150° C., preferably about −10 to about 100° C.

The reaction time is normally about 0.1 to about 20 hours.

Compound (II-6) thus obtained may be isolated and purified by known means of separation and purification such as concentration, concentration under reduced pressure, solvent extraction, crystallization, recrystallization, redissolution and chromatography.

Compound (II-5), which is used as the starting material in Method D above, is produced by, for example, Methods A through C above.

Compound (II-7) having $NR^9R^{10}$ for $R^3$ in the formula (II) can also be produced by Method E below.

[Method E]

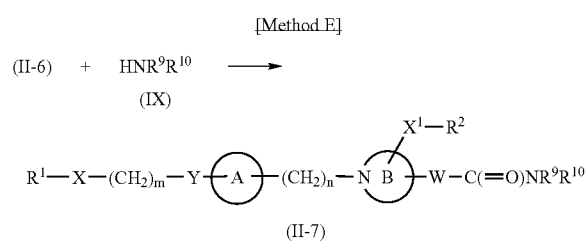

wherein the symbols have the same meanings as above.

In this method, Compound (II-7) is produced by amidating Compound (II-6). This reaction is carried out by a per se known method, e.g., a method wherein Compound (II-6) and Compound (IX) are directly condensed by means of a condensing agent (e.g., dicyclohexylcarbodiimide), a method wherein a reactive derivative of Compound (II-6) and Compound (IX) are reacted as appropriate, or the like. Here, the reactive derivative of Compound (II-6) is exemplified by acid anhydrides, acid halides (acid chlorides, acid bromides), imidazolides, or mixed acid anhydrides (e.g., anhydrides with methoxycarbonic acid, ethoxycarbonic acid, or isobutoxycarbonic acid).

When an acid halide is used, for example, the reaction is carried out in the presence of a base in a solvent which does not interfere with the reaction.

Examples of the base include triethylamine, N-methylmorpholine, N,N-dimethylaniline, sodium hydrogen carbonate, sodium carbonate, and potassium carbonate.

Examples of the solvent which does not interfere with the reaction include halogenated hydrocarbons such as chloroform and dichloromethane; aromatic hydrocarbons such as benzene and toluene; ethers such as tetrahydrofuran, dioxane, and diethyl ether; ethyl acetate, and water. These solvents may be used in mixture in appropriate ratios.

The amount of compound (IX) used is 0.1 to 10 mole equivalents, preferably 0.3 to 3 mole equivalents, relative to Compound (II-6).

The reaction temperature is normally −30 to 100° C.

The reaction time is normally 0.5 to 20 hours.

In addition, when a mixed acid anhydride is used, Compound (II-6) and a chlorocarbonic acid ester (e.g., methyl chlorocarbonate, ethyl chlorocarbonate, isobutyl chlorocarbonate) are reacted in the presence of a base (e.g., triethylamine, N-methylmorpholine, N,N-dimethylaniline, sodium hydrogen carbonate, sodium carbonate, potassium carbonate), and are further reacted with Compound (IX).

The amount of compound (IX) used is normally 0.1 to 10 mole equivalents, preferably 0.3 to 3 mole equivalents, relative to Compound (II-6).

The reaction temperature is normally −30 to 100° C.

The reaction time is normally 0.5 to 20 hours.

Compound (II-7) thus obtained may be isolated and purified by known means of separation and purification such as concentration, concentration under reduced pressure, solvent extraction, crystallization, recrystallization, redissolution and chromatography.

Compound (II-6), which is used as the starting compound in Method E above, can be produced by, for example, Methods A through D above.

[Method F]

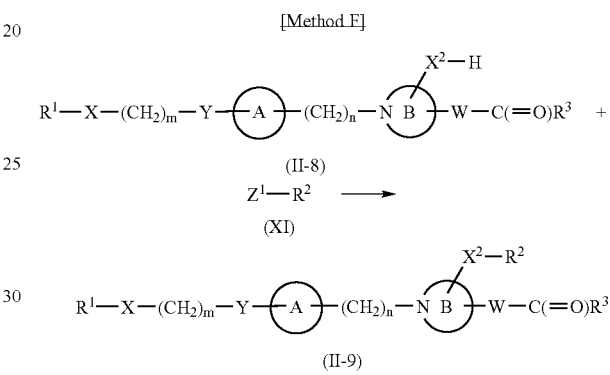

wherein $X^2$ represents an oxygen atom, a sulfur atom or a group of the formula: —$NR^6$— wherein $R^{16}$ has the same meaning as above; $Z^1$ represents a hydroxy group, a halogen atom or a group of the formula: $OSO_2R^{17}$ wherein $R^{17}$ represents an alkyl group having 1 to 4 carbon atoms or an aryl group having 6 to 10 carbon atoms which may be substituted by an alkyl group having 1 to 4 carbon atoms; the other symbols have the same meanings as above.

The "alkyl group having 1 to 4 carbon atoms" and "aryl group having 6 to 10 carbon atoms which may be substituted by an alkyl group having 1 to 4 carbon atoms" for $R^{17}$ are exemplified by those mentioned to exemplify $R^{15}$ above.

In this method, Compound (II-9) is produced by a reaction of Compound (II-8) and Compound (XI). This reaction is carried out in the same manner as the reaction of Compound (III) and Compound (IV) in Method A.

Compound (II-9) thus obtained may be isolated and purified by known means of separation and purification such as concentration, concentration under reduced pressure, solvent extraction, crystallization, recrystallization, redissolution and chromatography.

Compound (II-8), which is used as the starting compound in Method F above, can also be produced by, for example, the method described in Bioorganic & Medicinal Chemistry Letters, vol. 6, p. 1047 (1996), etc., or a method analogous thereto. Furthermore, Compound (II-8) can also be produced by Methods A through E above.

Compound (VIII), which is used as the starting compound in Method C, can be produced by, for example, Method G below.

[Method G]

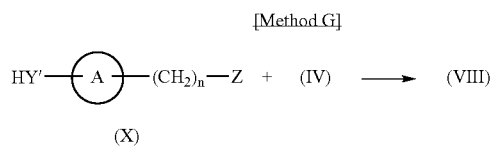

wherein the symbols have the same meaning as above.

This reaction is carried out in the same manner as the reaction of Compound (III) and Compound (IV) in Method A. The condensing reaction may be carried out with the —Y'H moiety of Compound (X) protected, which moiety may be deprotected after the reaction. Useful protective groups include benzyl group, methoxymethyl group, and silyl groups (e.g., trimethylsilyl group, tert-butyldimethylsilyl group).

Compound (II-10) having OH for $R^3$ and having —$CH_2$— for W in the formula (II) can also be produced by Method H below.

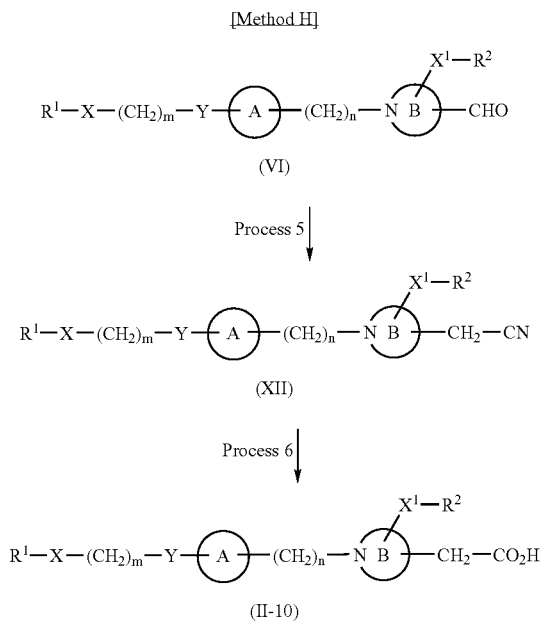

wherein the symbols have the same meaning as above.

(Process 5)

Compound (XII) can be produced by reacting Compound (VI) and p-toluenesulfonylmethylisocyanide in the presence of base such as potassium t-butoxide, sodium hydride, and lithium hydride, in a solvent which does not interfere with the reaction, and then conducting alcoholysis.

The amount of p-toluenesulfonylmethylisocyanide used is preferably about 0.5 to about 10 mole equivalents, relative to Compound (VI).

The amount of the base used is preferably about 0.5 to about 20 mole equivalents, relative to Compound (VI).

Examples of alcohols used in alcoholysis include methanol, ethanol, propanol, butanol, and isopropanol.

Examples of the solvent which does not interfere with the reaction include aromatic hydrocarbons such as benzene, toluene, and xylene; halogenated hydrocarbons such as chloroform and dichloromethane; and ethers such as tetrahydrofuran, dioxane, diethyl ether, 1,2-dimethoxyethane. These solvents may be used in mixture in appropriate ratios.

The reaction temperature is normally about −100 to about 150° C., preferably about −80 to about 100° C.

The reaction time is normally about 0.5 to about 20 hours.

Compound (XII) thus obtained may be isolated and purified by known means of separation and purification such as concentration, concentration under reduced pressure, solvent extraction, crystallization, recrystallization, redissolution and chromatography.

Compound (VI), which is used as the starting compound in Process 5 of Method H above, can be produced by, for example, Process 2 of Method B above.

(Process 6)

In this method, Compound (II-10) is produced by hydrolyzing Compound (XII).

This hydrolytic reaction is carried out by a conventional method in the presence of an acid or a base in a hydrated solvent.

Examples of the acid include hydrochloric acid, sulfuric acid, acetic acid, and hydrobromic acid.

Examples of the base include alkali metal carbonates such as potassium carbonate and sodium carbonate; alkali metal alkoxides such as sodium methoxide; and alkali metal hydroxides such as potassium hydroxide, sodium hydroxide, and lithium hydroxide.

The amount of the acid or base used is normally in excess to Compound (XII). Preferably, the amount of the acid used is about 2 to about 50 equivalents relative to Compound (XII), and the amount of the base used is about 1.2 to about 5 equivalents relative to Compound (XII).

Examples of the hydrated solvents include solvent mixtures of water and one or more solvents selected from alcohols such as methanol and ethanol; ethers such as tetrahydrofuran, dioxane, and diethyl ether; dimethyl sulfoxide and acetone.

The reaction temperature is normally about −20 to about 150° C., preferably about −10 to about 100° C.

The reaction time is normally about 0.1 to about 20 hours.

Compound (II-10) thus obtained may be isolated and purified by known means of separation and purification such as concentration, concentration under reduced pressure, solvent extraction, crystallization, recrystallization, redissolution and chromatography.

When the starting compound has amino, carboxy, hydroxy, or carbonyl as a substituent in the individual reactions described above, these groups may have a protective group in common use in peptide chemistry and other fields introduced therein. The desired compound can be obtained by removing the protective group after the reaction, if necessary.

Examples of the protective groups for amino include formyl, $C_{1-6}$alkyl-carbonyls (e.g., acetyl, propionyl), $C_{1-6}$ alkoxy-carbonyls (e.g., methoxycarbonyl, ethoxycarbonyl, tert-butoxycarbonyl), benzoyl, $C_{7-10}$ aralkyl-carbonyls (e.g., benzylcarbonyl), $C_{7-14}$ aralkyloxy-carbonyls (e.g., benzyloxycarbonyl, 9-fluorenylmethoxycarbonyl), trityl, phthaloyl, N,N-dimethylaminomethylene, silyls (e.g., trimethylsilyl, triethylsilyl, dimethylphenylsilyl, tert-butyldimethylsilyl, tert-butyldiethylsilyl), and $C_{2-6}$ alkenyls (e.g., 1-allyl). These groups may be substituted by 1 to 3 halogen atoms (e.g., fluorine, chlorine, bromine, iodine), $C_{1-6}$ alkoxys (e.g., methoxy, ethoxy, propoxy), nitro, or the like.

Examples of the protective groups for carboxy include $C_{1-6}$ alkyls (e.g., methyl, ethyl, propyl, isopropyl, butyl, tert-butyl), $C_{7-11}$ aralkyls (e.g., benzyl), phenyl, trityl, silyls (e.g., trimethylsilyl, triethylsilyl, dimethylphenylsilyl, tert-butyldimethylsilyl, tert-butyldiethylsilyl), and $C_{2-6}$ alkenyls (e.g., 1-allyl). These groups may be substituted by 1 to 3 halogen atoms (e.g., fluorine, chlorine, bromine, iodine), $C_{1-6}$ alkoxys (e.g., methoxy, ethoxy, propoxy), nitro, or the like.

Examples of the protective groups for hydroxy include $C_{1-6}$ alkyls (e.g., methyl, ethyl, propyl, isopropyl, butyl, tert-butyl), phenyl, trityl, $C_{7-10}$ aralkyls (e.g., benzyl), formyl, $C_{1-6}$ alkyl-carbonyls (e.g., acetyl, propionyl), benzoyl, $C_{7-10}$ aralkyl-carbonyls (e.g., benzylcarbonyl), 2-tetrahydropyranyl, 2-tetrahydrofuranyl, silyls (e.g., trimethylsilyl, triethylsilyl, dimethylphenylsilyl, tert-butyldimethylsilyl, tert-butyldiethylsilyl), and $C_{2-6}$ alkenyls (e.g., 1-allyl). These groups may be substituted by 1 to 3 halogen atoms (e.g., fluorine, chlorine, bromine, iodine), $C_{1-6}$ alkyls (e.g., methyl, ethyl, propyl), $C_{1-6}$ alkoxys (e.g., methoxy, ethoxy, propoxy), nitro, or the like.

Examples of the protective groups for carbonyl include cyclic acetals (e.g., 1,3-dioxane) and non-cyclic acetals (e.g., di-$C_{1-6}$ alkylacetals).

In addition, these protective groups can be removed by a per se known method, e.g., the method described in Protective Groups in Organic Synthesis, published by John Wiley and Sons (1980). For example, there may be used methods employing an acid, a base, ultraviolet rays, hydrazine, phenylhydrazine, sodium N-methyldithiocarbamate, tetrabutylammonium fluoride, palladium acetate, a trialkylsilyl halide (e.g., trimethylsilyl iodide, trimethylsilyl bromide), or the like, the reduction method, and the like.

When compound (II) contains an optical isomer, a stereomer, a position isomer, or a rotation isomer, these isomers are also contained as Compound (II) and can each be obtained as a single substance by means of a per se known method of synthesis or separation. For example, when an optical isomer is present in Compound (II), the optical isomer separated from said compound is also included in Compound (II).

Optical isomers can be produced by a per se known method. Specifically, optical isomers are obtained by using an optically active synthesis intermediate, or optically resolving a racemate of the final product by a conventional method.

Examples of the methods of optical resolution include per se known methods, such as the fractional recrystallization method, the chiral column method, and the diastereomer method.

1) Fractional Recrystallization Method

A method wherein a salt is formed between a racemate and an optically active compound [e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine], which salt is separated by fractional recrystallization, etc., and, if desired, subjected to a neutralization process, to yield a free optical isomer.

2) Chiral Column Method

A method wherein a racemate or a salt thereof is applied to a column for optical isomer separation (chiral column). In the case of liquid chromatography, for example, optical isomers are separated by adding a mixture of the optical isomers to a chiral column such as ENANTIO-OVM (produced by Tosoh Corporation) or CHIRAL series produced by DAICEL CHEMICAL IND., and developing it in water, various buffers (e.g., phosphate buffer), an organic solvent (e.g., ethanol, methanol, isopropanol, acetonitrile, trifluoroacetic acid, diethylamine), or a solvent mixture thereof. In the case of gas chromatography, for example, a chiral column such as CP-Chirasil-DeX CB (produced by GL Science) is used to separate optical isomers.

3) Diastereomer Method

A method wherein a racemate mixture and an optically active reagent are chemically reacted to yield a diastereomer mixture, which is then subjected to ordinary means of separation (e.g., fractional recrystallization, chromatography) to obtain single substances, which are subjected to a chemical reaction such as acid hydrolysis to cut off the optically active reagent moiety, whereby the desired optical isomer is obtained. For example, when Compound (I) has hydroxy or primary or secondary amino in the molecule thereof, said compound, an optically active organic acid (e.g., MTPA [α-methoxy-α-(trifluoromethyl)phenylacetic acid], (−)-menthoxyacetic acid) and the like may be subjected to a condensing reaction to yield a diastereomer of an ester or amide, respectively. On the other hand, when Compound (I) has a carboxyl group, said compound and an optically active amine or an alcohol reagent may be subjected to a condensing reaction to yield a diastereomer of an amide or ester, respectively. The diastereomer thus separated is converted to an optical isomer of the original compound by subjecting it to an acid hydrolysis or basic hydrolysis reaction.

BEST MODE FOR CARRYING OUT THE INVENTION

The present invention is hereinafter described in more detail by means of, but is not limited to, the following Test Examples, Reference Examples, Examples and Preparation Examples. In addition, % in the Reference Examples and Examples below means percent by weight, unless mentioned otherwise. Room temperature means the temperature of 1 to 30° C.

Abbreviations for bases, amino acids and others used in the present specification are based on abbreviations specified by the IUPAC-IUB Commission on Biochemical Nomenclature or abbreviations in common use in relevant fields. Some examples are given below. When an optical isomer may be present in amino acid, it is of the L-configuration, unless otherwise mentioned.

The sequence numbers in the sequence listing in the present specification show the following respective sequences.

[SEQ ID NO:1]

Shows the base sequence of the primer PAG-U used in Reference Example 1.

[SEQ ID NO:2]

Shows the base sequence of the primer PAG-L used in Reference Example 1.

[SEQ ID NO:3]

Shows the base sequence of the primer XRA-U used in Reference Example 2.

[SEQ ID NO:4]

Shows the base sequence of the primer XRA-L used in Reference Example 2.

[SEQ ID NO:5]

Shows the base sequence of the primer PPRE-U used in Reference Example 4.

[SEQ ID NO:6]
Shows the base sequence of the primer PPRE-L used in Reference Example 4.

[SEQ ID NO:7]
Shows the base sequence of the primer TK-U used in Reference Example 4.

[SEQ ID NO:8]
Shows the base sequence of the primer TK-L used in Reference Example 4.

Test Example 1

Hypoglycemic and Hypolipidemic Actions in Mice

Test compounds were mixed in a powdery diet (CE-2, Japan Clea) at the concentration of 0.01% (compounds of Examples 12, 30, 89, 186), 0.005% (compounds of Examples 7, 80, 82, 181, 182, 184, 256, 262, 283), 0.001% (compounds of Examples 9, 104, 110, 155, 156, 160, 167, 169, 172, 174, 176, 189), or 0.0003% (compounds of Examples 38, 40, 44), and freely given to KKA$^y$ mice (9 to 12 weeks old, 5 mice in a group), a model of obese and type 2 diabetes mellitus, for four days. During this period, water was given freely. Blood was sampled from orbital venous plexus, and glucose and triglyceride levels in plasma separated from blood were determined enzymatically using L type Wako Glu2 (Wako Pure Chemical Industries, Ltd.) or L type Wako TG•H (Wako Pure Chemical Industries, Ltd.), respectively. The results are given in Table 1.

In the Table, the value of each treatment group is represented as percent reduction compared with the non-treatment group.

TABLE 1

| Test compound (Example No.) | Hypoglycemic action (%) | Hypolipidemic action (%) |
|---|---|---|
| 7 | 54 | 60 |
| 9 | 48 | 70 |
| 12 | 46 | 63 |
| 30 | 54 | 77 |
| 38 | 44 | 69 |
| 40 | 41 | 66 |
| 44 | 47 | 74 |
| 80 | 42 | 22 |
| 82 | 50 | 58 |
| 89 | 48 | 70 |
| 104 | 43 | 42 |
| 110 | 50 | 70 |
| 155 | 49 | 56 |
| 156 | 45 | 80 |
| 160 | 54 | 57 |
| 167 | 48 | 60 |
| 169 | 48 | 39 |
| 172 | 42 | 62 |
| 174 | 40 | 52 |
| 176 | 40 | 66 |
| 181 | 56 | 63 |
| 182 | 34 | 12 |
| 184 | 56 | 82 |
| 186 | 57 | 78 |
| 189 | 44 | 75 |
| 256 | 57 | 16 |
| 262 | 45 | 61 |
| 283 | 52 | 78 |

These results indicated that the compounds of the present invention possess potent hypoglycemic and hypolipidemic actions. Therefore, the compounds are proved to be useful as agents for preventing or treating diabetes mellitus, hyperlipidemia (especially hypertriglyceridemia), impaired glucose tolerance, etc.

Test Example 2

Total Cholesterol Lowering Action and Plasma Anti-Arteriosclerosis Index-Enhancing Action in Mice Test compounds were mixed in a powdery diet (CE-2, Japan Clea) at the concentration of 0.01% (compounds of Examples 12, 30, 89), 0.005% (compounds of Examples 38, 40, 44, 181, 184, 262, 283), or 0.001% (compounds of Examples 9, 156, 167, 172, 174, 176, 189), and freely given to KKA$^y$ mice (9 to 12 weeks old, 5 mice per group), a model of obese and type 2 diabetes mellitus, for four days. During this period, water was given freely. Blood was sampled from orbital venous plexus and plasma was separated. Total cholesterol levels were determined by using L type Wako Cholesterol (Wako Pure Chemical Industries, Ltd.). Precipitation reagent for apoB containing lipoprotein was added to a part of the plasma to precipitate non-HDL lipoprotein, and cholesterol (HDL cholesterol) in the resulting supernatant was determined. The plasma anti-arteriosclerosis index [(HDL cholesterol/total cholesterol)×100] was calculated by using these cholesterol levels. The results are given in Table 2.

In the Table, "Total cholesterol lowering action (%)" represents the percent reduction (%) of total cholesterol level in the treatment group, when the total cholesterol level in the non-treatment group is taken as 100%. "Plasma anti-arteriosclerosis index-enhancing action (%)" represents the percent increase (%) of plasma anti-arteriosclerosis index in the treatment group, when the plasma anti-arteriosclerosis index in the non-treatment group is taken as 100%.

TABLE 2

| Test compound (Example No.) | Total cholesterol lowering action (%) | Plasma anti-arteriosclerosis index-enchancing action (%) |
|---|---|---|
| 9 | 16 | 12 |
| 12 | 15 | 24 |
| 30 | 27 | 16 |
| 38 | 24 | 21 |
| 40 | 19 | 22 |
| 44 | 23 | 21 |
| 89 | 8 | 15 |
| 156 | 20 | 15 |
| 167 | 19 | 9 |
| 172 | 20 | 11 |
| 174 | 19 | 10 |
| 176 | 23 | 11 |
| 181 | 25 | 21 |
| 184 | 27 | 17 |
| 189 | 21 | 20 |
| 262 | 22 | 9 |
| 283 | 24 | 19 |

These results indicated that the compounds of the present invention possess total cholesterol lowering and plasma anti-arteriosclerosis index-enhancing actions. Therefore, the compounds are proved to be useful as agents for preventing or treating arteriosclerosis by improving plasma lipoprotein profiles of hypercholesterolemia and/or hypo-HDL-cholesterolemia.

Test Example 3

(PPARγ-RXRα Heterodimer Ligand Activity)

A PPARγ:RXRα:4ERPP/CHO-K1 cells obtained in Reference Example 5 described later were cultured in HAM F12 medium (produced by NISSUI SEIYAKU) containing 10% Fetal bovine serum (produced by Life Technologies, Inc., USA) and then inoculated to a 96-well white plate (produced by Corning Costar Corporation, USA) at the density of $2 \times 10^4$ cells/well, and cultured in a $CO_2$ gas incubator at 37° C. overnight.

After washing the 96 well white plate with PBS (Phosphate-buffered saline), 90 μl of HAM F12 medium containing 0.1% fatty acid-free bovine serum albumin (BSA) and 10 μl of test compound were added, which was cultured in a $CO_2$ gas incubator at 37° C. for 48 hours. After removing the medium, 40 μl of PIKKAGENE 7.5 (produced by Wako Pure Chemical Industries, Ltd.) was added. After stirring, the luciferase activity was determined using Lumistar (produced by BMG Labtechnologies GmbH, Germany).

A fold induction was calculated based on the luciferase activity of each test compound by taking the luciferase activity in the non-treatment group as 1. The values of the test compound concentration and the fold induction were analyzed using PRISM 2.01 (produced by GraphPad Software Inc. USA) to calculate the $EC_{50}$ values, the effective concentration of a test compound for 50% of the maximum fold induction. The results are shown in Table 3.

TABLE 3

| Test compound (Example No.) | $EC_{50}$ (nM) |
|---|---|
| 7 | 3.8 |
| 8 | 2.7 |
| 9 | 1.5 |
| 12 | 320 |
| 30 | 9.7 |
| 38 | 38 |
| 40 | 57 |
| 44 | 13 |
| 80 | 2.5 |
| 82 | 1.4 |
| 89 | 0.23 |
| 100 | 1.8 |
| 104 | 2.0 |
| 110 | 3.5 |
| 256 | 53 |
| 262 | 33 |
| 283 | 0.22 |

These results indicated that the compounds of the present invention have potent PPARγ-RXRα heterodimer ligand activity.

Reference Example 1

(Human PPARγ Gene Cloning)

A human PPARγ gene was cloned using a heart cDNA (produced by Toyobo Co., Ltd., trade name: QUICK-Clone cDNA) as a template by means of a PCR method employing a primer set shown below which was prepared with reference to the base sequence of PPARγ gene reported by Greene et al (Gene Expr., 1995, Vol. 4(4–5), page 281–299).

PAG-U: 5'-GTG GGT ACC GAA ATG ACC ATG GTT GAC ACA GAG-3' (Sequence ID Number: 1)
PAG-L: 5'-GGG GTC GAC CAG GAC TCT CTG CTA GTA CAA GTC-3' (Sequence ID Number: 2)

The PCR reaction was performed by Hot Start method using AmpliWax PCR Gem 100 (produced by TAKARA SHUZO CO., LTD.). First, 2 μl of 10×LA PCR Buffer, 3 μL1 of 2.5 mM dNTP solution, 2.5 μl each of 12.5 μM primer solutions and 10 μl of sterilized distilled water were mixed to obtain a bottom layer solution mixture. 1 μl of human heart cDNA (1 ng/ml) as a template, 3 μl of 10×LA PCR Buffer, 1 μl of 2.5 mM dNTP solution, 0.5 μl of TaKaRa LA Taq DNA polymerase (produced by TAKARA SHUZO CO., LTD.) and 24.5 μl of sterilized distilled water were mixed to obtain a top layer solution mixture.

To the bottom layer solution mixture described above, added was one unit of AmpliWax PCR Gem 100 (produced by TAKARA SHUZO CO., LTD.), which was treated at 70° C. for 5 minutes and then in ice for 5 minutes. Then the top layer solution mixture was added to the mixture to prepare the reaction mixture of PCR. A tube containing the reaction mixture was set on a thermal cycler (produced by Perkin Elmer, USA) and treated at 95° C. for 2 minutes. After repeating the cycle of 95° C. for 15 seconds and 68° C. for 2 minutes a further 35 times, the tube was treated at 72° C. for 8 minutes.

The PCR product thus obtained was subjected to electrophoresis on agarose gel (1%), and 1.4 kb DNA fragment containing PPARγ gene was recovered from the gel, and then inserted into pT7 Blue-T vector (produced by TAKARA SHUZO CO., LTD.) to obtain a plasmid pTBT-hPPARγ.

Reference Example 2

(Human RXR α Gene Cloning)

A human RXRα gene was cloned using a kidney cDNA (produced by Toyobo Co., Ltd., trade name: QUICK-Clone cDNA) as a template by means of a PCR method employing a primer set shown below which was prepared with reference to the base sequence of RXRα gene reported by Mangelsdorf, D. J. et al (Nature, 1990, Vol. 345 (6272), page 224–229).

XRA-U: 5'-TTA GAA TTC GAC ATG GAC ACC AAA CAT TTC CTG-3' (Sequence ID Number: 3)
XRA-L: 5'-CCC CTC GAG CTA AGT CAT TTG GTG CGG CGC CTC-3' (Sequence ID Number: 4)

The PCR reaction was performed by Hot Start method using AmpliWax PCR Gem 100 (produced by TAKAEA SHUZO CO., LTD.). First, 2 μl of 10×LA PCR Buffer, 3 μl of 2.5 mM dNTP solution, 2.5 μl each of 12.5 μM primer solutions and 10 μl of sterilized distilled water were mixed to obtain a bottom layer solution mixture. 1 μl of human kidney cDNA (1 ng/ml) as a template, 3 μl of 10×LA PCR Buffer, 1 μl of 2.5 mM dNTP solution, 0.5 μl of TaKaRa LA Taq DNA polymerase (produced by TAKARA SHUZO CO., LTD.) and 24.5 μl of sterilized distilled water were mixed to obtain a top layer solution mixture.

To the bottom layer solution mixture described above, added was one unit of AmpliWax PCR Gem 100 (produced by TAKARA SHUZO CO., LTD.), which was treated at 70° C. for 5 minutes and then in ice for 5 minutes. Then, the top layer solution mixture was added to the mixture to prepare the reaction mixture of PCR. A tube containing the reaction mixture was set on a thermal cycler (produced by Perkin Elmer, USA) and treated at 95° C. for 2 minutes. After repeating the cycle of 95° C. for 15 seconds and 68° C. for 2 minutes a further 35 times, the tube was treated at 72° C. for 8 minutes.

The PCR product thus obtained was subjected to electrophoresis on agarose gel (1%), and 1.4 kb DNA fragment containing RXRα gene was recovered from the gel, and then inserted into pT7 Blue-T vector (produced by TAKARA SHUZO CO., LTD.) to obtain a plasmid pTBT-hRXRα.

Reference Example 3

(Construction of Plasmids for Expressing HUMAN PPARγ, RXR α)

7.8 kb FspI-NotI fragment of plasmid pVgRXR (produce by Invitrogen, USA) was ligated to a 0.9 kb FspI-NotI fragment containing RXRα gene of plasmid pTBT-hRXRα obtained in Reference Example 2 to prepare plasmid pVgRXR2. Then, pVgRXR2 was digested with BstXI and then treated with T4DNA polymerase (produced by TAKARA SHUZO CO., LTD.) to obtain a blunt terminal. Then digestion at KpnI gave a 6.5 kb DNA fragment.

On the other hand, plasmid pTBT-hPPARγ obtained in Reference Example 1 was digested with Sal I and then treated with T4DNA polymerase (produced by TAKARA SHUZO CO., LTD.) to obtain a blunt terminal. Then digestion at KpnI gave a 1.4 kb DNA fragment containing human PPARγ gene.

The both DNA fragments were ligated to construct plasmid pVgRXR2-hPPARγ.

Reference Example 4

(Construction of Reporter Plasmids)

A DNA fragment containing PPAR-responding element (PPRE) of an acyl CoA oxidase was prepared using the following 5'-terminal phosphorylated synthetic DNA.

PPRE-U: 5'-pTCGACAGGGGACCAGGACAAAGGT-CACGTTCGGGAG-3' (Sequence ID Number: 5)

PPRE-L: 5'-pTCGACTCCCGAACGTGACCTTTGTC-CTGGTCCCCTG-3' (Sequence ID Number: 6)

First, PPRE-U and PPRE-L were annealed and inserted to Sal I site of plasmid pBlue Script SK+. By determining the base sequence of the inserted fragment, plasmid pBSS-PPRE4 in which 4 PPREs were ligated in tandem was selected.

A HSV thymidine kinase minimum promoter (TK promoter) region was cloned using pRL-TK vector (produced by Promega, USA) as a template by means of a PCR method employing a primer set shown below which was prepared with reference to the base sequence of the promoter region of thymidine kinase reported by Luckow, B et al (Nucleic Acids Res., 1987, Vol. 15(13), p. 5490)

TK-U: 5'-CCCAGATCTCCCCAGCGTCTTGTCATTG-3' (Sequence ID Number: 7)

TK-L: 5'-TCACCATGGTCAAGCTTTTAAGCGGGTC-3' (Sequence ID Number: 8)

The PCR reaction was performed by Hot Start method using AmpliWax PCR Gem 100 (TAKARA SHUZO CO., LTD.). First, 2 μl of 10×LA PCR Buffer, 3 μl of 2.5 mM dNTP solution, 2.5 μl each of 12.5 μM primer solutions and 10 μl of sterilized distilled water were mixed to obtain a bottom layer solution mixture. 1 μl of pRL-TK vector (produced by Promega, USA) as a template, 3 μl of 10×LA PCR Buffer, 1 μl of 2.5 mM dNTP solution, 0.5 μl of TaKaRa LA Taq DNA polymerase (produced by TAKARA SHUZO CO., LTD.) and 24.5 μl of sterilized distilled water were mixed to obtain a top layer solution mixture.

To the bottom layer solution mixture described above, added was one unit of AmpliWax PCR Gem 100 (produced by TAKARA SHUZO CO., LTD.), which was treated at 70° C. for 5 minutes and then in ice for 5 minutes. Then, the top layer solution mixture was added to the mixture to prepare the reaction mixture of PCR. A tube containing the reaction mixture was set on a thermal cycler (produced by Perkin Elmer, USA) and treated at 95° C. for 2 minutes. After repeating the cycle of 95° C. for 15 seconds and 68° C. for 2 minutes a further 35 times, the tube was treated at 72° C. for 8 minutes.

The PCR product thus obtained was subjected to electrophoresis on agarose gel (1%), and 140 b DNA fragment containing TK promoter was recovered from the gel, and then inserted into pT7 Blue-T vector (produced by TAKARA SHUZO CO., LTD.). By digesting the plasmid thus obtained with the restriction enzymes Bgl II and NcoI, a fragment containing TK promoter was obtained, which was ligated to the Bgl II-NcoI fragment of plasmid pGL3-Basic vector (produced by Promega, USA) to obtain plasmid pGL3-TK.

A 4.9 kb NheI-XhoI fragment of plasmid pGL3-TK thus obtained was ligated to a 200 b NheI-XhoI fragment of plasmid pBSS-PPRE4 to obtain plasmid pGL3-4ERPP-TK.

This plasmid pGL3-4ERPP-TK thus obtained was digested with BamHI (produced by TAKARA SHUZO CO., LTD.) and then treated with T4DNA polymerase (produced by TAKARA SHUZO CO., LTD.) to form a blunt terminal, whereby obtaining a DNA fragment.

On the other hand, pGFP-C1 (produced by Toyobo Co., Ltd.) was digested with Bsu36I (NEB) and then treated with T4DNA polymerase (produced by TAKARA SHUZO CO., LTD.) to form a blunt terminal whereby obtaining a 1.6 kb of a DNA fragment.

The both DNA fragments were ligated to construct a reporter plasmid pGL3-4ERPP-TK neo.

Reference Example 5

(Introduction of Human PPARγ- and RXRα-Expressing Plasmid and Reporter Plasmid into CHO-K1 Cell and Establishment of Expressed Cell)

After a CHO-K1 cell cultured in a 750 ml tissue culture flask (produced by Corning Costar Corporation, USA) containing HAM F12 medium (produced by NISSUI SEIYAKU) supplemented with 10% Fetal Bovine Serum (produced by Life Technologies, Inc., USA) was scraped by treating with 0.5 g/L trypsin-0.2 g/L EDTA (ethylenediaminetetraacetic acid) (produced by Life Technologies, Inc., USA), the cell was washed with PBS (phosphate-buffered saline) (produced by Life Technologies, Inc., USA), centrifuged (1000 rpm, 5 minutes), and then suspended in PBS. Subsequently, a DNA was introduced into the cell under the condition shown below using GENE PULSER (produced by Bio-Rad Laboratories, USA).

Namely, to a cuvette having a 0.4 cm gap, added were $8 \times 10^6$ cells and 10 μg of plasmid pVgRXR2-hPPAR γ obtained in Reference Example 3 and 10 μg of reporter plasmid pGL3-4ERPP-TK neo obtained in Reference Example 4, which was subjected to electroporation at the voltage of 0.25 kV under the capacitance of 960 μF. Subsequently, the cell was transferred into a HAM F12 medium containing 10% Fetal Bovine Serum and cultured for 24 hours and then the cell was scraped again and centrifuged, and then suspended in HAM F12 medium containing 10% Fetal Bovine Serum supplemented with 500 μg/ml of GENETICIN (produced by Life Technologies, Inc., USA) and 250 μg/ml of ZEOCIN (produced by Invitrogen, USA) and diluted to the density of $10^4$ cells/ml upon inoculation to a 96-well plate (produced by Corning Costar Corporation, USA), which was cultured in a $CO_2$ gas incubator at 37° C., whereby obtaining a GENETICIN- and ZEOCIN-resistant transformant.

Subsequently, after the transformant cell line thus obtained was cultured in a 24-well plate (produced by Corning Costar Corporation, USA), selected was a cell line in which the luciferase was expressed and induced, i.e., PPARγ:RXRα:4ERPP/CHO-K1 cell by addition of 10 μM pioglitazone hydrochloride.

Reference Example 6

Lithium aluminium hydride (2.53 g) was added to a solution of methyl 1-(4-benzyloxybenzyl)-4-phenylpyrrole-3-carboxylate (21.52 g) in tetrahydrofuran (100 ml) at 0° C., and the mixture was stirred at room temperature for one hour. Sodium sulfate decahydrate (30.00 g) and hexane (100 ml) were added to the reaction mixture and the mixture was stirred at room temperature for one hour. After the precipitate was removed by filtration, the filtrate was concentrated. The residue was subjected to silica gel column chromatography, and [1-(4-benzyloxybenzyl)-4-phenyl-3-pyrrolyl]methanol (19.68 g, yield: 98%) was obtained as colorless crystals from the fraction eluted with ethyl acetate-hexane (1:1, volume ratio). This was recrystallized from ethyl acetate-hexane. Melting point: 122–123° C.

Reference Example 7

A mixture of [1-(4-benzyloxybenzyl)-4-phenyl-3-pyrrolyl]methanol (19.00 g), activated manganese dioxide (41.19 g), and tetrahydrofuran (300 ml) was stirred at room temperature overnight. After the manganese dioxide was removed by filtration, the filtrate was concentrated. The residue was subjected to silica gel column chromatography, and 1-(4-benzyloxybenzyl)-4-phenylpyrrole-3-carbaldehyde (18.56 g, yield: 98%) was obtained as colorless crystals from the fraction eluted with ethyl acetate-hexane (1:2, volume ratio). This was recrystallized from ethyl acetate-hexane. Melting point: 100–101° C.

Reference Example 8

A mixture of ethyl(E)-3-[1-(4-benzyloxybenzyl)-4-phenyl-3-pyrrolyl]propenoate (19.50 g), 5% palladium-carbon (20.00 g), and tetrahydrofuran (200 ml) was stirred overnight at room temperature under a hydrogen atmosphere. After the palladium-carbon was removed by filtration, the filtrate was concentrated. The residue was subjected to silica gel column chromatography, and ethyl 3-[1-(4-hydroxybenzyl)-4-phenyl-3-pyrrolyl]propionate (14.92 g, yield: 96%) was obtained as an oily substance from the fraction eluted with ethyl acetate-hexane (1:2, volume ratio).

NMR(CDCl$_3$) δ: 1.20(3H, t, J=7.0 Hz), 2.44–2.58(2H, m), 2.88–3.02(2H, m), 4.08(2H, q, J=7.0 Hz), 4.93(2H, s), 6.46–6.54(1H, m), 6.66–6.84(3H, m), 7.02–7.12(2H, m), 7.14–7.44(5H, m).

Reference Example 9

Lithium aluminium hydride (232 mg) was added to a mixture of methyl 1-[4-(5-methyl-2-phenyl-4-oxazolylmethoxy)benzyl]-4-phenylpyrrole-3-carboxylate (2.92 g), diethyl ether (50 ml), and tetrahydrofuran (25 ml) at 0° C., and the mixture was stirred at 0° C. for 3 hours. After water was added to the reaction mixture, the precipitate was removed by filtration. The filtrate was extracted with ethyl acetate. The ethyl acetate layer was washed with saturated aqueous sodium chloride solution, dried (MgSO$_4$), and then concentrated. The residue was subjected to silica gel column chromatography, and [1-[4-(5-methyl-2-phenyl-4-oxazolylmethoxy)benzyl]-4-phenyl-3-pyrrolyl]methanol (2.37 g, yield: 86%) was obtained as a colorless amorphous substance from the fraction eluted with ethyl acetate-hexane (2:3, volume ratio).

NMR(CDCl$_3$) δ: 2.43(3H, s), 4.64(2H, s), 4.99(4H, s like), 6.73–6.77(1H, m), 6.80–6.83(1H, m), 7.04(2H, d, J=8.6 Hz), 7.12–7.56(10H, m), 7.98–8.04(2H, m).

Reference Example 10

A mixture of [1-[4-(5-methyl-2-phenyl-4-oxazolylmethoxy)benzyl]-4-phenyl-3-pyrrolyl]methanol (3.98 g), activated manganese dioxide (8.00 g), and toluene (50 ml) was stirred at 80° C. for 10 hours. After the manganese dioxide was removed by filtration, the filtrate was concentrated. The residue was subjected to silica gel column chromatography, and 1-[4-(5-methyl-2-phenyl-4-oxazolylmethoxy)benzyl]-4-phenylpyrrole-3-carbaldehyde (2.85 g, yield: 72%) was obtained as colorless crystals from the fraction eluted with ethyl acetate-hexane (2:3, volume ratio). This was recrystallized from ethyl acetate-hexane. Melting point: 117–118° C.

Reference Example 11

Lithium aluminium hydride (305 mg) was added to a solution of methyl 1-[4-[2-[N-methyl-N-(2-pyridyl)amino]ethoxy]benzyl]-4-phenyl-3-pyrrolecarboxylate (1.78 g) in tetrahydrofuran (40 ml) at 0° C., and the mixture was stirred at room temperature for 6 hours. After water was added to the reaction mixture, the precipitate was removed by filtration and the filtrate was concentrated. The residue was subjected to silica gel column chromatography, and [1-[4-[2-[N-methyl-N-(2-pyridyl)amino]ethoxy]benzyl]-4-phenyl-3-pyrrolyl]methanol (1.45 g, yield: 87%) was obtained as an oily substance from the fraction eluted with ethyl acetate-hexane (1:1, volume ratio).

NMR(CDCl$_3$) δ: 1.35–1.5(1H, m), 3.15(3H, s), 3.99(2H, t, J=5.5 Hz), 4.18(2H, t, J=5.5 Hz), 4.63(2H, d, J=4.5 Hz), 4.96(2H, s), 6.45–6.6(2H, m), 6.73(1H, d, J=2.5 Hz), 6.79 (1H, d, J=2.5 Hz), 6.87(2H, d, J=9.0 Hz), 7.12(2H, d, J=9.0 Hz), 7.15–7.6(6H, m), 8.1–8.2(1H, m).

Reference Example 12

A mixture of [1-[4-[2-[N-methyl-N-(2-pyridyl)amino]ethoxy]benzyl]-4-phenyl-3-pyrrolyl]methanol (1.45 g), activated manganese dioxide (4.0 g), and tetrahydrofuran (60 ml) was stirred at room temperature for 3 hours. After the manganese dioxide was removed by filtration, the filtrate was concentrated to obtain 1-[4-[2-[N-methyl-N-(2-pyridyl)amino]ethoxy]benzyl]-4-phenylpyrrole-3-carbaldehyde (1.40 g, yield: 97%) as an oily substance.

NMR(CDCl$_3$) δ 3.15(3H, s), 3.99(2H, t, J=5.5 Hz), 4.19 (2H, t, J=5.5 Hz), 5.02(2H, s), 6.45–6.6(2H, m), 6.73(1H, d, J=2.0 Hz), 6.90(2H, d, J=8.5 Hz), 7.15(2H, d, J=8.5 Hz), 7.2–7.5(7H, m), 8.1–8.2(1H, m), 9.84(1H, s).

Reference Example 13

Lithium aluminium hydride (0.258 g) was added to a solution of methyl 1-(6-benzyloxy-2-naphthylmethyl)-4-phenylpyrrole-3-carboxylate (3.04 g) in tetrahydrofuran (30 ml) at 0° C., and the mixture was stirred at room temperature for one hour. Sodium sulfate decahydrate (2.19 g) and hexane (30 ml) were added to the reaction mixture and the mixture was stirred at room temperature for 30 minutes. After the precipitate was removed by filtration, the filtrate was concentrated. The colorless crystals obtained were collected by filtration to yield [1-(6-benzyloxy-2-naphthylmethyl)-4-phenyl-3-pyrrolyl]methanol (2.54 g, yield: 89%). This was recrystallized from ethyl acetate-hexane. Melting point: 116–117° C.

Reference Example 14

A mixture of [1-(6-benzyloxy-2-naphthylmethyl)-4-phenyl-3-pyrrolyl]methanol (2.39 g), activated manganese dioxide (4.80 g), and tetrahydrofuran (50 ml) was stirred at room temperature for one hour. After the manganese dioxide was removed by filtration, the filtrate was concentrated. The colorless crystals obtained were collected by filtration to yield 1-(6-benzyloxy-2-naphthylmethyl)-4-phenylpyrrole-3-carbaldehyde (2.24 g, yield: 94%). This was recrystallized from tetrahydrofuran-hexane. Melting point: 140–141° C.

Reference Example 15

A mixture of ethyl(E)-3-[1-(6-benzyloxy-2-naphthylmethyl)-4-phenyl-3-pyrrolyl]propenoate (1.46 g), 5% palladium-carbon (1.5 g), ethanol (15 ml), and tetrahydrofuran (15 ml) was stirred for 4 hours at room temperature under a hydrogen atmosphere. After the palladium-carbon was removed by filtration, the filtrate was concentrated. The residue was subjected to silica gel column chromatography, and ethyl 3-[1-(6-hydroxy-2-naphthylmethyl)-4-phenyl-3-pyrrolyl]propionate (1.08 g, yield: 90%) was obtained as an oily substance from the fraction eluted with ethyl acetate-hexane (1:1, volume ratio).

NMR(CDCl$_3$) δ 1.17(3H, t, J=7.2 Hz), 2.53(2H, t, J=7.6 Hz), 2.97(2H, t, J=7.6 Hz), 4.07(2H, q, J=7.2 Hz), 5.10(2H, s), 5.57(1H, br.s), 6.55(1H, d, J=2.4 Hz), 6.76(1H, d, J=2.4 Hz), 7.07–7.45(8H, m), 7.54(1H, s), 7.60–7.71(2H, m).

Reference Example 16

Lithium aluminium hydride (0.25 g) was added to a solution of ethyl 1-[4-(5-methyl-2-phenyl-4-oxazolylmethoxy)benzyl]-4-(2-pyridyl)pyrrole-3-carboxylate (2.40 g) in tetrahydrofuran (30 ml) at 0° C., and the mixture was stirred at 0° C. for 30 minutes. After sodium sulfate decahydrate (2.13 g) and hexane (30 ml) were added to the reaction mixture, the mixture was stirred at room temperature for 30 minutes. After the precipitate was removed by filtration, the filtrate was concentrated. The residue was subjected to silica gel column chromatography, and [1-[4-(5-methyl-2-phenyl-4-oxazolylmethoxy)benzyl]-4-(2-pyridyl)-3-pyrrolyl]methanol (2.09 g, yield: 95%) was obtained as an oily substance from the fraction eluted with ethyl acetate-hexane (1:1, volume ratio).

NMR(CDCl$_3$) δ: 2.44(3H, s), 4.55(2H, s), 4.99(4H, s), 6.68(1H, d, J=2.2 Hz), 6.94–7.22(6H, m), 7.36–7.69(5H, m), 7.96–8.08(2H, m), 8.46–8.53(1H, m).

Reference Example 17

A mixture of [1-[4-(5-methyl-2-phenyl-4-oxazolylmethoxy)benzyl]-4-(2-pyridyl)-3-pyrrolyl]methanol (2.01 g), activated manganese dioxide (5.09 g), and tetrahydrofuran (50 ml) was stirred at room temperature overnight. After the manganese dioxide was removed by filtration, the filtrate was concentrated. The residue was subjected to silica gel column chromatography, and 1-[4-(5-methyl-2-phenyl-4-oxazolylmethoxy)benzyl]-4-(2-pyridyl)pyrrole-3-carbaldehyde (1.71 g, yield: 85%) was obtained as an oily substance from the fraction eluted with ethyl acetate-hexane (1:2, volume ratio).

NMR(CDCl$_3$) δ: 2.44(3H, s), 5.00(2H, s), 5.06(2H, s), 6.96–7.28(6H, m), 7.38–7.49(4H, m), 7.62–7.74(1H, m), 7.79–7.86(1H, m), 7.96–8.08(2H, m), 8.54–8.60(1H, m), 10.16(1H, s).

Reference Example 18

Methanesulfonyl chloride (5.03 ml) was slowly added to a mixture of 3,5-dibenzyloxybenzyl alcohol (16.0 g), triethylamine (9.06 ml), and tetrahydrofuran (200 ml), and the mixture was stirred at room temperature for 30 minutes. The reaction mixture was poured into water, which was extracted with ethyl acetate. The ethyl acetate layer was washed with saturated aqueous sodium chloride solution, dried (MgSO$_4$), and then concentrated. The colorless crystals obtained were collected by filtration to yield 3,5-dibenzyloxybenzyl methanesulfonate (22.20 g, yield: 91%). This was recrystallized from ethyl acetate-hexane. Melting point: 85–86° C.

Reference Example 19

Lithium aluminium hydride (1.97 g) was added to a solution of methyl 1-(3,5-dibenzyloxybenzyl)-4-phenyl-3-pyrrolecarboxylate (26.2 g) in tetrahydrofuran (250 ml) at 0° C., and the mixture was stirred at room temperature for one hour. Sodium sulfate decahydrate (16.1 g) and hexane (250 ml) were added to the reaction mixture, and the mixture was stirred at room temperature for 30 minutes. After the precipitate was removed by filtration, the filtrate was concentrated. The colorless crystals obtained were collected by filtration to yield [1-(3,5-dibenzyloxybenzyl)-4-phenyl-3-pyrrolyl]methanol (24.20 g, yield: 98%). This was recrystallized from tetrahydrofuran-hexane. Melting point: 115–116° C.

Reference Example 20

A mixture of [1-(3,5-dibenzyloxybenzyl)-4-phenyl-3-pyrrolyl]methanol (23.8 g), activated manganese dioxide (50.00 g), and tetrahydrofuran (200 ml) was stirred at room temperature for two hours. After the manganese dioxide was removed by filtration, the filtrate was concentrated. The colorless crystals obtained were collected by filtration to yield 1-(3,5-dibenzyloxybenzyl)-4-phenylpyrrole-3-carbaldehyde (23.10 g, yield: 97%). This was recrystallized from tetrahydrofuran-hexane. Melting point: 117–118° C.

Reference Example 21

A mixture of ethyl(E)-3-[1-(3,5-dibenzyloxybenzyl)-4-phenyl-3-pyrrolyl]propenoate (19.0 g), 5% palladium-carbon (40.0 g), ethanol (200 ml), and tetrahydrofuran (200 ml) was stirred for 4 hours at room temperature under a hydrogen atmosphere. After the palladium-carbon was removed by filtration, the filtrate was concentrated. The residue was subjected to silica gel column chromatography, and ethyl 3-[1-(3,5-dihydroxybenzyl)-4-phenyl-3-pyrrolyl]propionate (12.10 g, yield: 95%) was obtained as an oily substance from the fraction eluted with ethyl acetate-hexane (3:2, volume ratio).

NMR(CDCl$_3$) δ: 1.13(3H, t, J=7.2 Hz), 2.49(2H, t, J=7.4 Hz), 2.93(2H, t, J=7.4 Hz), 4.01(2H, q, J=7.2 Hz), 4.77(2H, s), 6.09(2H, d, J=2.2 Hz), 6.24(1H, t, J=2.2 Hz), 6.33(2H, s), 6.42(1H, d, J=2.4 Hz), 6.65(1H, d, J=2.4 Hz), 7.14–7.37(5H, m).

Reference Example 22

Lithium aluminium hydride (884 mg) was added to a solution of ethyl 1-(4-benzyloxybenzyl)-3-phenyl-1H-pyrazole-4-carboxylate (9.61 g) in tetrahydrofuran (50 ml) at 0° C., and the mixture was stirred at 0° C. for one hour. After adding water, the reaction mixture was stirred at room temperature for one hour. After the precipitate was removed by filtration, the filtrate was extracted with ethyl acetate. The ethyl acetate layer was washed with saturated aqueous sodium chloride solution, dried ($MgSO_4$), and then concentrated. The crystals obtained were collected by filtration to yield [1-(4-benzyloxybenzyl)-3-phenyl-1H-pyrazol-4-yl]methanol (23.10 g, yield: 97%). This was recrystallized from ethyl acetate-hexane. Melting point: 88–89° C.

Reference Example 23

Thionyl chloride (1.83 ml) was added dropwise to a solution of [1-(4-benzyloxybenzyl)-3-phenyl-1H-pyrazol-4-yl]methanol (8.43 g) in toluene (100 ml) at 0° C., and the mixture was stirred at room temperature for 30 minutes. The reaction mixture was poured into water, which was extracted with ethyl acetate. The ethyl acetate layer was washed with saturated aqueous sodium chloride solution, dried ($MgSO_4$), and then concentrated. The residue was dissolved in tetrahydrofuran (30 ml), and this solution was added to a mixture of diethyl malonate (18.3 g), sodium hydride (60%, oily, 3.65 g), and tetrahydrofuran (100 ml) at 0° C. The above mixture was stirred at 0° C. for one hour and then at room temperature for 6 hours. The reaction mixture was acidified with diluted hydrochloric acid, which was extracted with ethyl acetate. The ethyl acetate layer was washed with saturated aqueous sodium chloride solution, dried ($MgSO_4$), and then concentrated. The residue was subjected to silica gel column chromatography, and diethyl 2-[1-(4-benzyloxybenzyl)-3-phenyl-1H-pyrazol-4-yl]mehtylmalonate (9.50 g, yield: 81%) was obtained as a colorless oily substance from the fraction eluted with ethyl acetate-hexane (1:3, volume ratio).

NMR($CDCl_3$) δ: 1.15(6H, t, J=7.1 Hz), 3.21(2H, d, J=8.0 Hz), 3.52(1H, t, J=8.0 Hz), 4.08(4H, q, J=7.1 Hz), 5.06(2H, s), 5.21(2H, s), 6.94(2H, d, J=8.8 Hz), 7.15–7.47(11H, m), 7.60–7.66(2H, m).

Reference Example 24

A mixture of methyl 3-[1-(4-benzyloxybenzyl)-3-phenyl-1H-pyrazol-4-yl]propionate (500 mg), 5% palladium-carbon (1.00 g), and tetrahydrofuran (10 ml) was stirred for 18 hours at room temperature under a hydrogen atmosphere. After the palladium-carbon was removed by filtration, the filtrate was concentrated. The residue was subjected to silica gel column chromatography, and methyl 3-[1-(4-hydroxybenzyl)-3-phenyl-1H-pyrazol-4-yl]propionate (325 mg, yield: 80%) was obtained as colorless crystals from the fraction eluted with ethyl acetate-hexane (2:3, volume ratio). This was recrystallized from ethyl acetate-hexane. Melting point: 87–88° C.

Reference Example 25

Methanesulfonyl chloride (3.37 g) was added dropwise to a mixture of 2-[4-(5-methyl-2-phenyl-4-oxazolylmethoxy)phenyl]ethan-1-ol (7.0 g), triethylamine (2.97 g), and ethyl acetate (300 ml) at 0° C., and the mixture was stirred for 3 hours at room temperature. The reaction mixture was poured into water, which was extracted with ethyl acetate. The ethyl acetate layer was washed with saturated aqueous sodium bicarbonate, 1N hydrochloric acid and then with saturated aqueous sodium chloride solution, then dried ($MgSO_4$), and concentrated. The crystals obtained were collected by filtration to yield 2-[4-(5-methyl-2-phenyl-4-oxazolylmethoxy)phenyl]ethyl methanesulfonate (8.44 g, yield: 96%). This was recrystallized from ethyl acetate-hexane. Melting point: 66–67° C.

Reference Example 26

A mixture of 4-[4-(3,5-dimethyl-1H-pyrazol-1-ylmethyl)phenoxymethyl]-5-methyl-2-phenyloxazole (1.62 g), phosphorus oxychloride (1.00 g), and N,N-dimethylformamide (20 ml) was stirred for 5 days at room temperature. The reaction mixture was poured into water, which was extracted with ethyl acetate. The ethyl acetate layer was washed with saturated aqueous sodium bicarbonate and with saturated aqueous sodium chloride solution, then dried ($MgSO_4$), and concentrated. The residue was subjected to silica gel column chromatography, and 3,5-dimethyl-1-[4-(5-methyl-2-phenyl-4-oxazolylmethoxy)benzyl]-1H-pyrazole-4-carbaldehyde (950 mg, yield: 55%) was obtained as an oily substance from the fraction eluted with ethyl acetate-hexane (1:1, volume ratio).

NMR($CDCl_3$) δ: 2.43(3H, s), 2.47(6H, s), 4.97(2H, s), 5.18(2H, s), 6.98(2H, d, J=9 Hz), 7.10(2H, d, J=9 Hz), 7.4–7.5(3H, m), 7.95–8.05(2H, m), 9.92(1H, s).

Reference Example 27

Lithium aluminium hydride (262 mg) was added to a solution of methyl 3-[1-[4-(5-methyl-2-phenyl-4-oxazolylmethoxy)benzyl]-3-phenyl-1H-pyrazol-4-yl]propionate (3.50 g) in diethyl ether (50 ml) at 0° C., and the mixture was stirred at 0° C. for one hour. After adding water, the reaction mixture was acidified with diluted hydrochloric acid, which was extracted with ethyl acetate. The ethyl acetate layer was washed with saturated aqueous sodium chloride solution, dried ($MgSO_4$), and then concentrated. The residue was subjected to silica gel column chromatography, and 3-[1-[4-(5-methyl-2-phenyl-4-oxazolylmethoxy)benzyl]-3-phenyl-1H-pyrazol-4-yl]propan-1-ol (3.04 g, yield: 92%) was obtained as a colorless oily substance from the fraction eluted with ethyl acetate-hexane (3:2, volume ratio).

NMR($CDCl_3$) δ: 1.72–1.87(2H, m), 2.44(3H, s), 2.65–2.74(2H, m), 3.63(2H, t, J=6.4 Hz), 4.99(2H, s), 5.25(2H, s), 7.00(2H, d, J=8.8 Hz), 7.17–7.46(9H, m), 7.62–7.68(2H, m), 7.98–8.04(2H, m).

Reference Example 28

Methanesulfonyl chloride (0.625 ml) was added to a mixture of 3-[1-[4-(5-methyl-2-phenyl-4-oxazolylmethoxy)benzyl]-3-phenyl-1H-pyrazol-4-yl]propan-1-ol (2.98 g), triethylamine (1.74 ml), and ethyl acetate (50 ml) at 0° C., and the mixture was stirred for 30 minutes. The reaction mixture was washed with water and then with saturated aqueous sodium chloride solution, dried ($MgSO_4$), and then concentrated. After the residue was dissolved in acetone (50 ml), sodium iodide (1.86 g) was added and the solution was stirred at 50° C. for 3 hours. After the solvent was removed under reduced pressure, the residue was dissolved in water, which was extracted with ether acetate. The ethyl acetate layer was washed with saturated aqueous sodium chloride solution, dried ($MgSO_4$), and then concentrated to obtain 1-iodo-3-[1-[4-(5-methyl-2-phenyl-4-oxazolylmethoxy)benzyl]-3-phenyl-1H-pyrazol-4-yl]propane (3.60 g, yield: 98%) as a colorless oily substance.

NMR($CDCl_3$) δ: 1.96–2.08(2H, m), 2.44(3H, s), 2.69–2.77(2H, m), 3.15(2H, t, J=6.8 Hz), 4.99(2H, s), 5.25 (2H, s), 7.01(2H, d, J=8.8 Hz), 7.19–7.48(9H, m), 7.60–7.66 (2H, m), 7.98–8.04(2H, m).

Reference Example 29

A mixture of 1-iodo-3-[1-[4-(5-methyl-2-phenyl-4-oxazolylmethoxy)benzyl]-3-phenyl-1H-pyrazol-4-yl]propane (1.75 g), sodium cyanide (291 mg), and dimethyl sulfoxide (5 ml) was stirred at 60° C. for 2 hours. The reaction mixture was poured into water, which was extracted with ethyl acetate. The ethyl acetate layer was washed with saturated aqueous sodium chloride solution, dried ($MgSO_4$), and then concentrated. The residue was subjected to silica gel column chromatography, and 4-[1-[4-(5-methyl-2-phenyl-4-oxazolylmethoxy)benzyl]-3-phenyl-1H-pyrazol-4-yl]butyronitrile (1.34 g, yield: 92%) was obtained as a colorless oily substance from the fraction eluted with ethyl acetate-hexane (2:3, volume ratio).

NMR($CDCl_3$) δ: 1.76–1.92(2H, m), 2.28(2H, t, J=7.0 Hz), 2.44(3H, s), 2.78(2H, t, J=7.5 Hz), 4.99(2H, s), 5.25 (2H, s), 7.01(2H, d, J=8.8 Hz), 7.19–7.47(9H, m), 7.58–7.64 (2H, m), 7.98–8.04(2H, m).

Reference Example 30

Sodium hydride (60%, oily, 476 mg) was added to a solution of diethyl malonate (2.37 g) in tetrahydrofuran (50 ml) at 0° C., and the mixture was stirred for 30 minutes. A solution of 1-iodo-3-[1-[4-(5-methyl-2-phenyl-4-oxazolylmethoxy)benzyl]-3-phenyl-1H-pyrazol-4-yl]propane (1.75 g) in tetrahydrofuran (15 ml) was added dropwise to the above mixture, which was stirred at room temperature for 13 hours. The reaction mixture was acidified with diluted hydrochloric acid, which was extracted with ethyl acetate. The ethyl acetate layer was washed with saturated aqueous sodium chloride solution, dried ($MgSO_4$), and then concentrated. The residue was subjected to silica gel column chromatography, and diethyl 2-[3-[1-[4-(5-methyl-2-phenyl-4-oxazolylmethoxy)benzyl]-3-phenyl-1H-pyrazol-4-yl]propyl]malonate (1.63 g, yield: 88%) was obtained as a colorless oily substance from the fraction eluted with ethyl acetate-hexane (1:2, volume ratio).

NMR($CDCl_3$) δ 1.23(6H, t, J=7.1 Hz), 1.50–1.65(2H, m), 1.86–1.98(2H, m), 2.43(3H, s), 2.63(2H, t, J=7.7 Hz), 3.29 (1H, t, J=7.6 Hz), 4.15(4H, q, J=7.1 Hz), 4.99(2H, s), 5.24(2H, s), 7.00(2H, d, J=8.8 Hz), 7.17–7.47(9H, m), 7.59–7.65(2H, m), 7.98–8.04(2H, m).

Reference Example 31

Lithium aluminium hydride (2.03 g) was added to a solution of ethyl 1-[4-(5-methyl-2-phenyl-4-oxazolylmethoxy)benzyl]-3-[4-(5-methyl-2-phenyl-4-oxazolylmethoxy)benzyloxy]-1H-pyrazole-4-carboxylate (40.00 g) in tetrahydrofuran (150 ml) at 0° C., and the mixture was stirred at room temperature for 30 minutes. After water was added to the reaction mixture, the precipitate was removed by filtration and the filtrate was extracted with ethyl acetate. The ethyl acetate layer was washed with saturated aqueous sodium chloride solution, dried ($MgSO_4$), and then concentrated. The crystals obtained were collected by filtration to yield [1-[4-(5-methyl-2-phenyl-4-oxazolylmethoxy)benzyl]-3-[4-(5-methyl-2-phenyl-4-oxazolylmethoxy)benzyloxy]-1H-pyrazol-4-yl]methanol (35.91 g, yield: 95%). This was recrystallized from tetrahydrofuran-hexane. Melting point: 157–158° C.

Reference Example 32

A mixture of [1-[4-(5-methyl-2-phenyl-4-oxazolylmethoxy)benzyl]-3-[4-(5-methyl-2-phenyl-4-oxazolylmethoxy)benzyloxy]-1H-pyrazol-4-yl]methanol (27.02 g), activated manganese dioxide (52.29 g), chloroform (50 ml), and tetrahydrofuran (300 ml) was stirred at room temperature for 3 hours. After the manganese dioxide was removed by filtration, the filtrate was concentrated. The crystals obtained were collected by filtration to yield 1-[4-(5-methyl-2-phenyl-4-oxazolylmethoxy)benzyl]-3-[4-(5-methyl-2-phenyl-4-oxazolylmethoxy)benzyloxy]-1H-pyrazole-4-carbaldehyde (25.69 g, yield: 95%). This was recrystallized from tetrahydrofuran-hexane. Melting point: 155–156° C.

Reference Example 33

Lithium aluminium hydride (0.98 g) was added to a solution of ethyl 1-[4-[2-(2-furyl)-5-methyl-4-oxazolylmethoxy]benzyl]-3-[4-[2-(2-furyl)-5-methyl-4-oxazolylmethoxy]benzyloxy]-1H-pyrazole-4-carboxylate (19.16 g) in tetrahydrofuran (75 ml) at 0° C., and the mixture was stirred at room temperature for 30 minutes. After water was added to the reaction mixture, the precipitate was removed by filtration and the filtrate was extracted with ethyl acetate. The ethyl acetate layer was washed with saturated aqueous sodium chloride solution, dried ($MgSO_4$), and then concentrated. The crystals obtained were collected by filtration to yield [1-[4-[2-(2-furyl)-5-methyl-4-oxazolylmethoxy]benzyl]-3-[4-[2-(2-furyl)-5-methyl-4-oxazolylmethoxy]benzyloxy]-1H-pyrazol-4-yl]methanol (17.25 g, yield: 96%). This was recrystallized from ethyl acetate-hexane. Melting point: 80–81° C.

Reference Example 34

A mixture of [1-[4-[2-(2-furyl)-5-methyl-4-oxazolylmethoxy]benzyl]-3-[4-[2-(2-furyl)-5-methyl-4-oxazolylmethoxy]benzyloxy]-1H-pyrazol-4-yl]methanol (16.59 g), activated manganese dioxide (35.19 g) and tetrahydrofuran (100 ml) was stirred at room temperature for 3 hours. After the manganese dioxide was removed by filtration, the filtrate was concentrated. The crystals obtained were collected by filtration to yield 1-[4-[2-(2-furyl)-5-methyl-4-oxazolylmethoxy]benzyl]-3-[4-[2-(2-furyl)-5-methyl-4-oxazolylmethoxy]benzyloxy]-1H-pyrazole-4-carbaldehyde (14.73 g, yield: 89%). This was recrystallized from ethyl acetate-hexane. Melting point: 109–110° C.

Reference Example 35

Lithium aluminium hydride (0.58 g) was added to a solution of methyl 3-isopropyl-1-[4-(5-methyl-2-phenyl-4-oxazolylmethoxy)benzyl]-1H-pyrazole-4-carboxylate (9.02 g) in tetrahydrofuran (50 ml) at 0° C., and the mixture was stirred at room temperature for 30 minutes. After water was added to the reaction mixture, the precipitate was removed by filtration and the filtrate was extracted with ethyl acetate. The ethyl acetate layer was washed with saturated aqueous sodium chloride solution, dried ($MgSO_4$), and then concentrated. The residue was subjected to silica gel column chromatography, and [3-isopropyl-1-[4-(5-methyl-2-phenyl-4-oxazolylmethoxy)benzyl]-1H-pyrazol-4-yl]methanol (8.20 g, yield: 97%) was obtained from the fraction eluted with ethyl acetate-hexane (1:1, volume ratio). This was recrystallized from ethyl acetate-hexane. Melting point: 98–99° C.

Reference Example 36

A mixture of ethyl 3-oxohexanoate (15.80 g) and N,N-dimethylformamidedimethylacetal (17.9 g) was refluxed for 2.5 hours and the reaction mixture was concentrated under reduced pressure. After the residue was dissolved in ethanol (200 ml) and degassed, benzylhydrazine dihydrochloride (22.0 g) was added and the solution was refluxed for 2 hours under a nitrogen atmosphere. The reaction mixture was concentrated under reduced pressure. The residue was dissolved in ethyl acetate and washed with water and then with saturated aqueous sodium chloride solution, dried ($MgSO_4$), and then concentrated. The residue was subjected to silica gel column chromatography, and ethyl 1-benzyl-5-propyl-1H-pyrazole-4-carboxylate (22.81 g, yield: 84%) was obtained as a colorless oily substance from the fraction eluted with ethyl acetate-hexane (1:9, volume ratio).

NMR($CDCl_3$) δ: 0.92(3H, t, J=7.2 Hz), 1.34(3H, t, J=7.2 Hz), 1.39–1.59(2H, m), 2.84–2.92(2H, m), 4.28(2H, q, J=7.2 Hz), 5.32(2H, s), 7.08–7.13(2H, m), 7.26–7.34(3H, m), 7.92(1H, s).

Reference Example 37

Lithium aluminium hydride (2.58 g) was added to a solution of ethyl 1-benzyl-5-propyl-1H-pyrazole-4-carboxylate (18.50 g) in tetrahydrofuran (300 ml) at 0° C., and the mixture was stirred at room temperature for one hour. Sodium sulfate decahydrate (21.88 g) and hexane (100 ml) were added to the reaction mixture and the mixture was stirred at room temperature for 30 minutes. After the precipitate was removed by filtration, the filtrate was concentrated to obtain (1-benzyl-5-propyl-1H-pyrazol-4-yl)methanol (14.99 g, yield: 96%) as a colorless oily substance.

NMR($CDCl_3$) δ: 0.90(3H, t, J=7.6 Hz), 1.38–1.57(2H, m), 2.59(2H, t, J=7.6 Hz), 4.52(2H, s), 5.29(2H, s), 7.06–7.11(2H, m), 7.21–7.36(3H, m), 7.51(1H, s).

Reference Example 38

A mixture of (1-benzyl-5-propyl-1H-pyrazol-4-yl)methanol (14.99 g), activated manganese dioxide (30.0 g) and, tetrahydrofuran (300 ml) was stirred at room temperature for 3 days. After the manganese dioxide was removed by filtration, the filtrate was concentrated. The residue was subjected to silica gel column chromatography, and 1-benzyl-5-propyl-1H-pyrazole-4-carbaldehyde (10.69 g, yield: 72%) was obtained as a colorless oily substance from the fraction eluted with ethyl acetate-hexane (1:2, volume ratio).

NMR($CDCl_3$) δ: 0.93(3H, t, J=7.0 Hz), 1.43–1.58(2H, m), 2.89(2H, t, J=8.0 Hz), 5.33(2H, s), 7.11–7.16(2H, m), 7.26–7.37(3H, m), 7.96(1H, s), 9.88(1H, s).

Reference Example 39

Sodium hydride (60%, oily, 2.25 g) was added to a mixture of 1-benzyl-5-propyl-1H-pyrazole-4-carbaldehyde (12.60 g), ethyl diethylphosphonoacetate (10.69 g), and N,N-dimethylformamide (150 ml) at 0° C., and the mixture was stirred at room temperature for 15 hours. The reaction mixture was poured into ice water, which was extracted with ethyl acetate. The ethyl acetate layer was washed with water and then with saturated aqueous sodium chloride solution, dried ($MgSO_4$), and then concentrated. The residue was subjected to silica gel column chromatography, and ethyl (E)-3-(1-benzyl-5-propyl-1H-pyrazol-4-yl)propenoate (11.90 g, yield: 85%) was obtained as a colorless oily substance from the fraction eluted with ethyl acetate-hexane (1:4, volume ratio).

NMR($CDCl_3$) δ: 0.90(3H, t, J=7.2 Hz), 1.32(3H, t, J=7.2 Hz), 1.36–1.60(2H, m), 2.65(2H, t, J=7.6 HZ)), 4.24(2H, q, J=7.2 Hz), 5.30(2H, s), 6.17(1H, d, J=15.6 Hz), 7.07–7.12 (2H, m), 7.26–7.37(3H, m), 7.50(1H, d, J=15.6 Hz), 7.77 (1H, s).

Reference Example 40

A mixture of ethyl(E)-3-(1-benzyl-5-propyl-1H-pyrazol-4-yl)propenoate (6.00 g), 5% palladium-carbon (12.0 g), formic acid (50 ml), and ethanol (100 ml) was refluxed for 16 hours. After the palladium-carbon was removed by filtration, the filtrate was concentrated. The residue was dissolved in ethyl acetate, washed with saturated aqueous sodium bicarbonate and then with saturated aqueous sodium chloride solution, dried ($MgSO_4$), and concentrated. The residue was subjected to silica gel column chromatography, and ethyl 3-(3-propyl-1H-pyrazol-4-yl)propionate (3.45 g, yield: 82%) was obtained as a colorless oily substance from the fraction eluted with ethyl acetate-hexane (1:1, volume ratio).

NMR($CDCl_3$) δ: 0.97(3H, t, J=7.2 Hz), 1.25(3H, t, J=7.2 Hz), 1.56–1.76(2H, m), 2.50–2.79(6H, m), 4.13(2H, q, J=7.2 Hz), 7.34(1H, s).

Reference Example 41

A mixture of ethyl benzoylacetate (20.0 g) and N,N-dimethylformamide dimethylacetal (18.59 g) was refluxed for 1.5 hours and the reaction mixture was concentrated under reduced pressure. After the residue was dissolved in ethanol (200 ml) and degassed, benzylhydrazine dihydrochloride (22.25 g) was added and the solution was refluxed for 2 hours under a nitrogen atmosphere. The reaction mixture was concentrated under reduced pressure. The residue was dissolved in ethyl acetate, washed with water and then with saturated aqueous sodium chloride solution, dried ($MgSO_4$), and then concentrated. The residue was subjected to silica gel column chromatography, and ethyl 1-benzyl-5-phenyl-1H-pyrazole-4-carboxylate (20.9 g, yield: 66%) was obtained as colorless crystals from the fraction eluted with ethyl acetate-hexane (1:6, volume ratio). This was recrystallized from ethyl acetate-hexane. Melting point: 78–79° C.

Reference Example 42

Lithium aluminium hydride (2.50 g) was added to a solution of ethyl 1-benzyl-5-phenyl-1H-pyrazole-4-carboxylate (20.2 g) in tetrahydrofuran (300 ml) at 0° C., and the mixture was stirred at room temperature for one hour. Sodium sulfate decahydrate (21.23 g) and hexane (100 ml) were added to the reaction mixture, and the mixture was stirred at room temperature for one hour. After the precipitate was removed by filtration, the filtrate was concentrated. The residue was subjected to silica gel column chromatography, and (1-benzyl-5-phenyl-1H-pyrazol-4-yl)methanol (17.4 g, yield: 100%) was obtained as a colorless oily substance from the fraction eluted with ethyl acetate-hexane (1:1, volume ratio). NMR($CDCl_3$) δ: 4.46(2H, s), 5.25(2H, s), 6.99–7.04(2H, m), 7.23–7.32(5H, m), 7.41–7.45(3H, m), 7.69(1H, s).

Reference Example 43

A mixture of (1-benzyl-5-phenyl-1H-pyrazol-4-yl)methanol (9.76 g), activated manganese dioxide (20.0 g), and tetrahydrofuran (200 ml) was stirred at room temperature for 12 hours. After the manganese dioxide was removed by filtration, the filtrate was concentrated. The residue was subjected to silica gel column chromatography, and 1-benzyl-5-phenyl-1H-pyrazole-4-carbaldehyde (7.30 g, yield: 75%) was obtained as colorless crystals from the fraction eluted with ethyl acetate-hexane (1:2, volume ratio). This was recrystallized from ethyl acetate-hexane. Melting point: 99–100° C.

Reference Example 44

Sodium hydride (60%, oily, 1.28 g) was added to a mixture of 1-benzyl-5-phenyl-1H-pyrazole-4-carbaldehyde (7.00 g), ethyl diethylphosphonoacetate (6.59 g), and N,N-dimethylformamide (100 ml) at 0° C., and the mixture was stirred at room temperature for 2.5 days. The reaction mixture was poured into ice water, which was extracted with ethyl acetate. The ethyl acetate layer was washed with water and then with saturated aqueous sodium chloride solution, dried ($MgSO_4$), and then concentrated. The residue was subjected to silica gel column chromatography, and ethyl (E)-3-(1-benzyl-5-phenyl-1H-pyrazol-4-yl)propenoate (6.30 g, yield: 71%) was obtained as colorless crystals from the fraction eluted with ethyl acetate-hexane (1:4, volume ratio). This was recrystallized from ethyl acetate-hexane. Melting point: 62–63° C.

Reference Example 45

A mixture of ethyl(E)-3-(1-benzyl-5-phenyl-1H-pyrazol-4-yl)propenoate (300 mg), 5% palladium-carbon (600 mg), formic acid (3 ml), and ethanol (10 ml) was refluxed for 2 hours. After the palladium-carbon was removed by filtration, the filtrate was concentrated. The residue was dissolved in ethyl acetate, washed with saturated aqueous sodium bicarbonate and then with saturated aqueous sodium chloride solution, dried ($MgSO_4$), and concentrated. The residue was subjected to silica gel column chromatography, and ethyl 3-(3-phenyl-1H-pyrazol-4-yl)propionate (120 mg, yield: 55%) was obtained as a colorless oily substance from the fraction eluted with ethyl acetate-hexane (2:3, volume ratio).

NMR($CDCl_3$) δ: 1.23(3H, t, J=7.2 Hz), 2.58(2H, t, J=7.6 Hz), 2.98(2H, t, J=7.6 Hz), 4.12(2H, q, J=7.2 Hz), 7.38–7.58 (6H, m).

Reference Example 46

Lithium aluminium hydride (1.93 g) was added to a solution of ethyl 3-methyl-1-(2-pyridyl)-1H-pyrazole-4-carboxylate (15.00 g) in tetrahydrofuran (150 ml) at 0° C., and the mixture was stirred at room temperature for one hour. Sodium sulfate decahydrate (21.03 g) and hexane (100 ml) were added to the reaction mixture, and the mixture was stirred at room temperature for one hour. After the precipitate was removed by filtration, the filtrate was concentrated. The crystals obtained were collected by filtration to yield [3-methyl-1-(2-pyridyl)-1H-pyrazol-4-yl]methanol (11.38 g). This was recrystallized from acetone-hexane. Melting point: 116–117° C.

Reference Example 47

Sodium hydride (60%, oily, 0.80 g) was added to a solution of [3-methyl-1-(2-pyridyl)-1H-pyrazol-4-yl]methanol (3.20 g) in N,N-dimethylformamide (50 ml) at 0° C., and the mixture was stirred at room temperature for one hour. 4-fluorobenzaldehyde (2 ml) was added to the reaction mixture, and the mixture was stirred overnight at 50° C. The reaction mixture was poured into water, which was extracted with ethyl acetate. The ethyl acetate layer was washed with saturated aqueous sodium chloride solution, dried ($MgSO_4$), and then concentrated. The residue was subjected to silica gel column chromatography, and 4-[3-methyl-1-(2-pyridyl)-1H-pyrazol-4-ylmethoxy]benzaldehyde (4.26 g, yield: 86%) was obtained as colorless crystals from the fraction eluted with ethyl acetate-hexane (1:2, volume ratio). This was recrystallized from ethyl acetate-hexane. Melting point: 84–85° C.

Reference Example 48

Sodium borohydride (0.25 g) was added to a mixture of 4-[3-methyl-1-(2-pyridyl)-1H-pyrazol-4-ylmethoxy]benzaldehyde (3.50 g), methanol (5 ml), and tetrahydrofuran (25 ml) at 0° C., and the mixture was stirred at room temperature for 30 minutes. After the reaction mixture was concentrated under reduced pressure, diluted hydrochloric acid was added to the residue, which was extracted with ethyl acetate. The ethyl acetate layer was washed with saturated aqueous sodium chloride solution, dried ($MgSO_4$), and then concentrated. The residue was subjected to silica gel column chromatography, and 4-[3-methyl-1-(2-pyridyl)-1H-pyrazol-4-ylmethoxy]benzyl alcohol (3.41 g, yield: 97%) was obtained as colorless crystals from the fraction eluted with ethyl acetate-hexane (1:2, volume ratio). This was recrystallized from ethyl acetate-hexane. Melting point: 83–84° C.

Reference Example 49

Sodium hydride (60%, oily, 180 mg) was added to a mixture of ethyl 3-(3-phenyl-1H-pyrazol-4-yl)propionate (1.00 g), benzyl 4-chloromethylbenzoate (1.17 g), and N,N-dimethylformamide (10 ml) at 0° C., and the mixture was stirred for 2.5 days at room temperature. The reaction mixture was poured into water, which was extracted with ethyl acetate. The ethyl acetate layer was washed with saturated aqueous sodium chloride solution, dried ($MgSO_4$), and then concentrated. The residue was subjected to silica gel column chromatography, and benzyl 4-[4-(3-ethoxy-3-oxo-1-propyl)-3-phenyl-1H-pyrazole-1-ylmethyl]benzoate (1.68 g, yield: 88%) was obtained as a colorless oily substance from the fraction eluted with ethyl acetate-hexane (1:4, volume ratio).

NMR($CDCl_3$) δ: 1.18 (3H, t, J=7.0 Hz), 2.53(2H, t, J=7.6 Hz), 2.96(2H, t, J=7.6 Hz), 4.07(2H, q, J=7.0 Hz), 5.35(4H, s), 7.25–7.46(11H, m), 7.60–7.66(2H, m), 8.02–8.07(2H, m).

Reference Example 50

A mixture of benzyl 4-[4-(3-ethoxy-3-oxo-1-propyl)-3-phenyl-1H-pyrazol-1-ylmethyl]benzoate (1.67 g), 5% palladium-carbon (2.00 g), and ethanol (50 ml) was stirred for 5 hours at room temperature under a hydrogen atmosphere. After the palladium-carbon was removed by filtration, the filtrate was concentrated. The crystals obtained were collected by filtration to yield 4-[4-(3-ethoxy-3-oxo-1-propyl)-3-phenyl-1H-pyrazol-1-ylmethyl]benzoate (1.08 g, yield: 79%). This was recrystallized from ethyl acetate-hexane. Melting point: 97–98° C.

Reference Example 51

Sodium hydride (60%, oily, 850 mg) was added to a mixture of ethyl 3-(3-phenyl-1H-pyrazol-4-yl)propionate (4.69 g), benzyl 3-chloromethylbenzoate (5.50 g), and N,N-dimethylformamide (50 ml) at 0° C., and the mixture was stirred for 2.5 days at room temperature. The reaction mixture was poured into water, which was extracted with ethyl acetate. The ethyl acetate layer was washed with saturated aqueous sodium chloride solution, dried ($MgSO_4$), and then concentrated. The residue was subjected to silica gel column chromatography, and a colorless oily substance was obtained from the fraction eluted with ethyl acetate-hexane (1:4, volume ratio). A mixture of the oily substance obtained, 5% palladium-carbon (12.0 g), and ethanol (200 ml) was stirred for 5 hours at room temperature under a hydrogen atmosphere. After the palladium-carbon was removed by filtration, the filtrate was concentrated. The crystals obtained were collected by filtration to yield 3-[4-(3-ethoxy-3-oxo-1-propyl)-3-phenyl-1H-pyrazol-1-ylmethyl]benzoate (2.41 g, yield: 33%). This was recrystallized from ethyl acetate-hexane. Melting point: 101–102° C.

Reference Example 52

Thionyl chloride (4.35 g) was added to a solution of (1-benzyl-5-phenyl-1H-pyrazol-4-yl)methanol (8.06 g) in toluene (100 ml) dropwise at 0° C., and the mixture was stirred at room temperature for one hour and then refluxed for ten minutes. The reaction mixture was concentrated under reduced pressure. The residue was dissolved in ethyl acetate, washed with saturated aqueous sodium bicarbonate and then with saturated aqueous sodium chloride solution, dried ($MgSO_4$), and then concentrated. The residue was subjected to silica gel column chromatography, and 1-benzyl-4-chloromethyl-5-phenyl-1H-pyrazole (8.31 g, yield: 96%) was obtained as a colorless oily substance from the fraction eluted with ethyl acetate-hexane (1:4, volume ratio).
NMR($CDCl_3$) δ: 4.44(2H, s), 5.23(2H, s), 6.99–7.04(2H, m), 7.22–7.36(5H, m), 7.42–7.47(3H, m), 7.72(1H, s).

Reference Example 53

A mixture of 1-benzyl-4-chloromethyl-5-phenyl-1H-pyrazole (8.31 g), potassium cyanide (2.87 g), and N,N-dimethylformamide (100 ml) was stirred for 15 hours at 90° C., and poured into water, which was extracted with ethyl acetate. The ethyl acetate layer was washed with water and then with saturated aqueous sodium chloride solution, dried ($MgSO_4$), and then concentrated. The residue was subjected to silica gel column chromatography, and (1-benzyl-5-phenyl-1H-pyrazol-4-yl)acetonitrile (3.50 g, yield: 44%) was obtained as a colorless oily substance from the fraction eluted with ethyl acetate-hexane (1:2, volume ratio).
NMR($CDCl_3$) δ: 3.45(2H, s), 5.21(2H, s), 6.97–7.02(2H, m), 7.19–7.30(5H, m), 7.43–7.50(3H, m), 7.67(1H, s).

Reference Example 54

A mixture of (1-benzyl-5-phenyl-1H-pyrazol-4-yl)acetonitrile (3.50 g), a 4N aqueous potassium hydroxide solution (16 ml), and ethanol (50 ml) was refluxed for 4 hours. The reaction mixture was acidified with 1N hydrochloric acid, which was extracted with ethyl acetate. The ethyl acetate layer was washed with saturated aqueous sodium chloride solution, dried ($MgSO_4$), and concentrated to obtain (1-benzyl-5-phenyl-1H-pyrazol-4-yl)acetic acid (3.70 g, yield: 99%) as a colorless oily substance.
NMR($CDCl_3$) δ: 3.42(2H, s), 5.22(2H, s), 6.97–7.02(2H, m), 7.22–7.26(5H, m), 7.40–7.44(3H, m), 7.65(1H, s).

Reference Example 55

A mixture of (1-benzyl-5-phenyl-1H-pyrazol-4-yl)acetic acid (3.70 g), concentrated sulfuric acid (0.5 ml), and ethanol (200 ml) was refluxed for 5 hours. The reaction mixture was alkalinized with saturated aqueous sodium bicarbonate, which was extracted with ethyl acetate. The ethyl acetate layer was washed with saturated aqueous sodium chloride solution, dried ($MgSO_4$), and concentrated. The residue was subjected to silica gel column chromatography, and ethyl(1-benzyl-5-phenyl-1H-pyrazol-4-yl)acetate (3.62 g, yield: 89%) was obtained as an oily substance from the fraction eluted with ethyl acetate-hexane (1:6, volume ratio).
NMR($CDCl_1$) δ: 1.22(3H, t, J=7.2 Hz), 3.38(2H, s), 4.11(2H, q, J=7.2 Hz), 5.21(2H, s), 6.98–7.03(2H, m), 7.21–7.28(5H, m), 7.37–7.44(3H, m), 7.63(1H, s).

Reference Example 56

A mixture of ethyl(1-benzyl-5-phenyl-1H-pyrazol-4-yl)acetate (3.60 g), 5% palladium-carbon (7.00 g), formic acid (40 ml), and ethanol (150 ml) was refluxed for 2 hours. After the palladium-carbon was removed by filtration, the filtrate was concentrated. The residue was dissolved in ethyl acetate, washed with saturated aqueous sodium bicarbonate and then with saturated aqueous sodium chloride solution, dried ($MgSO_4$), and concentrated to obtain ethyl (3-phenyl-1H-pyrazol-4-yl)acetate (2.33 g, yield: 90%) as a colorless oily substance.
NMR($CDCl_3$) δ: 1.23(3H, t, J=7.2 Hz), 3.61(2H, s), 4.15(2H, q, J=7.2 Hz), 7.36–7.64(6H, m).

Reference Example 57

A mixture of ethyl(1-[2-(4-benzyloxyphenyl)ethyl]-3-phenyl-1H-pyrazol-4-yl)acetate (800 mg), 5% palladium-carbon (1.50 g), tetrahydrofuran (20 ml), and ethanol (30 ml) was stirred for 3 hours at room temperature under a hydrogen atmosphere. After the palladium-carbon was removed by filtration, the filtrate was concentrated. The residue was subjected to silica gel column chromatography, and ethyl [1-[2-(4-hydroxyphenyl)ethyl]-3-phenyl-1H-pyrazol-4-yl]acetate (400 mg, yield: 63%) was obtained as an oily substance from the fraction eluted with ethyl acetate-hexane (1:4, volume ratio).
NMR($CDCl_3$) δ: 1.23(3H, t, J=7.0 Hz), 3.11(2H, t, J=7.2 Hz), 3.57(2H, s), 4.13(2H, q, J=7.0 Hz), 4.29(2H, t, J=7.2 Hz), 5.36(1H, br.s), 6.69–6.74(2H, m), 6.93–6.98(2H, m), 7.26–7.45(4H, m), 7.58–7.62(2H, m).

Reference Example 58

Lithium aluminium hydride (323 mg) was added to a mixture of ethyl 1-[4-(5-methyl-2-phenyl-4-oxazolylmethoxy)benzyl]-1H-pyrazole-4-carboxylate (3.55 g), diethyl ether (25 ml), and tetrahydrofuran (25 ml) at 0° C., and the mixture was stirred at room temperature for 2 hours. The reaction mixture was poured into a 1N aqueous sodium hydroxide solution, which was extracted with diethyl ether. The diethyl ether layer was washed with water and then with saturated aqueous sodium chloride solution, dried ($MgSO_4$), and then concentrated. The crystals obtained were filtrated to obtain [1-[4-(5-methyl-2-phenyl-4-oxazolylmethoxy)benzyl]-1H-pyrazol-4-yl]methanol (2.93 g, yield: 92%). This was recrystallized from ethyl acetate-hexane. Melting point: 100–101° C.

Reference Example 59

A mixture of [1-[4-(5-methyl-2-phenyl-4-oxazolylmethoxy)benzyl]-1H-pyrazol-4-yl]methanol (2.82 g), activated manganese dioxide (6.00 g), and tetrahydrofuran (50 ml) was stirred at room temperature for 2 hours. After the manganese dioxide was removed by filtration, the filtrate was concentrated. The residue was subjected to silica gel column chromatography, and 1-[4-(5-methyl-2-phenyl-4-oxazolylmethoxy)benzyl]-1H-pyrazole-4-carbaldehyde (2.63 g, yield: 94%) was obtained as a colorless oily substance from the fraction eluted with ethyl acetate-hexane (1:1, volume ratio).
NMR(CDCl$_3$) δ: 2.44(3H, s), 5.00(2H, s), 5.27(2H, s), 7.03(2H, d, J=8.8 Hz), 7.24(2H, d, J=8.8 Hz), 7.40–7.48(3H, m), 7.84(1H, s), 7.97–8.04(3H, m), 9.82(1H, s).

Reference Example 60

Sodium hydride (60%, oily, 880 mg) was added to a mixture of 3,5-dimethylpyrazole (2.11 g) and tetrahydrofuran (50 ml) at 0° C., and the mixture was stirred at room temperature for 30 minutes. After 4-(4-chloromethylphenoxymethyl)-5-methyl-2-phenyloxazole (6.28 g) was added to the reaction mixture, the mixture was refluxed for 24 hours. The reaction mixture was poured into water, which was extracted with ethyl acetate. The ethyl acetate layer was washed with saturated aqueous sodium chloride solution, dried (MgSO$_4$), and then concentrated. The residue was subjected to silica gel column chromatography, and 3,5-dimethyl-1-[4-(5-methyl-2-phenyl-4-oxazolylmethoxy)benzyl]-1H-pyrazole (5.49 g, yield: 74%) was obtained as colorless crystals from the fraction eluted with ethyl acetate-hexane (1:1, volume ratio). This was recrystallized from ethyl acetate-hexane. Melting point: 86–87° C.

Reference Example 61

A mixture of ethyl 3-hydroxy-1H-pyrazole-4-carboxylate (11.53 g), benzyl bromide (18 ml), potassium carbonate (21.12 g), and N,N-dimethylformamide (300 ml) was stirred for 5 hours at 80° C. The reaction mixture was poured into water, which was extracted with ethyl acetate. The ethyl acetate layer was washed with diluted hydrochloric acid and then with saturated aqueous sodium chloride solution, dried (MgSO$_4$), and then concentrated. The residue was subjected to silica gel column chromatography, and ethyl 1-benzyl-3-benzyloxy-1H-pyrazole-4-carboxylate (13.52 g, yield: 95%) was obtained as colorless crystals from the fraction eluted with ethyl acetate-hexane (1:4, volume ratio). This was recrystallized from ethyl acetate-hexane. Melting point: 71–72° C.

Reference Example 62

Lithium aluminium hydride (6.64 g) was added to a solution of ethyl 1-benzyl-3-benzyloxy-1H-pyrazole-4-carboxylate (58.90 g) in tetrahydrofuran (500 ml) at 0° C., and the mixture was stirred at room temperature for 30 minutes. After the reaction mixture was poured into water and the precipitate was removed by filtration, the filtrate was extracted with ethyl acetate. The ethyl acetate layer was washed with saturated aqueous sodium chloride solution, dried (MgSO$_4$), and then concentrated. The residue was subjected to silica gel column chromatography, and (1-benzyl-3-benzyloxy-1H-pyrazol-4-yl)methanol (45.30 g, yield: 88%) was obtained as colorless crystals from the fraction eluted with ethyl acetate. This was recrystallized from ethyl acetate-hexane. Melting point: 79–80° C.

Reference Example 63

A mixture of (1-benzyl-3-benzyloxy-1H-pyrazol-4-yl)methanol (14.70 g), activated manganese dioxide (30.00 g), and tetrahydrofuran (200 ml) was stirred at room temperature for 2 hours. After the manganese dioxide was removed by filtration, the filtrate was concentrated. The crystals obtained were collected by filtration to yield 1-benzyl-3-benzyloxy-1H-pyrazole-4-carbaldehyde (13.10 g, yield: 90%). This was recrystallized from tetrahydrofuran-hexane. Melting point: 85–86° C.

Reference Example 64

Sodium hydride (60%, oily, 1.94 g) was added to a mixture of 1-benzyl-3-benzyloxy-1H-pyrazole-4-carbaldehyde (12.90 g), ethyl diethylphosphonoacetate (9.60 ml), and N,N-dimethylformamide (200 ml) at 0° C., and the mixture was stirred at room temperature for 2 hours. The reaction mixture was poured into water, which was extracted with ethyl acetate. The ethyl acetate layer was washed with diluted hydrochloric acid and then with saturated aqueous sodium chloride solution, dried (MgSO$_4$), and then concentrated. The crystals obtained were collected by filtration to yield ethyl(E)-3-(1-benzyl-3-benzyloxy-1H-pyrazol-4-yl)propenoate (14.50 g, yield: 91%). This was recrystallized from ethyl acetate-hexane. Melting point: 88–89° C.

Reference Example 65

A mixture of ethyl(E)-3-(1-benzyl-3-benzyloxy-1H-pyrazol-4-yl)propenoate (14.30 g), 5% palladium-carbon (28.00 g), ethanol (150 ml), and tetrahydrofuran (150 ml) was stirred at room temperature for 3 hours under a hydrogen atmosphere. After the palladium-carbon was removed by filtration, the filtrate was concentrated. The crystals obtained were collected by filtration to yield ethyl 3-(1-benzyl-3-hydroxy-1H-pyrazol-4-yl)propionate (9.01 g, yield: 83%). This was recrystallized from ethyl acetate-hexane. Melting point: 75–76° C.

Reference Example 66

Sodium hydride (60%, oily, 1.28 g) was added to a solution of ethyl 3-(1-benzyl-3-hydroxy-1H-pyrazol-4-yl)propionate (8.78 g) in N,N-dimethylformamide (100 ml) at 0° C., and the mixture was stirred for 30 minutes. Iodoethane (2.82 ml) was added to the reaction mixture, and the mixture was stirred at room temperature for one hour. The reaction mixture was poured into water, which was extracted with ethyl acetate. The ethyl acetate layer was washed with 1N hydrochloric acid and then with saturated aqueous sodium chloride solution, dried (MgSO$_4$), and concentrated. The residue was subjected to silica gel column chromatography, and ethyl 3-(1-benzyl-3-ethoxy-1H-pyrazol-4-yl)propionate (8.80 g, yield: 91%) was obtained as a colorless oily substance from the fraction eluted with ethyl acetate-hexane (1:5, volume ratio).

NMR(CDCl$_3$) δ: 1.21 (3H, t, J=7.2 Hz), 1.37 (3H, t, J=7.0 Hz), 2.48–2.55 (2H, m), 2.62–2.70 (2H, m), 4.09 (2H, q, J=7.2 Hz), 4.22 (2H, q, J=7.0 Hz), 5.07 (2H, s), 6.96 (1H, s), 7.13–7.18 (2H, m), 7.26–7.37 (3H, m).

Reference Example 67

A mixture of ethyl 3-(1-benzyl-3-ethoxy-1H-pyrazol-4-yl)propionate (21.20 g), 5% palladium-carbon (40.00 g), ethanol (200 ml), and formic acid (100 ml) was refluxed for one hour. After the palladium-carbon was removed by filtration, the filtrate was concentrated. The residue was dissolved in ethyl acetate, which was washed with saturated aqueous sodium bicarbonate and then with saturated aqueous sodium chloride solution, dried (MgSO$_4$), and then concentrated. The residue was subjected to silica gel column chromatography, and ethyl 3-(3-ethoxy-1H-pyrazol-4-yl)propionate (10.70 g, yield: 72%) was obtained as a colorless oily substance from the fraction eluted with ethyl acetate-hexane (1:1, volume ratio).

NMR(CDCl$_3$) δ: 1.24 (3H, t, J=7.2 Hz), 1.39 (3H, t, J=7.0 Hz), 2.51–2.59 (2H, m), 2.66–2.74 (2H, m), 4.12 (2H, q, J=7.2 Hz), 4.24 (2H, q, J=7.0 Hz), 7.18 (1H, s), 9.15 (1H, s).

Reference Example 68

A mixture of ethyl 3-[1-(4-benzyloxybenzyl)-3-ethoxy-1H-pyrazol-4-yl]propionate (5.32 g), 5% palladium-carbon (3.45 g), and tetrahydrofuran (100 ml) was stirred for 3 hours at room temperature under a hydrogen atmosphere. After the palladium-carbon was removed by filtration, the filtrate was concentrated. The residue was subjected to silica gel column chromatography, and ethyl 3-[3-ethoxy-1-(4-hydroxybenzyl)-1H-pyrazol-4-yl]propionate (3.56 g, yield: 86%) was obtained as a colorless oily substance from the fraction eluted with ethyl acetate-hexane (1:1, volume ratio).

NMR(CDCl$_3$) δ: 1.22 (3H, t, J=7.4 Hz), 1.35 (3H, t, J=7.4 Hz), 2.44–2.72 (4H, m), 4.03–4.29 (4H, m), 4.96 (2H, s), 6.58–6.68 (2H, m), 6.90–7.03 (3H, m).

Reference Example 69

Lithium aluminium hydride (1.52 g) was added to a solution of ethyl 1-(4-benzyloxybenzyl)-3-(4-benzyloxybenzyloxy)-1H-pyrazole-4-carboxylate (11.00 g) in tetrahydrofuran (200 ml) at 0° C., and the mixture was stirred at room temperature for one hour. After water was added to the reaction mixture, the precipitate was removed by filtration and the filtrate was extracted with ethyl acetate. The ethyl acetate layer was washed with saturated aqueous sodium chloride solution, dried (MgSO$_4$), and then concentrated. The crystals obtained were collected by filtration to yield [1-(4-benzyloxybenzyl)-3-(4-benzyloxybenzyloxy)-1H-pyrazol-4-yl]methanol (7.11 g, yield: 70%). This was recrystallized from tetrahydrofuran-hexane. Melting point: 128–129° C.

Reference Example 70

A mixture of [1-(4-benzyloxybenzyl)-3-(4-benzyloxybenzyloxy)-1H-pyrazol-4-yl]methanol (6.84 g), activated manganese dioxide (14.00 g), and tetrahydrofuran (70 ml) was stirred at room temperature for one hour. After the manganese dioxide was removed by filtration, the filtrate was concentrated. The crystals obtained were collected by filtration to yield 1-(4-benzyloxybenzyl)-3-(4-benzyloxybenzyloxy)-1H-pyrazole-4-carbaldehyde (6.50 g, yield: 95%). This was recrystallized from tetrahydrofuran-hexane. Melting point: 138–139° C.

Reference Example 71

A mixture of ethyl(E)-3-[1-(4-benzyloxybenzyl)-3-(4-benzyloxybenzyloxy)-1H-pyrazol-4-yl]propenoate (6.61 g), 5% palladium-carbon (13.00 g), ethanol (150 ml), and tetrahydrofuran (150 ml) was stirred for one hour at room temperature under a hydrogen atmosphere. After the palladium-carbon was removed by filtration, the filtrate was concentrated. The crystals obtained were collected by filtration to yield ethyl 3-[1-(4-hydroxybenzyl)-3-hydroxy-1H-pyrazol-4-yl]propionate (2.98 g, yield: 89%). This was recrystallized from ethyl acetate-hexane. Melting point: 143–144° C.

Reference Example 72

Sodium hydride-(60%, oily, 2.40 g) was added to a solution of 5-methyl-2-phenyl-4-oxazolylmethanol (9.46 g) in N,N-dimethylformamide (50 ml) at 0° C., which was stirred for 15 minutes. A solution of methyl 2-chloro-4-pyridinecarboxylate (8.58 g) in tetrahydrofuran (50 ml) was added to the mixture. After being stirred at room temperature for 1 hour, the reaction mixture was poured into water, which was extracted with ethyl acetate. The ethyl acetate layer was washed with saturated aqueous sodium chloride solution, dried (MgSO$_4$), and concentrated. The residue was subjected to silica gel column chromatography to obtain methyl 2-(5-methyl-2-phenyl-4-oxazolylmethoxy)-4-pyridinecarboxylate (2190 mg, yield 14%) as colorless crystals from the fraction eluted with ethyl acetate-hexane (1:3, volume ratio). This was recrystallized from ethyl acetate-hexane. Melting point: 106–107° C.

Reference Example 73

Lithium aluminium hydride (228 mg) was added to a solution of methyl 2-(5-methyl-2-phenyl-4-oxazolylmethoxy)-4-pyridinecarboxylate (1.95 g) in tetrahydrofuran (20 ml) at 0° C., which was stirred at room temperature for 30 minutes. Sodium sulfate decahydrate (1.93 g) was added to the reaction mixture, which was stirred at room temperature for 30 minutes. The precipitates were removed by filtration, the filtrate was concentrated. The resulting colorless crystals were collected by filtration to obtain 2-(5-methyl-2-phenyl-4-oxazolylmethoxy)-4-pyridylmethanol (1.37 g, yield 77%). This was recrystallized from ethyl acetate-hexane. Melting point: 100–101° C.

Reference Example 74

A mixture of 2-(5-methyl-2-phenyl-4-oxazolylmethoxy)-4-pyridylmethanol (1.19 g) and thionyl chloride (4 ml) was stirred at room temperature for 1 hour. After the reaction mixture was concentrated, saturated aqueous sodium bicarbonate solution was added to the mixture, which was extracted with ethyl acetate. The ethyl acetate layer was washed with saturated aqueous sodium chloride solution, dried (MgSO$_4$), and concentrated. The residue was subjected to silica gel column chromatography to obtain 4-chloromethyl-2-(5-methyl-2-phenyl-4-oxazolylmethoxy)pyridine (680 mg, yield 54%) as colorless crystals from the fraction eluted with ethyl acetate-hexane (1:3, volume ratio). This was recrystallized from ethyl acetate-hexane. Melting point: 104–105° C.

Reference Example 75

A mixture of methyl 5-hydroxy-3-pyridinecarboxylate (9.84 g), 4-chloromethyl-5-methyl-2-phenyloxazole (13.40 g), potassium carbonate (8.90 g) and N,N-dimethylformamide (100 ml) was stirred at 80° C. overnight. The reaction mixture was poured into water, which was extracted with ethyl acetate. The ethyl acetate layer was washed with saturated aqueous sodium chloride solution, dried ($MgSO_4$), and concentrated. The residue was subjected to silica gel column chromatography to obtain methyl 5-(5-methyl-2-phenyl-4-oxazolylmethoxy)-3-pyridinecarboxylate (12.42 g, yield 59%) as pale yellow crystals from the fraction eluted with ethyl acetate-hexane (1:2, volume ratio). This was recrystallized from ethyl acetate-hexane. Melting point: 119–120° C.

Reference Example 76

Lithium aluminium hydride (1.02 g) was added to a solution of methyl 5-(5-methyl-2-phenyl-4-oxazolylmethoxy)-3-pyridinecarboxylate (10.70 g) in tetrahydrofuran (100 ml) at 0° C., which was stirred at room temperature for 30 minutes. Sodium sulfate decahydrate (8.93 g) was added to the reaction mixture, which was stirred at room temperature for 30 minutes. The precipitate was removed by filtration, and the filtrate was concentrated. The resulting colorless crystals were collected by filtration to obtain 5-(5-methyl-2-phenyl-4-oxazolylmethoxy)-3-pyridylmethanol (8.93 g g, yield 91%). This was recrystallized from ethyl acetate-hexane. Melting point: 111–112° C.

Reference Example 77

A mixture of 5-(5-methyl-2-phenyl-4-oxazolylmethoxy)-3-pyridylmethanol (1.33 g) and thionyl chloride (4 ml) was stirred at room temperature for 1 hour. After the reaction mixture was concentrated, saturated aqueous sodium bicarbonate solution was added to the mixture, which was extracted with ethyl acetate. The ethyl acetate layer was washed with saturated aqueous sodium chloride solution, dried ($MgSO_4$), and concentrated. The residue was subjected to silica gel column chromatography to obtain 3-chloromethyl-5-(5-methyl-2-phenyl-4-oxazolylmethoxy)pyridine (911 mg, yield 64%) as colorless crystals from the fraction eluted with tetrahydrofuran-hexane (1:1, volume ratio). This was recrystallized from tetrahydrofuran-hexane. Melting point: 98–99° C.

Reference Example 78

Sodium borohydride (0.378 g) was added to a mixture of 4-methoxy-3-(5-methyl-2-phenyl-4-oxazolylmethoxy)benzaldehyde (3.23 g), tetrahydrofuran (15 ml) and methanol (15 ml) at room temperature, which was stirred at room temperature for 30 minutes. The reaction mixture was poured into water, which was extracted with ethyl acetate. The organic layer was washed with saturated aqueous sodium chloride solution, dried with anhydrous magnesium sulfate and concentrated to obtain crystals of 4-methoxy-3-(5-methyl-2-phenyl-4-oxazolylmethoxy)benzyl alcohol. This was recrystallized from tetrahydrofuran-hexane to obtain pale yellow plates (3.22 g, 99%). Melting point: 144–145° C.

Reference Example 79

A mixture of 4-methoxy-3-(5-methyl-2-phenyl-4-oxazolylmethoxy)benzyl alcohol (3.22 g), thionyl chloride (0.73 ml) and toluene (50 ml) was refluxed for 1 hour. After the reaction mixture was concentrated, saturated aqueous sodium bicarbonate solution was added to the mixture, which was extracted with ethyl acetate. The ethyl acetate layer was washed with saturated aqueous sodium chloride solution, dried ($MgSO_4$), and concentrated. The residue was subjected to silica gel column chromatography to obtain 4-(5-chloromethyl-2-methoxyphenoxymethyl)-5-methyl-2-phenyloxazole (2.59 g, yield 75%) as colorless crystals. This was recrystallized from ethyl acetate-hexane. Melting point: 129–130° C.

Reference Example 80

Sodium borohydride (378 mg) was added slowly to a mixture of 3-ethoxy-4-(5-methyl-2-phenyl-4-oxazolylmethoxy)benzaldehyde (3.37 g), tetrahydrofuran (50 ml) and methanol (50 ml) at room temperature, which was stirred for 30 minutes. The reaction mixture was poured into water, which was extracted with ethyl acetate. The ethyl acetate layer was washed with saturated aqueous sodium chloride solution, dried ($MgSO_4$) and concentrated to obtain 3-ethoxy-4-(5-methyl-2-phenyl-4-oxazolylmethoxy)benzyl alcohol (3.28 g, yield 97%) as colorless crystals. This was recrystallized from tetrahydrofuran-hexane. Melting point: 130–131° C.

Reference Example 81

Thionyl chloride (0.73 ml) was added slowly to a mixture of 3-ethoxy-4-(5-methyl-2-phenyl-4-oxazolylmethoxy)benzyl alcohol (3.05 g), tetrahydrofuran (25 ml) and toluene (50 ml) at room temperature, which was stirred at 80° C. for 30 minutes. After cooling, the reaction mixture was poured into an aqueous saturated sodium bicarbonate solution, which was extracted with ethyl acetate. The ethyl acetate layer was washed with saturated sodium bicarbonate solution, dried ($MgSO_4$) and concentrated to obtain 4-(4-chloromethyl-2-ethoxyphenoxymethyl)-5-methyl-2-phenyloxazole (2.94 g, yield 91%) as colorless crystals. This was recrystallized from tetrahydrofuran-hexane. Melting point: 138–139° C.

Reference Example 82

Sodium hydride (60%, oily, 1.40 g) was added to a solution of methyl 3-hydroxyisoxazole-5-carboxylate (5.01 g) in N,N-dimethylformamide (70 ml) at 0° C., which was stirred for 15 minutes. 4-Chloromethyl-5-methyl-2-phenyloxazole (7.26 g) was added to the mixture. After being stirred at 60° C. for 2 hours, the reaction mixture was poured into water, which was extracted with ethyl acetate. The ethyl acetate layer was washed with saturated aqueous sodium chloride solution, dried ($MgSO_4$), and concentrated. The residue was subjected to silica gel column chromatography to obtain methyl 3-(5-methyl-2-phenyl-4-oxazolylmethoxy)-5-isoxazolecarboxylate (7.96 g, yield 72%) as colorless crystals. This was recrystallized from tetrahydrofuran-hexane. Melting point: 123–124° C.

Reference Example 83

Diisobutylaluminium hydride (1.0M tetrahydrofuran solution, 60 ml) was added slowly to a solution of methyl 3-(5-methyl-2-phenyl-4-oxazolylmethoxy)-5-isooxazole-carboxylate (7.86 g) in tetrahydrofuran (150 ml) at 0° C., which was stirred at room temperature for 30 minutes. The reaction mixture was poured into dilute hydrochloric acid, which was extracted with ethyl acetate. The ethyl acetate layer was washed with a saturated aqueous sodium chloride solution, dried (MgSO$_4$), and concentrated to obtain 3-(5-methyl-2-phenyl-4-oxazolylmethoxy)-5-isoxazolylmethanol (5.93 g, yield 86%) as colorless crystals. This was recrystallized from ethyl acetate-hexane. Melting point: 99–100° C.

Reference Example 84

Thionyl chloride (0.80 ml) was added slowly to a solution of 3-(5-methyl-2-phenyl-4-oxazolylmethoxy)-5-isoxazolylmethanol (2.86 g) in toluene (50 ml) at room temperature, which was stirred for 30 minutes under reflux. After cooling, the reaction mixture was poured into saturated aqueous sodium bicarbonate solution, which was extracted with ethyl acetate. The ethyl acetate layer was washed with saturated aqueous sodium chloride solution, dried (MgSO$_4$), and concentrated to obtain 5-chloromethyl-3-(5-methyl-2-phenyl-4-oxazolylmethoxy)isoxazole (2.70 g, yield 89%) as colorless crystals. This was recrystallized from ethyl acetate-hexane. Melting point: 105–106° C.

Reference Example 85

Sodium borohydride (620 mg) was added to a mixture of 4-[2-[1-oxo-2(1H)-phthaladinyl]ethoxy]benzaldehyde (4.90 g), methanol (20 ml) and tetrahydrofuran (20 ml) at 0° C., which was stirred at room temperature for 30 minutes. Dilute hydrochloric acid was added to the reaction mixture, and the resulting colorless crystals were collected by filtration to obtain 4-[2-[1-oxo-2(1H)-phthaladinyl]ethoxy]benzyl alcohol (4.53 g, yield 92%). This was recrystallized from acetone-hexane. Melting point: 142–143° C.

Reference Example 86

Sodium borohydride (600 mg) was added to a mixture of 3-[2-[1-oxo-2(1H)-phthaladinyl]ethoxy]benzaldehyde (5.00 g), methanol (30 ml) and tetrahydrofuran (30 ml) at 0° C., which was stirred at room temperature for 30 minutes. Dilute hydrochloric acid was added to the reaction mixture, and the resulting colorless crystals were collected by filtration to obtain 3-[2-[1-oxo-2(1H)-phthaladinyl]ethoxy]benzyl alcohol (4.80 g, yield 95%). This was recrystallized from ethyl acetate-hexane. Melting point: 133–134° C.

Reference Example 87

Thionyl chloride (1 ml) was added slowly to a solution of 4-[2-[1-oxo-2(1H)-phthaladinyl]ethoxy]benzyl alcohol (3.80 g) in toluene (40 ml) at room temperature, which was stirred at 90° C. for 30 minutes. After cooling, the reaction mixture was poured into saturated aqueous sodium bicarbonate solution, which was extracted with ethyl acetate. The ethyl acetate layer was washed with saturated aqueous sodium chloride solution, dried (MgSO$_4$), and concentrated to obtain 2-[2-(4-chloromethylphenoxy)ethyl]-1(2H)-phthaladinone (3.62 g, yield 95%) as a colorless oily substance.

NMR(CDCl$_3$) δ: 4.37–4.47(2H, m), 4.54(2H, s), 4.60–4.70(2H, m), 6.86–6.96(2H, m), 7.24–7.34(2H, m), 7.66–7.86(3H, m), 8.19(1H, s), 8.40–8.48(1H, m)

Reference Example 88

Thionyl chloride (1.3 ml) was added slowly to a solution of 3-[2-[1-oxo-2(1H)-phthaladinyl]ethoxy]benzyl alcohol (4.59 g) in toluene (30 ml) at room temperature, which was stirred at 90° C. for 30 minutes. After cooling, the reaction mixture was poured into saturated aqueous sodium bicarbonate solution, which was extracted with ethyl acetate. The ethyl acetate layer was washed with saturated aqueous sodium chloride solution, dried (MgSO$_4$), and concentrated to obtain 2-[2-(3-chloromethylphenoxy)ethyl]-[(2H)-phthaladinone (4.39 g, yield 95%) as a colorless oily substance.

NMR(CDCl$_3$) δ: 4.40–4.48(2H, m), 4.51(2H, s), 4.62–4.70(2H, m), 6.84–7.00(3H, m), 7.18–7.26(1H, m), 7.64–7.88(3H, m), 8.19(1H, s), 8.40–8.50(1H, m).

Reference Example 89

Sodium hydride (60%, oily, 1.80 g) was added to a solution of 5-methyl-2-phenyl-4-oxazolylmethanol (8.51 g) in tetrahydrofuran (100 ml) at 0° C., which was stirred at room temperature for 15 minutes. A solution of methyl 6-chloro-2-pyridinecarboxylate (7.72 g) in tetrahydrofuran (75 ml) was added to the mixture. After being stirred at 40° C. for 5 hours, the reaction mixture was poured into water, which was extracted with ethyl acetate. The ethyl acetate layer was washed with saturated aqueous sodium chloride solution, dried (MgSO$_4$), and concentrated to obtain methyl 6-(5-methyl-2-phenyl-4-oxazolylmethoxy)-2-pyridinecarboxylate (7.41 g, yield 51%) as yellow crystals. This was recrystallized from ethyl acetate-hexane. Melting point: 97–98° C.

Reference Example 90

Lithium aluminium hydride (759 mg) was added to a solution of methyl 6-(5-methyl-2-phenyl-4-oxazolylmethoxy)-2-pyridinecarboxylate (6.49 g) in tetrahydrofuran (60 ml) at 0° C., which was stirred at room temperature for 30 minutes. Sodium sulfate decahydrate (6.44 g) was added to the reaction mixture, which was stirred at room temperature for 30 minutes. The precipitate was removed by filtration, and the filtrate was concentrated. A mixture of the residue and thionyl chloride (20 ml) was stirred at room temperature for 1 hour. The reaction mixture was concentrated, saturated aqueous sodium bicarbonate solution was added, which was extracted with ethyl acetate. The ethyl acetate layer was washed with saturated aqueous sodium chloride solution, dried (MgSO$_4$), and concentrated. The residue was subjected to silica gel column chromatography to obtain 2-chloromethyl-6-(5-mehyl-2-phenyl-4-oxazolylmethoxy)pyridine (2.74 g, yield 44%) as colorless crystals. This was recrystallized from ethyl acetate-hexane. Melting point: 85–86° C.

Reference Example 91

Lithium aluminium hydride (2.43 g) was added to a solution of methyl 6-phenyl-3-pyridinecarboxylate (14.00 g) in tetrahydrofuran (200 ml) at 0° C., which was stirred at room temperature for 30 minutes. Sodium sulfate decahydrate (22.50 g) was added to the reaction mixture, which was stirred at room temperature for 30 minutes. The precipitate was removed by filtration, and the filtrate was concentrated to obtain 6-phenyl-3-pyridylmethanol (11.63 g, yield 96%) as a pale yellow oily substance.

NMR(CDCl$_3$) δ: 1.91(1H, br.s), 4.78(2H, d, J=5.6 Hz), 7.34–7.54(3H, m), 7.70–7.84(2H, m), 7.93–8.04(2H, m), 8.64–8.71(1H, m).

Reference Example 92

Thionyl chloride (10 ml) was slowly added to a solution of 6-phenyl-3-pyridylmethanol (11.60 g) in toluene (100 ml) at room temperature, which was stirred at 100° C. for 1 hour. After cooling, the reaction mixture was poured into saturated aqueous sodium bicarbonate solution, which was extracted with ethyl acetate. The ethyl acetate layer was washed with saturated aqueous sodium chloride solution, dried (MgSO$_4$) and concentrated to obtain 5-chloromethyl-2-phenylpyridine (11.49 g, yield 89%) as colorless crystals. This was recrystallized from ethyl acetate-hexane. Melting point: 95–96° C.

Reference Example 93

Sodium hydride (60%, oily, 2.88 g) was added to a mixture of 2-(2-furyl)-5-methyl-4-oxazolylmethanol (10.80 g), methyl 2-chloro-4-pyridinecarboxylate (10.30 g), tetrahydrofuran (100 ml) and N,N-dimethylformamide (100 ml) at 0° C., and the mixture was stirred at room temperature for 2 hours. The reaction mixture was poured into water, which was extracted with ethyl acetate. The ethyl acetate layer was washed with saturated aqueous sodium chloride solution, dried (MgSO$_4$), and concentrated. The residue was subjected to silica gel column chromatography to obtain ethyl 2-[2-(2-furyl)-5-methyl-4-oxazolylmethoxy]-4-pyridinecarboxylate (2.86 g, yield 15%) as colorless crystals. This was recrystallized from ethyl acetate-hexane. Melting point: 80–81° C.

Reference Example 94

Lithium aluminium hydride (304 mg) was added to a solution of ethyl 2-[2-(2-furyl)-5-methyl-4-oxazolylmethoxy]-4-pyridinecarboxylate (2.63 g) in tetrahydrofuran (30 ml) at 0° C., and the mixture was stirred at room temperature for 30 minutes. Sodium sulfate decahydrate (2.58 g) was added to the reaction mixture, which was stirred at room temperature for 30 minutes. The precipitate was removed by filtration, and the filtrate was concentrated. A mixture of the residue, thionyl chloride (10 ml) and toluene (5 ml) was stirred at room temperature for 1 hour. After the reaction mixture was concentrated, saturated aqueous sodium bicarbonate solution was added to the residue, which was extracted with ethyl acetate. The ethyl acetate layer was washed with saturated aqueous sodium chloride solution, dried (MgSO$_4$), and concentrated. The residue was subjected to silica gel column chromatography to obtain 4-chloromethyl-2-[2-(2-furyl)-5-methyl-4-oxazolylmethoxy]pyridine (1020 mg, yield 42%) as colorless crystals from the fraction eluted with ethyl acetate-hexane (1:3, volume ratio). This was recrystallized from ethyl acetate-hexane. Melting point: 107–108° C.

Reference Example 95

Sodium hydride (60%, oily, 2.00 g) was added to a mixture of 5-chloroimidazo[1,2-a]pyridin-2-ylmethanol (8.77 g), methyl 2-chloro-4-pyridinecarboxylate (8.24 g) and N,N-dimethylformamide (150 ml) at 0° C., and the mixture was stirred at room temperature for 3 hours. The reaction mixture was poured into water, which was extracted with ethyl acetate. The ethyl acetate layer was washed with a saturated aqueous sodium chloride solution, dried (MgSO4), and concentrated. The residue was subjected to silica gel column chromatography to obtain methyl 2-(5-chloroimidazo[1,2-a]pyridin-2-ylmethoxy)-4-pydinecarboxylate (2.78 g, yield 18%) as colorless crystals from the fraction eluted with tetrahydrofuran. This was recrystallized from tetrahydrofuran-hexane. Melting point: 157–158° C.

Reference Example 96

Diisobutylaluminium hydride (1.0M tetrahydrofuran solution, 30 ml) was added to a solution of methyl 2-(5-chloroimidazo[1,2-a]pyridin-2-ylmethoxy)-4-pyridinecarboxylate (3.97 g) in tetrahydrofuran (150 ml) at 0° C., which was stirred at room temperature for 30 minutes. Sodium sulfate decahydrate (12.2 g) was added to the reaction mixture, which was stirred at room temperature for 1 hour. The precipitate was removed by filtration, and the filtrate was concentrated. The resulting colorless crystals were collected by filtration to obtain 2-(5-chloroimidazo[1,2-a]pyridin-2-ylmethoxy)-4-pyridylmethanol (3.12 g, yield 86%). This was recrystallized from tetrahydrofuran-hexane. Melting point: 143–144° C.

Reference Example 97

A mixture of 2-(5-chloroimidazo[1,2-a]pyridin-2-ylmethoxy)-4-pyridylmethanol (2.90 g) and thionyl chloride (10 ml) was stirred at room temperature for 1 hour. After the reaction mixture was concentrated, saturated aqueous sodium bicarbonate solution was added to the residue, which was extracted with ethyl acetate. The ethyl acetate layer was washed with saturated aqueous sodium chloride solution, dried (MgSO$_4$), and concentrated. The residue was subjected to silica gel column chromatography to obtain 5-chloro-2-(4-chloromethyl-2-pyridyloxymethyl)imidazo[1,2-a]pyridine (2.63 g, yield 85%) as colorless crystals from the fraction eluted with tetrahydrofuran. This was recrystallized from tetrahydrofuran-hexane. Melting point: 118–119° C.

Reference Example 98

Sodium hydride (60%, oily, 2.88 g) was added to a solution of methyl 5-hydroxy-3-pyridinecarboxylate (10.00 g) and N-phenyltrifluoromethanesulfonimide (24.00 g) in tetrahydrofuran (200 ml) at 0° C., and the mixture was stirred at room temperature for 1 hour. The reaction mixture was poured into water, which was extracted with ethyl acetate. The ethyl acetate layer was washed with saturated aqueous sodium bicarbonate solution, then with saturated aqueous sodium chloride solution, dried (MgSO$_4$), and concentrated. The residue was subjected to silica gel column chromatography to obtain methyl 5-trifluoromethanesulfonyloxy-3-pyridinecarboxylate (18.06 g, yield 97%) as a colorless oily substance from the fraction eluted with ethyl acetate-hexane (1:4, volume ratio).

NMR(CDCl$_3$) δ: 4.01(3H, s), 8.23(1H, dd, J=1.4, 2.6 Hz), 8.77(1H, d, J=2.6 Hz), 9.26(1H, d, J=1.4 Hz).

Reference Example 99

A mixture of methyl 5-trifluoromethanesulfonyloxy-3-pyridinecarboxylate (18.00 g), phenylboronic acid (7.88 g), tetrakis(triphenylphosphine)palladium (3.01 g), sodium carbonate (13.51 g), ethanol (80 ml), water (80 ml) and toluene (500 ml) was refluxed overnight under an argon atmosphere. The reaction mixture was poured into water, which was extracted with ethyl acetate. The ethyl acetate layer was washed with saturated aqueous sodium chloride solution, dried (MgSO$_4$), and concentrated. The residue was subjected to silica gel column chromatography to obtain ethyl 5-phenyl-3-pyridinecarboxylate (8.63 g, yield 60%) as a colorless oily substance from the fraction eluted with ethyl acetate.

NMR(CDCl$_3$) δ: 1.44(3H, t, J=6.8 Hz), 4.46(2H, q, J=6.8 Hz), 7.42–7.70(5H, m), 8.44–8.56(1H, m), 9.00(1H, d, J=2.2 Hz), 9.20(1H, d, J=1.8 Hz).

Reference Example 100

Lithium aluminium hydride (1.45 g) was added to a solution of ethyl 5-phenyl-3-pyridinecarboxylate (8.60 g) in tetrahydrofuran (100 ml) at 0° C., which was stirred at room temperature for 30 minutes. Sodium sulfate decahydrate (13.40 g) was added to the reaction mixture, which was stirred at room temperature for 30 minutes. The precipitate was removed by filtration, and the filtrate was concentrated. The resulting colorless crystals were collected by filtration to obtain 5-phenyl-3-pyridylmethanol (4.82 g, yield 69%). This was recrystallized from ethyl acetate-hexane. Melting point: 71–72° C.

Reference Example 101

A mixture of 5-phenyl-3-pyridylmethanol (4.50 g) and thionyl chloride (5 ml) was stirred at room temperature for 1 hour. After the reaction mixture was concentrated, saturated aqueous sodium bicarbonate solution was added to the mixture, which was extracted with ethyl acetate. The ethyl acetate layer was washed with saturated aqueous sodium chloride solution, dried (MgSO$_4$), and concentrated. The residue was subjected to silica gel column chromatography to obtain 3-chloromethyl-5-phenylpyridine (4.28 g, yield 86%) as colorless crystals from the fraction eluted with tetrahydrofuran. This was recrystallized from ethyl acetate-hexane. Melting point: 75–76° C.

Reference Example 102

A mixture of methyl 3-hydroxyisoxazole-5-carboxylate (5.01 g), 2-chloromethylquinoline hydrochloride (8.99 g), potassium carbonate (14.50 g) and N,N-dimethylformamide (100 ml) was stirred at 60° C. for 2 hours. The reaction mixture was poured into water, which was extracted with ethyl acetate. The ethyl acetate layer was washed with saturated aqueous sodium chloride solution, dried (MgSO$_4$), and concentrated. The residue was subjected to silica gel column chromatography to obtain methyl 3-(2-quinolylmethoxy)-5-isoxazolecarboxylate (7.78 g, yield 78%) as colorless crystals. This was recrystallized from tetrahydrofuran-hexane. Melting point: 133–134° C.

Reference Example 103

Diisobutylaluminium hydride (1.0M tetrahydrofuran solution, 60 ml) was added slowly to a solution of methyl 3-(2-quinolylmethoxy)-5-isoxazolecarboxylate (7.39 g) in tetrahydrofuran (150 ml) at 0° C., which was stirred at room temperature for 30 minutes. The reaction mixture was poured into dilute hydrochloric acid, which was extracted with ethyl acetate. The ethyl acetate layer was washed with saturated aqueous sodium chloride solution, dried (MgSO$_4$), and concentrated to obtain 3-(2-quinolylmethoxy)-5-isoxazolylmethanol (4.95 g, yield 74%) as colorless crystals. This was recrystallized from tetrahydrofuran-hexane. Melting point: 111–112° C.

Reference Example 104

A mixture of 3-(2-quinolylmethoxy)-5-isoxazolylmethanol (1.54 g) and thionyl chloride (5 ml) was stirred at room temperature for 1 hour. The reaction mixture was concentrated under reduced pressure, and saturated aqueous sodium bicarbonate solution was added to the residue, which was extracted with ethyl acetate. The ethyl acetate layer was washed with saturated aqueous sodium chloride solution, dried (MgSO$_4$), and concentrated to obtain 2-(5-chloromethyl-3-isoxazolyloxymethyl)quinoline (1.61 g, yield 98%) as colorless crystals. This was recrystallized from ethyl acetate-hexane. Melting point: 126–127° C.

Reference Example 105 tert-Butyl Lithium (1.7M pentane solution, 15 ml) was added slowly to a solution of 5-chloro-2-phenylpyridine (4.70 g) in tetrahydrofuran (50 ml) at −78° C. under a nitrogen atmosphere, which was stirred for 1 hour. N,N-Dimethylformamide (2.3 ml) was added to the mixture slowly, which was stirred for 1 hour while raising the temperature to room temperature. After addition of dilute hydrochloric acid the mixture was stirred at room temperature for 30 minutes. The reaction mixture was neutralized with saturated aqueous sodium bicarbonate solution, which was extracted with ethyl acetate. The ethyl acetate layer was washed with saturated aqueous sodium chloride solution, dried (MgSO$_4$), and concentrated. Sodium borohydride (946 mg) was added slowly to a mixture of the residue, tetrahydrofuran (50 ml) and methanol (50 ml) at room temperature, which was stirred for 1 hour. The reaction mixture was poured into water, which was extracted with ethyl acetate. The ethyl acetate layer was washed with saturated aqueous sodium chloride solution, dried (MgSO$_4$), and concentrated. The residue was subjected to silica gel column chromatography to obtain 3-chloro-6-phenyl-2-pyridylmethanol (2.35 g, yield 43%) as pale yellow crystals from the fraction eluted with ethyl acetate-hexane (1:6, volume ratio). This was recrystallized from ethyl acetate-hexane. Melting point: 69–70° C.

Reference Example 106

A mixture of 3-chloro-6-phenyl-2-pyridylmethanol (2.20 g), 5% palladium-carbon (1.10 g), triethylamine (1.4 ml), methanol (20 ml) and tetrahydrofuran (20 ml) was stirred at room temperature under a hydrogen atmosphere. After palladium-carbon was removed by filtration, the filtrate was concentrated. The residue was subjected to silica gel column chromatography to obtain 6-phenyl-2-pyridylmethanol (1.76 g, yield 95%) as a colorless oily substance from the fraction eluted with ethyl acetate-hexane (1:5, volume ratio).

NMR(CDCl$_3$) δ: 4.20(1H, t, J=3.8 Hz), 4.82(2H, d, J=3.8 Hz), 7.16(1H, dd, J=0.8, 7.6 Hz), 7.38–7.54(3H, m), 7.64 (1H, dd, J=0.8, 7.6 Hz), 7.76(1H, t, J=7.6 Hz), 7.99–8.05 (2H, m).

Reference Example 107

A mixture of 3-chloro-6-phenyl-2-pyridylmethanol (2.20 g) and thionyl chloride (15 ml) was stirred at room temperature for 1 hour. The reaction mixture was concentrated under reduced pressure, and aqueous saturated sodium bicarbonate solution was added to the residue, which was extracted with ethyl acetate. The ethyl acetate layer was washed with saturated aqueous sodium chloride solution, dried (MgSO$_4$), and concentrated to obtain 3-chloro-2-chloromethyl-5-phenylpyridine (2.25 g, yield 94%) as colorless crystals. This was recrystallized from ethyl acetate-hexane. Melting point: 74–75° C.

Reference Example 108

A mixture of 6-phenyl-2-pyridylmethanol (1.76 g) and thionyl chloride (10 ml) was stirred at room temperate for 1 hour. The reaction mixture was concentrated under reduced pressure, and aqueous saturated sodium bicarbonate solution was added to the residue, which was extracted with ethyl acetate. The ethyl acetate layer was washed with saturated aqueous sodium chloride solution, dried ($MgSO_4$), and concentrated. The residue was subjected to silica gel column chromatography to obtain 2-chloromethyl-5-phenylpyridine (1.91 g, yield 99%) as a colorless oily substance from the fraction eluted with ethyl acetate-hexane (1:5, volume ratio).
NMR($CDCl_3$) δ: 4.75(2H, s), 7.36–7.52(4H, m), 7.64(1H, dd, J=1.0, 7.6 Hz), 7.77(1H, t, J=7.6 Hz), 7.96–8.02(2H, m).

Reference Example 109

Sodium hydride (60%, oily, 1.40 g) was added to a solution of 2-phenyl-4-thiazolylmethanol (6.69 g) and methyl 6-chloro-3-pyridinecarboxylate (6.01 g) in N,N-dimethylformamide (100 ml) at 0° C., and the mixture was stirred for 30 minutes. The reaction mixture was poured into water, which was extracted with ethyl acetate. The ethyl acetate layer was washed with saturated aqueous sodium chloride solution, dried ($MgSO_4$), and concentrated. Lithium aluminium hydride (1.33 g) was added to a solution of the residue in tetrahydrofuran (150 ml) at 0° C., which was stirred at room temperature for 10 minutes. Sodium sulfate decahydrate (11.3 g) was added to the reaction mixture, which was stirred for 30 minutes at room temperature. The precipitate was removed by filtration, and the filtrate was concentrated. The residue was subjected to silica gel column chromatography to obtain 6-(2-phenyl-4-thiazolylmethoxy)-3-pyridylmethanol (5.81 g, yield 56%) as colorless crystals from the fraction eluted with tetrahydrofuran. This was recrystallized from tetrahydrofuran-hexane. Melting point: 134–135° C.

Reference Example 110

Sodium hydride (60%, oily, 1.58 g) was added to a solution of 2-quinolylmethanol (6.29 g) and methyl 6-chloro-3-pyridinecarboxylate (6.78 g) in N,N-dimethylformamide (100 ml) at 0° C., and the mixture was stirred for 1 hour. The reaction mixture was poured into water, which was extracted with ethyl acetate. The ethyl acetate layer was washed with saturated aqueous sodium chloride solution, dried ($MgSO_4$), and concentrated. Lithium aluminium hydride (1.50 g) was added to a solution of the residue in tetrahydrofuran (150 ml) at 0° C., which was stirred at room temperature for 10 minutes. Sodium sulfate decahydrate (12.7 g) was added to the reaction mixture, which was stirred at room temperature for 1 hour. The precipitate was removed by filtration, and the filtrate was concentrated. The residue was subjected to silica gel column chromatography to obtain 2-(2-quinolylmethoxy)-5-pyridylmethanol (5.31 g, yield 50%) as colorless crystals from the fraction eluted with ethyl acetate. This was recrystallized from ethyl acetate-hexane. Melting point: 124–125° C.

Reference Example 111

A mixture of 6-(2-quinolylmethoxy)-3-pyridylmethanol (2.66 g) and thionyl chloride (10 ml) was stirred at room temperature for 1 hour. The reaction mixture was concentrated under reduced pressure, and saturated aqueous sodium bicarbonate solution was added to the residue, which was extracted with ethyl acetate. The ethyl acetate layer was washed with saturated aqueous sodium chloride solution, dried ($MgSO_4$) and concentrated. The residue was subjected to silica gel column chromatography to obtain 2-(5-chloromethyl-2-pyridyloxymethyl)quinoline (2.50 g, yield 88%) as colorless crystals from the fraction eluted with ethyl acetate-hexane (1:1, volume ratio). This was recrystallized from ethyl acetate-hexane. Melting point: 118–119° C.

Reference Example 112

A mixture of 6-(2-phenyl-4-thiazolylmethoxy)-3-pyridylmethanol (2.98 g) and thionyl chloride (15 ml) was stirred at room temperature for 1 hour. The reaction mixture was concentrated under reduced pressure, and saturated aqueous sodium bicarbonate solution was added to the residue, which was extracted with ethyl acetate. The ethyl acetate layer was washed with saturated aqueous sodium chloride solution, dried ($MgSO_4$) and concentrated. The residue was subjected to silica gel column chromatography to obtain 5-chloromethyl-2-(2-phenyl-4-thiazolylmethoxy)pyridine (2.40 g, yield 76%) as colorless crystals from the fraction eluted with ethyl acetate. This was recrystallized from tetrahydrofuran-hexane. Melting point: 117–118° C.

Reference Example 113

A mixture of 3-methyl-1-(2-pyridyl)-1H-pyrazol-4-ylmethanol (3.00 g), thionyl chloride (2.5 ml) and toluene (50 ml) was stirred at 70° C. for 2 hours. The reaction mixture was concentrated under reduced pressure, and saturated aqueous sodium bicarbonate solution was added to the residue, which was extracted with ethyl acetate. The ethyl acetate layer was washed with saturated aqueous sodium chloride solution, dried ($MgSO_4$) and concentrated to obtain 4-chloromethyl-3-methyl-1-(2-pyridyl)-1H-pyrazole (3.10 g, yield 94%) as a colorless oily substance.
NMR($CDCl_3$) δ: 2.44(3H, s), 4.58(2H, s), 7.46–7.60(1H, m), 8.18–8.42(2H, m), 8.50–8.60(1H, m), 9.43(1H, s)

Reference Example 114

A mixture of 2-methyl-5-(5-methyl-2-phenyl-4-oxazolylmethoxy)pyridine (18.04 g), 3-chloroperbenzoic acid (18.85 g) and tetrahydrofuran (100 ml) was stirred at room temperature overnight, and concentrated. The residue was subjected to silica gel column chromatography to obtain a colorless oily substance from the fraction eluted with tetrahydrofuran. A solution of the obtained colorless oily substance in acetic anhydride (100 ml) was added slowly to acetic anhydride (200 ml) heated at 130° C., which was stirred for 2 hours, and concentrated. The residue was dissolved in ethyl acetate, which was washed with an aqueous saturated sodium bicarbonate solution, then with a saturated aqueous sodium chloride solution, dried ($MgSO_4$) and concentrated. The residue was subjected to silica gel column chromatography to obtain [5-(5-methyl-2-phenyl-4-oxazolylmethoxy)-2-pyridylmethyl]acetate (18.09 g, yield 83%) as a colorless oily substance from the fraction eluted with ethyl acetate-hexane (1:2, volume ratio).
NMR($CDCl_3$) δ: 2.13(3H, s), 2.45(3H, s), 5.05(2H, s), 5.16(2H, s), 7.26–7.50(5H, m), 7.94–8.05(2H, m), 8.38–8.43(1H, m).

Reference Example 115

A mixture of [5-(5-methyl-2-phenyl-4-oxazolylmethoxy)-2-pyridylmethyl]acetate (18.00 g), 1N aqueous sodium hydroxide solution (75 ml) and methanol (100 ml) was stirred at room temperature for 3 hours, and concentrated. The residue was dissolved in ethyl acetate, which was washed with water and saturated aqueous sodium chloride solution. The organic layer was dried ($MgSO_4$) and concentrated. The resulting colorless crystals were collected by filtration to obtain 5-(5-methyl-2-phenyl-4-oxazolylmethoxy)-2-pyridylmethanol (14.29 g, yield 91%). This was recrystallized from ethyl acetate-hexane. Melting point: 125–126° C.

Reference Example 116

Sodium borohydride (835 mg) was added gradually to a solution of 6-(5-methyl-2-phenyl-4-oxazolylmethoxy)nicotinaldehyde (13.0 g) in tetrahydrofuran (150 ml)-methanol (10 ml) at 0° C. After stirring for 30 minutes, water was added to the reaction mixture, which was extracted with ethyl acetate. The organic layer was washed with water, dried over anhydrous magnesium sulfate and concentrated to obtain crystals of 6-(5-methyl-2-phenyl-4-oxazolylmethoxy)-3-pyridylmethanol. This was recrystallized from acetone-isopropyl ether to obtain colorless prism crystals (12.4 g, yield 95%). Melting point: 121–122° C.

Reference Example 117

Thionyl chloride (5.39 g) was added to a mixture of 6-(5-methyl-2-phenyl-4-oxazolylmethoxy)-3-pyridylmethanol (12.2 g) and toluene (200 ml), which was stirred at room temperature for 1 hour. Ice water was added to the reaction mixture, which was neutralized with saturated aqueous sodium bicarbonate solution, and was extracted with ethyl acetate. The organic layer was washed with water, dried over anhydrous magnesium sulfate, and concentrated. The residue was subjected to silica gel column chromatography to obtain 5-chloromethyl-2-(5-methyl-2-phenyl-4-oxazolylmethoxy)pyridine (11.7 g, yield 90%) as colorless crystals from the fraction eluted with ethyl acetate-hexane (1:3, volume ratio). This was recrystallized from ethyl acetate-hexane to obtain colorless prism crystals. Melting point: 86–87° C.

Reference Example 118

Sodium borohydride (410 mg) was added to a mixture of 6-[2-(2-furyl)-5-methyl-4-oxazolylmethoxy]nicotinaldehyde (3.10 g), tetrahydrofuran (50 ml) and ethanol (50 mL) at room temperature, which was stirred at room temperature for 30 minutes. The reaction mixture was poured into water, which was extracted with ethyl acetate. The organic layer was washed with saturated aqueous sodium chloride solution, dried over anhydrous magnesium sulfate, and concentrated to obtain 6-[2-(2-furyl)-5-methyl-4-oxazolylmethoxy]-3-pyridylmethanol (2.86 g, yield 92%) as colorless crystals. This was recrystallized from ethyl acetate-hexane. Melting point: 120–121° C.

Reference Example 119

A mixture of 6-[2-(2-furyl)-5-methyl-4-oxazolylmethoxy]-3-pyridylmethanol (1.87 g) and thionyl chloride (15 ml) was stirred at room temperature for 1-hour. The reaction mixture was concentrated under reduced pressure, and saturated aqueous sodium bicarbonate solution was added to the residue, which was extracted with ethyl acetate. The ethyl acetate layer was washed with saturated aqueous sodium chloride solution, dried ($MgSO_4$) and concentrated. The residue was subjected to silica gel column chromatography to obtain 5-chloromethyl-2-[2-(2-furyl)-5-methyl-4-oxazolylmethoxy]pyridine (1.41 g, yield 71%) as colorless crystals from the fraction eluted with ethyl acetate-hexane (1:3, volume ratio). This was recrystallized from ethyl acetate-hexane. Melting point: 95–96° C.

Reference Example 120

Lithium aluminium hydride (1.33 g) was added to a solution of ethyl 1-(4-benzyloxybenzyl)-3-(4-fluorophenyl)-1H-pyrazole-4-carboxylate (15.1 g) in tetrahydrofuran (300 ml) at 0° C., which was stirred at room temperature for 1 hour. Sodium sulfate decahydrate (12.26 g) and hexane (100 ml) was added to the reaction mixture, which was stirred at room temperature for 1 hour. After the precipitate was removed by filtration, the filtrate was concentrated to obtain 1-(4-benzyloxybenzyl)-3-(4-fluorophenyl)-1H-pyrazol-4-ylmethanol (12.9 g, yield 95%) as colorless crystals. This was recrystallized from ethyl acetate-hexane. Melting point: 112–113° C.

Reference Example 121

A mixture of 1-(4-benzyloxybenzyl)-3-(4-fluorophenyl)-1H-pyrazol-4-ylmethanol (11.7 g), active manganese dioxide (20.0 g) and tetrahydrofuran (150 ml) was stirred at room temperature for 2 hours. After the manganese dioxide was removed by filtration, the filtrate was concentrated to obtain 1-(4-benzyloxybenzyl)-3-(4-fluorophenyl)-1H-pyrazole-4-carbaldehyde (10.9 g, yield 94%) as colorless crystals. This was recrystallized from ethyl acetate-hexane. Melting point: 97–98° C.

Reference Example 122

A mixture of 5-hydroxy-2-methylpyridine (8.46 g), 4-chloromethyl-5-methyl-2-phenyloxazole (15.20 g), potassium carbonate (15.98 g) and N,N-dimethylformamide (200 ml) was stirred at 80° C. for 3 hours, poured into water, and extracted with ethyl acetate. The ethyl acetate layer was washed with saturated aqueous sodium chloride solution, dried ($MgSO_4$) and concentrated. The residue was subjected to silica gel column chromatography to obtain 2-methyl-5-(5-methyl-2-phenyl-4-oxazolylmethoxy)pyridine (19.68 g, yield 96%) as pale yellow crystals from the fraction eluted with tetrahydrofuran-hexane (1:1, volume ratio). This was recrystallized from acetone-hexane. Melting point: 103–104° C.

Reference Example 123

A mixture of ethyl 3-[1-(4-hydroxybenzyl)-3-phenyl-1H-pyrazol-4-yl]propionate (2.02 g), 1,2-dibromoethane (20 ml), potassium carbonate (1.68 g) and N,N-dimethylformamide (20 ml) was stirred at 90° C. for 24 hours. The reaction mixture was poured into water, which was extracted with ethyl acetate. The ethyl acetate layer was washed with saturated aqueous sodium chloride solution, dried ($MgSO_4$), and concentrated. The residue was subjected to silica gel column chromatography to obtain ethyl 3-[1-[4-(2-bromoethoxy)benzyl]-3-phenyl-1H-pyrazol-4-yl]propionate (1530 mg, yield 58%) as a colorless oily substance from the fraction eluted with ethyl acetate-hexane (1:4, volume ratio).

NMR(CDCl$_3$) δ: 1.19(3H, t, J=7.0 Hz), 2.46–2.58(2H, m) 2.88–3.00(2H, m), 3.59–3.70(2H, m), 4.08(2H, q, J=7.0 Hz), 4.24–4.35(2H, m), 5.24(2H, s), 6.84–6.94(2H, m), 7.16–7.52(6H, m), 7.58–7.68(2H, m).

Reference Example 124

A solution of p-toluenesulfonylmethylisocyanide (12.3 g) in dimethoxyethane (60 ml) was added to a mixture of potassium t-butoxide (13.5 g) and dimethoxyethane (60 ml) at −78° C., and the resultant was stirred for 5 minutes. A solution of 1-benzyl-5-phenyl-1H-pyrazol-4-carbaldehyde (13.0 g) in dimethoxyethane (60 ml) was added to the mixture. After stirring at the same temperature for 1 hour, the mixture was stirred for 1 hour while raising the temperature. Methanol (180 ml) was added to the mixture, and refluxed for 1 hour. After cooling, the reaction solution was poured into saturated aqueous ammonium chloride solution, which was extracted with ethyl acetate. The ethyl acetate layer was washed with saturated aqueous sodium chloride solution, dried (MgSO$_4$), and concentrated. The residue was subjected to silica gel column chromatography to obtain a colorless oily substance from the fraction eluted with ethyl acetate-hexane (1:2, volume ratio). A mixture of the resulting colorless oily substance, 4N aqueous sodium hydroxide solution (100 ml), tetrahydrofuran (100 ml) and ethanol (100 ml) was refluxed for 3 days. After cooling, the mixture was neutralized with dilute hydrochloric acid, which was extracted with ethyl acetate. The ethyl acetate layer was washed with saturated aqueous sodium chloride solution, dried (MgSO$_4$) and concentrated. A mixture of the residue, ethyl iodide (6.5 ml), potassium carbonate (14.9 g) and N,N-dimethylformamide (150 ml) was stirred at room temperature for 3 hours. The reaction mixture was poured into water, which was extracted with ethyl acetate. The ethyl acetate layer was washed with saturated aqueous sodium chloride solution, dried (MgSO$_4$), and concentrated. The residue was subjected to silica gel column chromatography to obtain a colorless oily substance from the fraction eluted with ethyl acetate-hexane (1:2, volume ratio). A mixture of the resulting oily substance, 5% palladium-carbon (30.0 g), formic acid (80 ml) and ethanol (160 ml) was refluxed for 1 hour. After cooling, the palladium-carbon was removed by filtration, and the filtrate was concentrated. The residue was dissolved in ethyl acetate, which was washed with saturated aqueous sodium bicarbonate solution, then with saturated aqueous sodium chloride solution, dried (MgSO$_4$) and concentrated. The residue was subjected to silica gel column chromatography to obtain ethyl 3-phenyl-1H-pyrazol-4-ylacetate (4.65 g, yield 34%) as a colorless oily substance from the fraction eluted with ethyl acetate-hexane (1:1, volume ratio).

NMR(CDCl$_3$) δ: 1.23(3H, t, J=7.0 Hz), 3.61(2H, s), 4.14(2H, q, J=7.0 Hz), 7.32–7.47(3H, m), 7.51–7.59(3H, m), 11.38(1H, br.s).

Reference Example 125

Lithium aluminium hydride (300 mg) was added gradually to a solution of ethyl 1-[6-(5-methyl-2-phenyl-4-oxazolylmethoxy)-3-pyridylmethyl]-3-phenyl-1H-pyrazole-4-carboxylate (1.56 g) in tetrahydrofuran (70 ml) at 0° C., which was stirred for 2 hours. Sodium sulfate-decahydrate (3.40 g) was added to the reaction mixture, and the precipitate was filtered. The filtrate was concentrated, and residue was subjected to silica gel column chromatography to obtain 1-(6-(5-methyl-2-phenyl-4-oxazolylmethoxy)-3-pyridylmethyl]-3-phenyl-1H-pyrazol-4-ylmethanol (1.27 g, yield 89%) as a colorless oily substance from the fraction eluted with acetone-hexane (2:3, volume ratio).

NMR(CDCl$_3$) δ: 1.60(1H, t, J=5.5 Hz), 2.48(3H, s), 4.68(2H, d, J=5.5 Hz), 5.26(2H, s), 5.30(2H, s), 6.82(1H, d, J=8.5 Hz), 7.25–7.5 (7H, m), 7.56(1H, dd, J=8.5, 2 Hz), 7.7–7.8(2H, m), 7.95–8.05(1H, m), 8.15(1H, d, J=2 Hz).

Reference Example 126

A mixture of 1-[6-(5-methyl-2-phenyl-4-oxazolylmethoxy)-3-pyridylmethyl]-3-phenyl-1H-pyrazol-4-yl-methanol (1.25 g), active manganese dioxide (3.00 g) and ethyl acetate (80 ml) was stirred at room temperature for 3 hours. After manganese dioxide was separated by filtration, the filtrate was concentrated. The residue was subjected to silica gel column chromatography to obtain 1-[6-(5-methyl-2-phenyl-4-oxazolylmethoxy)-3-pyridylmethyl]-3-phenyl-1H-pyrazole-4-carboaldehyde (1.20 g, yield 96%) as a colorless oily substance from the fraction eluted with ethyl acetate-hexane (1:1, volume ratio).

NMR(CDCl$_3$) δ: 2.48(3H, s), 5.30(2H, s), 5.31(2H, s), 6.85(1H, d, J=8.5 Hz), 7.4–7.6(7H, m), 7.59(1H, dd, J=8.5, 2.5 Hz), 7.65–7.8(2H, m), 7.97(1H, s), 8.0–8.05(2H, m), 8.21(1H, d, J=2 Hz), 9.93(1H, s).

Reference Example 127

A solution of p-toluenesulfonylmethylisocyanide (3.08 g) in dimethoxyethane (15 ml) was added to a mixture of potassium t-butoxide (3.37 g) and dimethoxyethane (15 ml) at −78° C., and the resultant was stirred for 5 minutes. A solution of 1-(4-benzyloxybenzyl)-3-(4-fluorophenyl)-1H-pyrazole-4-carbaldehyde (5.80 g) in dimethoxyethane (30 ml) was added to the mixture. After stirring at the same temperature, the mixture was stirred for 1 hour while raising the temperature. Methanol (45 ml) was added to the mixture, which was refluxed for 1 hour. After cooling, the reaction mixture was poured into saturated aqueous ammonium chloride solution, which was extracted with ethyl acetate. The ethyl acetate layer was washed with saturated aqueous sodium chloride solution, dried (MgSO$_4$), and concentrated. The residue was subjected to silica gel column chromatography to obtain 1-(4-benzyloxybenzyl)-3-(4-fluorophenyl)-1H-pyrazol-4-ylacetonitrile (4.52 g, yield 76%) as colorless crystals from the fraction eluted with ethyl acetate-hexane (1:2, volume ratio). This was recrystallized from ethyl acetate-hexane. Melting point: 86–87° C.

Reference Example 128

A mixture of ethyl 1-(4-phenoxybenzyl)-3-(4-phenoxybenzyloxy)-1H-pyrazole-4-carboxylate (21.50 g), 5% palladium-carbon (10.43 g) and tetrahydrofuran (300 ml) was stirred overnight under a hydrogen atmosphere. After the palladium-carbon was removed by filtration, the filtrate was concentrated to obtain ethyl 3-hydroxy-1-(4-phenoxybenzyl)-1H-pyrazole-4-carboxylate (13.35 g, yield 96%) as colorless crystals. This was recrystallized from acetone-hexane. Melting point: 117–118° C.

Reference Example 129

Lithium aluminium hydride (205 mg) was added gradually to a solution of methyl 1-[6-(5-methyl-2-phenyl-4- oxazolylmethoxy)-3-pyridylmethyl]-4-phenylpyrrole-3-carboxylate (1.30 g) in tetrahydrofuran (40 ml) at 0° C., and the resultant was stirred for 3 hours. Sodium sulfate decahydrate (2.80 g) was added to the reaction mixture, and the precipitate was removed by filtration. The filtrate was concentrated, and the residue was subjected to silica gel column chromatography to obtain [1-[6-(5-methyl-2-phenyl-4-oxazolylmethoxy)-3-pyridylmethyl]-4-phenyl-3-pyrrolyl]methanol (1.15 g, yield 94%) as a colorless oily substance from the fraction eluted with ethyl acetate-hexane (3:2, volume ratio).

NMR(CDCl$_3$) δ: 2.48(3H, s), 4.63(2H, br s), 4.98(2H, s), 5.30(2H, s), 6.7–6.85(2H, m), 7.2–7.55(10H, m), 7.95–8.1 (3H, m).

Reference Example 130

A mixture of [1-[6-(5-methyl-2-phenyl-4-oxazolylmethoxy)-3-pyridylmethyl]-4-phenyl-3-pyrrolyl]methanol (1.15 g), active manganese dioxide (2.30 g) and ethyl acetate (80 ml) was stirred at room temperature for 2 hours. After the manganese dioxide was removed by filtration, the filtrate was concentrated to obtain 1-[6-(5-methyl-2-phenyl-4-oxazolylmethoxy)-3-pyridylmethyl]-4-phenylpyrrole-3-carbaldehyde (1.06 g, yield 93%) as a colorless oily substance.

NMR(CDCl$_3$) δ: 2.48(3H, s), 5.04(2H, s), 5.31(2H, s), 6.75(1H, d, J=2 Hz), 6.84(1H, d, J=8.5 Hz), 7.25–7.5(10H, m), 7.95–8.15(3H, m), 9.86(1H, s).

Reference Example 131

A mixture of ethyl(E)-3-[1-(4-benzyloxybenzyl)-3-phenyl-1H-pyrazol-4-yl]propenoate (12.13 g), 5% palladium-carbon (10.22 g) and tetrahydrofuran (100 ml) was stirred for 5 hours under a hydrogen atmosphere. After the palladium-carbon was removed by filtration, the filtrate was concentrated to obtain ethyl 3-[1-(4-hydroxybenzyl)-3-phenyl-1H-pyrazol-4-yl]propionate (9.52 g, yield 98%) as a colorless oily substance.

NMR(CDCl$_3$) δ: 1.19(3H, t, J=7.2 Hz), 2.48–2.58(2H, m), 2.88–3.00(2H, m), 4.08(2H, q, J=7.2 Hz), 5.19(2H, s), 6.62–6.74(2H, m), 6.98–7.10(2H, m), 7.18–7.45(4H, m), 7.56–7.66(2H, m).

Reference Example 132

A mixture of ethyl(E)-3-[1-(4-benzyloxybenzyl)-3-(4-fluorophenyl)-1H-pyrazol-4-yl]propenoate (10.0 g), 5% palladium-carbon (20.0 g), ethanol (100 ml) and tetrahydrofuran (100 ml) was stirred for 1 hour under a hydrogen atmosphere. After the palladium-carbon was removed by filtration, the filtrate was concentrated to obtain ethyl 3-[3-(4-fluorophenyl)-1-(4-hydroxybenzyl)-1H-pyrazol-4-yl] propionate (7.15 g, yield 88%) as a colorless oily substance.

NMR(CDCl$_3$) δ: 1.19(3H, t, J=7.2 Hz), 2.52(2H, t, J=7.6 Hz), 2.90(2H, t, J=7.6 Hz), 4.08(2H, q, J=7.2 Hz), 5.15(2H, s), 6.57(2H, d, J=8.4 Hz), 6.97(2H, d, J=8.4 Hz), 7.07(2H, t, J=8.8 Hz), 7.24(1H, s), 7.56(2H, dd, J=5.4, 8.8 Hz), 7.59(1H, s).

Reference Example 133

A mixture of 5-phenyl-2-pyridylmethyl acetate (3.68 g), a 1N aqueous sodium hydroxide solution (30 ml), tetrahydrofuran (30 ml) and methanol (300 ml) was stirred at room temperature for 3 hours, which was concentrated. The residue was dissolved in ethyl acetate, and then the solution was washed with water, then with saturated aqueous sodium chloride solution, dried (MgSO$_4$), and concentrated. The residual colorless crystals were collected by filtration to obtain 5-phenyl-2-pyridylmethanol (2.84 g, yield 95%). This was recrystallized from ethyl acetate-hexane. Melting point: 86–87° C.

Reference Example 134

A mixture of 5-phenyl-2-pyridylmethanol (1.98 g), thionyl chloride (1.6 ml) and toluene (30 ml) was stirred at 70° C. for 2 hours. After the reaction mixture was concentrated, saturated aqueous sodium bicarbonate solution was added to the residue, which was extracted with ethyl acetate. The ethyl acetate layer was washed with saturated aqueous sodium chloride solution, dried (MgSO$_4$), and concentrated. A mixture of the residue, 4-hydroxybenzyl alcohol (1.37 g), potassium carbonate (3.18 g) and N,N-dimethylformamide (50 ml) was stirred at 80° C. overnight. The reaction mixture was poured into water, which was extracted with ethyl acetate. The ethyl acetate layer was washed with saturated aqueous sodium chloride solution, dried (MgSO$_4$) and concentrated. The residue was subjected to silica gel column chromatography to obtain 4-(5-phenyl-2-pyridylmethoxy) benzyl alcohol (2.69 g, yield 86%) as colorless crystals from the fraction eluted with ethyl acetate-hexane (1:1, volume ratio). This was recrystallized from ethyl acetate-hexane. Melting point: 159–160° C.

Reference Example 135

Sodium borohydride (0.36 g) was added to a mixture of 4-(2-phenyl-4-oxazolylmethoxy)benzaldehyde (2.65 g) and methanol (50 ml) under ice-cooling, which was stirred at room temperature for 1 hour. Dilute hydrochloric acid and water were added to the reaction mixture, which was extracted with ethyl acetate. The ethyl acetate layer was washed with saturated aqueous sodium chloride solution, dried (MgSO$_4$) and concentrated to obtain 4-(2-phenyl-4-oxazolylmethoxy)benzyl alcohol (2.43 g, yield 91%) as colorless crystals. This was recrystallized from ethyl acetate-hexane. Melting point: 141–142° C.

Reference Example 136

A mixture of 4-(2-phenyl-4-oxazolylmethoxy)benzylalcohol (2.39 g), thionyl chloride (0.69 ml) and toluene (50 ml) was stirred at 40° C. overnight, and then the reaction mixture was concentrated. Saturated aqueous sodium bicarbonate solution was added to the residue, which was extracted with ethyl acetate. The ethyl acetate layer was washed with saturated aqueous sodium chloride solution, dried (MgSO$_4$), and concentrated. The residue was subjected to silica gel column chromatography to obtain 4-(4-chloromethylphenoxymethyl)-2-phenyloxazole (2.34 g, yield 92%) as colorless crystals from the fraction eluted with ethyl acetate-hexane (1:3, volume ratio). This was recrystallized from ethyl acetate-hexane. Melting point: 129–130° C.

Reference Example 137

Lithium aluminum hydride (320 mg) was added gradually to a solution of methyl 3-(5-methyl-2-phenyl-4-oxazolylmethoxy)-1-(4-phenoxybenzyl)-1H-pyrazole-4-carboxylate (4.00 g) in tetrahydrofuran (30 ml) at 0° C., which was stirred for 2 hours. Sodium sulfate decahydrate (2.95 g) was added to the reaction mixture, and the precipitate was separated by filtration. The filtrate was concentrated, and the residue was subjected to silica gel column chromatography to obtain [3-(5-methyl-2-phenyl-4-oxazolylmethoxy)-1-(4-phenoxybenzyl)-1H-pyrazol-4-yl]methanol (3.56 g, yield 97%) as colorless crystals. This was recrystallized from ethyl acetate-hexane. Melting point: 103–104° C.

Reference Example 138

A mixture of [3-(5-methyl-2-phenyl-4-oxazolylmethoxy)-1-(4-phenoxybenzyl)-1H-pyrazol-4-yl]methanol (2.85 g), active manganese dioxide (8.42 g) and tetrahydrofuran (50 ml) was stirred at room temperature overnight. After the manganese dioxide was separated by filtration, the filtrate was concentrated. The residue was subjected to silica gel column chromatography to obtain 3-(5-methyl-2-phenyl-4-oxazolylmethoxy)-1-(4-phenoxybenzyl)-1H-pyrazole-4-carbaldehyde (2.61 g, yield 92%) as colorless crystals from the fraction eluted with ethyl acetate-hexane (1:1, volume ratio). This was recrystallized from ethyl acetate-hexane. Melting point: 129–130° C.

Reference Example 139

A mixture of 4-(2-bromoethoxy)benzaldehyde (4.97 g), 1(2H)-phthalazinone (3.27 g), potassium carbonate (6.20 g) and N,N-dimethylformamide (50 ml) was stirred at 80° C. for 5 hours. After cooling, the reaction mixture was poured into water, which was extracted with ethyl acetate. The ethyl acetate layer was washed with saturated aqueous sodium chloride solution, dried (MgSO$_4$) and concentrated to obtain 4-[2-[1-oxo-2(1H)-phthalazinyl]ethoxy]benzaldehyde (5.36 g, yield 84%) as colorless crystals. This was recrystallized from ethyl acetate-hexane. Melting point: 126–127° C.

Reference Example 140

A mixture of 3-(2-bromoethoxy)benzaldehyde (6.00 g), 1(2H)-phthalazinone (4.21 g), potassium carbonate (7.24 g) and N,N-dimethylformamide (40 ml) was stirred at 80° C. for 5 hours. After cooling, the reaction mixture was poured into water, which was extracted with ethyl acetate. The ethyl acetate layer was washed with saturated aqueous sodium chloride solution, dried (MgSO$_4$) and concentrated to obtain 3-[2-[1-oxo-2(1H)-phthalazinyl]ethoxy]benzaldehyde (6.94 g, yield 90%) as colorless crystals. This was recrystallized from acetone-hexane. Melting point: 110–111° C.

Reference Example 141

A mixture of ethyl 3-methyl-1H-pyrazole-4-carboxylate (7.59 g), 2-chloropyridine (5 ml), sodium hydride (60%, oily, 2.32 g) and N,N-dimethylformamide (150 ml) was stirred at 180° C. overnight. The reaction mixture was poured into water, which was extracted with ethyl acetate. The ethyl acetate layer was washed with saturated aqueous sodium chloride solution, dried (MgSO$_4$) and concentrated. The residue was subjected to silica gel column chromatography to obtain ethyl 3-methyl-1-(2-pyridyl)-1H-pyrazole-4-carboxylate (8.31 g, yield 73%) from the fraction eluted with ethyl acetate-hexane (1:9, volume ratio). This was recrystallized from ethyl acetate-hexane. Melting point: 79–80° C.

Reference Example 142

Sodium borohydride (0.45 g) was added to a mixture of 4-(2-phenyl-4-thiazolylmethoxy)benzaldehyde (6.35 g), tetrahydrofuran (30 ml) and methanol (20 ml) under ice-cooling, which was stirred at room temperature for 30 minutes. The reaction mixture was neutralized with dilute hydrochloric acid and water to give a precipitate, which was collected by filtration and then air-dried to obtain crystals of 4-(2-phenyl-4-thiazolylmethoxy)benzyl alcohol (5.76 g, yield 90%). This was recrystallized from ethyl acetate-hexane to obtain colorless needles. Melting point: 145–146° C.

Reference Example 143

A solution of thionyl chloride (1.5 ml) in toluene (5 ml) was added to a mixture of 4-(2-phenyl-4-thiazolylmethoxy) benzyl alcohol (4.35 g), tetrahydrofuran (50 ml) and toluene (50 ml) under ice-cooling, which was stirred at room temperature for 2 hours. The reaction mixture was concentrated. The residue was dissolved in ethyl acetate, and the solution was washed with saturated aqueous sodium bicarbonate solution, then with saturated aqueous sodium chloride solution. The organic layer was dried over anhydrous magnesium sulfate and concentrated to obtain colorless crystals of 4-(4-chloromethylphenoxymethyl)-2-phenylthiazole (4.10 g, yield 89%). Melting point: 98–99° C.

Reference Example 144

A mixture of 4-chloromethyl-5-methyl-2-phenylthiazole (5.40 g), 4-hydroxybenzaldehyde (2.91 g), anhydrous potassium carbonate (4.95 g) and N,N-dimethylformamide (50 ml) was stirred at 80° C. for 3 hours. The reaction mixture was poured into water, the precipitated solid was collected by filtration, and air-dried to obtain crystals of 4-(5-methyl-2-phenyl-4-thiazolylmethoxy)benzaldehyde (6.85 g, yield 93%). This was recrystallized from ethyl acetate-hexane to obtain colorless prisms. Melting point: 118–119° C.

Reference Example 145

Sodium borohydride (0.38 g) was added to a mixture of 4-(5-methyl-2-phenyl-4-thiazolylmethoxy)benzaldehyde (6.00 g), tetrahydrofuran (30 ml) and methanol (20 ml) under ice-cooling, which was stirred at room temperature for 30 minutes. The reaction mixture was neutralized with dilute hydrochloric acid and water to give a precipitate, which was collected by filtration and air-dried to obtain crystals of 4-(5-methyl-2-phenyl-4-thiazolylmethoxy)benzyl alcohol (5.68 g, yield 94%). This was recrystallized from ethyl acetate-hexane to obtain colorless prisms. Melting point: 94–95° C.

Reference Example 146

A solution of thionyl chloride (1.5 mL) in toluene (5 mL) was added to a mixture of 4-(5-methyl-2-phenyl-4-thiazolylmethoxy)benzyl alcohol (4.50 g), tetrahydrofuran (50 mL) and toluene (50 mL) under ice-cooling, which was stirred at room temperature for 2 hours. The reaction mixture was concentrated. The residue was dissolved in ethyl acetate, which was washed with saturated aqueous sodium bicarbonate solution, then with saturated aqueous sodium chloride solution. The organic layer was dried over anhydrous magnesium sulfate, and concentrated to obtain colorless crystals of 4-(4-chloromethylphenoxymethyl)-5-methyl-2-phenylthiazole (4.50 g, yield 94%). Melting point: 100–101° C.

Reference Example 147

A mixture of 4-chloromethyl-2-phenylthiazole (8.60 g), sodium acetate (10.1 g) and N,N-dimethylformamide (80 ml) was stirred at 80° C. for 6 hours. After cooling, the reaction solution was poured into water, which was extracted with ethyl acetate. The ethyl acetate layer was washed with saturated aqueous sodium chloride solution, dried (MgSO$_4$), and concentrated. A mixture of the residue, 4N aqueous sodium hydroxide solution (25 ml), tetrahydrofuran (50 ml) and methanol (50 ml) was stirred at room temperature for 5 minutes, and poured into water, which was extracted with ethyl acetate. The ethyl acetate layer was washed with saturated aqueous sodium chloride solution, dried (MgSO$_4$), and concentrated. The residue was subjected to silica gel column chromatography to obtain 2-phenyl-4-thiazolylmethanol (7.05 g, yield 90%) as colorless crystals from the fraction eluted with ethyl acetate-hexane (1:1, volume ratio). This was recrystallized from hexane. Melting point: 71–72° C.

Reference Example 148

A mixture of 2-chloromethylquinoline hydrochloride (21.4 g), sodium acetate (32.8 g) and N,N-dimethylformamide (200 ml) was stirred at 60° C. overnight. After cooling, the reaction solution was poured into water, which was extracted with ethyl acetate. The ethyl acetate layer was washed with saturated aqueous sodium chloride solution, dried (MgSO$_4$), and concentrated. A mixture of the residue, 4N aqueous sodium hydroxide solution (50 ml), tetrahydrofuran (100 ml) and methanol (100 ml) was stirred at room temperature for 1 hour, and poured into water, which was extracted with ethyl acetate. The ethyl acetate layer was washed with saturated aqueous sodium chloride solution, dried (MgSO$_4$) and concentrated. The residue was subjected to silica gel column chromatography to obtain 2-quinolylmethanol (14.0 g, yield 88%) as colorless crystals from the fraction eluted with ethyl acetate-hexane (1:2, volume ratio). This was recrystallized from ethyl acetate-hexane. Melting point: 68–69° C.

Reference Example 149

Sodium hydride (60%, oily, 5.01 g) was added to a solution of 5-hydroxy-2-methylpyridine (12.45 g) and N-phenyltrifluoromethanesulfonimide (40.80 g) in tetrahydrofuran (500 ml) at 0° C., which was stirred at room temperature for 1 hour, and concentrated. The residue was dissolved in ethyl acetate, which was washed with saturated aqueous sodium bicarbonate solution, and with saturated aqueous sodium chloride solution, and then dried (MgSO$_4$) and concentrated. The residue was subjected to silica gel column chromatography to obtain 6-methyl-3-pyridyl trifluoromethanesulfonate (23.10 g, yield 84%) as a colorless oily substance from the fraction eluted with ethyl acetate-hexane (1:4, volume ratio).

NMR(CDCl$_3$) δ: 2.61(3H, s), 7.27(1H, d, J=8.4 Hz), 7.52(1H, dd, J=2.8, 8.4 Hz), 8.47(1H, d, J=2.8 Hz).

Reference Example 150

A mixture of 6-methyl-3-pyridyl tifluoromethanesulfonate (23.00 g), phenylboronic acid (11.83 g), tetrakis(triphenylphosphine)palladium (5.00 g), sodium carbonate (22.43 g), ethanol (100 ml), water (100 ml) and toluene (500 ml) was refluxed overnight under an argon atmosphere. The reaction mixture was poured into water, which was extracted with ethyl acetate. The ethyl acetate layer was washed with saturated aqueous sodium chloride solution, dried (MgSO$_4$) and concentrated. The residue was subjected to silica gel column chromatography to obtain 2-methyl-5-phenylpyridine (15.24 g, yield 94%) as a colorless oily substance from the fraction eluted with ethyl acetate.

NMR(CDCl$_3$) δ: 2.61(3H, s), 7.23(1H, d, J=8.0 Hz), 7.32–7.63(5H, m), 7.78(1H, dd, J=2.6, 8.0 Hz), 8.73(1H, d, J=2.6 Hz).

Reference Example 151

A mixture of 2-methyl-5-phenylpyridine (3.00 g), 3-chloroperbenzoic acid (4.79 g) and tetrahydrofuran (50 ml) was stirred at room temperature overnight, and concentrated. The residue was subjected to silica gel column chromatography to obtain a colorless oily substance from the fraction eluted with tetrahydrofuran. A solution of the resulting colorless oily substance in acetic anhydride (50 ml) was added slowly to acetic anhydride (50 ml) heated at 130° C., which was stirred at 2 hours, and concentrated. The residue was dissolved in ethyl acetate, which was washed with saturated aqueous sodium bicarbonate solution, and with saturated aqueous sodium chloride solution, and then dried (MgSO$_4$) and concentrated. The residue was subjected to silica gel column chromatography to obtain 5-phenyl-2-pyridylmethyl acetate (3.68 g, yield 92%) as colorless crystals from the fraction eluted with ethyl acetate-hexane (1:2, volume ratio). This was recrystallized from ethyl acetate-hexane. Melting point: 71–72° C.

Reference Example 152

A solution of p-toluenesufonylmethylisocyanide (10.3 g) in dimethoxyethane (50 ml) was added to a mixture of potassium t-butoxide (11.2 g) and dimethoxyethane (50 ml) at −78° C., and the mixture was stirred for 5 minutes. A solution of 1-benzyl-3-benzyloxy-1H-pyrazole-4-carbaldehyde (14.6 g) in dimethoxyethane (50 ml) was added to the mixture. After stirring at the same temperature for 1 hour, the mixture was stirred for 1 hour while raising the temperature. Methanol (150 ml) was added to the mixture, which was refluxed for 1 hour. After cooling, the reaction solution was poured into saturated aqueous ammonium chloride solution, which was extracted with ethyl acetate. The ethyl acetate layer was washed with saturated aqueous sodium chloride solution, dried (MgSO$_4$), and concentrated. The residue was subjected to silica gel column chromatography to obtain 1-benzyl-3-benzyloxy-1H-pyrazol-4-ylacetonitrile (13.1 g, yield 86%) as a colorless oily substance from the fraction eluted with ethyl acetate-hexane (1:3, volume ratio).

NMR(CDCl$_3$) δ: 3.42(2H, s), 5.11(2H, s), 5.24(2H, s), 7.18–7.24(3H, m), 7.27–7.47(8H, m).

Reference Example 153

A mixture of 1-benzyl-3-benzyloxy-1H-pyrazol-4-ylacetonitrile (13.0 g), 4N aqueous sodium hydroxide solution (100 ml), tetrahydrofuran (100 ml) and ethanol (100 ml) was refluxed for 3 days. After cooling, the mixture was neutralized with dilute hydrochloric acid, which was extracted with ethyl acetate. The ethyl acetate layer was washed with saturated aqueous sodium chloride solution, dried (MgSO$_4$) and concentrated. A mixture of the residue, ethyl iodide (5.2 ml), potassium carbonate (11.9 g) and N,N-dimethylformamide (100 ml) was stirred at room temperature for 3 hours.

The reaction mixture was poured into water, which was extracted with ethyl acetate. The ethyl acetate layer was washed with saturated aqueous sodium chloride solution, dried ($MgSO_4$), and concentrated. The residue was subjected to silica gel column chromatography to obtain ethyl 1-benzyl-3-benzyloxy-1H-pyrazol-4-ylacetate (14.9 g, yield 99%) as a colorless oily substance from the fraction eluted with ethyl acetate-hexane (1:2, volume ratio).

NMR($CDCl_3$) δ: 1.22(3H, t, J=7.2 Hz), 3.39(2H, s), 4.12(2H, q, J=7.2 Hz), 5.12(2H, s), 5.24(2H, s), 7.17–7.26 (3H, m), 7.28–7.49(8H, m).

Reference Example 154

A mixture of ethyl 1-benzyl-3-benzyloxy-1H-pyrazol-4-ylacetate (14.9 g), 5% palladium-carbon (15.0 g), tetrahydrofuran (150 ml) and ethanol (150 ml) was stirred for 2 hours under a hydrogen atmosphere. After the palladium-carbon was removed by filtration, the filtrate was concentrated to obtain ethyl 1-benzyl-3-hydroxy-1H-pyrazol-4-ylacetate (9.76 g, yield 88%) as colorless crystals. This was recrystallized from tetrahydrofuran-hexane. Melting point: 156–157° C.

Reference Example 155

Sodium hydride (60%, oily, 1.20 g) was added to a solution of ethyl 1-benzyl-3-hydroxy-1H-pyrazol-4-ylacetate (7.81 g) in N,N-dimethylformamide (100 ml) at 0° C., which was stirred at room temperature for 15 minutes. Ethyl iodide (2.40 ml) was added to the mixture, which was stirred at room temperature for 1 hour. The reaction mixture was poured into water, which was extracted with ethyl acetate. The ethyl acetate layer was washed with saturated aqueous sodium chloride solution, dried ($MgSO_4$), and concentrated. The residue was subjected to silica gel column chromatography to obtain ethyl 1-benzyl-3-ethoxy-1H-pyrazol-4-ylacetate (7.52 g, yield 87%) as a colorless oily substance from the fraction eluted with ethyl acetate-hexane (1:3, volume ratio).

NMR($CDCl_3$) δ: 1.25(3H, t, J=77.0 Hz), 1.35(3H, t, J=7.0 Hz), 3.36(2H, s), 4.14(2H, q, J=7.0 Hz), 4.23(2H, q, J=7.0 Hz), 5.10(2H, s), 7.16–7.38(6H, m).

Reference Example 156

A mixture of ethyl 1-benzyl-3-ethoxy-1H-pyrazol-4-ylacetate (7.50 g), 5% palladium-carbon (15.0 g), formic acid (50 ml) and ethanol (100 ml) was refluxed for 1 hour. After cooling, the palladium-carbon was removed by filtration, and the filtrate was concentrated. The residue was dissolved in ethyl acetate, which was washed with saturated aqueous sodium bicarbonate solution, and with a saturated aqueous sodium chloride solution, dried ($MgSO_4$) and concentrated. The residue was subjected to silica gel column chromatography to obtain ethyl 3-ethoxy-1H-pyrazol-4-ylacetate (2.79 g, yield 54%) as a colorless oily substance from the fraction eluted with ethyl acetate-hexane (1:1, volume ratio).

NMR($CDCl_3$) δ: 1.27(3H, t, J=7.2 Hz), 1.38(3H, t, J=7.0 Hz), 3.41(2H, s), 4.14(2H, q, J=7.2 Hz), 4.25(2H, q, J=7.0 Hz), 7.38(1H, s), 9.38(1H, br.s).

Reference Example 157

Lithium aluminium hydride (1100 mg) was added gradually to a solution of ethyl 1-[4-(5-methyl-2-phenyl-4-oxazolylmethoxy)benzyl]-3-(2-thienyl)-1H-pyrazole-4-carboxylate (14.39 g) in tetrahydrofuran (50 ml) at 0° C., which was stirred for 30 minutes. Sodium sulfate decahydrate (12.14 g) was added to the reaction mixture, and the precipitate was removed by filtration. The filtrate was concentrated, and the residue was subjected to silica gel column chromatography to obtain [1-[4-(5-methyl-2-phenyl-4-oxazolylmethoxy)benzyl]-3-(2-thienyl)-1H-pyrazol-4-yl]methanol (12.20 g, yield: 93%) as pale yellow oily substance from the fraction eluted with ethyl acetate-hexane (1:1, volume ratio).

NMR($CDCl_3$) δ: 2.44(3H, s), 4.69(2H, d, J=5.4 Hz), 4.99(2H, s), 5.24(2H, s), 6.96–7.13(3H, m), 7.20–7.34(4H, m), 7.38–7.48(4H, m), 7.96–8.06(2H, m).

Reference Example 158

A mixture of [1-[4-(5-methyl-2-phenyl-4-oxazolylmethoxy)benzyl]-3-(2-thienyl)-1H-pyrazol-4-yl]methanol (12.15 g), activated manganese dioxide (37.03 g), and tetrahydrofuran (200 ml) was stirred at room temperature overnight. After the manganese dioxide was removed by filtration, the filtrate was concentrated to obtain 1-[4-(5-methyl-2-phenyl-4-oxazolylmethoxy)benzyl]-3-(2-thienyl)-1H-pyrazole-4-carbaldehyde (11.68 g, yield: 96%) as colorless crystals. This was recrystallized from ethyl acetate-hexane. Melting point: 136~137° C.

Reference Example 159

Lithium aluminium hydride (540 mg) was added gradually to a solution of ethyl 1-[4-(2-phenyl-4-thiazolylmethoxy)benzyl]-3-(2-thienyl)-1H-pyrazole-4-carboxylate (7.10 g) in tetrahydrofuran (50 ml) at 0° C., which was stirred for 30 minutes. Sodium sulfate decahydrate (4.33 g) was added to the reaction mixture, and the precipitate was removed by filtration. The filtrate was concentrated, and the residue was subjected to silica gel column chromatography to obtain [1-[4-(2-phenyl-4-thiazolylmethoxy)benzyl]-3-(2-thienyl)-1H-pyrazol-4-yl]methanol (6.31 g, yield: 96%) as colorless crystals from the fraction eluted with ethyl acetate-hexane (1:1, volume ratio). This was recrystallized from ethyl acetate-hexane. Melting point: 147~148° C.

Reference Example 160

A mixture of [1-[4-(2-phenyl-4-thiazolylmethoxy)benzyl]-3-(2-thienyl)-1H-pyrazol-4-yl]methanol (5.57 g), activated manganese dioxide (16.11 g), and tetrahydrofuran (100 ml) was stirred at room temperature overnight. After the manganese dioxide was removed by filtration, the filtrate was concentrated to obtain 1-[4-(2-phenyl-4-thiazolylmethoxy)benzyl]-3-(2-thienyl)-1H-pyrazole-4-carbaldehyde (5.39 g, yield: 98%) as colorless crystals. This was recrystallized from acetone-hexane. Melting point: 115~116° C.

Reference Example 161

A solution of p-toluenesulfonylmethylisocyanide (0.95 g) in dimethoxyethane (10 ml) was added to a mixture of potassium tert-butoxide (1.01 g) and dimethoxyethane (10 ml) at −78° C., and the mixture was stirred for 5 minutes. A solution of 1-[4-(5-methyl-2-phenyl-4-oxazolylmethoxy)benzyl]-3-(2-thienyl)-1H-pyrazole-4-carbaldehyde (2.01 g) in dimethoxyethane (20 ml) was added to the mixture, and then stirred at the same temperature for 1 hour, and at room temperature for 1 hour. Methanol (40 ml) was added to the mixture, and reflux was conducted for 1 hour. After cooling, the reaction mixture was poured into saturated aqueous ammonium chloride solution, and extracted with ethyl acetate. The ethyl acetate layer was washed with saturated aqueous sodium chloride solution, dried (MgSO$_4$), and concentrated. The residue was subjected to silica gel chromatography to obtain [1-[4-(5-methyl-2-phenyl-4-oxazolylmethoxy)benzyl]-3-(2-thienyl)-1H-pyrazol-4-yl]acetonitrile (1.69 g, yield: 78%) as a colorless oily substance from the fraction eluted with ethyl acetate-hexane (1:3, volume ratio).

NMR(CDCl$_3$) δ: 2.44(3H, s), 3.69(2H, s), 4.99(2H, s), 5.24(2H, s), 6.96–7.48(11H, m), 7.95–8.08(2H, m).

Reference Example 162

A mixture of 1-[4-(5-methyl-2-phenyl-4-oxazolylmethoxy)benzyl]-3-(2-thienyl)-1H-pyrazole-4-carbaldehyde (5.02 g), diethyl malonate (2.12 g), piperidine (0.35 ml), benzoic acid (0.27 g), and toluene (50 ml) was subjected to azeotropic dehydration for 1 hour. The reaction mixture was poured into dilute hydrochloric acid, and extracted with ethyl acetate. The ethyl acetate layer was washed with saturated aqueous sodium chloride solution, dried (MgSO$_4$), and concentrated. The residue was subjected to silica gel-chromatography to obtain a colorless oily substance from the fraction eluted with ethyl acetate-hexane (1:2, volume ratio). Sodium borohydride (170 mg) was added to a mixture of the obtained colorless oily substance, ethanol (20 ml), and tetrahydrofuran (20 ml) at 0° C., and the mixture was stirred at room temperature for 30 minutes. The reaction mixture was poured into dilute hydrochloric acid, and extracted with ethyl acetate. The ethyl acetate layer was washed with saturated aqueous sodium chloride solution, dried (MgSO$_4$), and concentrated. The residue was subjected to silica gel chromatography to obtain diethyl [1-[4-(5-methyl-2-phenyl-4-oxazolylmethoxy)benzyl]-3-(2-thienyl)-1H-pyrazol-4-yl]methylmalonate (6.08 g, yield: 92%) as a pale yellow oily substance from the fraction eluted with ethyl acetate-hexane (1:2, volume ratio).

NMR(CDCl$_3$) δ: 1.14–1.35(6H, m), 2.44(3H, s), 3.24(2H, d, J=7.6 Hz), 3.61(1H, t, J=7.6 Hz), 4.05–4.18(4H, m), 4.98(2H, s), 5.20(2H, s), 6.92–7.34(8H, m), 7.38–7.48(3H, m), 7.96–8.06(2H, m).

Reference Example 163

A mixture of 1-[4-(2-phenyl-4-thiazolylmethoxy)benzyl]-3-(2-thienyl)-1H-pyrazole-4-carbaldehyde (3.70 g), diethyl malonate (1.56 g), piperidine (0.25 ml), benzoic acid (0.20 g), and toluene (50 ml) was subjected to azeotropic dehydration for 1 hour. The reaction mixture was poured into dilute hydrochloric acid, and extracted with ethyl acetate. The ethyl acetate layer was washed with saturated aqueous sodium chloride solution, dried (MgSO$_4$), and concentrated. The residue was subjected to silica gel chromatography to obtain a colorless oily substance from the fraction eluted with ethyl acetate-hexane (1:2, volume ratio). Sodium borohydride (150 mg) was added to a mixture of the obtained colorless oily substance, ethanol (30 ml), and tetrahydrofuran (30 ml) at 0° C., and the mixture was stirred at room temperature for 30 minutes. The reaction mixture was poured into dilute hydrochloric acid, and extracted with ethyl acetate. The ethyl acetate layer was washed with saturated aqueous sodium chloride solution, dried (MgSO$_4$), and concentrated. The residue was subjected to silica gel chromatography to obtain diethyl [1-[4-(2-phenyl-4-thiazolylmethoxy)benzyl]-3-(2-thienyl)-1H-pyrazol-4-yl]methyl malonate (4.09 g, yield: 84%) as a pale yellow oily substance from the fraction eluted with ethyl acetate-hexane (1:2, volume ratio).

NMR(CDCl$_3$) δ: 1.18(6H, t, J=7.0 Hz), 3.24(2H, d, J=7.6 Hz), 3.62(1H, t, J=7.6 Hz), 4.12(4H, q, J=7.0 Hz), 5.20(2H, s), 5.26(2H, s), 6.94–7.04(2H, m), 7.09(1H, dd, J=3.6, 5.2 Hz), 7.15–7.36(6H, m), 7.40–7.48(3H, m), 7.90–7.99(2H, m).

Reference Example 164

Lithium aluminium hydride (210 mg) was added portionwise to a solution of ethyl 1-[4-(2-phenyl-4-oxazolylmethoxy)benzyl]-3-(2-thienyl)-1H-pyrazole-4-carboxylate (2.73 g) in tetrahydrofuran (50 ml) at 0° C., which was stirred for 30 minutes. After sodium sulfate decahydrate (1.80 g) was added to the reaction mixture, and the precipitate was removed by filtration, the filtrate was concentrated. The residue was subjected to silica gel column chromatography to obtain [1-[4-(2-phenyl-4-oxazolylmethoxy)benzyl]-3-(2-thienyl)-1H-pyrazol-4-yl]methanol (2.33 g, yield: 94%) as colorless crystals from the fraction eluted with ethyl acetate-hexane (1:1, volume ratio). This was recrystallized from ethyl acetate-hexane. Melting point: 155~156° C.

Reference Example 165

A mixture of [1-[4-(2-phenyl-4-oxazolylmethoxy)benzyl]-3-(2-thienyl)-1H-pyrazol-4-yl]methanol (2.03 g), activated manganese dioxide (6.00 g), and tetrahydrofuran (50 ml) was stirred at room temperature overnight. After the manganese dioxide was removed by filtration, the filtrate was concentrated to obtain 1-[4-(2-phenyl-4-oxazolylmethoxy)benzyl]-3-(2-thienyl)-1H-pyrazole-4-carbaldehyde (1.74 g, yield: 86%) as colorless crystals. This was recrystallized from ethyl acetate-hexane. Melting point: 153~154° C.

Reference Example 166

A mixture of 1-[4-(2-phenyl-4-oxazolylmethoxy)benzyl]-3-(2-thienyl)-1H-pyrazole-4-carbaldehyde (1.60 g), diethyl malonate (0.69 g), piperidine (0.12 ml), benzoic acid (0.09 g), and toluene (50 ml) was subjected to azeotropic dehydration for 1 hour. The reaction mixture was poured into dilute hydrochloric acid, and extracted with ethyl acetate. The ethyl acetate layer was washed with saturated aqueous sodium chloride solution, dried (MgSO$_4$), and concentrated. The residue was subjected to silica gel chromatography to obtain a colorless oily substance from the fraction eluted with ethyl acetate-hexane (1:2, volume ratio). Sodium borohydride (105 mg) was added to a mixture of the obtained colorless oily substance, ethanol (20 ml), and tetrahydrofuran (20 ml) at 0° C., and the mixture was stirred at room temperature for 1 hour. The reaction mixture was poured into dilute hydrochloric acid, and extracted with ethyl acetate. The ethyl acetate layer was washed with saturated aqueous sodium chloride solution, dried (MgSO$_4$), and concentrated. The residue was subjected to silica gel chromatography to obtain diethyl [1-[4-(2-phenyl-4-oxazolylmethoxy)benzyl]-3-(2-thienyl)-1H-pyrazol-4-yl]methylmalonate (1.76 g, yield: 83%) as a colorless oily substance from the fraction eluted with ethyl acetate-hexane (1:2, volume ratio).

NMR(CDCl$_3$) δ: 1.18(6H, t, J=7.0 Hz), 3.24(2H, d, J=7.8 Hz), 3.61(1H, J=7.8 Hz), 4.11(2H, q, J=7.0 Hz), 4.12(2H, q, J=7.2 Hz), 5.07(2H, d, J=1.0 Hz), 5.20(2H, s), 6.95–7.01

(2H, m), 7.0(1H, dd, J=5.0, 3.6 Hz), 7.17–7.32 (5H, m), 7.42–7.50(3H, m), 7.73(1H, J=1.0 Hz), 8.02–8.08(2H, m).

Reference Example 167

A mixture of 2-acetylthiophene (50.75 g), sodium hydride (60%, oily, 16.33 g), and diethyl carbonate (500 ml) was stirred at 80° C. for 1 hour. Water was added to the reaction mixture and the water layer was neutralized with dilute hydrochloric acid. After stirring at room temperature for 30 minutes, the reaction mixture was extracted with ethyl acetate. The ethyl acetate layer was washed with saturated aqueous sodium chloride solution, dried (MgSO$_4$), and concentrated. A mixture of the residue and N,N-dimethylformamide dimethyl acetal (52.46 g) was refluxed for 1.5 hours. The reaction mixture was concentrated and the residue was dissolved in ethanol (500 ml). Hydrazine hydrate (20.09 g) was added to the solution, and refluxed for 3 hours. The reaction mixture was concentrated and saturated aqueous sodium bicarbonate solution was added to the residue. The mixture was extracted with ethyl acetate. The ethyl acetate layer was washed with saturated aqueous sodium chloride solution, dried (MgSO$_4$), and concentrated. The resulting crystals were collected by filtration to obtain ethyl 3-(2-thienyl)-1H-pyrazole-4-carboxylate (73.22 g, yield: 82%). This was recrystallized from ethyl acetate-hexane. Melting point: 123~124° C.

EXAMPLE 1

Sodium hydride (60%, oily, 2.55 g) was added to a mixture of methyl 4-phenylpyrrole-3-carboxylate (11.61 g), 4-benzyloxybenzyl chloride (15.23 g) and N,N-dimethylformamide (100 ml) at 0° C., and the mixture was stirred for one hour. The reaction mixture was poured into dilute hydrochloric acid, which was extracted with ethyl acetate. The ethyl acetate layer was washed with saturated aqueous sodium chloride solution, dried (MgSO$_4$), and then concentrated. The residue was subjected to silica gel column chromatography, and methyl 1-(4-benzyloxybenzyl)-4-phenylpyrrole-3-carboxylate (22.16 g, yield: 97%) was obtained from the fraction eluted with ethyl acetate-hexane (1:4, volume ratio). This was recrystallized from ethyl acetate-hexane. Melting point: 97–98° C.

EXAMPLE 2

Sodium hydride (60%, oily, 2.13 g) was added to a mixture of 1-(4-benzyloxybenzyl)-4-phenylpyrrole-3-carbaldehyde (18.00 g), ethyl diethylphosphonoacetate (12.09 g) and N,N-dimethylformamide (150 ml) at 0° C., and the mixture was stirred at room temperature for 2 hours. The reaction mixture was poured into dilute hydrochloric acid, which was extracted with ethyl acetate. The ethyl acetate layer was washed with saturated aqueous sodium chloride solution, dried (MgSO$_4$), and then concentrated. The residue was subjected to silica gel column chromatography, and ethyl(E)-3-[1-(4-benzyloxybenzyl)-4-phenyl-3-pyrrolyl]propenoate (20.16 g, yield: 94%) was obtained as colorless crystals from the fraction eluted with ethyl acetate-hexane (1:4, volume ratio). This was recrystallized from ethyl acetate-hexane. Melting point: 111–112° C.

EXAMPLE 3

Sodium hydride (60%, oily, 298 mg) was added to a mixture of methyl 4-phenylpyrrole-3-carboxylate (1.50 g), 4-(4-chloromethylphenoxymethyl)-5-methyl-2-phenyloxazole (2.34 g) and N,N-dimethylformamide (15 ml) at 0° C., and the mixture was stirred for one hour. The reaction mixture was poured into dilute hydrochloric acid, which was extracted with ethyl acetate. The ethyl acetate layer was washed with saturated aqueous sodium chloride solution, dried (MgSO$_4$), and then concentrated. The residue was subjected to silica gel column chromatography, and methyl 1-[4-(5-methyl-2-phenyl-4-oxazolylmethoxy)benzyl]-4-phenylpyrrole-3-carboxylate (3.12 g, yield: 88%) was obtained as colorless crystals from the fraction eluted with ethyl acetate-hexane (1:3, volume ratio). This was recrystallized from ethyl acetate-hexane. Melting point: 115–116° C.

EXAMPLE 4

Sodium hydride (60%, oily, 222 mg) was added to a mixture of 1-[4-(5-methyl-2-phenyl-4-oxazolylmethoxy)benzyl]-4-phenylpyrrole-3-carbaldehyde (2.37 g), ethyl diethylphosphonoacetate (1.1 ml) and tetrahydrofuran (30 ml) at 0° C., and the mixture was stirred at room temperature for 5 hours. The reaction mixture was poured into dilute hydrochloric acid, which was extracted with ethyl acetate. The ethyl acetate layer was washed with saturated aqueous sodium chloride solution, dried (MgSO$_4$), and then concentrated. The residue was subjected to silica gel column chromatography, and ethyl(E)-3-[1-[4-(5-methyl-2-phenyl-4-oxazolylmethoxy)benzyl]-4-phenyl-3-pyrrolyl]propenoate (2.13 g, yield: 78%) was obtained as colorless crystals from the fraction eluted with ethyl acetate-hexane (1:4, volume ratio). This was recrystallized from ethyl acetate-hexane. Melting point: 120–121° C.

EXAMPLE 5

A mixture of ethyl(E)-3-[1-[4-(5-methyl-2-phenyl-4-oxazolylmethoxy)benzyl]-4-phenyl-3-pyrrolyl]propenoate (600 mg), a 1N aqueous sodium hydroxide solution (5 ml), tetrahydrofuran (5 ml) and ethanol (5 ml) was stirred at 60° C. for 3 hours and 1N hydrochloric acid (7 ml) was added, which was extracted with ethyl acetate. The ethyl acetate layer was washed with saturated aqueous sodium chloride solution, dried (MgSO$_4$), and then concentrated. The crystals obtained were collected by filtration to yield (E)-3-[1-[4-(5-methyl-2-phenyl-4-oxazolylmethoxy)benzyl]-4-phenyl-3-pyrrolyl]propenoic acid (521 mg, yield: 92%). This was recrystallized from ethyl acetate-hexane. Melting point: 154–155° C.

EXAMPLE 6

A mixture of ethyl(E)-3-[1-[4-(5-methyl-2-phenyl-4-oxazolylmethoxy)benzyl]-4-phenyl-3-pyrrolyl]propenoate (700 mg), 5% palladium-carbon (1.00 g) and tetrahydrofuran (15 ml) was stirred for one hour at room temperature under a hydrogen atmosphere. After the palladium-carbon was removed by filtration, the filtrate was concentrated. The residue was subjected to silica gel column chromatography, and ethyl 3-[1-[4-(5-methyl-2-phenyl-4-oxazolylmethoxy)benzyl]-4-phenyl-3-pyrrolyl]propionate (618 mg, yield: 88%) was obtained as a colorless oily substance from the fraction eluted with ethyl acetate-hexane (2:7, volume ratio).
NMR(CDCl$_3$) δ: 1.20(3H, t, J=7.1 Hz), 2.43(3H, s), 2.47–2.56(2H, m), 2.91–3.00(2H, m), 4.08(2H, q, J-7.1 Hz), 4.95(2H, s), 4.98(2H, s), 6.51(1H, d, J=2.2 Hz), 6.71(1H, d, J=2.2 Hz), 6.98(2H, d, J=8.8 Hz), 7.10–7.47(10H, m), 7.97–8.04(2H, m).

EXAMPLE 7

A mixture of ethyl 3-[1-[4-(5-methyl-2-phenyl-4-oxazolylmethoxy)benzyl]-4-phenyl-3-pyrrolyl]propionate (531 mg), lithium hydroxide monohydrate (128 mg), tetrahydrofuran (6 ml), ethanol (4 ml) and water (4 ml) was stirred at room temperature for 2 hours and acidified by adding 1N hydrochloric acid, which was extracted with ethyl acetate. The ethyl acetate layer was washed with saturated aqueous sodium chloride solution, dried ($MgSO_4$), and then concentrated. The colorless crystals obtained were collected by filtration to yield 3-[1-[4-(5-methyl-2-phenyl-4-oxazolylmethoxy)benzyl]-4-phenyl-3-pyrrolyl]propionic acid (451 mg, yield: 90%). This was recrystallized from ethyl acetate-hexane. Melting point: 124–125° C.

EXAMPLE 8

A mixture of ethyl 3-[1-(4-hydroxybenzyl)-4-phenyl-3-pyrrolyl]propionate (1.01 g), 4-chloromethyl-2-(2-furyl)-5-methyloxazole (0.75 g), potassium carbonate (0.63 g) and N,N-dimethylformamide (15 ml) was stirred at room temperature overnight. The reaction mixture was poured into dilute hydrochloric acid, which was extracted with ethyl acetate. The ethyl acetate layer was washed with saturated aqueous sodium chloride solution, dried ($MgSO_4$), and then concentrated. The residue was subjected to silica gel column chromatography, and an oily substance was obtained from the fraction eluted with ethyl acetate-hexane (1:2, volume ratio). A mixture of the oily substance obtained, 1N aqueous sodium hydroxide solution (6 ml), tetrahydrofuran (5 ml) and ethanol (10 ml) was stirred at room temperature for 3 hours and the organic solvent was removed under reduced pressure. After adding water, the residue was acidified by adding 1N hydrochloric acid. The colorless crystals obtained were collected by filtration to yield 3-[1-[4-[2-(2-furyl)-5-methyl-4-oxazolylmethoxy]benzyl]-4-phenyl-3-pyrrolyl]propionic acid (1.02 g, yield: 73%). This was recrystallized from ethyl acetate-hexane. Melting point: 86–87° C.

EXAMPLE 9

A mixture of ethyl 3-[1-(4-hydroxybenzyl)-4-phenyl-3-pyrrolyl]propionate (1.30 g), 4-chloromethyl-5-methyl-2-(2-thienyl)oxazole (0.95 g), potassium carbonate (1.20 g) and N,N-dimethylformamide (15 ml) was stirred at room temperature overnight. The reaction mixture was poured into dilute hydrochloric acid, which was extracted with ethyl acetate. The ethyl acetate layer was washed with saturated aqueous sodium chloride solution, dried ($MgSO_4$), and then concentrated. The residue was subjected to silica gel column chromatography, and an oily substance was obtained from the fraction eluted with ethyl acetate-hexane (1:2, volume ratio). A mixture of the oily substance obtained, 1N aqueous sodium hydroxide solution (8 ml), tetrahydrofuran (10 ml) and ethanol (8 ml) was stirred at room temperature for 3 hours and the organic solvent was removed under reduced pressure. After adding water, the residue was acidified by adding 1N hydrochloric acid. The colorless crystals obtained were collected by filtration to yield 3-[1-[4-[5-methyl-2-(2-thienyl)-4-oxazolylmethoxy]benzyl]-4-phenyl-3-pyrrolyl]propionic acid (1.43 g, yield: 77%). This was recrystallized from ethyl acetate-hexane. Melting point: 117–118° C.

EXAMPLE 10

A mixture of ethyl 3-[1-(4-hydroxybenzyl)-4-phenyl-3-pyrrolyl]propionate (1.55 g), benzyl bromide (0.7 ml), potassium carbonate (0.92 g) and N,N-dimethylformamide (15 ml) was stirred at room temperature overnight. The reaction mixture was poured into dilute hydrochloric acid, which was extracted with ethyl acetate. The ethyl acetate layer was washed with saturated aqueous sodium chloride solution, dried ($MgSO_4$), and then concentrated. The residue was subjected to silica gel column chromatography, and an oily substance was obtained from the fraction eluted with ethyl acetate-hexane (1:4, volume ratio). A mixture of the oily substance obtained, 1N aqueous sodium hydroxide solution (8 ml), tetrahydrofuran (8 ml) and ethanol (8 ml) was stirred at room temperature for 3 hours and the organic solvent was removed under reduced pressure. After adding water, the residue was acidified by adding 1N hydrochloric acid. The colorless crystals obtained were collected by filtration to yield 3-[1-(4-benzyloxybenzyl)-4-phenyl-3-pyrrolyl]propionic acid (1.53 g, yield: 84%). This was recrystallized from ethyl acetate-hexane. Melting point: 130–131° C.

EXAMPLE 11

A mixture of ethyl 3-[1-(4-hydroxybenzyl)-4-phenyl-3-pyrrolyl]propionate (1.31 g), 2-picolyl chloride hydrochloride (0.73 g), potassium carbonate (0.69 g) and N,N-dimethylformamide (15 ml) was stirred at room temperature overnight. The reaction mixture was poured into water, which was extracted with ethyl acetate. The ethyl acetate layer was washed with saturated aqueous sodium chloride solution, dried ($MgSO_4$), and then concentrated. The residue was subjected to silica gel column chromatography, and an oily substance was obtained from the fraction eluted with ethyl acetate-hexane (1:2, volume ratio). A mixture of the oily substance obtained, 1N aqueous sodium hydroxide solution (8 ml), tetrahydrofuran (8 ml) and ethanol (8 ml) was stirred at room temperature for 3 hours and the organic solvent was removed under reduced pressure. After adding water, the residue was neutralized by adding 1N hydrochloric acid. The colorless crystals obtained were collected by filtration to yield 3-[4-phenyl-1-[4-(2-pyridylmethoxy)benzyl]-3-pyrrolyl]propionic acid (1.06 g, yield: 69%). This was recrystallized from ethanol-water. Melting point: 109–110° C.

EXAMPLE 12

A mixture of ethyl 3-[1-(4-hydroxybenzyl)-4-phenyl-3-pyrrolyl]propionate (1.35 g), 3-picolyl chloride hydrochloride (0.76 g), potassium carbonate (0.85 g) and N,N-dimethylformamide (15 ml) was stirred at room temperature overnight. The reaction mixture was poured into water, which was extracted with ethyl acetate. The ethyl acetate layer was washed with saturated aqueous sodium chloride solution, dried ($MgSO_4$), and then concentrated. The residue was subjected to silica gel column chromatography, and an oily substance was obtained from the fraction eluted with ethyl acetate-hexane (1:1, volume ratio). A mixture of the oily substance obtained, 1N aqueous sodium hydroxide solution (8 ml), tetrahydrofuran (8 ml) and ethanol (8 ml) was stirred at room temperature for 3 hours and the organic solvent was removed under reduced pressure. After adding water, the residue was neutralized by adding 1N hydrochloric acid. The colorless crystals obtained were collected by filtration to yield 3-[4-phenyl-1-[4-(3-pyridylmethoxy)benzyl]-3-pyrrolyl]propionic acid (0.76 g, yield: 48%). This was recrystallized from ethanol-water. Melting point: 131–132° C.

EXAMPLE 13

A mixture of ethyl 3-[1-(4-hydroxybenzyl)-4-phenyl-3-pyrrolyl]propionate (1.10 g), 4-picolyl chloride hydrochloride (0.60 g), potassium carbonate (0.88 g) and N,N-dimethylformamide (15 ml) was stirred at room temperature overnight. The reaction mixture was poured into water, which was extracted with ethyl acetate. The ethyl acetate layer was washed with saturated aqueous sodium chloride solution, dried (MgSO$_4$), and then concentrated. The residue was subjected to silica gel column chromatography, and an oily substance was obtained from the fraction eluted with ethyl acetate-hexane (1:1, volume ratio). A mixture of the oily substance obtained, 1N aqueous sodium hydroxide solution (6 ml), tetrahydrofuran (6 ml) and ethanol (6 ml) was stirred at room temperature for 3 hours and the organic solvent was removed under reduced pressure. After adding water, the residue was neutralized by adding 1N hydrochloric acid. The colorless crystals obtained were collected by filtration to yield 3-[4-phenyl-1-[4-(4-pyridylmethoxy)benzyl]-3-pyrrolyl]propionic acid (0.98 g, yield: 75%). This was recrystallized from acetone-hexane. Melting point: 124–125° C.

EXAMPLE 14

A toluene solution (5.66 g) of 40% diethyl azodicarboxylate was added dropwise slowly to a mixture of ethyl 3-[1-(4-hydroxybenzyl)-4-phenyl-3-pyrrolyl]propionate (2.84 g), 2-(5-methyl-2-phenyl-4-oxazolyl)ethanol (2.48 g), triphenylphosphine (3.31 g) and tetrahydrofuran (25 ml) at room temperature. After the above solution was stirred at room temperature for 2 hours, the reaction solvent was removed under reduced pressure. The residue was subjected to silica gel column chromatography, and an oily substance was obtained from the fraction eluted with ethyl acetate-hexane (1:4, volume ratio). A mixture of the oily substance obtained, 1N aqueous sodium hydroxide solution (15 ml), tetrahydrofuran (15 ml) and ethanol (15 ml) was stirred at room temperature for 3 hours and the organic solvent was removed under reduced pressure. After adding water, the residue was acidified by adding 1N hydrochloric acid. The colorless crystals obtained were collected by filtration to yield 3-[1-[4-[2-(5-methyl-2-phenyl-4-oxazolyl)ethoxy]benzyl]-4-phenyl-3-pyrrolyl]propionic acid (2.72 g, yield: 57%). This was recrystallized from ethanol-water. Melting point: 147–148° C.

EXAMPLE 15

Sodium hydride (60%, oily, 60.0 mg) was added to a solution of ethyl 3-[1-(4-hydroxybenzyl)-4-phenyl-3-pyrrolyl]propionate (524 mg) in N,N-dimethylformamide (10 ml) at 0° C., and the mixture was stirred at room temperature for 15 minutes. 2-(4-Chloromethyl-2-thiazolyl)pyrazine (349 mg) was added to the mixture, which was stirred at room temperature for 15 minutes. The reaction mixture was poured into water, which was extracted with ethyl acetate. The ethyl acetate layer was washed with saturated aqueous sodium chloride solution, dried (MgSO$_4$), and then concentrated. The residue was subjected to silica gel column chromatography, and ethyl 3-[4-phenyl-1-[4-[2-(2-pyradinyl)-4-thiazolylmethoxy]benzyl]-3-pyrrolyl]propionate (629 mg, yield: 80%) was obtained as an oily substance from the fraction eluted with ethyl acetate-hexane (1:1, volume ratio).

NMR(CDCl$_3$) δ: 1.20(3H, t, J=7.2 Hz), 2.52(2H, t, J=7.8 Hz), 2.95(2H, t, J=7.8 Hz), 4.08(2H, q, J=7.2 Hz), 4.96(2H, s), 5.28(2H, s), 6.51(1H, d, J=2.4 Hz), 6.72(1H, d, J=2.4 Hz), 6.99(2H, d, J=8.8 Hz), 7.16(2H, d, J=8.8 Hz), 7.19–7.42(5H, m), 7.50(1H, s), 8.56(1H, dd, J=2.4, 1.6 Hz), 8.61(1H, d, J=2.4 Hz), 9.43(1H, d, J=1.6 Hz).

EXAMPLE 16

A mixture of ethyl 3-[4-phenyl-1-[4-[2-(2-pyrazinyl)-4-thiazolylmethoxy]benzyl]-3-pyrrolyl]propionate (629 mg), 1N aqueous sodium hydroxide solution (2.5 ml), tetrahydrofuran (5 ml) and ethanol (5 ml) was stirred at room temperature overnight and 1N hydrochloric acid (2.5 ml) was added, which was extracted with ethyl acetate. The ethyl acetate layer was washed with saturated aqueous sodium chloride solution, dried (MgSO$_4$), and then concentrated. The colorless crystals obtained were collected by filtration to yield 3-[4-phenyl-1-[4-[2-(2-pyrazinyl)-4-thiazolylmethoxy]benzyl]-3-pyrrolyl]propionic acid (523 mg, yield: 88%) as colorless crystals. This was recrystallized from ethanol. Melting point: 137–138° C.

EXAMPLE 17

A toluene solution (1.04 g) of 40% diethyl azodicarboxylate was added dropwise slowly to a mixture of ethyl 3-[1-(4-hydroxybenzyl)-4-phenyl-3-pyrrolyl]propionate (699 mg), 3-furanmethanol (0.172 ml), triphenylphosphine (577 mg) and tetrahydrofuran (20 ml) at room temperature. After the solution was stirred at room temperature overnight, the reaction solvent was removed under reduced pressure. The residue was subjected to silica gel column chromatography, and ethyl 3-[1-[4-(3-furylmethoxy)benzyl]-4-phenyl-3-pyrrolyl]propionate (385 mg, yield: 45%) was obtained as an oily substance from the fraction eluted with ethyl acetate-hexane (1:4, volume ratio).

NMR(CDCl$_3$) δ: 1.19(3H, t, J=7.0 Hz), 2.51(2H, t, J=7.8 Hz), 2.94(2H, t, J=7.8 Hz), 4.08(2H, q, J=7.0 Hz), 4.91(2H, s), 4.94(2H, s), 6.48(1H, d, J=1.8 Hz), 6.50(1H, d, J=2.6 Hz), 6.71(1H, d, J=2.6 Hz), 6.92(2H, d, J=8.8 Hz), 7.12(2H, d, J=8.8 Hz), 7.16–7.43(5H, m), 7.49(1H, d, J=1.8 Hz).

EXAMPLE 18

A mixture of ethyl 3-[1-[4-(3-furylmethoxy)benzyl]-4-phenyl-3-pyrrolyl]propionate (382 mg), 1N aqueous sodium hydroxide solution (2 ml), tetrahydrofuran (4 ml), and ethanol (4 ml) was stirred at room temperature overnight, and 1N hydrochloric acid (2 ml) was added to the mixture, which was extracted with ethyl acetate. The ethyl acetate layer was washed with saturated aqueous sodium chloride solution, and dried (MgSO$_4$), then concentrated.

The colorless crystals obtained were collected by filtration to yield 3-[1-[4-(3-furylmethoxy)benzyl]-4-phenyl-3-pyrrolyl]propionic acid (257 mg, yield: 72%).

This was recrystallized from ethanol-hexane. Melting point: 110–111° C.

EXAMPLE 19

A toluene solution (1.74 g) of 40% diethyl azodicarboxylate was added dropwise slowly to a mixture of ethyl 3-[1-(4-hydroxybenzyl)-4-phenyl-3-pyrrolyl]propionate (873 mg), 2-thiophenemethanol (0.237 ml), triphenyl phosphine (984 mg), and tetrahydrofuran (20 ml) at room temperature. After the solution was stirred overnight at room temperature, the reaction solvent was removed under reduced pressure. The residue was subjected to silica gel column chromatography, and ethyl 3-[1-[4-(2-thienylmethoxy)benzyl]-4-phenyl-3-pyrrolyl]propionate (620 mg, yield: 56%) was obtained as an oily substance from the fraction eluted with ethyl acetate-hexane (1:4, volume ratio).

NMR(CDCl$_3$) δ: 1.19(3H, t, J=7.3 Hz), 2.51(2H, t, J=7.8 Hz), 2.95(2H, t, J=7.8 Hz), 4.08(2H, q, J=7.2 Hz), 4.94(2H, s), 5.20(2H, s), 6.50(1H, d, J=2.2 Hz), 6.70(1H, d, J=2.2 Hz), 6.90–7.02(3H, m), 7.14–7.25(4H, m), 7.30–7.41(5H, m).

EXAMPLE 20

A mixture of ethyl 3-[4-phenyl-1-[4-(2-thienylmethoxy)benzyl]-3-pyrrolyl]propionate (620 mg), 1N aqueous sodium hydroxide solution (3 ml), tetrahydrofuran (6 ml), and ethanol (6 ml) was stirred at room temperature for 7 hours, and 1N hydrochloric acid (3 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[4-phenyl-1-[4-(2-thienylmethoxy)benzyl]-3-pyrrolyl]propionic acid (272 mg, yield: 47%). This was recrystallized from ethyl acetate-hexane. Melting point: 127–128° C.

EXAMPLE 21

A toluene solution (1.74 g) of 40% diethyl azodicarboxylate was added dropwise slowly to a mixture of ethyl 3-[1-(4-hydroxybenzyl)-4-phenyl-3-pyrrolyl]propionate (873 mg), 3-thiophenemethanol (0.236 ml), triphenyl phosphine (984 mg), and tetrahydrofuran (20 ml) at room temperature. After the solution was stirred overnight at room temperature, the reaction solvent was removed under reduced pressure. The residue was subjected to silica gel column chromatography, and ethyl 3-[1-[4-(3-thienylmethoxy)benzyl]-4-phenyl-3-pyrrolyl]propionate (629 mg, yield: 56%) was obtained as an oily substance from the fraction eluted with ethyl acetate-hexane (1:4, volume ratio).

NMR(CDCl$_3$) δ: 1.19(3H, t, J=7.2 Hz), 2.51(2H, t, J=7.8 Hz), 2.95(2H, t, J=7.8 Hz), 4.08(2H, q, J=7.0 Hz), 4.93(2H, s), 5.05(2H, s), 6.50(1H, d, J=2.2 Hz), 6.71(1H, d, J=2.2 Hz), 6.92(2H, d, J=8.8 Hz), 7.08–7.22(4H, m), 7.31–7.41 (6H, m).

EXAMPLE 22

A mixture of ethyl 3-[4-phenyl-1-[4-(3-thienylmethoxy)benzyl]-3-pyrrolyl]propionate (624 mg), 1N aqueous sodium hydroxide solution (3 ml), tetrahydrofuran (6 ml), and ethanol (6 ml) was stirred at room temperature for 5 hours, and 1N hydrochloric acid (3 ml) was added to the mixture, which was extracted with ethyl acetate. The ethyl acetate layer was washed with saturated aqueous sodium chloride solution, dried (MgSO$_4$), and then concentrated. The colorless crystals obtained were collected by filtration to yield 3-[4-phenyl-1-[4-(3-thienylmethoxy)benzyl]-3-pyrrolyl]propionic acid (421 mg, yield: 72%). This was recrystallized from ethyl acetate-hexane. Melting point: 118–119° C.

EXAMPLE 23

A toluene solution (1.74 g) of 40% diethyl azodicarboxylate was added dropwise slowly to a mixture of ethyl 3-[1-(4-hydroxybenzyl)-4-phenyl-3-pyrrolyl]propionate (873 mg), furfuryl alcohol (0.216 ml), triphenyl phosphine (984 mg), and tetrahydrofuran (20 ml) at room temperature. After the solution was stirred overnight at room temperature, the reaction solvent was removed under reduced pressure. The residue was subjected to silica gel column chromatography, and ethyl 3-[1-[4-(2-furylmethoxy)benzyl]-4-phenyl-3-pyrrolyl]propionate (624 mg, yield: 58%) was obtained as an oily substance from the fraction eluted with ethyl acetate-hexane (1:4, volume ratio).

NMR(CDCl$_3$) δ: 1.20(3H, t, J=7.2 Hz), 2.52(2H, t, J=7.8 Hz), 2.95(2H, t, J=7.8 Hz), 4.08(2H, q, J=7.2 Hz), 4.94(2H, s), 4.99(2H, s), 6.38(1H, dd, J=3.2, 1.4 Hz), 6.43(1H, d, J=3.2 Hz), 6.50(1H, d, J=2.4 Hz), 6.71(1H, d, J=2.4 Hz), 6.95(2H, d, J=8.8 Hz), 7.10–7.45(8H, m).

EXAMPLE 24

A mixture of ethyl 3-[1-[4-(2-furylmethoxy)benzyl]-4-phenyl-3-pyrrolyl]propionate (624 mg), 1N aqueous sodium hydroxide solution (3 ml), tetrahydrofuran (6 ml), and ethanol (6 ml) was stirred at room temperature for 3 hours, and 1N hydrochloric acid (3 ml) was added to the mixture, which was extracted with ethyl acetate. The ethyl acetate layer was washed with saturated aqueous sodium chloride solution, dried (MgSO$_4$), then concentrated. The residue was subjected to silica gel column chromatography, and 3-[1-[4-(2-furylmethoxy)benzyl]-4-phenyl-3-pyrrolyl]propionic acid (386 mg, yield: 66%) was obtained as an oily substance from the fraction eluted with ethyl acetate-hexane (1:1, volume ratio).

NMR(CDCl$_3$) δ: 2.58(2H, t, J=7.8 Hz), 2.96(2H, t, J=7.8 Hz), 4.94(2H, s), 4.98(2H, s), 6.37(1H, dd, J=3.4, 1.8 Hz), 6.42(1H, d, J=3.4 Hz), 6.52(1H, d, J=2.4 Hz), 6.71(1H, d, J=2.4 Hz), 6.94(2H, d, J=8.8 Hz), 7.12(2H, d, J=8.8 Hz), 7.19–7.44(8H, m).

EXAMPLE 25

Sodium hydride (60%, oily, 60.0 mg) was added to a solution of ethyl 3-[1-(4-hydroxybenzyl)-4-phenyl-3-pyrrolyl]propionate (524 mg) in N,N-dimethylformamide (10 ml) at 0° C., and the mixture was stirred at room temperature for 15 minutes. 3-Chloromethyl-2-methylpyridine (212 mg) was added to the mixture, which was stirred at room temperature for 15 minutes. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and ethyl 3-[1-[4-(2-methyl-3-pyridylmethoxy)benzyl]-4-phenyl-3-pyrrolyl]propionate (581 mg, yield: 85%) was obtained as an oily substance from the fraction eluted with ethyl acetate-hexane (1:1, volume ratio).

NMR(CDCl$_3$) δ: 1.20(3H, t, J=7.0 Hz), 2.52(2H, t, J=7.8 Hz), 2.59(3H, s), 2.96(2H, t, J=7.8 Hz), 4.08(2H, q, J=7.0 Hz), 4.96(2H, s), 5.03(2H, s), 6.51(1H, d, J=2.6 Hz), 6.72 (1H, d, J=2.6 Hz), 6.72(1H, d, J=2.6 Hz), 6.94(2H, d, J=8.8 Hz), 7.11–7.42(8H, m), 7.71(1H, dd, J=7.8, 1.8 Hz), 8.48 (1H, dd, J=4.8, 1.8 Hz).

EXAMPLE 26

A mixture of ethyl 3-[1-[4-(2-methy-3-pyridylmethoxy)benzyl]-4-phenyl-3-pyrrolyl]propionate (568 mg), 1N aqueous sodium hydroxide solution (3 ml), tetrahydrofuran (6 ml), and ethanol (6 ml) was stirred at room temperature for 4 hours, and 1N hydrochloric acid (3 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[1-[4-(2-methyl-3-pyridylmethoxy)benzyl]-4-phenyl-3-pyrrolyl]propionic acid (465 mg, yield: 87%). This was recrystallized from ethyl acetate-hexane. Melting point: 158–159° C.

EXAMPLE 27

Sodium hydride (60%, oily, 60.0 mg) was added to a solution of ethyl 3-[1-(4-hydroxybenzyl)-4-phenyl-3-pyrrolyl]propionate (524 mg) in N,N-dimethylformamide (10 ml) at 0° C., and the mixture was stirred at room temperature for 15 minutes. 4-Chloromethyl-5-methyl-2-phenylthiazole (336 mg) was added to the mixture, which was stirred at room temperature for 30 minutes. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and ethyl 3-[1-[4-(5-methyl-2-phenyl-4-thiazolylmethoxy)benzyl]-4-phenyl-3-pyrrolyl]propionate (690 mg, yield: 86%) was obtained as an oily substance from the fraction eluted with ethyl acetate-hexane (1:2, volume ratio).

NMR(CDCl$_3$) δ: 1.19(3H, t, J=7.2 Hz), 2.51(2H, t, J=7.8 Hz), 2.52(3H, s), 2.95(2H, t, J=7.8 Hz), 4.08(2H, q, J=7.2 Hz), 4.94(2H, s), 5.15(2H, s), 6.50(1H, d, J=2.4 Hz), 6.71 (1H, d, J=2.4 Hz), 7.00(2H, d, J=8.8 Hz), 7.13(2H, d, J=8.8 Hz), 7.16–7.25(1H, m), 7.29–7.46(7H, m), 7.86–7.91(2H, m).

EXAMPLE 28

A mixture of ethyl 3-[1-[4-(5-methyl-2-phenyl-4-thiazolylmethoxy)benzyl]-4-phenyl-3-pyrrolyl]propionate (671 mg), 1N aqueous sodium hydroxide solution (2.5 ml), tetrahydrofuran (5 ml), and ethanol (5 ml) was stirred at room temperature overnight, and 1N hydrochloric acid (2.5 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[1-[4-(5-methyl-2-phenyl-4-thiazolylmethoxy)benzyl]-4-phenyl-3-pyrrolyl]propionic acid (495 mg, yield: 78%). This was recrystallized from ethyl acetate-hexane. Melting point: 157–158° C.

EXAMPLE 29

Sodium hydride (60%, oily, 60.0 mg) was added to a solution of ethyl 3-[1-(4-hydroxybenzyl)-4-phenyl-3-pyrrolyl]propionate (524 mg) in N,N-dimethylformamide (10 ml) at 0° C., and the mixture was stirred at room temperature for 15 minutes. 4-Chloromethyl-2-phenylthiazole (315 mg) was added to the mixture, which was stirred at room temperature for 30 minutes. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and ethyl 3-[4-phenyl-1-[4-(2-phenyl-4-thiazolylmethoxy)benzyl]-3-pyrrolyl]propionate (717 mg, yield: 91%) was obtained as an oily substance from the fraction eluted with ethyl acetate-hexane (1:3, volume ratio).

NMR(CDCl$_3$) δ: 1.20(3H, t, J=7.2 Hz), 2.52(2H, t, J=7.8 Hz), 2.95(2H, t, J=7.8 Hz), 4.08(2H, q, J=7.2 Hz), 4.95(2H, s), 5.25(2H, s), 6.51(1H, d, J=2.4 Hz), 6.71(1H, d, J=2.4 Hz), 6.98(2H, d, J=8.8 Hz), 7.13(2H, d, J=8.8 Hz), 7.18–7.25(1H, m), 7.30–7.49(8H, m), 7.91–7.99(2H, m).

EXAMPLE 30

A mixture of ethyl 3-[4-phenyl-1-[4-(2-phenyl-4-thiazolylmethoxy)benzyl]-3-pyrrolyl]propionate (706 mg), 1N aqueous sodium hydroxide solution (2.5 ml), tetrahydrofuran (5 ml), and ethanol (5 ml) was stirred at room temperature for 6 hours, and 1N hydrochloric acid (2.5 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[4-phenyl-1-[4-(2-phenyl-4-thiazolylmethoxy)benzyl]-3-pyrrolyl]propionic acid (619 mg, yield: 93%). This was recrystallized from ethanol-hexane. Melting point: 111–112° C.

EXAMPLE 31

Sodium hydride (60%, oily, 60.0 mg) was added to a solution of ethyl 3-[1-(4-hydroxybenzyl)-4-phenyl-3-pyrrolyl]propionate (524 mg) in N,N-dimethylformamide (10 ml) at 0° C., and the mixture was stirred at room temperature for 15 minutes. 4-Chloromethyl-2-(2-pyridyl)thiazole (316 mg) was added to the mixture, which was stirred at room temperature for 30 minutes. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography and ethyl 3-[4-phenyl-1-[4-[2-(2-pyridyl)-4-thiazolylmethoxy]benzyl]-3-pyrrolyl]propionate (590 mg, yield: 75%) was obtained as colorless crystals from the fraction eluted with ethyl acetate-hexane (1:2, volume ratio). This was recrystallized from ethyl acetate-hexane. Melting point: 81–82° C.

EXAMPLE 32

A mixture of ethyl 3-[4-phenyl-1-[4-[2-(2-pyridyl)-4-thiazolylmethoxy)benzyl]-3-pyrrolyl]propionate (471 mg), 1N aqueous sodium hydroxide solution (2 ml), tetrahydrofuran (5 ml), and ethanol (5 ml) was stirred at room temperature overnight, and 1N hydrochloric acid (2 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[4-phenyl-1-[4-[2-(2-pyridyl)-4-thiazolylmethoxy)benzyl]-3-pyrrolyl]propionic acid (408 mg, yield: 91%). This was recrystallized from ethanol-hexane. Melting point: 117–118° C.

EXAMPLE 33

Sodium hydride (60%, oily, 60.0 mg) was added to a solution of ethyl 3-[1-(4-hydroxybenzyl)-4-phenyl-3-pyrrolyl]propionate (524 mg) in N,N-dimethylformamide (10 ml) at 0° C., and the mixture was stirred at room temperature for 15 minutes. 4-Chloromethyl-2-(4-pyridyl)thiazole (316 mg) was added to the mixture, which was stirred at room temperature for 30 minutes. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and ethyl 3-[4-phenyl-1-[4-[2-(4-pyridyl)-4-thiazolylmethoxy)benzyl]-3-pyrrolyl]propionate (867 mg, yield: 89%) was obtained as an oily substance from the fraction eluted with ethyl acetate-hexane (2:1, volume ratio).

NMR(CDCl$_3$) δ: 1.20(3H, t, J=7.2 Hz), 2.51(2H, t, J=7.8 Hz), 2.95(2H, t, J=7.8 Hz), 4.08(2H, q, J=7.2 Hz), 4.95(2H, s), 5.27(2H, s), 6.51(1H, d, J=2.4 Hz), 6.71(1H, d, J=2.4 Hz), 6.98(2H, d, J=8.8 Hz), 7.14(2H, d, J=8.8 Hz), 7.18–7.26(1H, m), 7.29–7.41(4H, m), 7.45(1H, s), 7.81(2H, dd, J=4.8, 1.4 Hz), 8.71(2H, dd, J=4.8, 1.4 Hz).

EXAMPLE 34

A mixture of ethyl 3-[4-phenyl-1-[4-[2-(4-pyridyl)-4-thiazolylmethoxy)benzyl]-3-pyrrolyl]propionate (864 mg), 1N aqueous sodium hydroxide solution (3 ml), tetrahydrofuran (6 ml), and ethanol (6 ml) was stirred at room temperature overnight, and 1N hydrochloric acid (3 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[4-phenyl-1-[4-[2-(4-pyridyl)-4-thiazolylmethoxy)benzyl]-3-pyrrolyl]propionic acid (771 mg, yield: 94%). This was recrystallized from ethanol. Melting point: 149–150° C.

EXAMPLE 35

Sodium hydride (60%, oily, 60.0 mg) was added to a solution of ethyl 3-[1-(4-hydroxybenzyl)-4-phenyl-3-pyrrolyl]propionate (524 mg) in N,N-dimethylformamide (10 ml) at 0° C., and the mixture was stirred at room temperature for 15 minutes. 2-(3-Chloromethylphenyl)pyrazine (307 mg) was added to the mixture, which was stirred at room temperature for 30 minutes. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and ethyl 3-[4-phenyl-1-[4-[3-(2-pyrazinyl)benzyloxy]benzyl]-3-pyrrolyl]propionate (647 mg, yield: 83%) was obtained as an oily substance from the fraction eluted with ethyl acetate-hexane (1:1, volume ratio).

NMR(CDCl$_3$) δ: 1.19(3H, t, J=7.2 Hz), 2.52(2H, t, J=7.8 Hz), 2.95(2H, t, J=7.8 Hz), 4.08(2H, q, J=7.2 Hz), 4.94(2H, s), 5.15(2H, s), 6.51(1H, d, J=2.2 Hz), 6.71(1H, d, J=2.2 Hz), 6.96(2H, d, J=8.8 Hz), 7.13(2H, d, J=8.8 Hz), 7.18–7.41(5H, m), 7.49–7.56(2H, m), 7.92–8.00(1H, m), 8.10(1H, s), 8.52(1H, d, J=2.6 Hz), 8.64(1H, dd, J=2.6, 1.4 Hz), 9.04(1H, d, J=1.4 Hz).

EXAMPLE 36

A mixture of ethyl 3-[4-phenyl-1-[4-[3-(2-pyrazinyl)benzyloxy]benzyl]-3-pyrrolyl]propionate (647 mg), 1N aqueous sodium hydroxide solution (2.5 ml), tetrahydrofuran (5 ml), and ethanol (5 ml) was stirred at room temperature overnight, and 1N hydrochloric acid (2.5 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[4-phenyl-1-[4-[3-(2-pyrazinyl)benzyloxy]benzyl]-3-pyrrolyl]propionic acid (470 mg, yield: 77%). This was recrystallized from ethyl acetate-hexane. Melting point: 91–92° C.

EXAMPLE 37

Sodium hydride (60%, oily, 60.0 mg) was added to a solution of ethyl 3-[1-(4-hydroxybenzyl)-4-phenyl-3-pyrrolyl]propionate (524 mg) in N,N-dimethylformamide (10 ml) at 0° C., and the mixture was stirred at room temperature for 15 minutes. 4-Chloromethyl-2-(2-furyl)thiazole (299 mg) was added to the mixture, which was stirred at room temperature for 30 minutes. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and ethyl 3-[1-[4-[2-(2-furyl)-4-thiazolylmethoxy]benzyl]-4-phenyl-3-pyrrolyl]propionate (643 mg, yield: 84%) was obtained as an oily substance from the fraction eluted with ethyl acetate-hexane (1:3, volume ratio).

NMR(CDCl$_3$) δ: 1.20(3H, t, J=7.0 Hz), 2.52(2H, t, J=7.8 Hz), 2.95(2H, t, J=7.8 Hz), 4.08(2H, q, J=7.0 Hz), 4.95(2H, s), 5.23(2H, s), 6.52–6.55(2H, m), 6.71(1H, d, J=2.2 Hz), 6.96(2H, d, J=8.8 Hz), 7.01(1H, d, J=2.2 Hz), 7.13(2H, d, J=8.8 Hz), 7.16–7.41(6H, m), 7.51(1H, dd, J=1.8, 0.6 Hz).

EXAMPLE 38

A mixture of ethyl 3-[1-[4-[2-(2-furyl)-4-thiazolylmethoxy]benzyl]-4-phenyl-3-pyrrolyl]propionate (641 mg), 1N aqueous sodium hydroxide solution (2.5 ml), tetrahydrofuran (5 ml), and ethanol (5 ml) was stirred at room temperature for 5 hours, and 1N hydrochloric acid (2.5 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[1-[4-[2-(2-furyl)-4-thiazolylmethoxy]benzyl]-4-phenyl-3-pyrrolyl]propionic acid (485 mg, yield: 78%). This was recrystallized from ethanol-hexane. Melting point: 114–115° C.

EXAMPLE 39

Sodium hydride (60%, oily, 60.0 mg) was added to a solution of ethyl 3-[1-(4-hydroxybenzyl)-4-phenyl-3-pyrrolyl]propionate (524 mg) in N,N-dimethylformamide (10 ml) at 0° C., and the mixture was stirred at room temperature for 15 minutes. 4-Chloromethyl-2-(2-thienyl)thiazole (324 mg) was added to the mixture, which was stirred at room temperature for 30 minutes. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and ethyl 3-[4-phenyl-1-[4-[2-(2-thienyl)-4-thiazolylmethoxy]benzyl]-3-pyrrolyl]propionate (590 mg, yield: 74%) was obtained as an oily substance from the fraction eluted with ethyl acetate-hexane (1:3, volume ratio).

NMR(CDCl$_3$) δ: 1.20(3H, t, J=7.0 Hz), 2.52(2H, t, J=7.8 Hz), 2.95(2H, t, J=7.8 Hz), 4.08(2H, q, J=7.0 Hz), 4.94(2H, s), 5.22(2H, s), 6.51(1H, d, J=2.2 Hz), 6.70(1H, d, J=2.2 Hz), 6.96(2H, d, J=8.8 Hz), 7.03–7.40(10H, m), 7.52(1H, dd, J=3.6, 1.0 Hz).

EXAMPLE 40

A mixture of ethyl 3-[4-phenyl-1-[4-[2-(2-thienyl)-4-thiazolylmethoxy]benzyl]-3-pyrrolyl]propionate (582 mg), 1N aqueous sodium hydroxide solution (2.5 ml), tetrahydrofuran (5 ml), and ethanol (5 ml) was stirred at room temperature overnight, and 1N hydrochloric acid (2.5 ml) was added to the mixture, which was extracted with ethyl acetate. The ethyl acetate layer was washed with saturated aqueous sodium chloride solution, dried (MgSO$_4$), and concentrated. The colorless crystals obtained were collected by filtration to yield 3-[4-phenyl-1-[4-[2-(2-thienyl)-4-thiazolylmethoxy]benzyl]-3-pyrrolyl]propionic acid (421 mg, yield: 76%). This was recrystallized from ethyl acetate-hexane. Melting point: 106–107° C.

EXAMPLE 41

A mixture of ethyl 3-[1-(4-hydroxybenzyl)-4-phenyl-3-pyrrolyl]propionate (349 mg), 4-chloromethyl-2-methylthiazole hydrochloride (276 mg), potassium carbonate (276 mg) and N,N-dimethylformamide (5 ml) was stirred at 90° C. for 6 hours. The reaction mixture was poured into water, which was extracted with ethyl acetate. The ethyl acetate layer was washed with saturated aqueous sodium chloride solution, dried (MgSO$_4$), and concentrated. The residue was subjected to silica gel column chromatography, and ethyl 3-[1-[4-(2-methyl-4-thiazolylmethoxy)benzyl]-4-phenyl-3-pyrrolyl]propionate (373 mg, yield: 81%) was obtained as an oily substance from the fraction eluted with ethyl acetate-hexane (1:2, volume ratio).

NMR(CDCl$_3$) δ: 1.20(3H, t, J=7.2 Hz), 2.52(2H, t, J=7.8 Hz), 2.73(3H, s), 2.95(2H, t, J=7.8 Hz), 4.08(2H, q, J=7.2 Hz), 4.94(2H, s), 5.15(2H, s), 6.50(1H, d, J=2.2 Hz), 6.71 (1H, d, J=2.2 Hz), 6.95(2H, d, J=8.8 Hz), 7.12(2H, d, J=8.8 Hz), 7.14–7.41(6H, m).

EXAMPLE 42

A mixture of ethyl 3-[1-[4-(2-methyl-4-thiazolylmethoxy]benzyl]-4-phenyl-3-pyrrolyl]propionate (368 mg), 1N aqueous sodium hydroxide solution (2 ml), tetrahydrofuran (4 ml), and ethanol (4 ml) was stirred at room temperature for 4 hours, and 1N hydrochloric acid (2 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[1-[4-(2-methyl-4-thiazolylmethoxy]benzyl]-4-phenyl-3-pyrrolyl]propionic acid (251 mg, yield: 73%). This was recrystallized from ethanol-hexane. Melting point: 113–114° C.

EXAMPLE 43

Sodium hydride (60%, oily, 60.0 mg) was added to a solution of ethyl 3-[1-(4-hydroxybenzyl)-4-phenyl-3-pyrrolyl]propionate (524 mg) in N,N-dimethylformamide (10 ml) at 0° C., and the mixture was stirred at room temperature for 15 minutes. 4-Chloromethyl-2-phenyloxazole (290 mg) was added to the mixture, which was stirred at room temperature for 30 minutes. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatograpy, and ethyl 3-[4-phenyl-1-[4-(2-phenyl-4-oxazolylmethoxy)benzyl]-3-pyrrolyl]propionate (550 mg, yield: 72%) was obtained as an oily substance from the fraction eluted with ethyl acetate-hexane (1:3, volume ratio).

NMR(CDCl$_3$) δ: 1.20(3H, t, J=7.2 Hz), 2.52(2H, t, J=7.8 Hz), 2.95(2H, t, J=7.8 Hz), 4.08(2H, q, J=7.2 Hz), 4.95(2H, s), 5.07(2H, s), 6.51(1H, d, J-2.4 Hz), 6.71(1H, d, J=2.4 Hz), 6.97(2H, d, J=8.8 Hz), 7.01–7.50(10H, m), 7.73(1H, s), 8.01–8.10(2H, m).

EXAMPLE 44

A mixture of ethyl 3-[4-phenyl-1-[4-(2-phenyl-4-oxazolylmethoxy]benzyl]-3-pyrrolyl]propionate (532 mg), 1N aqueous sodium hydroxide solution (2.5 ml), tetrahydrofuran (5 ml), and ethanol (5 ml) was stirred at room temperature overnight, and 1N hydrochloric acid (2.5 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[4-phenyl-1-[4-(2-phenyl-4-oxazolylmethoxy]benzyl]-3-pyrrolyl]propionic acid (428 mg, yield: 85%). This was recrystallized from ethanol-hexane. Melting point: 139–140° C.

EXAMPLE 45

Sodium hydride (60%, oily, 60.0 mg) was added to a solution of ethyl 3-[1-(4-hydroxybenzyl)-4-phenyl-3-pyrrolyl]propionate (524 mg) in N,N-dimethylformamide (10 ml) at 0° C., and the mixture was stirred at room temperature for 15 minutes. 4-Chloromethyl-2-(3-pyridyl)thiazole (316 mg) was added to the mixture, which was stirred at room temperature for 30 minutes. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatograpy, and ethyl 3-[4-phenyl-1-[4-[2-(3-pyridyl)-4-thiazolylmethoxy]benzyl]-3-pyrrolyl]propionate (657 mg, yield: 84%) was obtained as an oily substance from the fraction eluted with ethyl acetate-hexane (1:1, volume ratio).

NMR(CDCl$_3$) δ: 1.20(3H, t, J=7.2 Hz), 2.52(2H, t, J=7.8 Hz), 2.95(2H, t, J=7.8 Hz), 4.08(2H, q, J=7.2 Hz), 4.96(2H, s), 5.27(2H, s), 6.51(1H, d, J=2.4 Hz), 6.71(1H, d, J=2.4 Hz), 6.99(2H, d, J=8.6 Hz), 7.02–7.42(9H, m), 8.24(1H, ddd, J=8.2, 2.0, 1.2 Hz), 8.66(1H, dd, J=4.8, 1.2 Hz), 9.17(1H, d, J=2.0 Hz).

EXAMPLE 46

A mixture of ethyl 3-[4-phenyl-1-[4-[2-(3-pyridyl)-4-thiazolylmethoxy]benzyl]-3-pyrrolyl]propionate (655 mg), 1N aqueous sodium hydroxide solution (2.5 ml), tetrahydrofuran (5 ml), and ethanol (5 ml) was stirred at room temperature for 6 hours, and 1N hydrochloric acid (2.5 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[4-phenyl-1-[4-[2-(3-pyridyl)-4-thiazolylmethoxy]benzyl]-3-pyrrolyl]propionic acid (537 mg, yield: 92%). This was recrystallized from ethanol. Melting point: 118–119° C.

EXAMPLE 47

Thionyl chloride (830 mg) was added dropwise to a solution of 4-[2-[N-methyl-N-(2-pyridyl)amino]ethoxy]benzyl alcohol (1.50 g) in toluene (40 ml) at 0° C. After stirring at room temperature for 2 hours, the reaction mixture was concentrated. The residue and methyl 4-phenylpyrrole-3-carboxylate (1.40 g) were dissolved in N,N-dimethylformamide (40 ml). Sodium hydride (60%, oily, 465 mg) was added to the solution at 0° C., which was stirred at room temperature for 3 days. The reaction mixture was poured into saturated aqueous sodium chloride solution, which was extracted with ethyl acetate. The ethyl acetate layer was washed with water, then with saturated aqueous sodium chloride solution, then dried (MgSO$_4$), and concentrated. The residue was subjected to silica gel column chromatograpy, and methyl 1-[4-[2-[N-methyl-N-(2-pyridyl)amino]ethoxy]benzyl]-4-phenylpyrrole-3-carboxylate (1.80 g, yield: 7 0%) was obtained as an oily substance from the fraction eluted with ethyl acetate-hexane (1:3, volume ratio).

NMR(CDCl$_3$) δ: 3.15(3H, s), 3.70(3H, s), 3.99(2H, t, J=5.0 Hz), 4.19(2H, t, J=5.0 Hz), 4.97(2H, s), 6.5–6.6(2H, m), 6.64(1H, d, J=2.5 Hz), 6.88(2H, d, J=8.5 Hz), 7.13(2H, d, J=8.5 Hz), 7.2–7.55(7H, m), 8.1–8.2(1H, m).

EXAMPLE 48

Sodium hydride (60%, oily, 200.0 mg) was added to a solution of 1-[4-[2-[N-methyl-N-(2-pyridyl)amino]ethoxy]benzyl]-4-phenylpyrrole-3-carbaldehyde (1.35 g) and ethyl diethylphosphonoacetate (1.10 g) in N,N-dimethylformamide (30 ml) at 0° C., and the mixture was stirred at room temperature for 1 hour. The reaction mixture was poured into ice water, then neutralized using 2N hydrochloric acid, which was extracted with ethyl acetate. The ethyl acetate layer was washed with water, then with saturated aqueous sodium chloride solution, dried (MgSO$_4$), then concentrated. The residue was subjected to silica gel column chromatograpy, and ethyl (E)-3-[1-[4-[2-[N-methyl-N-(2-pyridyl)amino]ethoxy]benzyl]-4-phenyl-3-pyrrolyl]propenoate (1.35 g, yield: 85%) was obtained as an oily substance from the fraction eluted with acetone-hexane (1:2, volume ratio).

NMR(CDCl$_3$) δ: 1.26(3H, t, J=7 Hz), 3.16(3H, s), 3.95–4.25(6H, m), 4.98(2H, s), 6.05(1H, d, J=16 Hz), 6.5–6.6(2H, m), 6.69(1H, d, J=2.5 Hz), 6.88(2H, d, J=9 Hz), 7.03(1H, d, J=2.5 Hz), 7.14(2H, d, J=9 Hz), 7.2–7.55(6H, m), 7.69(2H, d, J=16 Hz), 8.1–8.2(1H, m).

EXAMPLE 49

Catalytic hydrogenation of a mixture of ethyl(E)-3-[1-[4-[2-[N-methyl-N-(2-pyridyl)amino]ethoxy]benzyl]-4-phenyl-3-pyrrolyl]propenoate (1.32 g), 5% palladium-carbon (1.0 g), tetrahydrofuran (40 ml) and ethanol (40 ml) was conducted at ordinary temperature and ordinary pressure. After the palladium-carbon was removed by filtration, the filtrate was concentrated. The residue was dissolved in a mixed solution of tetrahydrofuran (10 ml) and ethanol (10 ml), then 1N aqueous sodium hydroxide solution (10 ml) was added to the solution, which was stirred at room temperature for 2 hours. The reaction mixture was poured into water, then neutralized with 1N hydrochloric acid (10 ml), which was extracted with ethyl acetate. The ethyl acetate layer was washed with saturated aqueous sodium chloride solution, dried (MgSO$_4$), and concentrated. The colorless crystals obtained were collected by filtration to yield 3-[1-[4-[2-[N-methyl-N-(2-pyridyl)amino]ethoxy]benzyl]-4-phenyl-3-pyrrolyl]propionic acid (900 mg, yield: 72%). This was recrystallized from acetone-ethyl acetate. Melting point: 110–111° C.

EXAMPLE 50

3-Phenoxybenzyl chloride (11.32 g) and ethyl 3-phenyl-1H-pyrazole-4-carboxylate (11.30 g) were dissolved in N,N-dimethylformamide (100 ml). Sodium hydride (60%, oily, 2.49 g) was added to the solution at 0° C., and the solution was stirred at room temperature for 20 hours. The reaction mixture was poured into saturated aqueous sodium chloride solution, which was extracted with ethyl acetate. The ethyl acetate layer was washed with water, then with saturated aqueous sodium chloride solution, dried (MgSO$_4$), then concentrated. The residue was subjected to silica gel column chromatograpy, and an oily substance was obtained from the fraction eluted with ethyl acetate-hexane (1:2, volume ratio). A mixture of the oily substance obtained, potassium hydroxide (8.53 g) and ethanol (150 ml) was refluxed for 5 hours. After the reaction solvent was removed under reduced pressure, water was added to the mixture, then the mixture was acidified using 1N hydrochloric acid. The colorless crystals obtained were collected by filtration to yield 1-(3-phenoxybenzyl)-3-phenyl-1H-pyrazole-4-carboxylic acid (14.83 g, yield: 77%). This was recrystallized from acetone-hexane. Melting point: 148–149° C.

EXAMPLE 51

Sodium hydride (60%, oily, 0.36 g) was added to a mixture of methyl 4-phenylpyrrole-3-carboxylate (1.81 g), 6-benzyloxy-2-chloromethylnaphthalene (2.54 g) and N,N-dimethylformamide (35 ml), and the mixture was stirred at room temperature for 30 minutes. The reaction mixture was poured into water, which was extracted with ethyl acetate. The ethyl acetate layer was washed with water, then with saturated aqueous sodium chloride solution, dried (MgSO$_4$), then concentrated. The residue was subjected to silica gel column chromatograpy, and methyl 1-(6-benzyloxy-2-naphthylmethyl)-4-phenylpyrrole-3-carboxylate (3.20 g, yield: 80%) was obtained as colorless crystals from the fraction eluted with tetrahydrofuran-hexane (1:2, volume ratio). This was recrystallized from ethyl acetate-hexane. Melting point: 109–110° C.

EXAMPLE 52

Sodium hydride (60%, oily, 0.20 g) was added to a mixture of ethyl diethylphosphonoacetate (0.992 ml) and tetrahydrofuran (20 ml) at 0° C., and the mixture was stirred at room temperature for 30 minutes. A solution of 1-(6-benzyloxy-2-naphthylmethyl)-4-phenylpyrrole-3-carbaldehyde (2.09 g) in tetrahydrofuran (20 ml) was slowly added to the mixture, which was stirred at room temperature for 1 hour. The reaction mixture was poured into water, which was extracted with ethyl acetate. The ethyl acetate layer was washed with saturated aqueous sodium chloride solution, dried (MgSO$_4$), then concentrated. The colorless crystals obtained were collected by filtration to yield ethyl(E)-3-[1-(6-benzyloxy-2-naphthylmethyl)-4-phenyl-3-pyrrolyl]propenoate (1.65 g, yield: 68%). This was recrystallized from ethyl acetate-hexane. Melting point: 119–120° C.

EXAMPLE 53

Sodium hydride (60%, oily, 36.0 mg) was added to a solution of ethyl 3-[1-(6-hydroxy-2-naphthylmethyl)-4-phenyl-3-pyrrolyl]propionate (360 mg) in N,N-dimethylformamide (10 ml) at 0° C., and the mixture was stirred at room temperature for 30 minutes. 4-Chloromethyl-5-methyl-2-phenyloxazole (207 mg) was added to the mixture, which was stirred at room temperature for 1 hour. The reaction mixture was poured into water, which was extracted with ethyl acetate. The ethyl acetate layer was washed with saturated aqueous sodium chloride solution, dried ($MgSO_4$), and concentrated. The residue was subjected to silica gel column chromatograpy, and ethyl 3-[1-[6-(5-methyl-2-phenyl-4-oxazolylmethoxy)-2-naphthylmethyl]-4-phenyl-3-pyrrolyl]propionate (304 mg, yield: 59%) was obtained as an oily substance from the fraction eluted with ethyl acetate-hexane (1:3, volume ratio).

NMR($CDCl_3$) δ: 1.17(3H, t, J=7.0 Hz), 2.47(3H, s), 2.52(2H, t, J=7.8 Hz), 2.97(2H, t, J=7.8 Hz), 4.06(2H, q, J=7.0 Hz), 5.11(2H, s), 5.13(2H, s), 6.56(1H, d, J=2.2 Hz), 6.77(1H, d, J=2.2 Hz), 7.15–7.48(11H, m), 7.56(1H, s), 7.71(2H, d, J=8.8 Hz), 7.99–8.06(2H, m).

EXAMPLE 54

A mixture of ethyl 3-[1-[6-(5-methyl-2-phenyl-4-oxazolylmethoxy)-2-naphthylmethyl]-4-phenyl-3-pyrrolyl]propionate (304 mg), 1N aqueous sodium hydroxide solution (2 ml), tetrahydrofuran (4 ml) and ethanol (4 ml) was stirred at room temperature for 7 hours, and 1N hydrochloric acid (2 ml) was added to the mixture, which was extracted with ethyl acetate. The ethyl acetate layer was washed with saturated aqueous sodium chloride solution, dried ($MgSO_4$), then concentrated. The colorless crystals obtained were collected by filtration to yield 3-[1-[6-(5-methyl-2-phenyl-4-oxazolylmethoxy)-2-naphthylmethyl]-4-phenyl-3-pyrrolyl]propionic acid (243 mg, yield: 84%). This was recrystallized from tetrahydrofuran-hexane. Melting point: 122–123° C.

EXAMPLE 55

Sodium hydride (60%, oily, 36.0 mg) was added to a solution of ethyl 3-[1-(6-hydroxy-2-naphthylmethyl)-4-phenyl-3-pyrrolyl]propionate (360 mg) in N,N-dimethylformamide (10 ml) at 0° C., and the mixture was stirred at room temperature for 15 minutes. 2-Fluorobenzyl chloride (0.119 ml) was added to this mixture, which was stirred at room temperature for 1 hour. The reaction mixture was poured into water, which was extracted with ethyl acetate. The ethyl acetate layer was washed with saturated aqueous sodium chloride solution, dried ($MgSO_4$), and concentrated. The residue was subjected to silica gel column chromatograpy, and ethyl 3-[1-[6-(2-fluorobenzyloxy)-2-naphthylmethyl]-4-phenyl-3-pyrrolyl]propionate (404 mg, yield: 88%) was obtained as an oily substance from the fraction eluted with ethyl acetate-hexane (1:3, volume ratio).

NMR($CDCl_3$) δ: 1.17(3H, t, J=7.2 Hz), 2.52(2H, t, J=7.8 Hz), 2.96(2H, t, J=7.8 Hz), 4.06(2H, q, J=7.2 Hz), 5.12(2H, s), 5.24(2H, s), 6.55(1H, d, J=2.4 Hz), 6.76(1H, d, J=2.4 Hz), 7.06–7.43(11H, m), 7.51–7.59(2H, m), 7.68–7.75(2H, m).

EXAMPLE 56

A mixture of ethyl 3-[1-[6-(2-fluorobenzyloxy)-2-naphthylmethyl]-4-phenyl-3-pyrrolyl]propionate (401 mg), 1N aqueous sodium hydroxide solution (2 ml), tetrahydrofuran (4 ml) and ethanol (4 ml) was stirred at room temperature for 7 hours, and 1N hydrochloric acid (2 ml) was added to the mixture, which was extracted with ethyl acetate. The ethyl acetate layer was washed with saturated aqueous sodium chloride solution, dried ($MgSO_4$), then concentrated. The colorless crystals obtained were collected by filtration to yield 3-[1-[6-(2-fluorobenzyloxy)-2-naphthylmethyl]-4-phenyl-3-pyrrolyl]propionic acid (289 mg, yield: 76%). This was recrystallized from ethanol-hexane. Melting point: 143–144° C.

EXAMPLE 57

Sodium hydride (60%, oily, 60.0 mg) was added to a solution of ethyl 3-[1-(6-hydroxy-2-naphthylmethyl)-4-phenyl-3-pyrrolyl]propionate (599 mg) in N,N-dimethylformamide (10 ml) at 0° C., and the mixture was stirred at room temperature for 15 minutes. 3-Picolyl chloride (230 mg) was added to the mixture, which was stirred at room temperature for 15 minutes. The reaction mixture was poured into water, which was extracted with ethyl acetate. The ethyl acetate layer was washed with saturated aqueous sodium chloride solution, dried ($MgSO_4$), and concentrated. The residue was subjected to silica gel column chromatography, and ethyl 3-[4-phenyl-1-[6-(3-pyridylmethoxy)-2-naphthylmethyl]-3-pyrrolyl]propionate (647 mg, yield: 88%) was obtained as an oily substance from the fraction eluted with ethyl acetate-hexane (1:1, volume ratio).

NMR($CDCl_3$) δ: 1.17(3H, t, J=7.0 Hz), 2.52(2H, t, J-7.6 Hz), 2.97(2H, t, J=7.6 Hz), 4.06(2H, q, J=7.0 Hz), 5.13(2H, s), 5.19(2H, s), 6.56(1H, d, J=2.6 Hz), 6.76(1H, d, J=2.6 Hz), 7.16–7.43(9H, m), 7.57(1H, s), 7.68–7.84(3H, m), 8.60(1H, d, J=4.4 Hz), 8.74(1H, s).

EXAMPLE 58

A mixture of ethyl 3-[4-phenyl-1-[6-(3-pyridylmethoxy)-2-naphthylmethyl]-3-pyrrolyl]propionate (638 mg), 1N aqueous sodium hydroxide solution (2.5 ml), tetrahydrofuran (5 ml) and ethanol (5 ml) was stirred at room temperature overnight, and 1N hydrochloric acid (2.5 ml) was added to the mixture, which was extracted with ethyl acetate. The ethyl acetate layer was washed with saturated aqueous sodium chloride solution, dried ($MgSO_4$), then concentrated. The colorless crystals obtained were collected by filtration to obtain 3-[4-phenyl-1-[6-(3-pyridylmethoxy)-2-naphthylmethyl]-3-pyrrolyl]propionic acid (508 mg, yield: 84%). This was recrystallized from ethanol. Melting point: 158–159° C.

EXAMPLE 59

Sodium hydride (60%, oily, 80.0 mg) was added to a solution of ethyl 3-[1-(6-hydroxy-2-naphthylmethyl)-4-phenyl-3-pyrrolyl]propionate (799 mg) in N,N-dimethylformamide (10 ml) at 0° C., and the mixture was stirred at room temperature for 15 minutes. 3-Chloromethyl-2-methylpyridine (283 mg) was added to the mixture, which was stirred at room temperature for 30 minutes. The reaction mixture was poured into water, which was extracted with ethyl acetate. The ethyl acetate layer was washed with saturated aqueous sodium chloride solution, dried ($MgSO_4$), then concentrated. The residue was subjected to silica gel column chromatograpy, and ethyl 3-[1-[6-(2-methyl-3-pyridylmethoxy)-2-naphthylmethyl]-4-phenyl-3-pyrrolyl]propionate (959 mg, yield: 95%) was obtained as an oily substance from the fraction eluted with ethyl acetate-hexane (1:2, volume ratio).

NMR($CDCl_3$) δ: 1.17(3H, t, J=7.2 Hz), 2.52(2H, t, J=7.8 Hz), 2.63(3H, s), 2.97(2H, t, J=7.8 Hz), 4.07(2H, q, J=7.2

Hz), 5.13(2H, s), 5.15(2H, s), 6.56(1H, d, J=2.6 Hz), 6.77 (1H, d, J=2.6 Hz), 7.14–7.48(9H, m), 7.57(1H, s), 7.69–7.79 (3H, m), 8.49(1H, dd, J=4.8, 1.8 Hz).

EXAMPLE 60

A mixture of ethyl 3-[1-[6-(2-methyl-3-pyridylmethoxy)-2-naphthylmethyl]-4-phenyl-3-pyrrolyl]propionate (959 mg), 1N aqueous sodium hydroxide solution (4 ml), tetrahydrofuran (8 ml) and ethanol (8 ml) was stirred at room temperature overnight, and 1N hydrochloric acid (4 ml) was added to the mixture, which was extracted with ethyl acetate. The ethyl acetate layer was washed with saturated aqueous sodium chloride solution, dried ($MgSO_4$), then concentrated. The colorless crystals obtained were collected by filtration to yield 3-[1-[6-(2-methyl-3-pyridylmethoxy)-2-naphthylmethyl]-4-phenyl-3-pyrrolyl]propionic acid (750 mg, yield: 83%). This was recrystallized from ethanol. Melting point: 163–164° C.

EXAMPLE 61

Sodium hydride (60%, oily, 0.22 g) was added to a mixture of ethyl 4-(2-pyridyl)pyrrole-3-carboxylate (1.10 g), 4-(4-chlorometylphenoxymethyl)-5-methyl-2-phenyloxazole (1.83 g) and N,N-dimethylformamide (25 ml) at 0° C., and the mixture was stirred for 1 hour. The reaction mixture was poured into water, which was extracted with ethyl acetate. The ethyl acetate layer was washed with water, then with saturated aqueous sodium chloride solution, dried ($MgSO_4$), and concentrated. The residue was subjected to silica gel column chromatograpy, and ethyl 1-[4-(5-methyl-2-phenyl-4-oxazolylmethoxy)benzyl]-4-(2-pyridyl)pyrrole-3-carboxylate (2.43 g, yield: 97%) was obtained as an oily substance from the fraction eluted with tetrahydrofuran-hexane (1:1, volume ratio).

NMR($CDCl_3$) δ: 1.28(3H, t, J=7.2 Hz), 2.44(3H, s), 4.22(2H, q, J=7.2 Hz), 4.99(2H, s), 5.02(2H, s), 6.94–7.24 (6H, m), 7.35–7.48(4H, m), 7.60–7.72(1H, m), 7.84–7.92 (1H, m), 7.96–8.08(2H, m), 8.51–8.58(1H, m).

EXAMPLE 62

Sodium hydride (60%, oily, 0.17 g) was added to a mixture of ethyl diethylphosphonoacetate (1.00 g) and N,N-dimethylformamide (5 ml) at 0° C., and the mixture was stirred at room temperature for 30 minutes. A solution of 1-[4-(5-methyl-2-phenyl-4-oxazolylmethoxy)benzyl]-4-phenylpyrrole-3-carbaldehyde (1.65° g) in N,N-dimethylformamide (10 ml) was added slowly to the mixture, which was stirred at room temperature for 3 hours. The reaction mixture was poured into water, which was extracted with ethyl acetate. The ethyl acetate layer was washed with saturated aqueous sodium chloride solution, dried ($MgSO_4$), then concentrated. The residue was subjected to silica gel column chromatograpy, and ethyl(E)-3-[1-[4-(5-methyl-2-phenyl-4-oxazolylmethoxy)benzyl]-4-(2-pyridyl)-3-pyrrolyl]propenoate (1.83 g, yield: 96%) was obtained as an oily substance from the fraction eluted with ethyl acetate-hexane (1:1 volume ratio).

NMR($CDCl_3$) δ: 1.29(3H, t, J=7.2 Hz), 2.44(3H, s), 4.21(2H, q, J=7.2 Hz), 4.99(2H, s), 5.02(2H, s), 6.14(1H, d, J=16.0 Hz), 6.94–7.24(7H, m), 7.34–7.52(4H, m), 7.58–7.72 (1H, m), 7.86–8.16(3H, m), 8.58–8.66(1H, m).

EXAMPLE 63

A mixture of ethyl(E)-3-[1-[4-(5-methyl-2-phenyl-4-oxazolylmethoxy)benzyl]-4-(2-pyridyl)-3-pyrrolyl]propenoate (1.80 g), 5% palladium-carbon (2.32 g) and tetrahydrofuran (30 ml) was stirred overnight in a hydrogen atmosphere at room temperature. After the palladium-carbon was removed by filtration, the filtrate was concentrated. The residue was subjected to silica gel column chromatograpy, and ethyl 3-[1-[4-(5-methyl-2-phenyl-4-oxazolylmethoxy)benzyl]-4-(2-pyridyl)-3-pyrrolyl]propionate (1.61 g, yield: 89%) was obtained as an oily substance from the fraction eluted with ethyl acetate-hexane (1:2, volume ratio).

NMR($CDCl_3$) δ: 1.21(3H, t, J=7.0 Hz), 2.43(3H, s), 2.56–2.66(2H, m), 3.04–3.16(2H, m), 4.09(2H, q, J=7.0 Hz), 4.96(2H, s), 4.98(2H, s), 6.51(1H, d, J=2.6 Hz), 6.92–7.18 (6H, m), 7.34–7.66(5H, m), 7.94–8.04(2H, m), 8.50–8.56 (1H, m).

EXAMPLE 64

A mixture of ethyl 3-[1-[4-(5-methyl-2-phenyl-4-oxazolylmethoxy)benzyl]-4-(2-pyridyl)-3-pyrrolyl propionate (1.46 g), 1N aqueous sodium hydroxide solution (6 ml), tetrahydrofuran (5 ml) and ethanol (10 ml) was stirred at room temperature for 5 hours, and 1N hydrochloric acid (6 ml) was added to the mixture, which was extracted with ethyl acetate. The ethyl acetate layer was washed with saturated aqueous sodium chloride solution, dried ($MgSO_4$), and concentrated. The colorless crystals obtained were collected by filtration to obtain 3-[1-[4-(5-methyl-2-phenyl-4-oxazolylmethoxy)benzyl]-4-(2-pyridyl)-3-pyrrolyl]propionic acid (1.20 g, yield: 87%). This was recrystallized from N,N-dimethylformamide-water. Melting point: 155–156° C.

EXAMPLE 65

Sodium hydride (60%, oily, 2.20 g) was added to a mixture of methyl 4-phenylpyrrole-3-carboxylate (11.10 g), 3,5-dibenzyloxybenzyl methanesulfonate (21.9 g) and N,N-dimethylformamide (200 ml) at 0° C., and the mixture was stirred at room temperature for 30 minutes. The reaction mixture was poured into water, which was extracted with ethyl acetate. The ethyl acetate layer was washed with water, then with saturated aqueous sodium chloride solution, dried ($MgSO_4$), and concentrated. The residue was subjected to silica gel column chromatography, and methyl 1-(3,5-dibenzyloxybenzyl)-4-phenylpyrrole-3-carboxylate (26.4 g, yield: 95%) was obtained as an oily substance from the fraction eluted with tetrahydrofuran-hexane (1:2, volume ratio).

NMR($CDCl_3$) δ: 3.72(3H, s), 4.95(2H, s), 4.99(4H, s), 6.41(1H, d, J=2.6 Hz), 6.56(1H, t, J=2.2 Hz), 6.64(1H, d, J=2.6 Hz), 7.21–7.42(15H, m), 7.44–7.50(2H, m).

EXAMPLE 66

Sodium hydride (60%, oily, 2.11 g) was added to a mixture of ethyl diethylphosphonoacetate (10.5 ml) and tetrahydrofuran (150 ml) at 0° C., which was stirred at room temperature for 30 minutes. A solution of 1-(3,5-dibenzyloxybenzyl)-4-phenylpyrrole-3-carbaldehyde (22.7 g) in tetrahydrofuran (20 ml) was slowly added to the mixture, which was stirred at room temperature for 1 hour. The reaction mixture was poured into water, which was extracted with ethyl acetate. The ethyl acetate layer was washed with saturated aqueous sodium chloride solution, dried ($MgSO_4$), then concentrated. The residue was subjected to silica gel column chromatography, and ethyl (E)-3-[1-(3,5-dibenzyloxybenzyl)-4-phenyl-3-pyrrolyl]propenoate (21.9 g, yield: 84%) was obtained. This was recrystallized from ethyl acetate-hexane. Melting point: 98–99° C.

EXAMPLE 67

After a mixture of ethyl(E)-3-[1-(3,5-dibenzyloxybenzyl)-4-phenyl-3-pyrrolyl]propenoate (544 mg), 1N aqueous sodium hydroxide solution (2 ml), tetrahydrofuran (6 ml) and ethanol (6 ml) was stirred overnight at 50° C., and 1N hydrochloric acid (2 ml) was added to the mixture, which was extracted with ethyl acetate. The ethyl acetate layer was washed with saturated aqueous sodium chloride solution, dried ($MgSO_4$), then concentrated. The colorless crystal obtained was filtered, and E-3-[1-(3,5-dibenzyloxybenzyl)-4-phenyl-3-pyrrolyl]propenoic acid (479 mg, yield: 93%) was obtained. This was recrystallized from ethanol. Melting point: 182–183° C.

EXAMPLE 68

Sodium hydride (60%, oily, 0.54 g) was added to a solution of ethyl 3-[(1-(3,5-dihydroxybenzyl)-4-phenyl-3-pyrrolyl]propionate (4.93 g) in N,N-dimethylformamide (50 ml) at 0° C., and this solution was stirred at room temperature for 15 minutes. 2-(4-Chloromethyl-2-thiazolyl)pyrazine (2.86 g) was added to the solution, which was stirred at room temperature for 30 minutes. The reaction mixture was poured into water, which was extracted with ethyl acetate. The ethyl acetate layer was washed with saturated aqueous sodium chloride solution, dried ($MgSO_4$), then concentrated. The residue was subjected to silica gel column chromatography, and ethyl 3-[1-β-hydroxy-5-[2-(2-pyrazinyl)-4-thiazolylmethoxy]benzyl]-4-phenyl-pyrrolyl]propionate (2.00 g, yield: 27%) was obtained as colorless crystals. This was recrystallized from tetrahydofuran-hexane. Melting point: 156–157° C.

EXAMPLE 69

A mixture of ethyl 3-[1-β-hydroxy-5-[2-(2-pyrazinyl)-4-thiazolylmethoxy]benzyl]-4-phenyl-pyrrolyl]propionate (324 mg), 1N aqueous sodium hydroxide solution (1.5 ml), tetrahydrofuran (3 ml), and ethanol (3 ml) was stirred at 50° C. for 2 hours, and 1N hydrochloric acid (1.5 ml) was added to the mixture, which was extracted with ethyl acetate. The ethyl acetate layer was washed with saturated aqueous sodium chloride solution, dried ($MgSO_4$), then concentrated. The colorless crystals obtained were collected by filtration to yield 3-[1-β-hydroxy-5-[2-(2-pyrazinyl)-4-thiazolyl-methoxy]benzyl]-4-phenyl-pyrrolyl]propionic acid (277 mg, yield: 90%). This was recrystallized from ethanol-hexane. Melting point: 206–207° C.

EXAMPLE 70

Sodium hydride (60%, oily, 28.0 mg) was added to a solution of ethyl 3-[1-β-hydroxy-5-[2-(2-pyrazinyl)-4-thiazolylmethoxy]benzyl]-4-phenyl-3-pyrrolyl]propionate (378 mg) in N,N-dimethylformamide (5 ml) at 0° C., and the mixture was stirred at room temperature for 15 minutes. Iodomethane (0.0523 ml) was added to the mixture, which was stirred at room temperature for 1 hour. The reaction mixture was poured into water, which was extracted with ethyl acetate. The ethyl acetate layer was washed with saturated aqueous sodium chloride solution, dried ($MgSO_4$), then concentrated. The residue was subjected to silica gel column chromatography, and ethyl 3-[1-[3-methoxy-5-[2-(2-pyrazinyl)-4-thiazolylmethoxy]benzyl]-4-phenyl-3-pyrrolyl]propionate (361 mg, yield: 93%) was obtained as an oily substance from the fraction eluted with ethyl acetate-hexane (1:1, volume ratio).

NMR($CDCl_3$) δ: 1.20(3H, t, J=7.2 Hz), 2.52(2H, t, J=7.8 Hz), 2.96(2H, t, J=7.8 Hz), 3.77(3H, s), 4.09(2H, q, J=7.2 Hz), 4.95(2H, s), 5.23(2H, s), 6.36(1H, s), 6.43(1H, s), 6.52(1H, t, J=2.2 Hz), 6.53(1H, d, J=2.2 Hz), 6.73(1H, d, J=2.2 Hz), 7.16–7.42(5H, m), 7.48 (1H, s), 8.56(1H, dd, J=2.6, 1.4 Hz), 8.61(1H, d, J=2.6 Hz), 9.43(1H, d, J=1.4 Hz).

EXAMPLE 71

A mixture of ethyl 3-[1-[3-methoxy-5-[2-(2-pyrazinyl)-4-thiazolylmethoxy]benzyl]-4-phenyl-3-pyrrolyl]propionate (361 mg), 1N aqueous sodium hydroxide solution (1.5 ml), tetrahydrofuran (3 ml), and ethanol (3 ml) was stirred at room temperature for 4 hours, and 1N hydrochloric acid (1.5 ml) was added to the mixture, which was extracted with ethyl acetate. The ethyl acetate layer was washed with saturated aqueous sodium chloride solution, dried ($MgSO_4$), then concentrated. The colorless crystals obtained were collected by filtration to yield 3-[1-[3-methoxy-5-[2-(2-pyrazinyl)-4-thiazolylmethoxy]benzyl]-4-phenyl-3-pyrrolyl]propionic acid (338 mg, yield: 99%). This was recrystallized from ethanol-hexane. Melting point: 111–112° C.

EXAMPLE 72

Sodium hydride (60%, oily, 28.0 mg) was added to a solution of ethyl 3-[1-[3-hydroxy-5-[2-(2-pyrazinyl)-4-thiazolylmethoxy]benzyl]-4-phenyl-3-pyrrolyl]propionate (378 mg) in N,N-dimethylformamide (5 ml) at 0° C., which was stirred at room temperature for 15 minutes. Iodoethane (0.0672 ml) was added to the mixture, which was stirred at room temperature for 1 hour. The reaction mixture was poured into water, which was extracted with ethyl acetate. The ethyl acetate layer was washed with saturated aqueous sodium chloride solution, dried ($MgSO_4$), then concentrated. The residue was subjected to silica gel column chromatography, and ethyl 3-[1-[3-ethoxy-5-[2-(2-pyrazinyl)-4-thiazolylmethoxy]benzyl]-4-phenyl-3-pyrrolyl]propionate (385 mg, yield: 97%) was obtained as an oily substance from the fraction eluted with ethyl acetate-hexane (1:1, volume ratio).

NMR($CDCl_3$) δ: 1.20(3H, t, J=7.2 Hz), 1.39(3H, t, J=7.0 Hz), 2.52(2H, t, J=7.8 Hz), 2.96(2H, t, J=7.8 Hz), 3.98(2H, q, J=7.0 Hz), 4.09(2H, q, J=7.2 Hz), 4.94(2H, s), 5.23(2H, s), 6.35(1H, s), 6.42(1H, s), 6.50–6.53(2H, m), 6.73(1H, d, J=2.6 Hz), 7.16–7.42(5H, m), 7.48(1H, s), 8.56(1H, dd, J=2.4, 1.2 Hz), 8.61(1H, d, J=2.4 Hz), 9.42(1H, d, J=1.2 Hz).

EXAMPLE 73

A mixture of ethyl 3-[1-[3-ethoxy-5-[2-(2-pyrazinyl)-4-thiazolylmethoxy]benzyl]-4-phenyl-3-pyrrolyl]propionate (370 mg), 1N aqueous sodium hydroxide solution (6 ml), tetrahydrofuran (6 ml), and ethanol (6 ml) was stirred overnight under reflux conditions, and then 1N hydrochloric acid (6 ml) was added to the mixture, which was extracted with ethyl acetate. The ethyl acetate layer was washed with saturated aqueous sodium chloride solution, dried ($MgSO_4$), then concentrated. The colorless crystals obtained were collected by filtration to yield 3-[1-[3-ethoxy-5-[2-(2-pyrazinyl)-4-thiazolylmethoxy]benzyl]-4-phenyl-3-pyrrolyl]propionic acid (210 mg, yield: 60%). This was recrystallized from ethanol. Melting point: 97–98° C.

EXAMPLE 74

Sodium hydride (60%, oily, 28.0 mg) was added to a solution of ethyl 3-[1-[3-hydroxy-5-[2-(2-pyrazinyl)-4-thiazolylmethoxy]benzyl]-4-phenyl-3-pyrrolyl]propionate (378 mg) in N,N-dimethylformamide (5 ml) at 0° C., and the mixture was stirred at room temperature for 15 minutes. Benzyl bromide (0.10 ml) was added to the mixture, which was stirred at room temperature for 1 hour. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and ethyl 3-[1-[3-benzyloxy-5-[2-(2-pyrazinyl)-4-thiazolyl methoxy]benzyl]-4-pheny-3-pyrrolyl]propionate (419 mg, yield: 95%) was obtained as colorless crystals from the fraction eluted with ethyl acetate-hexane (1:1, volume ratio). This was recrystallized from ethyl acetate-hexane. Melting point: 126–127° C.

EXAMPLE 75

A mixture of ethyl 3-[1-[3-benzyloxy-5-[2-(2-pyrazinyl)-4-thiazolylmethoxy]benzyl]-4-pheny-3-pyrrolyl]propionate (347 mg), 1N aqueous sodium hydroxide solution (5 ml), tetrahydrofuran (5 ml), and ethanol (5 ml) was stirred overnight under reflux conditions, and then 1N hydrochloric acid (5 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[1-[3-benzyloxy-5-[2-(2-pyrazinyl)-4-thiazolylmethoxy]benzyl]-4-phenyl-3-pyrrolyl]propionic acid (274 mg, yield: 83%). This was recrystallized from ethanol-hexane. Melting point: 109–110° C.

EXAMPLE 76

Sodium hydride (60%, oily, 1.85 g) was added to a mixture of 4-benzyloxybenzyl chloride (10.8 g), ethyl 3-phenyl-1H-pyrazole-4-carboxylate (10.0 g) and N,N-dimethylformamide (50 ml) at 0° C., and the mixture was stirred for 1.5 hours. The reaction mixture was poured into water, which was extracted with ethyl acetate. The ethyl acetate layer was washed with saturated aqueous sodium chloride solution, dried (MgSO$_4$), then concentrated. The colorless crystals obtained were collected by filtration to yield ethyl 1-(4-benzyloxybenzyl)-3-phenyl-1H-pyrazole-4-carboxylate (15.3 g, yield: 80%). This was crystallized from ethyl acetate-diisopropyl ether. Melting point: 102–103° C.

EXAMPLE 77

A mixture of diethyl 2-[1-(4-benzyloxybenzyl)-3-phenyl-1H-pyrazol-4-ylmethyl]malonate (9.41 g), 4N aqueous potassium hydroxide solution (30 ml), and ethanol (30 ml) was refluxed for 1 hour. The reaction mixture was acidified with dilute hydrochloric acid, which was extracted with ethyl acetate. The ethyl acetate layer was washed with saturated aqueous sodium chloride solution, dried (MgSO$_4$), then concentrated. The residue was dissolved in pyridine (20 ml), which was stirred at 110° C. for 2 hours. After removal of the solvent under reduced pressure, the residue was extracted with ethyl acetate. The ethyl acetate layer was washed with dilute hydrochloric acid, then with saturated aqueous sodium chloride solution, dried (MgSO$_4$), then concentrated. The crystals obtained were collected by filtration to yield 3-[1-(4-benzyloxybenzyl)-3-phenyl-1H-pyrazol-4-yl]propionic acid (7.52 g, yield: 99%). This was recrystallized from ethyl acetate-hexane. Melting point: 147–148° C.

EXAMPLE 78

A mixture of 3-[1-(4-benzyloxybenzyl)-3-phenyl-1H-pyrazol-4-yl]propionic acid (7.01 g), iodomethane (2.12 ml), potassium carbonate (4.70 g) and N,N-dimethylformamide (30 ml) was stirred at room temperature for 48 hours. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and methyl 3-[1-(4-benzyloxybenzyl)-3-phenyl-1H-pyrazol-4-yl]propionate (6.51 g, yield: 90%) was obtained as an oily substance from the fraction eluted with ethyl acetate-hexane (1:3, volume ratio).

NMR(CDCl$_3$) δ: 2.48–2.57(2H, m), 2.90–2.98(2H, m), 3.61(3H, s), 5.06(2H, s), 5.23(2H, s), 6.95(2H, d, J=8.8 Hz), 7.17–7.46(11H, m), 7.59–7.66(2H, m).

EXAMPLE 79

A mixture of 4-chloromethyl-2-(2-furyl)-5-methyloxazole (312 mg), methyl 3-[1-(4-hydroxybenzyl)-3-phenyl-1H-pyrazol-4-yl]propionate (500 mg), potassium carbonate (397 mg) and N,N-dimethylformamide (7 ml) was stirred at room temperature for 18 hours. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and methyl 3-[1-[4-[2-(2-furyl)-5-methyl-4-oxazolylmethoxy]benzyl]-3-phenyl-1H-pyrazol-4-yl]propionate (687 mg, yield: 87%) was obtained as an oily substance from the fraction eluted with ethyl acetate-hexane (5:6, volume ratio).

NMR(CDCl$_3$) δ: 2.42(3H, s), 2.49–2.58(2H, m), 2.90–2.99(2H, m), 3.61(3H, s), 4.98(2H, s), 5.24(2H, s), 6.51–6.54(1H, m), 6.94–7.02(3H, m), 7.18–7.46(6H, m), 7.52–7.55(1H, m), 7.60–7.66(1H, m).

EXAMPLE 80

A mixture of methyl 3-[1-[4-[2-(2-furyl)-5-methyl-4-oxazolylmethoxy]benzyl]-3-phenyl-1H-pyrazol-4-yl]propionate (610 mg), lithium hydroxide monohydrate (154 mg), tetrahydrofuran (6 ml), water (4 ml) and methanol (4 ml) was stirred at room temperature for 2 hours, and 1N hydrochloric acid (3.7 ml) was added to the mixture, which was extracted with ethyl acetate. The ethyl acetate layer was washed with saturated aqueous sodium chloride solution, dried (MgSO$_4$), then concentrated. Colorless crystals were collected by filtration to yield 3-[1-[4-[2-(2-furyl)-5-methyl-4-oxazolylmethoxy]benzyl]-3-phenyl-1H-pyrazol-4-yl]propionic acid (583 mg, yield: 98%). This was recrystallized from ethyl acetate-hexane. Melting point: 152–153° C.

EXAMPLE 81

A mixture of 4-chloromethyl-5-methyl-2-(2-thienyl)oxazole (338 mg), methyl 3-[1-(4-hydroxybenzyl)-3-phenyl-1H-pyrazol-4-yl]propionate (500 mg), potassium carbonate (397 mg) and N,N-dimethylformamide (7 ml) was stirred at room temperature for 18 hours. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and methyl 3-[1-[4-[5-methyl-2-(2-thienyl)-4-oxazolylmethoxy]benzyl]-3-phenyl-1H-pyrazol-4-yl]propionate (715 mg, yield: 88%) was obtained as a colorless oily substance from the fraction eluted with ethyl acetate-hexane (2:3, volume ratio).

NMR(CDCl$_3$) δ: 2.41(3H, s), 2.49–2.58(2H, m), 2.90–2.99(2H, m), 3.61(3H, s), 4.96(2H, s), 5.24(2H, s), 6.98(2H, d, J=8.8 Hz), 7.06–7.12(1H, m), 7.17–7.46(7H, m), 7.60–7.66(3H, m).

EXAMPLE 82

A mixture of methyl 3-[1-[4-[5-methyl-2-(2-thienyl)-4-oxazolylmethoxy]benzyl]-3-phenyl-1H-pyrazol-4-yl]propionate (633 mg), lithium hydroxide monohydrate (155 mg), tetrahydrofuran (6 ml), water (4 ml) and methanol (4 ml) was stirred at room temperature for 2 hours, and 1N hydrochloric acid (3.7 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[1-[4-[5-methyl-2-(2-thienyl)-4-oxazolylmethoxy]benzyl]-3-phenyl-1H-pyrazol-4-yl]propionic acid (581 mg, yield: 95%). This was recrystallized from ethyl acetate-hexane. Melting point: 159–160° C.

EXAMPLE 83

Diethyl azodicarboxylate (40% in toluene, 753 mg) was added dropwise slowly to a mixture of methyl 3-[1-(4-hydroxybenzyl)-3-phenyl-1H-pyrazol-4-yl]propionate (500 mg), [5-methyl-2-(4-pyridyl)-4-oxazolyl]methanol (274 mg), triphenylphosphine (414 mg) and tetrahydrofuran (7 ml) at room temperature. After stirring at room temperature for 4 hours, the reaction solvent was removed under reduced pressure. The residue was subjected to silica gel column chromatography, and an oily substance was obtained from the fraction eluted with ethyl acetate-hexane (3:1, volume ratio). A mixture of the oily substance obtained, lithium hydroxide monohydrate (181 mg), tetrahydrofuran (6 ml), water (4 ml) and methanol (4 ml) was stirred at room temperature for 2 hours, and 1N hydrochloric acid (4.3 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[1-[4-[5-methyl-2-(4-pyridyl)-4-oxazolylmethoxy]benzyl]-3-phenyl-1H-pyrazol-4-yl]propionic acid (470 mg, yield: 68%). This was recrystallized from tetrahydrofuran-hexane. Melting point: 154–155° C.

EXAMPLE 84

A mixture of 3-chloromethyl-5-phenyl-1,2,4-oxadiazole (307 mg), methyl 3-[1-(4-hydroxybenzyl)-3-phenyl-1H-pyrazol-4-yl]propionate (500 mg), potassium carbonate (397 mg) and N,N-dimethylformamide (7 ml) was stirred at room temperature for 18 hours. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and methyl 3-[3-phenyl-1-[4-(5-phenyl-1,2,4-oxadiazole-3-ylmethoxy)benzyl]-1H-pyrazol-4-yl]propionate (651 mg, yield: 89%) was obtained as a colorless oily substance from the fraction eluted with ethyl acetate-hexane (1:2, volume ratio).

NMR(CDCl$_3$) δ: 2.49–2.57(2H, m), 2.90–2.99(2H, m), 3.61(3H, s), 5.25(4H, s), 7.04(2H, d, J=8.8 Hz), 7.18–7.66 (11H, m), 8.13–8.19(2H, m).

EXAMPLE 85

A mixture of methyl 3-[3-phenyl-1-[4-(5-phenyl-1,2,4-oxadiazole-3-ylmethoxy)benzyl]-1H-pyrazol-4-yl propionate (560 mg), lithium hydroxide monohydrate (139 mg), tetrahydrofuran (6 ml), water (4 ml) and methanol (4 ml) was stirred at room temperature for 2 hours, and 1N hydrochloric acid (3.4 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[3-phenyl-1-[4-(5-phenyl-1,2,4-oxadiazole-3-ylmethoxy)benzyl]-1H-pyrazol-4-yl]propionic acid (529 mg, yield: 97%). This was recrystallized from ethyl acetate-hexane. Melting point: 166–167° C.

EXAMPLE 86

Diethyl azodicarboxylate (40% in toluene, 1.00 g) was added dropwise slowly to a mixture of methyl 3-[1-(4-hydroxybenzyl)-3-phenyl-1H-pyrazol-4-yl]propionate (500 mg), (2,5-dimethyl-4-oxazolyl]methanol (275 mg), triphenylphosphine (585 mg) and tetrahydrofuran (10 ml) at room temperature. After the mixture was stirred at room temperature for 8 hours, the reaction solvent was removed under reduced pressure. The residue was subjected to silica gel column chromatography, and methyl 3-[1-[4-(2,5-dimethyl-4-oxazolylmethoxy)benzyl]3-phenyl-1H-pyrazol-4-yl]propionate (288 mg, yield: 44%) was obtained as an oily substance from the fraction eluted with ethyl acetate-hexane (6:5, volume ratio).

NMR(CDCl$_3$) δ: 2.31(3H, s), 2.41(3H, s), 2.49–2.58(2H, m), 2.90–2.99(2H, m), 3.62(3H, s), 4.86(2H, s), 5.24(2H, s), 6.97(2H, d, J=8.8 Hz), 7.18–7.47(6H, m), 7.59–7.66(2H, m).

EXAMPLE 87

A mixture of methyl 3-[1-[4-(2,5-dimethyl-4-oxazolylmethoxy)benzyl]3-phenyl-1H-pyrazol-4-yl]propionate (254 mg), lithium hydroxide monohydrate (69.9 mg), tetrahydrofuran (6 ml), water (4 ml) and methanol (4 ml) was stirred at room temperature for 2 hours, and 1N hydrochloric acid (1.7 ml) was added to the mixture, which was extracted with ethyl acetate. The ethyl acetate layer was washed with saturated aqueous sodium chloride solution, dried (MgSO$_4$), then concentrated to yield 3-[1-[4-(2,5-dimethyl-4-oxazolylmethoxy)benzyl]3-phenyl-1H-pyrazol-4-yl]propionic acid (243 mg, yield: 99%) as an amorphous substance.

NMR(CDCl$_3$) δ: 2.30(3H, s), 2.41(3H, s), 2.54(2H, t, J=7.4 Hz), 2.92(2H, t, J=7.4 Hz), 4.85(2H, s), 5.21(2H, s), 6.94(2H, d, J=8.4 Hz), 7.15–7.47(6H, m), 7.61(2H, d, J=7.0 Hz).

EXAMPLE 88

A mixture of 3-chloromethyl-5-methyl-2-phenyloxazole (324 mg), methyl 3-[1-(4-hydroxybenzyl)-3-phenyl-1H-pyrazol-4-yl]propionate (500 mg), potassium carbonate (397 mg) and N,N-dimethylformamide (7 ml) was stirred at room temperature for 18 hours. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and methyl 3-[1-[4-(5-methyl-2-phenyl-4-oxazolylmethoxy)benzyl]-3-phenyl-1H-pyrazol-4-yl]propionate (657 mg, yield: 90%) was obtained as a colorless oily substance from the fraction eluted with ethyl acetate-hexane (1:2, volume ratio).

NMR(CDCl$_3$) δ: 2.43(3H, s), 2.49–2.58(2H, m), 2.95(2H, t, J=7.7 Hz), 3.61(3H, s), 4.99(2H, s), 5.24(2H, s), 7.00(2H, d, J=8.8 Hz), 7.18–7.47(9H, m), 7.60–7.66(2H, m), 7.98–8.04(2H, m).

EXAMPLE 89

A mixture of methyl 3-[1-[4-(5-methyl-2-phenyl-4-oxazolylmethoxy)benzyl]-3-phenyl-1H-pyrazol-4-yl]propionate (640 mg), lithium hydroxide monohydrate (363 mg), tetrahydrofuran (6 ml), water (4 ml) and methanol (4 ml) was stirred at room temperature for 2 hours, and 1N hydrochloric acid (9 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[1-[4-(5-methyl-2-phenyl-4-oxazolylmethoxy)benzyl]-3-phenyl-1H-pyrazol-4-yl]propionic acid (592 mg, yield: 97%). This was recrystallized from ethyl acetate-hexane. Melting point: 179–180° C.

EXAMPLE 90

4-[3-Methyl-1-(2-pyridyl)-1H-pyrazol-4-ylmethoxy]benzyl alcohol (400 mg) was added to thionyl chloride (1 ml) at 0° C., which was stirred at room temperature for 1 hour. After thionyl chloride was removed under reduced pressure, the residue was dissolved in ethyl acetate, which was washed successively with saturated aqueous sodium hydrogen carbonate solution and saturated aqueous sodium chloride solution, dried (MgSO$_4$), then concentrated. Sodium hydride (60%, oily, 60 mg) was added to a mixture of the residue, ethyl 3-(3-phenyl-1H-pyrazol-4-yl)propionate (320 mg) and N,N-dimethylformamide (20 ml), and the mixture was stirred at room temperature for 2 hours. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and ethyl 3-[1-[4-[3-methyl-1-(2-pyridyl)-1H-pyrazol-4-ylmethoxy]benzyl]-3-phenyl-1H-pyrazol-4-yl]propionate (340 mg, yield: 50%) was obtained as a colorless oily substance from the fraction eluted with ethyl acetate-hexane (1:3, volume ratio).

NMR(CDCl$_3$) δ: 1.18(3H, t, J=7.2 Hz), 2.39(3H, s), 2.52(2H, t, J=7.7 Hz), 2.94(2H, t, J=7.7 Hz), 4.07(2H, q, J=7.2 Hz), 4.97(2H, s), 5.24(2H, s), 6.94–6.99(2H, m), 7.11–7.45(7H, m), 7.61–7.65(2H, m), 7.74–7.82(1H, m), 7.91(1H, d, J=8.4 Hz), 8.36–8.39(1H, m), 8.53(1H, s).

EXAMPLE 91

A mixture of 3-picolyl chloride hydrochloride (148 mg), methyl 3-[1-(4-hydroxybenzyl)-3-phenyl-1H-pyrazol-4-yl]propionate (300 mg), potassium carbonate (357 mg) and N,N-dimethylformamide (5 ml) was stirred at 50° C. for 3 hours. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and a colorless oily substance was obtained from the fraction eluted with ethyl acetate. A mixture of the oily substance obtained, lithium hydroxide monohydrate (108 mg), tetrahydrofuran (6 ml), water (4 ml), and methanol (4 ml) was stirred at room temperature for 2 hours, and 1N hydrochloric acid (2.6 ml) was added to the mixture, which was extracted with ethyl acetate. The ethyl acetate layer was washed with saturated aqueous sodium chloride solution, dried (MgSO$_4$), then concentrated. The colorless crystals obtained were collected by filtration to yield 3-[3-phenyl-1-[4-(3-pyridylmethoxy)benzyl]-1H-pyrazol-4-yl]propionic acid (279 mg, yield: 78%). This was recrystallized from acetone-hexane. Melting point: 112–113° C.

EXAMPLE 92

A mixture of ethyl 1-(4-benzyloxybenzyl)-3-phenyl-1H-pyrazole-4-carboxylate (1.79 g), potassium hydroxide (0.75 g) and ethanol (30 ml) was refluxed for 5 hours. After removal of the solvent under reduced pressure, water was added to the reaction mixture, then the mixture was acidified with 1N hydrochloric acid. The crystals obtained were collected by filtration to yield 1-(4-benzyloxybenzyl)-3-phenyl-1H-pyrazol-4-carboxylic acid (1.36 g, yield: 82%). This was recrystallized from acetone-hexane. Melting point: 152–153° C.

EXAMPLE 93

A mixture of 4-chloromethyl-5-methyl-2-phenyloxazole (2.42 g), ethyl 1-(4-hydroxybenzyl)-3-phenyl-1H-pyrazol-4-carboxylate (3.40 g), potassium carbonate (2.51 g) and N,N-dimethylformamide (50 ml) was stirred overnight at 80° C. The reaction mixture was poured into water, which was extracted with ethyl acetate. The ethyl acetate layer was washed with saturated aqueous sodium chloride solution, dried (MgSO$_4$), then concentrated. A mixture of the residue, potassium hydroxide (1.78 g) and ethanol (50 ml) was refluxed for 5 hours. After the reaction solvent was removed under reduced pressure, water was added to the reaction mixture, then the mixture was acidified with 1N hydrochloric acid. The crystals obtained were collected by filtration to yield 1-[4-(5-methyl-2 phenyl-4-oxazolylmethoxy)benzyl]-3-phenyl-1H-pyrazol-4-carboxylic acid (3.66 g, yield: 75%). This was recrystallized from acetone-hexane. Melting point: 165–166° C.

EXAMPLE 94

A mixture of 4-chloromethyl-2-phenylthiazole (1.19 g), ethyl 1-(4-hydroxybenzyl)-3-phenyl-1H-pyrazol-4-carboxylate (1.65 g), potassium carbonate (1.18 g) and N,N-dimethylformamide (25 ml) was stirred overnight at 80° C. The reaction mixture was poured into water, which was extracted with ethyl acetate. The ethyl acetate layer was washed with saturated aqueous sodium chloride solution, dried (MgSO$_4$), then concentrated. A mixture of the residue, potassium hydroxide (0.93 g) and ethanol (50 ml) was refluxed for 5 hours. After the reaction solvent was removed under reduced pressure, water was added to the reaction mixture, then the mixture was acidified with 1N hydrochloric acid. The crystals obtained were collected by filtration to yield 3-phenyl-1-[4-(2-phenyl-4-thiazolylmethoxy)benzyl]-1H-pyrazol-4-carboxylic acid (1.82 g, yield: 76%). This was recrystallized from acetone-hexane. Melting point: 119–120° C.

EXAMPLE 95

Thionyl chloride (1 ml) was added dropwise to a solution of [1-[4-(5-methyl-2-phenyl-4-oxazolylmethoxy)benzyl]-3-phenyl-1H-pyrazol-4-yl]methanol (3.01 g) in toluene (50 ml) at 0° C., and then the mixture was stirred at room temperature for 1 hour. The reaction mixture was concentrated under reduced pressure. The residue was dissolved in ethyl acetate. The solution was washed with water, then with saturated aqueous sodium chloride solution, dried (MgSO$_4$), then concentrated. The residue was dissolved in N,N-dimethylformamide (50 ml). After sodium cyanide (0.82 g) was added to the solution at 0° C., the solution was stirred overnight at 70° C. The reaction mixture was poured into water, which was extracted with ethyl acetate. The ethyl acetate layer was washed with water, then with saturated aqueous sodium chloride solution, dried (MgSO$_4$), then concentrated. The residue was subjected to silica gel column chromatography, and an amorphous substance was obtained from the fraction eluted with ethyl acetate-hexane (1:2, volume ratio). A mixture of the amorphous substance obtained, 4N aqueous potassium hydroxide solution (10 ml) and ethanol (20 ml) was refluxed overnight. After removal of the solvent, water was added to the mixture, then the mixture was acidified with 1N hydrochloric acid. The crystals obtained were collected by filtration to yield [1-[4-(5-methyl-2-phenyl-4-oxazolylmethoxy)benzyl]-3-phenyl-1H-pyrazol-4-yl]acetate (2.38 g, yield: 74%). This was recrystallized from ethyl acetate-hexane. Melting point: 156–157° C.

EXAMPLE 96

A mixture of 4-[1-[4-(5-methyl-2-phenyl-4-oxazolylmethoxy)benzyl]-3-phenyl-1H-pyrazol-4-yl]butyronitrile (1.27 g), 4N aqueous potassium hydroxide solution (5 ml) and ethanol (10 ml) was refluxed for 18 hours. The reaction mixture was acidified with dilute hydrochloric acid, which was extracted with ethyl acetate. The ethyl acetate layer was washed with saturated aqueous sodium chloride solution, dried (MgSO$_4$), then concentrated. The colorless crystals obtained were collected by filtration to yield 4-[1-[4-(5-methyl-2-phenyl-4-oxazolylmethoxy)benzyl]-3-phenyl-1H-pyrazole-4-yl]butanoic acid (709 mg, yield: 54%). This was recrystallized from ethyl acetate-hexane. Melting point: 118–119° C.

EXAMPLE 97

A mixture of diethyl 2-[3-[1-[4-(5-methyl-2-phenyl-4-oxazolylmethoxy)benzyl]-3-phenyl-1H-pyrazol-4-yl]propyl]malonate (1.56 g), 4N aqueous potassium hydroxide solution (5 ml) and ethanol (10 ml) was refluxed for 30 minutes. The reaction mixture was acidified with dilute hydrochloric acid, which was extracted with ethyl acetate. The ethyl acetate layer was washed with saturated aqueous sodium chloride solution, dried (MgSO$_4$), then concentrated. A mixture of the residue and pyridine (10 ml) was stirred at 110° C. for 2 hours. After removal of the solvent under reduced pressure, the mixture was extracted with ethyl acetate. The ethyl acetate layer was washed with dilute hydrochloric acid, then with saturated aqueous sodium chloride solution, dried (MgSO$_4$), then concentrated. The colorless crystals obtained were collected by filtration to yield 5-[1-[4-(5-methyl-2-phenyl-4-oxazolylmethoxy)benzyl]-3-phenyl-1H-pyrazol-4-yl]pentanoic acid (857 mg, yield: 65%). This was recrystallized from ethyl acetate-hexane. Melting point: 109–110° C.

EXAMPLE 98

Tetrakis(triphenolphosphine)palladium (120 mg) was added to a mixture of ethyl 3-[1-[4-(5-methyl-2-phenyl-4-oxazolylmethoxy)benzyl]-3-trifluoromethanesulfonyloxy-1H-pyrazol-4-yl]propionate (1.20 g), 4-trifluoromethylphenylboronic acid (0.46 g), 2N aqueous sodium carbonate solution (2.6 ml), ethanol (3 ml), and toluene (50 ml). This mixture was refluxed under an argon atmosphere for 13 hours. Ethyl acetate was added to the reaction mixture, and the mixture was washed with saturated aqueous sodium chloride solution, dried (MgSO$_4$), then concentrated. The residue was subjected to silica gel column chromatography, and a colorless oily substance was obtained from the fraction eluted with ethyl acetate-hexane (1:3, volume ratio). A mixture of the oily substance obtained, 1N aqueous sodium hydroxide solution (5 ml), ethanol (5 ml) and tetrahydrofuran (5 ml) was stirred at room temperature for 2 hours. The reaction mixture was acidified with dilute hydrochloric acid, which was extracted with ethyl acetate. The ethyl acetate layer was washed with saturated aqueous sodium chloride solution, dried (MgSO$_4$), then concentrated. The colorless crystals obtained were collected by filtration to yield 3-[1-[4-(5-methyl-2-phenyl-4-oxazolylmethoxy)benzyl]-3-(4-trifluoromethylphenyl)-1H-pyrazol-4-yl]propionic acid (250 mg, yield: 22%). This was recrystallized from ethyl acetate-hexane. Melting point: 149–150° C.

EXAMPLE 99

Tetrakis(triphenolphosphine)palladium (130 mg) was added to a mixture of ethyl 3-[1-[4-(5-methyl-2-phenyl-4-oxazolylmethoxy)benzyl]-3-trifluoromethanesulfonyloxy-1H-pyrazol-4-yl]propionate (1.31 g), 4-fluorophenylboronic acid (0.31 g), 2N aqueous sodium carbonate solution (2.9 ml), ethanol (3 ml), and toluene (50 ml). This mixture was refluxed under an argon atmosphere for 13 hours. Ethyl acetate was added to this reaction mixture, and the mixture was washed with saturated aqueous sodium chloride solution, dried (MgSO$_4$), then concentrated. The residue was subjected to silica gel column chromatography, and ethyl 3-[3-(4-fluorophenyl)-1-[4-(5-methyl-2-phenyl-4-oxazolylmethoxy)benzyl]-1H-pyrazol-4-yl]propionate (540 mg, yield 45%) was obtained as colorless crystals from the fraction eluted with ethyl acetate-hexane (1:3, volume ratio). This was recrystallized from ethyl acetate-hexane. Melting point: 93–94° C.

EXAMPLE 100

A mixture of ethyl 3-[3-(4-fluorophenyl)-1-[4-(5-methyl-2-phenyl-4-oxazolylmethoxy)benzyl]-1H-pyrazol-4-yl]propionate (500 mg), 1N aqueous sodium hydroxide solution (2 ml), ethanol (3 ml), and tetrahydrofuran (5 ml) was stirred at room temperature for 1 hour. The reaction mixture was acidified with 1N hydrochloric acid, which was extracted with ethyl acetate. The ethyl acetate layer was washed with saturated aqueous sodium chloride solution, dried (MgSO$_4$), then concentrated. The colorless crystals obtained were collected by filtration to yield 3-[3-(4-fluorophenyl)-1-[4-(5-methyl-2-phenyl-4-oxazolylmethoxy)benzyl]-1H-pyrazol-4-yl]propionic acid (330 mg, yield: 69%). This was recrystallized from ethyl acetate-hexane. Melting point: 139–140° C.

EXAMPLE 101

Tetrakis(triphenylphosphine)palladium (790 mg) was added to a mixture of ethyl 3-[1-[4-(5-methyl-2-phenyl-4-oxazolylmethoxy)benzyl]-3-trifluoromethanesulfonyloxy-1H-pyrazol-4-yl]propionate (2.00 g), 4-methoxyphenylboronic acid (0.77 g), 2N aqueous sodium carbonate solution (5.0 ml), ethanol (5 ml), and toluene (100 ml). This mixture was refluxed under an argon atmosphere for 13 hours. Ethyl acetate was added to the reaction mixture, which was washed with saturated aqueous sodium chloride solution, dried (MgSO$_4$), then concentrated. The residue was subjected to silica gel column chromatography, and ethyl 3-[3-(4-methoxyphenyl)-1-[4-(5-methyl-2-phenyl-4-oxazolylmethoxy)benzyl]-1H-pyrazol-4-yl]propionate (450 mg, yield: 24%) was obtained as an oily substance from the fraction eluted with ethyl acetate-hexane (1:1, volume ratio).

NMR(CDCl$_3$) δ: 1.19(3H, t, J=7.0 Hz), 2.44(3H, s), 2.51(2H, t, J=7.5 Hz), 2.92(2H, t, J=7.5 Hz), 3.84(3H; s), 4.08(2H, q, J=7.0 Hz), 4.99(2H, s), 5.22(2H, s), 6.93–7.02 (4H, m), 7.16–7.26(3H, m), 7.52–7.59(2H, m), 7.99–8.04 (2H, m).

EXAMPLE 102

A mixture of ethyl 3-[3-(4-methoxyphenyl)-1-[4-(5-methyl-2-phenyl-4-oxazolylmethoxy)benzyl]-1H-pyrazol-4-yl]propionate (450 mg), 1N aqueous sodium hydroxide solution (2 ml), ethanol (3 ml), and tetrahydrofuran (3 ml) was stirred at room temperature for 1 hour. The reaction mixture was acidified with 1N hydrochloric acid, which was extracted with ethyl acetate. The ethyl acetate layer was washed with saturated aqueous sodium chloride solution, dried (MgSO$_4$), then concentrated. The colorless crystals obtained were collected by filtration to yield 3-[3-(4-methoxyphenyl)-1-[4-(5-methyl-2-phenyl-4-oxazolylmethoxy)benzyl]-1H-pyrazol-4-yl]propionic acid (350 mg, yield: 81%). This was recrystallized from ethyl acetate-hexane. Melting point: 137–138° C.

EXAMPLE 103

Tetrakis(triphenylphosphine)palladium (990 mg) was added to a mixture of ethyl 3-[1-[4-[2-(2-furyl)-5-methyl-4-oxazolylmethoxy)benzyl]-3-trifluoromethanesulfonyloxy-1H-pyrazol-4-yl]propionate (2.50 g), 4-trifluoromethylphenylboronic acid (1.23 g), 2N aqueous sodium carbonate solution (6.5 ml), ethanol (7 ml), and toluene (100 ml). This mixture was refluxed under an argon atmosphere for 13 hours. Ethyl acetate was added to this reaction mixture, which was washed with saturated aqueous sodium chloride solution, dried (MgSO$_4$), then concentrated. The residue was subjected to silica gel column chromatography, and a colorless oily substance was obtained from the fraction eluted with ethyl acetate-hexane (1:3, volume ratio). A mixture of the oily substance obtained, 1N aqueous sodium hydroxide solution (5 ml), ethanol (5 ml), and tetrahydrofuran (5 ml) was stirred at room temperature for 2 hours. The reaction mixture was acidified with dilute hydrochloric acid, which was extracted with ethyl acetate. The ethyl acetate layer was washed with saturated aqueous sodium chloride solution, dried (MgSO$_4$), then concentrated. The colorless crystals obtained were collected by filtration to yield 3-[1-[4-[2-(2-furyl)-5-methyl-4-oxazolylmethoxy)benzyl]-3-(4-trifluoromethylphenyl)-1H-pyrazol-4-yl]propionic acid (680 mg, yield: 29%). This was recrystallized from ethyl acetate-hexane. Melting point: 92–93° C.

EXAMPLE 104

Tetrakis(triphenylphosphine)palladium (878 mg) was added to a mixture of ethyl 3-[1-[4-[2-(2-furyl)-5-methyl-4-oxazolylmethoxy)benzyl]-3-trifluoromethanesulfonyloxy-1H-pyrazol-4-yl]propionate (2.22 g), 4-fluorophenylboronic acid (798 mg), 2N aqueous sodium carbonate solution (10 ml), ethanol (10 ml), and toluene (30 ml). This mixture was refluxed under an argon atmosphere for 13 hours. Ethyl acetate was added to this reaction mixture, which was washed with saturated aqueous sodium chloride solution, dried (MgSO$_4$), then concentrated. The residue was subjected to silica gel column chromatography, and ethyl 3-[3-(4-fluorophenyl)-1-[4-[2-(2-furyl)-5-methyl-4-oxazolylmethoxy]benzyl]-1H-pyrazol-4-yl]propionate (350 mg, yield: 17%) was obtained as a colorless oily substance from the fraction eluted with ethyl acetate-hexane (1:2, volume ratio).

NMR(CDCl$_3$) δ: 1.19(3H, t, J=7.2 Hz), 2.42(3H, s), 2.51(2H, t, J=7.6 Hz), 2.91(2H, t, J=7.6 Hz), 4.08(2H, q, J=7.2 Hz), 4.98(2H, s), 5.22(2H, s), 6.53(1H, dd, J=3.4, 1.8 Hz), 6.96–7.01(3H, m), 7.05–7.23(5H, m), 7.53–7.63(2H, m).

EXAMPLE 105

A mixture of ethyl 3-[3-(4-fluorophenyl)-1-[4-[2-(2-furyl)-5-methyl-4-oxazolylmethoxy)benzyl]-1H-pyrazol-4-yl]propionate (350 mg), 1N aqueous sodium hydroxide solution (2 ml), ethanol (4 ml), and tetrahydrofuran (4 ml) was stirred at room temperature for 2 hours. The reaction mixture was acidified with dilute hydrochloric acid, which was extracted with ethyl acetate. The ethyl acetate layer was washed with saturated aqueous sodium chloride solution, dried (MgSO$_4$), then concentrated. The colorless crystals obtained were collected by filtration to yield 3-[3-(4-fluorophenyl)-1-[4-[2-(2-furyl)-5-methyl-4-oxazolylmethoxy)benzyl]-1H-pyrazol-4-yl]propionic acid (150 mg, yield: 45%). This was recrystallized from ethyl acetate-hexane. Melting point: 125–126° C.

EXAMPLE 106

A mixture of 4-(4-chloromethylphenoxy)methyl-5-methyl-2-phenyloxazole (7.13 g), ethyl 3-isopropyl-1H-pyrazol-4-carboxylate (6.17 g), potassium carbonate (4.72 g) and N,N-dimethylformamide (70 ml) was stirred at 80° C. overnight. The reaction mixture was poured into water, which was extracted with ethyl acetate. The ethyl acetate layer was washed with saturated aqueous sodium chloride solution, dried (MgSO$_4$), then concentrated. A mixture of the residue, potassium hydroxide (4.83 g) and ethanol (150 ml) was refluxed for 5 hours. After the reaction solvent was removed under reduced pressure, water was added to the mixture, then the mixture was acidified with dilute hydrochloric acid. The crystals obtained were collected by filtration to yield 3-isopropyl-1-[4-(5-methyl-2-phenyl-4-oxazolylmethoxy)benzyl]-1H-pyrazol-4-carboxylic acid (11.39 g, yield: 78%). This was recrystallized from tetrahydrofuran-hexane. Melting point: 194–195° C.

EXAMPLE 107

A mixture of 3-isopropyl-1-[4-(5-methyl-2-phenyl-4-oxazolylmethoxy)benzyl]-1H-pyrazol-4-carboxylic acid (10.09 g), iodomethane (2 ml), potassium carbonate (4.83 g) and N,N-dimethylformamide (50 ml) was stirred at 80° C.

for 5 hours. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and methyl 3-isopropyl-1-[4-(5-methyl-2-phenyl-4-oxazolylmethoxy) benzyl]-1H-pyrazol-4-carboxylate (9.80 g, yield: 94%) was obtained as colorless crystals from the fraction eluted with ethyl acetate-hexane (1:2, volume ratio). This was recrystallized from ethyl acetate-hexane. Melting point: 90–91° C.

EXAMPLE 108

Methanesulfonyl chloride was added dropwise to a mixture of [3-isopropyl-1-[4-(5-methyl-2-phenyl-4-oxazolylmethoxy)benzyl]-1H-pyrazol-4-yl]methanol (2.02 g), triethylamine (0.8 ml) and ethyl acetate (30 ml) at 0° C., which was stirred at room temperature for 3 hours. The reaction mixture was poured into water, which was extracted with ethyl acetate. The ethyl acetate layer was washed with saturated aqueous sodium chloride solution, dried (MgSO$_4$), then concentrated. The residue was dissolved in tetrahydrofuran (20 ml). This solution was added dropwise at 0° C. to separately-prepared tetrahydrofuran solution (30 ml) of sodium diethyl malonate using diethyl malonate (2.35 g) and sodium hydride (60%, oily, 0.55 g). The reaction mixture was poured into dilute hydrochloric acid, which was extracted with ethyl acetate. The ethyl acetate layer was washed with saturated aqueous sodium chloride solution, dried (MgSO$_4$), then concentrated. The residue was dissolved in ethanol (50 ml), then 1N aqueous sodium hydroxide solution (15 ml) was added to the solution, which was stirred at 60° C. for 2 hours. After the reaction solvent was removed under reduced pressure, water was added to the mixture, which was acidified with dilute hydrochloric acid. After the crystals obtained were filtered and washed with water, the crystals were dissolved in pyridine (50 ml), which was stirred at 120° C. for 2 hours. After pyridine was removed under reduced pressure, the residue was dissolved in ethyl acetate, which was washed with dilute hydrochloric acid, then with saturated aqueous sodium chloride solution, and dried (MgSO$_4$), then concentrated. The crystals obtained were collected by filtration to yield 3-[3-isopropyl-1-[4-(5-methyl-2-phenyl-4-oxazolylmethoxy) benzyl]-1H-pyrazol-4-yl]propionic acid (1.23 g, yield: 55%). This was recrystallized from ethyl acetate-hexane. Melting point: 97–98° C.

EXAMPLE 109

Sodium hydride (60%, oily, 110 mg) was added to a mixture of 4-[(4-chloromethylphenoxy)methyl]-5-methyl-2-phenyloxazole (910 mg), ethyl 3-(3-propyl-1H-pyrazol-4-yl)propionate (500 mg) and N,N-dimethylformamide (10 ml), which was stirred for 12 hours. The reaction mixture was poured into water, which was extracted with ethyl acetate. The ethyl acetate layer was washed with saturated aqueous sodium chloride solution, dried (MgSO$_4$), then concentrated. The residue was subjected to silica gel column chromatography, and ethyl 3-[1-[4-(5-methyl-2-phenyl-4-oxazolylmethoxy)benzyl]-3-propyl-1H-pyrazol-4-yl]propionate (620 mg, yield: 53%) was obtained as a colorless oily substance.

NMR(CDCl$_3$) δ: 0.97(3H, t, J=7.2 Hz), 1.21(3H, t, J=7.2 Hz), 1.60–1.75(2H, m), 2.43(3H, s), 2.45–2.59(4H, m), 2.66–2.75(2H, m), 4.10(2H, q, J=7.2 Hz), 4.98(2H, s), 5.14(2H, s), 6.94–7.04(3H, m), 7.11–7.16(2H, m), 7.42–7.45(3H, m), 7.98–8.04(2H, m).

EXAMPLE 110

A mixture of ethyl 3-[1-[4-(5-methyl-2-phenyl-4-oxazolylmethoxy)benzyl]-3-propyl-1H-pyrazol-4-yl]propionate (610 mg), 1N aqueous sodium hydroxide solution (2.6 ml), ethanol (3 ml), and tetrahydrofuran (3 ml) was stirred at room temperature for 2 hours. The reaction mixture was acidified with dilute hydrochloric acid, which was extracted with ethyl acetate. The ethyl acetate layer was washed with saturated aqueous sodium chloride solution, dried (MgSO$_4$), then concentrated. The crystals obtained were collected by filtration to yield 3-[1-[4-(5-methyl-2-phenyl-4-oxazolylmethoxy)benzyl]-3-propyl-1H-pyrazol-4-yl]propionic acid (480 mg, yield: 80%). This was recrystallized from ethyl acetate-hexane. Melting point: 153–154° C.

EXAMPLE 111

Ethyl 3-[1-[4-(5-methyl-2-phenyl-4-oxazolylmethoxy)benzyl]-5-propyl-1H-pyrazol-4-yl]propionate (240 mg, yield: 21%) was obtained as a colorless oily substance from the fraction eluted subsequent to elution of the compound of Example 109, in the silica gel column chromatography in Example 109.

NMR(CDCl$_3$) δ: 0.89(3H, t, J=7.2 Hz), 1.24(3H, t, J=7.2 Hz), 1.35–1.47(2H, m), 2.42(3H, s), 2.43–2.58(4H, m), 2.67–2.75(2H, m), 4.13(2H, q, J=7.2 Hz), 4.96(2H, s), 5.20(2H, s), 6.91–7.06(4H, m), 7.33(1H, s), 7.41–7.45(3H, m), 7.98–8.03(2H, m).

EXAMPLE 112

A mixture of ethyl 3-[1-[4-(5-methyl-2-phenyl-4-oxazolylmethoxy)benzyl]-5-propyl-1H-pyrazol-4-yl]propionate (210 mg), 1N aqueous sodium hydroxide solution (1 ml), ethanol (1 ml), and tetrahydrofuran (1 ml) was stirred at room temperature for 2 hours. The reaction mixture was acidified with dilute hydrochloric acid, which was extracted with ethyl acetate. The ethyl acetate layer was washed with saturated aqueous sodium chloride solution, dried (MgSO$_4$), then concentrated. The crystals obtained were collected by filtration to yield 3-[1-[4-(5-methyl-2-phenyl-4-oxazolylmethoxy)benzyl]-5-propyl-1H-pyrazol-4-yl]propionic acid (170 mg, yield: 85%). This was recrystallized from ethyl acetate-hexane. Melting point: 158–159° C.

EXAMPLE 113

A mixture of ethyl 3-[1-[4-[3-methyl-1-(2-pyridyl)-)-4-ylmethoxy]benzyl]-3-phenyl-1H-pyrazol-4-yl]propionate (340 mg), 1N aqueous sodium hydroxide solution (1.5 ml), ethanol (2 ml) and tetrahydofuran (2 ml) was stirred at room temperature for 1 hour. The reaction mixture was acidified with dilute hydrochloric acid, which was extracted with ethyl acetate. The ethyl acetate layer was washed with saturated aqueous sodium chloride solution, dried (MgSO$_4$), then concentrated. The crystals obtained were collected by filtration to yield 3-[1-[4-(3-methyl-1-(2-pyridyl)-1H-pyrazol-4-ylmethoxy]benzyl]-3-phenyl-)-4-yl]propionic acid (320 mg, yield: 88%). This was recrystallized from ethyl acetate-hexane. Melting point: 131–132° C.

EXAMPLE 114

Sodium hydride (60%, oily, 200 mg) was added to an N,N-dimethylformamide solution (15 ml) of ethyl 3-(3-phenyl-1H-pyrazole-4-yl)propionate (1.04 g) at 0° C., which was stirred at 0° C. for 30 minutes. 4-[2-(4-Chloromethylphenoxy)ethyl]-5-methyl-2-phenyloxazole (1.43 g) was added to the reaction mixture, which was stirred at room temperature overnight. The reaction mixture was poured into water, which was extracted with ethyl acetate. The ethyl acetate layer was washed with saturated aqueous sodium chloride solution, dried ($MgSO_4$), then concentrated. The residue was subjected to silica gel column chromatography, and an oily substance was obtained from the fraction eluted with ethyl acetate-hexane (1:2, volume ratio). A mixture of the substance obtained, 1N aqueous sodium hydroxide solution (4 ml), ethanol (5 ml) and tetrahydrofuran (5 ml) was stirred for 2 hours at room temperature. The reaction mixture was acidified with dilute hydrochloric acid, which was extracted with ethyl acetate. The ethyl acetate layer was washed with saturated aqueous sodium chloride solution, dried ($MgSO_4$), then concentrated. The crystals obtained were collected by filtration to yield 3-[1-[4-[2-(5-methyl-2-phenyl-4-oxazolyl)ethoxy]benzyl]-3-phenyl-1H-pyrazol-4-yl]propionic acid (930 mg, yield: 71%). This was recrystallized from acetone-hexane. Melting point: 142–143° C.

EXAMPLE 115

Sodium hydride (60%, oily, 170 mg) was added to an N,N-dimethylformamide solution (50 ml) of ethyl 3-(3-phenyl-1H-pyrazole-4-yl)propionate (890 mg) at 0° C., and this mixture was stirred at 0° C. for 30 minutes. 2-[4-(5-Methyl-2-phenyl-4-oxazolylmethoxy)phenyl]ethyl methane sulfonate (2.79 g) was added to the reaction mixture, which was stirred at 90° C. for 1 hour. The reaction mixture was poured into water, which was extracted with ethyl acetate. The ethyl acetate layer was washed with saturated aqueous sodium chloride solution, dried ($MgSO_4$), then concentrated. The residue was subjected to silica gel column chromatography, and ethyl 3-[1-[2-[4-(5-methyl-2-phenyl-4-oxazolylmethoxy)phenyl]ethyl]-3-phenyl-1H-pyrazol-4-yl]propionate (1.19 g, yield: 62%) was obtained as colorless crystals. This was recrystallized from ethyl acetate-hexane. Melting point: 81–82° C.

EXAMPLE 116

A mixture of ethyl 3-[1-[2-[4-(5-methyl-2-phenyl-4-oxazolylmethoxy)phenyl]ethyl]-3-phenyl-1H-pyrazol-4-yl]propionate (900 mg), 1N aqueous sodium hydroxide solution (3.4 ml), ethanol (3 ml) and tetrahydrofuran (3 ml) was stirred at room temperature for 2 hours. The reaction mixture was acidified with dilute hydrochloric acid, which was extracted with ethyl acetate. The ethyl acetate layer was washed with saturated aqueous sodium chloride solution, dried ($MgSO_4$), then concentrated. The crystals obtained were collected by filtration to yield 3-[1-[2-[4-(5-methyl-2-phenyl-4-oxazolylmethoxy)phenyl]ethyl]-3-phenyl-1H-pyrazol-4-yl]propionic acid (860 mg, yield: 91%). This was recrystallized from ethyl acetate-hexane. Melting point: 85–86° C.

EXAMPLE 117

Thionyl chloride (0.31 ml) was added dropwise to a toluene solution (30 ml) of 4-[2-[N-methyl-N-(2-pyridyl)amino]ethoxy]benzyl alcohol (900 mg) at 0° C. The reaction mixture was stirred at room temperature for 2 hours, then concentrated. The residue was dissolved in ethyl acetate, which was washed with saturated aqueous sodium hydrogen carbonate solution, then with saturated aqueous sodium chloride solution, and dried ($MgSO_4$), then concentrated. The residue and ethyl 3-(3-phenyl-1H-pyrazol-4-yl)propionate (860 mg) were dissolved in N,N-dimethylformamide (15 ml). Sodium hydride (60%, oily, 100 mg) was added to the solution, which was then stirred at room temperature for 12 hours. The reaction mixture was poured into saturated aqueous sodium chloride solution, which was extracted with ethyl acetate. The ethyl acetate layer was washed with water, then with saturated aqueous sodium chloride solution, and dried ($MgSO_4$), then concentrated. The residue was subjected to silica gel column chromatography, and ethyl 3-[1-[4-[2-[N-methyl-N-(2-pyridyl)amino]ethoxy]benzyl]-3-phenyl-1H-pyrazol-4-yl]propionate (0.75 g, yield: 68%) was obtained as a colorless oily substance.

NMR($CDCl_3$) δ: 1.17(3H, t, J=7.0 Hz), 2.46–2.54(2H, m), 2.89–2.97(2H, m), 3.16(3H, s), 3.99(2H, t, J=5.4 Hz), 4.06(2H, q, J=7.0 Hz), 4.19(2H, t, J=5.4 Hz), 5.21(2H, s), 6.51–6.59(2H, m), 6.83–6.89(2H, m), 7.15–7.51(7H, m), 7.59–7.64(2H, m), 8.13–8.17(1H, m).

EXAMPLE 118

A mixture of ethyl 3-[1-[4-[2-[N-methyl-N-(2-pyridyl)amino]ethoxy]benzyl]-3-phenyl-1H-pyrazol-4-yl]propionate (750 mg), 1 N aqueous sodium hydroxide solution (3 ml), ethanol (3 ml), and tetrahydrofuran (3 ml) was stirred at room temperature for one hour. The reaction mixture was acidified with dilute hydrochloric acid, which was extracted with ethyl acetate. The ethyl acetate layer was washed with saturated aqueous sodium chloride solution, dried ($MgSO_4$), and concentrated. The obtained crystals were collected by filtration, and 3-[1-[4-[2-[N-methyl-N-(2-pyridyl)amino]ethoxy]benzyl]-3-phenyl-1H-pyrazol-4-yl]propionic acid (610 mg, yield: 90%) was obtained. This was recrystallized from ethyl acetate-hexane. Melting point: 110–111° C.

EXAMPLE 119

2-Chloromethyl-6-(2-fluorobenzyloxy)naphthalene (540 mg) and ethyl 3-(3-phenyl-1H-pyrazol-4-yl)propionate (390 mg) were dissolved in N,N-dimethylformamide (10 ml). Sodium hydride (60%, oily, 70 mg) was added to the solution at 0° C., which was stirred at room temperature for two hours. The reaction mixture was poured into saturated aqueous sodium chloride solution, which was extracted with ethyl acetate. The ethyl acetate layer was washed with water, then with saturated aqueous sodium chloride solution, dried ($MgSO_4$), and concentrated. The residue was subjected to silica gel column chromatography, and ethyl 3-[1-[6-(2-fluorobenzyloxy)-2-naphthylmethyl]-3-phenyl-1H-pyrazole-4-yl]propionate (0.58 g, yield: 72%) was obtained as a colorless oily substance from the fraction eluted with ethyl acetate-hexane (1:4, volume ratio).

NMR($CDCl_3$) δ: 1.14(3H, t, J=7.0 Hz), 2.47–2.50(2H, m), 2.91–2.98(2H, m), 4.04(2H, q, J=7.0 Hz), 5.25(2H, s), 7.06–7.77(16H, m).

EXAMPLE 120

A mixture of ethyl 3-[1-[6-(2-fluorobenzyloxy-2-naphthylmethyl]-3-phenyl-1H-pyrazol-4-yl]propionate (580 mg), 1N aqueous sodium hydroxide solution (2.2 ml), ethanol (3 ml), and tetrahydrofuran (3 ml) was stirred at room temperature for two hours. The reaction mixture was acidified with dilute hydrochloric acid, and the obtained colorless crystals were collected by filtration, and 3-[1-[6-(2-fluorobenzyloxy)-2-naphthylmethyl]-3-phenyl-1H-pyrazol-4-

EXAMPLE 121

A mixture of 4-[4-(2-ethoxycarbonylethyl)-3-phenyl-1H-pyrazol-1-ylmethyl]benzoic acid (500 mg), 4-trifluoromethylbenzylamine (250 mg), 1-hydroxybenzotriazole monohydrate (210 mg), WSC (270 mg), and N,N-dimethylformamide (10 ml) was stirred at room temperature for 13 hours. The reaction mixture was poured into water, which was extracted with ethyl acetate. The ethyl acetate layer was washed with saturated aqueous sodium bicarbonate solution, 1 N hydrochloric acid, then, with saturated aqueous sodium chloride solution, and dried (MgSO$_4$) and concentrated. The residue was subjected to silica gel column chromatography, and ethyl 3-[3-phenyl-1-[4-(4-trifluoromethylbenzylaminocarbonyl)benzyl]-1H-pyrazol-4-yl]propionate (550 mg, yield: 77%) was obtained as a colorless amorphous substance from the fraction eluted with ethyl acetate-hexane (3:1, volume ratio).

NMR(CDCl$_3$) δ: 1.18(3H, t, J=7.0 Hz), 2.47(3H, s), 2.53(2H, t, J=7.6 Hz), 2.95(2H, t, J=7.6 Hz), 4.07(2H, q, J=7.0 Hz), 4.52(2H, d, J=5.2 Hz), 5.33(2H, s), 6.83(1H, br.s), 7.24–7.47(9H, m), 7.60–7.65(2H, m), 7.76–7.81(2H, m), 7.96–8.01(2H, m).

EXAMPLE 122

A mixture of ethyl 3-[3-phenyl-1-[4-(4-trifluoromethylbenzylaminocarbonyl)benzyl]-1H-pyrazol-4-yl]propionate (680 mg), 1 N aqueous sodium hydroxide solution (1.7 ml), ethanol (2 ml), and tetrahydrofuran (2 ml) was stirred at room temperature for two hours. The reaction mixture was acidified with dilute hydrochloric acid, which was extracted with ethyl acetate. The ethyl acetate layer was washed with saturated aqueous sodium chloride solution, dried (MgSO$_4$), and concentrated. The obtained crystals were collected by filtration, and 3-[3-phenyl-1-[4-(4-trifluoromethylbenzylaminocarbonyl)benzyl]-1H-pyrazol-4-yl]propionic acid (620 mg, yield: 94%) was obtained. This was recrystallized from ethyl acetate-hexane. Melting point: 151–152° C.

EXAMPLE 123

A mixture of 4-[4-(2-ethoxycarbonylethyl)-3-phenyl-1H-pyrazol-1-ylmethyl]benzoic acid (500 mg), (5-methyl-2-phenyl-4-oxazolyl)methylamine (260 mg), 1-hydroxybenzotriazole monohydrate (210 mg), WSC (270 mg), and N,N-dimethylformamide (10 ml) was stirred at room temperature for 13 hours. The reaction mixture was poured into water, which was extracted with ethyl acetate. The ethyl acetate layer was washed with saturated aqueous sodium bicarbonate solution, 1 N hydrochloric acid, then, with saturated aqueous sodium chloride solution, and dried (MgSO$_4$) and concentrated. The obtained yellow crystals were collected by filtration, and ethyl 3-[1-[4-(5-methyl-2-phenyl-4-oxazolylmethylaminocarbonyl)benzyl]-3-phenyl-1H-pyrazol-4-yl]propionate (600 mg, yield: 87%) was obtained. This was recrystallized from ethyl acetate-hexane. Melting point: 190–191° C.

EXAMPLE 124

A mixture of ethyl 3-[1-[4-(5-methyl-2-phenyl-4-oxazolylmethylaminocarbonyl)benzyl]-3-phenyl-1H-pyrazol-4-yl]propionate (550 mg), 1 N aqueous sodium hydroxide solution (1.3 ml), ethanol (2 ml), and tetrahydrofuran (2 ml) was stirred at room temperature for two hours. The reaction mixture was acidified with dilute hydrochloric acid, and extracted with ethyl acetate. The ethyl acetate layer was washed with saturated aqueous sodium chloride solution, dried (MgSO$_4$), and concentrated. The obtained crystals were collected by filtration, and 3-[1-[4-(5-methyl-2-phenyl-4-oxazolylmethylaminocarbonyl)benzyl]-3-phenyl-1H-pyrazol-4-yl]propionic acid (500 mg, yield: 96%) was obtained. This was recrystallized from acetone-methanol. Melting point: 177–178° C.

EXAMPLE 125

A mixture of 3-[4-(2-ethoxycarbonylethyl)-3-phenyl-1H-pyrazol-1-ylmethyl]benzoic acid (700 mg), 4-trifluoromethylbenzylamine (390 mg), 1-hydroxybenzotriazole monohydrate (340 mg), WSC (430 mg), and N,N-dimethylformamide (30 ml) was stirred at room temperature for 18 hours. The reaction mixture was poured into water, which was extracted with ethyl acetate. The ethyl acetate layer was washed with water, dried (MgSO$_4$), and concentrated. The residue was subjected to silica gel column chromatography, and ethyl 3-[3-phenyl-1-[3-(4-trifluoromethylbenzylaminocarbonyl)benzyl]-1H-pyrazol-4-yl]propionate (900 mg, yield: 91%) was obtained as an oily substance from the fraction eluted with acetone-hexane (1:2, volume ratio).

NMR(CDCl$_3$) δ: 1.13(3H, t, J=7 Hz), 2.52(2H, t, J=7.3 Hz), 2.96(2H, t, J=7.3 Hz), 3.98(2H, q, J=7 Hz), 4.68(2H, d, J=6 Hz), 5.35(2H, s), 6.80(1H, br.s), 7.25–7.65(13H, m), 7.7–7.8(1H, m).

EXAMPLE 126

A mixture of ethyl 3-[3-phenyl-1-[3-(4-trifluoromethylbenzylaminocarbonyl)benzyl]-1H-pyrazol-4-yl]propionate (870 mg), 1 N aqueous sodium hydroxide solution (2 ml), ethanol (6 ml), and tetrahydrofuran (4 ml) was stirred at room temperature for one hour. The reaction mixture was poured into water, then 1 N hydrochloric acid (2 ml) was added to the mixture, which was extracted with ethyl acetate. The ethyl acetate layer was washed with water, dried (MgSO$_4$), and concentrated. The obtained crystals were collected by filtration, and 3-[3-phenyl-1-[3-(4-trifluoromethylbenzylaminocarbonyl)benzyl]-1H-pyrazol-4-yl]propionic acid (730 mg, yield: 89%) was obtained. This was recrystallized from acetone-isopropyl ether. Melting point: 165–166° C.

EXAMPLE 127

A mixture of 4-[4-(2-ethoxycarbonylethyl)-3-phenyl-1H-pyrazol-1-ylmethyl]benzoic acid (300 mg), 2-picolylamine (95 mg), 1-hydroxybenzotriazole monohydrate (130 mg), WSC (170 mg), and N,N-dimethylformamide (10 ml) was stirred at room temperature for 2.5 days. The reaction mixture was poured into water, which was extracted with ethyl acetate. The ethyl acetate layer was washed with saturated aqueous sodium chloride solution, dried (MgSO$_4$), and concentrated. The residue was subjected to silica gel column chromatography, and ethyl 3-[3-phenyl-1-[3-(2-picolylaminocarbonyl)benzyl]-1H-pyrazol-4-yl]propionate (200 mg, yield: 54%) was obtained as a colorless oily substance from the fraction eluted with ethyl acetate-methanol (50:1, volume ratio).

NMR(CDCl$_3$) δ: 1.17(3H, t, J=7.2 Hz), 2.53(2H, t, J=7.6 Hz), 2.96(2H, t, J=7.6 Hz), 4.06(2H, q, J=7.2 Hz), 4.76(2H, d, J=4.8 Hz), 5.36 (2H, s), 7.18–7.49 (7H, m), 7.61–7.84 (6H, m) 8.53(1H, d, J=4.0 Hz).

EXAMPLE 128

A mixture of ethyl 3-[3-phenyl-1-[3-(2-picolylaminocarbonyl)benzyl]-1H-pyrazol-4-yl]propionate (180 mg), 1 N aqueous sodium hydroxide solution (0.77 ml), ethanol (1 ml), and tetrahydrofuran (1 ml) was stirred at room temperature for one hour. 1 N hydrochloric acid (0.77 ml) was added to the reaction mixture, which was extracted with ethyl acetate. The ethyl acetate layer was washed with saturated aqueous sodium chloride solution, dried (MgSO$_4$), and concentrated. The obtained crystals were collected by filtration, and 3-[3-phenyl-1-[3-(2-picolylaminocarbonyl)benzyl]-1H-pyrazol-4-yl]propionic acid (120 mg, yield: 71%) was obtained. This was recrystallized from ethyl acetate-hexane. Melting point: 83–85° C. (decomposition).

EXAMPLE 129

A mixture of 4-[4-(2-ethoxycarbonylethyl)-3-phenyl-1H-pyrazol-1-ylmethyl]benzoic acid (400 mg), 2-aminopyridine (120 mg), 1-hydroxybenzotriazole monohydrate (200 mg), WSC (250 mg), and N,N-dimethylformamide (10 ml) was stirred at room temperature for 2.5 days. The reaction mixture was poured into water, which was extracted with ethyl acetate. The ethyl acetate layer was washed with saturated aqueous sodium bicarbonate solution, 1 N hydrochloric acid, then, with saturated sodium chloride solution, and dried (MgSO$_4$) and concentrated. The residue was subjected to silica gel column chromatography, and ethyl 3-[3-phenyl-1-[3-(2-pyridylaminocarbonyl)benzyl]-1H-pyrazol-4-yl]propionate (200 mg, yield: 40%) was obtained as a colorless oily substance from the fraction eluted with ethyl acetate-hexane (5:1, volume ratio).

NMR(CDCl$_3$) δ: 1.18(3H, t, J=7.0 Hz), 2.54(2H, t, J=7.4 Hz), 2.97(2H, t, J=7.4 Hz), 4.08(2H, q, J=7.0 Hz), 5.37(2H, s), 7.05–7.12(1H, m), 7.26–7.86(11H, m), 8.30–8.39(2H, m), 8.56(1H, br s).

EXAMPLE 130

A mixture of ethyl 3-[3-phenyl-1-[3-(2-pyridylaminocarbonyl)benzyl]-1H-pyrazol-4-yl]propionate (200 mg), 1 N aqueous sodium hydroxide solution (0.88 ml), ethanol (1 ml), and tetrahydrofuran (1 ml) was stirred at room temperature for one hour. 1 N hydrochloric acid (0.88 ml) was added to the reaction mixture, which was extracted with ethyl acetate. The ethyl acetate layer was washed with saturated aqueous sodium chloride solution, dried (MgSO$_4$), and concentrated. The obtained crystals were collected by filtration, and 3-[3-phenyl-1-[3-(2-pyridylaminocarbonyl)benzyl]-1H-pyrazol-4-yl]propionic acid (110 mg, yield: 58%) was obtained. This was recrystallized from tetrahydrofuran-hexane. Melting point: 187–188° C.

EXAMPLE 131

A mixture of 4-[4-(2-ethoxycarbonylethyl)-3-phenyl-1H-pyrazol-1-ylmethyl]benzoic acid (400 mg), 2-(2-pyridyl)ethylamine (170 mg), 1-hydroxybenzotriazole monohydrate (200 mg), WSC (250 mg), and N,N-dimethylformamide (10 ml) was stirred at room temperature for 2.5 days. The reaction mixture was poured into water, which was extracted with ethyl acetate. The ethyl acetate layer was washed with saturated aqueous sodium bicarbonate solution, 1 N hydrochloric acid, then, with saturated aqueous sodium chloride solution, and dried (MgSO$_4$) and concentrated. The residue was subjected to silica gel column chromatography, and ethyl 3-[3-phenyl-1-[3-[2-(2-pyridyl)ethylaminocarbonyl)benzyl]-1H-pyrazol-4-yl]propionate (460 mg, yield: 87%) was obtained as a colorless oily substance from the fraction eluted with ethyl acetate-methanol (50:1, volume ratio).

NMR(CDCl$_3$) δ: 1.17(3H, t, J=7.0 Hz), 2.52(2H, t, J=7.6 Hz), 2.95(2H, t, J=7.6 Hz), 3.08(2H, t, J=6.0 Hz), 3.85(2H, q, J=6.0 Hz), 4.06(2H, q, J=7.0 Hz), 5.33(2H, s), 7.07–7.72 (13H, m), 8.49(1H, d, J=4.0 Hz).

EXAMPLE 132

A mixture of ethyl 3-[3-phenyl-1-[3-[2-(2-pyridyl)ethylaminocarbonyl]benzyl]-1H-pyrazol-4-yl]propionate (450 mg), 1 N aqueous sodium hydroxide solution (2 ml), ethanol (2 ml), and tetrahydrofuran (2 ml) was stirred at room temperature for one hour. After 1 N hydrochloric acid (2 ml) was added to the reaction mixture, the reaction mixture was extracted with ethyl acetate. The ethyl acetate layer was washed with saturated aqueous sodium chloride solution, dried (MgSO$_4$), and concentrated. The obtained crystals were collected by filtration, and 3-[3-phenyl-1-[3-[2-(2-pyridyl)ethylaminocarbonyl]benzyl]-1H-pyrazol-4-yl]propionic acid (400 mg, yield: 95%) was obtained. This was recrystallized from tetrahydrofuran-hexane. Melting point: 166–167° C.

EXAMPLE 133

A mixture of 4-[4-(2-ethoxycarbonylethyl)-3-phenyl-1H-pyrazol-1-ylmethyl]benzoic acid (400 mg), 3-aminopyridine (160 mg), 1-hydroxybenzotriazole monohydrate (200 mg), WSC (250 mg), and N,N-dimethylformamide (10 ml) was stirred at room temperature for 2.5 days. The reaction mixture was poured into water, which was extracted with ethyl acetate. The ethyl acetate layer was washed with saturated aqueous sodium bicarbonate solution, 1 N hydrochloric acid, then, with saturated aqueous sodium chloride solution, and dried (MgSO$_4$) and concentrated. The residue was subjected to silica gel column chromatography, and ethyl 3-[3-phenyl-1-[3-(3-pyridylaminocarbonyl)benzyl]-1H-pyrazol-4-yl]propionate (280 mg, yield: 56%) was obtained as colorless crystals from the fraction eluted with ethyl acetate-methanol (50:1, volume ratio). Melting point: 111–112° C.

EXAMPLE 134

A mixture of ethyl 3-[3-phenyl-1-[3-(3-pyridylaminocarbonyl)benzyl]-1H-pyrazol-4-yl]propionate (230 mg), 1 N aqueous sodium hydroxide solution (1.2 ml), ethanol (2 ml), and tetrahydrofuran (2 ml) was stirred at room temperature for one hour. After 1 N hydrochloric acid (1.2 ml) was added to the reaction mixture, the reaction mixture was extracted with ethyl acetate. The ethyl acetate layer was washed with saturated aqueous sodium chloride solution, dried (MgSO$_4$), and concentrated. The obtained crystals were collected by filtration, and 3-[3-phenyl-1-[3-(3-pyridylaminocarbonyl)benzyl]-1H-pyrazol-4-yl]propionic acid (190 mg, yield: 86%) was obtained. This was recrystallized from tetrahydrofuran-hexane. Melting point: 131–132° C.

EXAMPLE 135

To a mixture of 2-(4-benzyloxyphenyl)ethanol (1.19 g), triethylamine (700 mg), and ethyl acetate (30 ml), methanesulfonyl chloride (790 mg) was added dropwise at 0° C., and the mixture was stirred at room temperature for two hours. The reaction mixture was washed with water, saturated aqueous sodium bicarbonate solution, 1 N hydrochloric acid, then, with saturated sodium chloride solution, and dried ($MgSO_4$) and concentrated. To a mixture of the residue, ethyl(3-phenyl-1H-pyrazol-4-yl)acetate (1.0 g), and N,N-dimethylformamide (50 ml), sodium hydride (60%, oily, 190 mg) was added at 0° C., and the mixture was stirred at room temperature for one hour. The reaction mixture was poured into water, which was extracted with ethyl acetate. The ethyl acetate layer was washed with saturated aqueous sodium chloride solution, dried ($MgSO_4$), and concentrated. The residue was subjected to silica gel column chromatography, and ethyl [1-[2-(4-benzyloxyphenyl)ethyl]-3-phenyl-1H-pyrazol-4-yl]acetate (0.45 g, yield: 24%) was obtained as a colorless oily substance in the fraction eluted with diethyl ether-hexane (2:3, volume ratio).

NMR($CDCl_3$) δ: 1.22(3H, t, J=7.0 Hz), 3.15(2H, t, J=7.4 Hz), 3.57(2H, s), 4.13(2H, q, J=7.0 Hz), 4.31(2H, t, J=7.4 Hz), 5.05(2H, s), 6.87–6.92(2H, m), 7.02–7.07(2H, m), 7.31–7.47(9H, m), 7.58–7.64(2H, m).

EXAMPLE 136

To a solution of ethyl 1-[2-(4-hydroxyphenyl)ethyl]-3-phenyl-1H-pyrazol-4-yl]acetate (400 mg) in N,N-dimethylformamide (10 ml), sodium hydride (60%, oily, 50 mg) was added at 0° C., and the solution was stirred at room temperature for 30 minutes. To this solution, 4-chloromethyl-5-methyl-2-phenyloxazole (290 mg) was added, and the mixture was stirred at room temperature for 15 hours. The reaction mixture was poured into water, which was extracted with ethyl acetate. The ethyl acetate layer was washed with saturated sodium chloride solution, dried ($MgSO_4$), and concentrated. The residue was subjected to silica gel column chromatography, and ethyl [1-[2-[4-(5-methyl-2-phenyl-4-oxazolylmethoxy)phenyl]ethyl]-3-phenyl-1H-pyrazol-4-yl]acetate (260 mg, yield: 46%) was obtained as a colorless oily substance from the fraction eluted with ethyl acetate-hexane (1:3, volume ratio).

NMR($CDCl_3$) δ: 1.22(3H, t, J=7.0 Hz), 2.43(3H, s), 3.15(2H, t, J=7.4 Hz), 3.57(2H, s), 4.13(2H, q, J=7.0 Hz), 4.31(2H, t, J=7.4 Hz), 4.97(2H, s), 6.91–6.96(2H, m), 7.03–7.08(2H, m), 7.26–7.45(7H, m), 7.58–7.63(2H, m), 7.99–8.04(2H, m).

EXAMPLE 137

A mixture of ethyl [1-[2-[4-(5-methyl-2-phenyl-4-oxazolylmethoxy)phenyl]ethyl]-3-phenyl-1H-pyrazol-4-yl]acetate (260 mg), 1 N aqueous sodium hydroxide solution (1 ml), ethanol (2 ml), and tetrahydrofuran (2 ml) was stirred at room temperature for one hour. After 1 N hydrochloric acid (1 ml) was added to the reaction mixture, the reaction mixture was extracted with ethyl acetate. The ethyl acetate layer was washed with saturated aqueous sodium chloride solution, dried ($MgSO_4$), and concentrated. The obtained crystals were collected by filtration, and 1-[2-[4-(5-methyl-2-phenyl-4-oxazolylmethoxy)phenyl]ethyl-3-phenyl-1H-pyrazol-4-ylacetic acid (170 mg, yield: 68%) was obtained. This was recrystallized from ethyl acetate-hexane. Melting point: 104–105° C.

EXAMPLE 138

A mixture of 4-(4-chloromethylphenoxy)methyl-5-methyl-2-phenyloxazole (3.55 g), ethyl 1H-pyrazol-4-carboxylate (1.50 g), potassium carbonate (2.76 g), and N,N-dimethylformamide (25 ml) was stirred at room temperature for 24 hours. The reaction mixture was poured into water, which was extracted with ethyl acetate. The ethyl acetate layer was washed with water, then, with saturated aqueous sodium chloride solution, dried ($MgSO_4$) and concentrated. The obtained crystals were collected by filtration, and ethyl 1-[4-(5-methyl-2-phenyl-4-oxazolylmethoxy)benzyl]-1H-pyrazol-4-carboxylate (3.79 g, yield: 91%) was obtained. This was recrystallized from ethyl acetate-hexane. Melting point: 108–109° C.

EXAMPLE 139

Sodium hydride (60%, oily, 336 mg) was added at 0° C. to a solution of ethyl diethylphosphonoacetate (1.67 ml) in tetrahydrofuran (20 ml), which was stirred at 0° C. for 30 minutes. To this solution, a solution of 1-[4-(5-methyl-2-phenyl-4-oxazolylmethoxy)benzyl]-1H-pyrazol-4-carbaldehyde (2.61 g) in tetrahydrofuran (20 ml) was added dropwise at 0° C., and the mixture was stirred at room temperature for 15 minutes. The reaction mixture was poured into water, which was extracted with ethyl acetate. The ethyl acetate layer was washed with saturated sodium chloride solution, dried ($MgSO_4$), and concentrated. The obtained crystals were collected by filtration, and ethyl (E)-3-[1-[4-(5-methyl-2-phenyl-4-oxazolylmethoxy)benzyl]-1H-pyrazole-4-yl]propenoate (2.78 g, yield: 90%) was obtained. This was recrystallized from ethyl acetate-hexane. Melting point: 112–113° C.

EXAMPLE 140

A mixture of ethyl(E)-3-[1-[4-(5-methyl-2-phenyl-4-oxazolylmethoxy)benzyl]-1H-pyrazole-4-yl]propenoate (887 mg), 1 N aqueous sodium hydroxide solution (4 ml), ethanol (8 ml), and tetrahydrofuran (8 ml) was stirred at 40° C. for 3 hours. After the reaction mixture was acidified with 1 N hydrochloric acid, the obtained crystals were collected by filtration, and (E)-3-[1-[4-(5-methyl-2-phenyl-4-oxazolylmethoxy)benzyl]-1H-pyrazol-4-yl]propenoic acid (672 mg, yield: 81%) was obtained. This was recrystallized from ethanol. Melting point: 186–187° C.

EXAMPLE 141

A mixture of ethyl(E)-3-[1-[4-(5-methyl-2-phenyl-4-oxazolylmethoxy)benzyl]-1H-pyrazol-4-yl]propenoate (1.78 g), 5% palladium-carbon (2.0 g), ethanol (20 ml), and tetrahydrofuran (20 ml) was stirred at room temperature for one hour under a hydrogen atmosphere. After removal of the catalyst by filtration, the filtrate was concentrated. The residue was subjected to silica gel column chromatography, and ethyl 3-[1-[4-(5-methyl-2-phenyl-4-oxazolylmethoxy)benzyl]-1H-pyrazol-4-yl]propionate (1.57 g, yield: 88%) was obtained as a colorless oily substance from the fraction eluted with ethyl acetate-hexane (1:1, volume ratio).

NMR($CDCl_3$) δ: 1.21(3H, t, J=7.0 Hz), 2.42(3H, s), 2.52(2H, t, J=7.2 Hz), 2.77(2H, t, J=7.2 Hz), 4.10(2H, q, J=7.0 Hz), 4.97(2H, s), 5.17(2H, s), 6.98(2H, d, J=8.6 Hz), 7.15(1H, s), 7.18(2H, d, J=8.6 Hz), 7.36(1H, s), 7.39–7.46 (3H, m), 7.97–8.03(2H, m).

EXAMPLE 142

A mixture of ethyl 3-[1-[4-(5-methyl-2-phenyl-4-oxazolylmethoxy)benzyl]-1H-pyrazol-4-yl]propionate (1.34 g), 1 N aqueous sodium hydroxide solution (6 ml), ethanol (12 ml), and tetrahydrofuran (12 ml) was stirred at room temperature for two hours. After 1 N hydrochloric acid (6 ml) was added to the reaction mixture, the reaction mixture was extracted with ethyl acetate. The ethyl acetate layer was washed with saturated aqueous sodium chloride solution, dried (MgSO$_4$), and concentrated. The obtained crystals were collected by filtration, 3-[1-[4-(5-methyl-2-phenyl-4-oxazolylmethoxy)benzyl]-1H-pyrazol-4-yl]propionic acid (1.21 g, yield: 97%) was obtained. This was recrystallized from ethanol-hexane. Melting point: 124–125° C.

EXAMPLE 143

To a solution of 3,5-dimethyl-1-[4-(5-methyl-2-phenyl-4-oxazolylmethoxy)benzyl]-1H-pyrazol-4-carbaldehyde (900 mg) and ethyl diethylphosphonoacetate (1.10 g) in N,N-dimethylformamide (20 ml), sodium hydride (60%, oily, 200 mg) was added at 0, and the mixture was stirred at room temperature for 5 hours. The reaction mixture was poured into water, which was extracted with ethyl acetate. The ethyl acetate layer was washed with water, dried (MgSO$_4$), and concentrated. The obtained crystals were collected by filtration, and ethyl(E)-3-[3,5-dimethyl-1-[4-(5-methyl-2-phenyl-4-oxazolylmethoxy)benzyl]-1H-pyrazol-4-yl]propenoate (740 mg) was obtained. After the mother liquor was concentrated, the residue was subjected to silica gel column chromatography, and 150 mg of crystals were additionally obtained from the fraction eluted with ethyl acetate-hexane (2:3, volume ratio). The total was 890 mg (yield: 87%). This was recrystallized from ethyl acetate-isopropyl ether. Melting point: 98–99° C.

EXAMPLE 144

A mixture of ethyl(E)-3-[3,5-dimethyl-1-[4-(5-methyl-2-phenyl-4-oxazolylmethoxy)benzyl]-1H-pyrazol-4-yl]propenoate (800 mg), 5% palladium-carbon (400 mg), ethanol (30 ml), and tetrahydrofuran (10 ml) was stirred at room temperature for one hour under a hydrogen atmosphere. After removal of the catalyst by filtration, and the filtrate was concentrated. The residue was subjected to silica gel column chromatography, and ethyl 3-[3,5-dimethyl-1-[4-(5-methyl-2-phenyl-4-oxazolylmethoxy)benzyl]-1H-pyrazol-4-yl]propionate (770 mg, yield: 96%) was obtained as a colorless oily substance from the fraction eluted with ethyl acetate-hexane (1:1, volume ratio).

NMR(CDCl$_3$) δ: 1.22(3H, t, J=7 Hz), 2.09(3H, s), 2.22 (3H, s), 2.35–2.5(5H, m), 2.6–2.75(2H, m), 4.09(2H, q, J=7 Hz), 4.96(2H, s), 5.14(2H, s), 6.94(2H, d, J=9 Hz), 7.02(2H, d, J=9 Hz), 7.4–7.5(3H, m), 7.95–8.1(2H, m).

EXAMPLE 145

A mixture of ethyl 3-[3,5-dimethyl-1-[4-(5-methyl-2-phenyl-4-oxazolylmethoxy)benzyl]-1H-pyrazol-4-yl]propionate (760 mg), 1 N aqueous sodium hydroxide solution (5 ml), ethanol (5 ml), and tetrahydrofuran (5 ml) was stirred at room temperature for two hours. The reaction mixture was poured into water, which was acidified with 1 N hydrochloric acid, and precipitated crystals were collected by filtration. This was recrystallized from methanol-ethyl acetate, and 3-[3,5-dimethyl-1-[4-(5-methyl-2-phenyl-4-oxazolylmethoxy)benzyl]-1H-pyrazol-4-yl]propionic acid was obtained (550 mg, yield: 77%). Melting point: 170–171° C.

EXAMPLE 146

A mixture of ethyl [1-[2-(4-benzyloxyphenyl)ethyl]-3-phenyl-1H-pyrazol-4-yl]acetate (440 mg), 1 N aqueous sodium hydroxide solution (2 ml), ethanol (2 ml), and tetrahydrofuran (2 ml) was stirred at room temperature for 2 hours. The reaction mixture was acidified with 1 N hydrochloric acid. The obtained crystals were collected by filtration, and [1-[2-(4-benzyloxyphenyl)ethyl]-3-phenyl-1H-pyrazol-4-yl]acetic acid was obtained (350 mg, yield: 85%). This was recrystallized from tetrahydrofuran-hexane. Melting point: 199–200° C.

EXAMPLE 147

A mixture of ethyl 3-hydroxy-1H-pyrazol-4-carboxylate (12.18 g), 4-(4-chloromethylphenoxymethyl)-5-methyl-2-phenyloxazole (55.11 g), potassium carbonate (25.52 g), and N,N-dimethylformamide (300 ml) was stirred at 90° C. for 8 hours. The reaction mixture was poured into water, which was extracted with ethyl acetate. The ethyl acetate layer was washed with dilute hydrochloric acid, then, with saturated aqueous sodium chloride solution, and dried (MgSO$_4$) and concentrated. The residue was subjected to silica gel column chromatography, and ethyl 1-[4-(5-methyl-2-phenyl-4-oxazolylmethoxy)benzyl]-3-[4-(5-methyl-2-phenyl-4-oxazolylmethoxy)benzyloxy]-1H-pyrazol-4-carboxylate (48.16 g, yield: 87%) was obtained as colorless crystals from the fraction eluted with ethyl acetate-hexane (1:1, volume ratio). This was recrystallized from acetone-hexane. Melting point: 118–119° C.

EXAMPLE 148

To a mixture of 1-[4-(5-methyl-2-phenyl-4-oxazolylmethoxy)benzyl]-3-[4-(5-methyl-2-phenyl-4-oxazolylmethoxy)benzyloxy]-1H-pyrazol-4-carbaldehyde (25.20 g), ethyl diethylphosphonoacetate (9.50 g), and N,N-dimethylformamide (200 ml), sodium hydride (60%, oily, 1.68 g) was added at 0° C., and the mixture was stirred at room temperature for 2 hours. The reaction mixture was added to ice water, and the obtained crystals were collected by filtration, and ethyl(E)-3-[1-[4-(5-methyl-2-phenyl-4-oxazolylmethoxy)benzyl]-3-[4-(5-methyl-2-phenyl-4-oxazolylmethoxy)benzyloxy]-1H-pyrazol-4-yl]propenoate (25.58 g, yield: 92%) was obtained. This was recrystallized from tetrahydrofuran-hexane. Melting point: 148–149° C.

EXAMPLE 149

A mixture of ethyl(E)-3-[1-[4-(5-methyl-2-phenyl-4-oxazolylmethoxy)benzyl]-3-[4-(5-methyl-2-phenyl-4-oxazolylmethoxy)benzyloxy]-1H-pyrazol-4-yl]propenoate (24.15 g), 5% palladium-carbon (34.22 g), and tetrahydrofuran (400 ml) was stirred at room temperature under a hydrogen atmosphere overnight. After removal of the catalyst by filtration, and the filtrate was concentrated. The residue was subjected to silica gel column chromatography, and ethyl 3-[3-hydroxy-1-[4-(5-methyl-2-phenyl-4-oxazolylmethoxy)benzyl]-1H-pyrazol-4-yl]propionate was obtained from the fraction eluted with ethyl acetate-hexane (2:1, volume ratio) as colorless crystals (13.93 g, yield: 92%). This was recrystallized from tetrahydrofuran-hexane. Melting point: 137–138° C.

EXAMPLE 150

After a mixture of ethyl 3-[3-hydroxy-1-[4-(5-methyl-2-phenyl-4-oxazolylmethoxy)benzyl]-1H-pyrazol-4-yl]propionate (650 mg), 1 N aqueous sodium hydroxide solution (5 ml), tetrahydrofuran (5 ml), and ethanol (10 ml) was stirred at room temperature for three hours, 1 N hydrochloric acid (5 ml) was added to the mixture, which was extracted with ethyl acetate. The ethyl acetate layer was washed with saturated aqueous sodium chloride solution, dried ($MgSO_4$), and concentrated. The obtained colorless crystals were collected by filtration, and 3-[3-hydroxy-1-[4-(5-methyl-2-phenyl-4-oxazolylmethoxy) benzyl]-1H-pyrazol-4-yl]propionic acid was obtained (560 mg, yield: 91%). This was recrystallized from tetrahydrofuran-hexane. Melting point: 197–198° C.

EXAMPLE 151

To a solution of ethyl 3-[3-hydroxy-1-[4-(5-methyl-2-phenyl-4-oxazolylmethoxy)benzyl]-1H-pyrazol-4-yl]propionate (1.00 g) in tetrahydrofuran (80 ml), sodium hydride (60%, oily, 100 mg) was added at 0° C., and the solution was stirred for 30 minutes. N-Phenyltrifluoromethanesulfonimide (930 mg) was added to the reaction mixture, which was stirred at room temperature for two hours. The reaction mixture was poured into water, which was extracted with ethyl acetate. The ethyl acetate was washed with saturated aqueous sodium bicarbonate solution, 1 N hydrochloric acid, then, with saturated sodium chloride solution, and dried ($MgSO_4$) and concentrated. The residue was subjected to silica gel column chromatography, and ethyl 3-[1-[4-(5-methyl-2-phenyl-4-oxazolylmethoxy)benzyl]-3-trifluoromethanesulfonyloxy-1H-pyrazol-4-yl]propionate was obtained (1.31 g, yield: 100%) as a colorless oily substance from the fraction eluted with ethyl acetate-hexane (1:2, volume ratio).
NMR($CDCl_3$) δ: 1.20 (3H, t, J=7.0 Hz), 2.43 (3H, s), 2.48–2.56 (2H, m), 2.69–2.76 (2H, m), 4.09 (2H, q, J=7.0 Hz), 4.99 (2H, s), 5.10 (2H, s), 6.98–7.02 (2H, m), 7.11–7.20 (3H, m), 7.42–7.46 (3H, m), 7.99–8.04 (2H, m).

EXAMPLE 152

To a solution of ethyl 3-[3-hydroxy-1-[4-(5-methyl-2-phenyl-4-oxazolylmethoxy)benzyl]-1H-pyrazol-4-yl]propionate (462 mg) in N,N-dimethylformamide (10 ml), sodium hydride (60%, oily, 40.0 mg) was added at 0° C., and the solution was stirred at room temperature for 30 minutes. Iodomethane (0.187 ml) was added to the reaction mixture, which was stirred at room temperature for one hour. The reaction mixture was poured into water, which was extracted with ethyl acetate. The ethyl acetate layer was washed with water, then, with saturated aqueous sodium chloride solution, and dried ($MgSO_4$) and concentrated. The residue was subjected to silica gel column chromatography, and ethyl 3-[3-methoxy-1-[4-(5-methyl-2-phenyl-4-oxazolylmethoxy)benzyl]-1H-pyrazol-4-yl]propionate was obtained (382 mg, yield: 80%) as a colorless oily substance from the fraction eluted with ethyl acetate-hexane (1:1, volume ratio).
NMR($CDCl_3$) δ: 1.21 (3H, t, J=7.2 Hz), 2.43 (3H, s), 2.46–2.54 (2H, m), 2.60–2.68 (2H, m), 3.90 (3H, s), 4.09 (2H, q, J=7.2 Hz), 4.98 (2H, s), 5.01 (2H, s), 6.93 (1H, s), 6.98 (2H, d, J=8.8 Hz), 7.15 (2H, d, J=8.8 Hz), 7.40–7.47 (3H, m), 7.99–8.04 (2H, m).

EXAMPLE 153

A mixture of ethyl 3-[3-methoxy-1-[4-(5-methyl-2-phenyl-4-oxazolylmethoxy)benzyl]-1H-pyrazole-4-yl]propionate (380 mg), 1 N aqueous sodium hydroxide solution (2 ml), tetrahydrofuran (4 ml), and ethanol (4 ml) was stirred at room temperature for 2 hours, diluted with 1 N hydrochloric acid (2 ml), and extracted with ethyl acetate. The ethyl acetate layer was washed with saturated aqueous sodium chloride solution, dried ($MgSO_4$), and concentrated. The obtained colorless crystals were collected by filtration, and 3-[3-methoxy-1-[4-(5-methyl-2-phenyl-4-oxazolylmethoxy)benzyl]-1H-pyrazol-4-yl]propionic acid was obtained (319 mg, yield: 89%). This was recrystallized from ethanol-hexane. Melting point: 127–128° C.

EXAMPLE 154

To a solution of ethyl 3-[3-hydroxy-1-[4-(5-methyl-2-phenyl-4-oxazolylmethoxy)benzyl]-1H-pyrazol-4-yl]propionate (462 mg) in N,N-dimethylformamide (10 ml), sodium hydride (60%, oily, 40.0 mg) was added at 0° C., and the solution was stirred at room temperature for 30 minutes. Iodoethane (0.240 ml) was added to the reaction mixture, which was stirred at room temperature for one hour. The reaction mixture was poured into water, which was extracted with ethyl acetate. The ethyl acetate layer was washed with water, then, with saturated aqueous sodium chloride solution, and dried ($MgSO_4$) and concentrated. The residue was subjected to silica gel column chromatography, and ethyl 3-[3-ethoxy-1-[4-(5-methyl-2-phenyl-4-oxazolylmethoxy)benzyl]-1H-pyrazol-4-yl]propionate was obtained (452 mg, yield: 92%) as a colorless oily substance from the fraction eluted with ethyl acetate-hexane (1:1, volume ratio).
NMR($CDCl_3$) δ: 1.21 (3H, t, J=7.2 Hz), 1.36 (3H, t, J=7.0 Hz), 2.43 (3H, s), 2.47–2.55 (2H, m), 2.61–2.69 (2H, m), 4.09 (2H, q, J=7.2 Hz), 4.23 (2H, q, J=7.0 Hz), 4.98 (2H, s), 5.00 (2H, s), 6.93 (1H, s), 6.97 (2H, d, J=8.8 Hz), 7.14 (2H, d, J=8.8 Hz), 7.40–7.47 (3H, m), 7.97–8.06 (2H, m).

EXAMPLE 155

A mixture of ethyl 3-[3-ethoxy-1-[4-(5-methyl-2-phenyl-4-oxazolylmethoxy)benzyl]-1H-pyrazole-4-yl]propionate (441 mg), 1 N aqueous sodium hydroxide solution (2 ml), tetrahydrofuran (4 ml), and ethanol (4 ml) was stirred at room temperature for two hours, diluted with 1 N hydrochloric acid (2 ml), and extracted with ethyl acetate. The ethyl acetate layer was washed with saturated aqueous sodium chloride solution, dried ($MgSO_4$), and concentrated. The obtained colorless crystals were collected by filtration, and 3-[3-ethoxy-1-[4-(5-methyl-2-phenyl-4-oxazolylmethoxy)benzyl]-1H-pyrazol-4-yl]propionic acid was obtained (328 mg, yield: 79%). This was recrystallized from ethanol-hexane. Melting point: 96–97° C.

EXAMPLE 156

To a solution of ethyl 3-[3-hydroxy-1-[4-(5-methyl-2-phenyl-4-oxazolylmethoxy)benzyl]-1H-pyrazol-4-yl]propionate (710 mg) in N,N-dimethylformamide (10 ml), sodium hydride (60%, oily, 72.0 mg) was added at 0° C., and the solution was stirred at room temperature for 30 minutes. Iodopropane (0.33 g) was added to the reaction mixture, which was stirred at room temperature for two hours. The reaction mixture was poured into water, which was extracted with ethyl acetate. The ethyl acetate layer was washed with water, then, with saturated aqueous sodium chloride solution, and dried ($MgSO_4$) and concentrated. The residue was subjected to silica gel column chromatography, and a colorless oily substance was obtained from the fraction eluted with ethyl acetate-hexane (1:2, volume ratio). A mixture of the obtained oily substance, 1 N aqueous sodium hydroxide solution (3 ml), tetrahydrofuran (5 ml), and ethanol (5 ml) was stirred at room temperature for two hours, diluted with 1 N hydrochloric acid (3 ml), and extracted with ethyl acetate. The ethyl acetate layer was washed with saturated aqueous sodium chloride solution, dried (MgSO$_4$), and concentrated. The obtained colorless crystals were collected by filtration, and 3-[1-[4-(5-methyl-2-phenyl-4-oxazolylmethoxy)benzyl]-3-propyloxy-1H-pyrazol-4-yl]propionic acid was obtained (0.59 g, yield. 81%). This was recrystallized from acetone-hexane. Melting point: 108–109° C.

EXAMPLE 157

A mixture of ethyl 3-[3-hydroxy-1-[4-(5-methyl-2-phenyl-4-oxazolylmethoxy)benzyl]-1H-pyrazol-4-yl]propionate (700 mg), potassium carbonate (250 mg), iodoisopropane (1.03 g), and N,N-dimethylformamide (15 ml) was stirred at 80–90° C. for four hours. The reaction mixture was poured into water, which was extracted with ethyl acetate. The ethyl acetate layer was washed with water, dried (MgSO$_4$), and concentrated. The residue was subjected to silica gel column chromatography, and ethyl 3-[3-isopropoxy-1-[4-(5-methyl-2-phenyl-4-oxazolylmethoxy)benzyl]-1H-pyrazol-4-yl]propionate was obtained as a colorless oily substance (460 mg, yield: 60%) from the fraction eluted with ethyl acetate-hexane (1:2, volume ratio).

NMR(CDCl$_3$) δ: 1.21 (3H, t, J=7 Hz), 1.32 (6H, d, J=6 Hz), 2.43 (3H, s), 2.45–2.7 (4H, m), 4.09 (2H, q, J=7 Hz), 4.75–4.95 (1H, m), 4.98 (2H, s), 5.00 (2H, s), 6.92 (1H, s), 6.97 (2H, d, J=9 Hz), 7.14 (2H, d, J=9 Hz), 7.4–7.5 (3H, m), 7.95–8.1 (2H, m).

EXAMPLE 158

A mixture of ethyl 3-[3-isopropoxy-1-[4-(5-methyl-2-phenyl-4-oxazolylmethoxy)benzyl]-1H-pyrazole-4-yl]propionate (440 mg), 1 N aqueous sodium hydroxide solution (5 ml), tetrahydrofuran (5 ml), and ethanol (5 ml) was stirred at room temperature for one hour, diluted with 1 N hydrochloric acid (5 ml), and extracted with ethyl acetate. The ethyl acetate layer was washed with saturated aqueous sodium chloride solution, dried (MgSO$_4$), and concentrated. The obtained colorless crystals were collected by filtration, and 3-[3-isopropoxy-1-[4-(5-methyl-2-phenyl-4-oxazolylmethoxy)benzyl]-1H-pyrazol-4-yl]propionic acid was obtained (380 mg, yield: 91%). This was recrystallized from acetone-isopropyl ether. Melting point: 106–107° C.

EXAMPLE 159

A mixture of ethyl 3-[3-hydroxy-1-[4-(5-methyl-2-phenyl-4-oxazolylmethoxy)benzyl]-1H-pyrazol-4-yl]propionate (500 mg), potassium carbonate (165 mg), benzyl bromide (205 mg), and N,N-dimethylformamide (10 ml) was stirred at 80° C. for one hour. The reaction mixture was poured into water, which was extracted with ethyl acetate. The ethyl acetate layer was washed with water, dried (MgSO$_4$), and concentrated. The residue was subjected to silica gel column chromatography, and ethyl 3-[3-benzyloxy-1-[4-(5-methyl-2-phenyl-4-oxazolylmethoxy)benzyl]-1H-pyrazol-4-yl]propionate (385 mg, yield: 64%) was obtained as a colorless oily substance from the fraction eluted with ethyl acetate-hexane (1:2, volume ratio).

NMR(CDCl$_3$) δ: 1.19 (3H, t, J=7 Hz), 2.44 (3H, s), 2.45–2.7 (4H, m), 4.07 (2H, q, J=7 Hz), 4.99 (2H, s), 5.03 (2H, s), 5.24 (2H, s), 6.96 (1H, s), 6.98 (2H, d, J=9 Hz), 7.14 (2H, d, J=9 Hz), 7.3–7.5 (8H, m), 7.95–8.1 (2H, m).

EXAMPLE 160

A mixture of ethyl 3-[3-benzyloxy-1-[4-(5-methyl-2-phenyl-4-oxazolylmethoxy)benzyl]-1H-pyrazol-4-yl]propionate (380 mg), 1 N aqueous sodium hydroxide solution (3 ml), tetrahydrofuran (3 ml), and ethanol (3 ml) was stirred at room temperature for one hour, and then diluted with 1 N hydrochloric acid (5 ml) to give colorless crystals, which were collected by filtration. This was recrystallized from ethyl acetate-hexane, to yield 3-[3-benzyloxy-1-[4-(5-methyl-2-phenyl-4-oxazolylmethoxy)benzyl]-1H-pyrazol-4-yl]propionic acid (300 mg, yield: 83%). Melting point: 108–109° C.

EXAMPLE 161

To a solution of ethyl 3-[3-hydroxy-1-[4-(5-methyl-2-phenyl-4-oxazolylmethoxy)benzyl]-1H-pyrazol-4-yl]propionate (1.00 g) in N,N-dimethylformamide (80 ml), sodium hydride (60%, oily, 100 mg) was added at 0° C., and the solution was stirred at room temperature for 30 minutes. 2-Chloro-5-trifluoromethylpyridine (0.45 g) was added to the reaction mixture, which was stirred at 90° C. for two hours. The reaction mixture was poured into water, which was extracted with ethyl acetate. The ethyl acetate layer was washed with water, then, with saturated aqueous sodium chloride solution, and dried (MgSO$_4$) and concentrated. The residue was subjected to silica gel column chromatography, and a colorless oily substance was obtained from the fraction eluted with ethyl acetate-hexane (1:1, volume ratio). A mixture of the obtained oily substance, 1 N aqueous sodium hydroxide solution (5 ml), tetrahydrofuran (5 ml), and ethanol (10 ml) was stirred at room temperature overnight, diluted with 1 N hydrochloric acid (5 ml), and extracted with ethyl acetate. The ethyl acetate layer was washed with saturated aqueous sodium chloride solution, dried (MgSO$_4$), and concentrated. The obtained colorless crystals were collected by filtration, and 3-[1-[4-(5-methyl-2-phenyl-4-oxazolylmethoxy)benzyl]-3-(5-trifluoromethyl-2-pyridyloxy)-1H-pyrazol-4-yl]propionic acid was obtained (960 mg, yield: 76%). This was recrystallized from ethyl acetate-hexane. Melting point: 107–108° C.

EXAMPLE 162

A mixture of ethyl 3-hydroxy-1H-pyrazol-4-carboxylate (5.50 g), 4-(4-chloromethylphenoxymethyl)-2-(2-furyl)-5-methyloxazole (22.85 g), potassium carbonate (15.11 g), and N,N-dimethylformamide (200 ml) was stirred at 90° C. for 8 hours. The reaction mixture was poured into water, which was extracted with ethyl acetate. The ethyl acetate layer was washed with dilute hydrochloric acid, then, with saturated aqueous sodium chloride solution, and dried (MgSO$_4$) and concentrated. The residue was subjected to silica gel column chromatography, and ethyl 1-[4-[2-(2-furyl)-5-methyl-4-oxazolylmethoxy]benzyl]-3-[4-[2-(2-furyl)-5-methyl-4-oxazolylmethoxy]benzyloxy]-1H-pyrazol-4-carboxylate (19.96 g, yield: 82%) was obtained as colorless crystals from the fraction eluted with ethyl acetate-hexane (1:1, volume ratio). This was recrystallized from ethyl acetate-hexane. Melting point: 133–134° C.

EXAMPLE 163

To a mixture of 1-[4-[2-(2-furyl)-5-methyl-4-oxazolylmethoxy]benzyl]-3-[4-[2-(2-furyl)-5-methyl-4-oxazolylmethoxy]benzyloxy]-1H-pyrazol-4-carbaldehyde (14.09 g), ethyl diethylphosphonoacetate (5.88 g), and N,N-dimethylformamide (100 ml), sodium hydride (60%, oily, 1.01 g) was added at 0° C., and the mixture was stirred at room temperature for two hours. The reaction mixture was poured into ice water, and the obtained crystals were collected by filtration, and ethyl(E)-3-[1-[4-[2-(2-furyl)-5-methyl-4-oxazolylmethoxy]benzyl]-3-[4-[2-(2-furyl)-5-methyl-4-oxazolylmethoxy]benzyloxy]-1H-pyrazol-4-yl]propenoate was obtained (13.91 g, yield: 89%). This was recrystallized from ethyl acetate-hexane. Melting point: 138–139° C.

EXAMPLE 164

A mixture of ethyl(E)-3-[1-[4-[2-(2-furyl)-5-methyl-4-oxazolylmethoxy]benzyl]-3-[4-[2-(2-furyl)-5-methyl-4-oxazolylmethoxy]benzyloxy]-1H-pyrazol-4-yl]propenoate (12.5 g), 5% palladium-carbon (20.0 g), ethanol (200 ml), and tetrahydrofuran (200 ml) was stirred under a hydrogen atmosphere at room temperature for 7 hours. After removal of the catalyst by filtration, the filtrate was concentrated. The obtained crystals were collected by filtration, and ethyl 3-[1-[4-[2-(2-furyl)-5-methyl-4-oxazolylmethoxy]benzyl]-3-hydroxy-1H-pyrazol-4-yl]propionate (4.40 g, yield: 56%) was obtained. This was recrystallized from tetrahydrofuran-hexane. Melting point: 145–146° C.

EXAMPLE 165

To a solution of ethyl 3-[1-[4-[2-(2-furyl)-5-methyl-4-oxazolylmethoxy]benzyl]-3-hydroxy-1H-pyrazol-4-yl]propionate (4.29 g) in tetrahydrofuran (100 ml), sodium hydride (60%, oily, 420 mg) was added at 0° C., and the solution was stirred for 10 minutes. N-Phenyltrifluoromethanesulfonimide (3.75 g) was added to the reaction mixture, which was stirred at 0° C. for 20 minutes. The reaction mixture was poured into water, which was extracted with ethyl acetate. The ethyl acetate layer was washed with saturated aqueous sodium bicarbonate solution, 1 N hydrochloric acid, then with saturated aqueous sodium chloride solution, and dried ($MgSO_4$) and concentrated. The residue was subjected to silica gel column chromatography, and ethyl 3-[1-[4-[2-(2-furyl)-5-methyl-4-oxazolylmethoxy]benzyl]-3-trifluoromethanesulfonyloxy-1H-pyrazol-4-yl]propionate (5.02 g, yield: 91%) was obtained as a colorless oily substance from the fraction eluted with ethyl acetate-hexane (1:2, volume ratio).

NMR($CDCl_3$) δ: 1.20 (3H, t, J=7.2 Hz), 2.42 (3H, s), 2.53 (2H, t, J=7.0 Hz), 2.73 (2H, t, J=7.0 Hz), 4.09 (2H, q, J=7.2 Hz), 4.98 (2H, s), 5.10 (2H, s), 6.52 (1H, dd, J=3.6, 1.8 Hz), 6.96–7.01 (3H, m), 7.12 (1H, s), 7.17 (2H, d, J=8.8 Hz), 7.53 (1H, dd, J=1.8, 0.8 Hz).

EXAMPLE 166

To a solution of ethyl 3-[1-[4-[2-(2-furyl)-5-methyl-4-oxazolylmethoxy]benzyl]-3-hydroxy-1H-pyrazol-4-yl]propionate (452 mg) in N,N-dimethylformamide (10 ml), sodium hydride (60%, oily, 40.0 mg) was added at 0° C., and the solution was stirred at room temperature for 30 minutes. Iodoethane (0.240 ml) was added to the reaction mixture, which was stirred at room temperature for one hour. The reaction mixture was poured into water, which was extracted with ethyl acetate. The ethyl acetate layer was washed with water, then, with saturated aqueous sodium chloride solution, and dried ($MgSO_4$) and concentrated. The residue was subjected to silica gel column chromatography, and ethyl 3-[3-ethoxy-1-[4-[2-(2-furyl)-5-methyl-4-oxazolylmethoxy]benzyl]-1H-pyrazol-4-yl]propionate (348 mg, yield: 73%) was obtained as a colorless oily substance from the fraction eluted with ethyl acetate-hexane (1:1, volume ratio).

NMR($CDCl_3$) δ: 1.21 (3H, t, J=7.0 Hz), 1.36 (3H, t, J=7.0 Hz), 2.47 (3H, s), 2.48–2.55 (2H, m), 2.61–2.69 (2H, m), 4.09 (2H, q, J=77.0 Hz), 4.22 (2H, q, J=7.0 Hz), 4.97 (2H, s), 5.00 (2H, s), 6.52 (1H, dd, J=3.6, 2.0 Hz), 6.92–6.99 (4H, m), 7.13 (2H, d, J=8.8 Hz), 7.54 (1H, dd, J=2.0, 0.6 Hz).

EXAMPLE 167

A mixture of ethyl 3-[3-ethoxy-1-[4-[2-(2-furyl)-5-methyl-4-oxazolylmethoxy]benzyl]-1H-pyrazole-4-yl]propionate (381 mg), 1 N aqueous sodium hydroxide solution (2 ml), tetrahydrofuran (4 ml), and ethanol (4 ml) was stirred at room temperature for four hours, diluted with 1 N hydrochloric acid (2 ml), and extracted with ethyl acetate. The ethyl acetate layer was washed with saturated aqueous sodium chloride solution, dried ($MgSO_4$), and concentrated. The obtained colorless crystals were collected by filtration, and 3-[3-ethoxy-1-[4-[2-(2-furyl)-5-methyl-4-oxazolylmethoxy]benzyl]-1H-pyrazol-4-yl]propionic acid was obtained (327 mg, yield: 91%). This was recrystallized from ethanol-hexane. Melting point: 129–130° C.

EXAMPLE 168

To a solution of ethyl 3-[1-[4-[2-(2-furyl)-5-methyl-4-oxazolylmethoxy]benzyl]-3-hydroxy-1H-pyrazol-4-yl]propionate (452 mg) in N,N-dimethylformamide (10 ml), sodium hydride (60%, oily, 40.0 mg) was added at 0° C., and the solution was stirred at room temperature for 30 minutes. Benzyl bromide (0.178 ml) was added to the reaction mixture, which was stirred at room temperature for one hour. The reaction mixture was poured into water, which was extracted with ethyl acetate. The ethyl acetate layer was washed with water, then, with saturated aqueous sodium chloride solution, and dried ($MgSO_4$) and concentrated. The residue was subjected to silica gel column chromatography, and ethyl 3-[3-benzyloxy-1-[4-[2-(2-furyl)-5-methyl-4-oxazolylmethoxy]benzyl]-1H-pyrazol-4-yl]propionate (383 mg, yield: 71%) was obtained as a colorless oily substance from the fraction eluted with ethyl acetate-hexane (1:1, volume ratio).

NMR($CDCl_3$) δ: 1.19 (3H, t, J=7.2 Hz), 2.42 (3H, s), 2.47–2.55 (2H, m), 2.63–2.71 (2H, m), 4.07 (2H, q, J=7.2 Hz), 4.97 (2H, s), 5.02 (2H, s), 5.23 (2H, s), 6.52 (1H, dd, J=3.6, 1.8 Hz), 6.90–6.99 (4H, m), 7.13 (2H, d, J=8.4 Hz), 7.27–7.47 (5H, m), 7.54 (1H, dd, J=1.8, 1.0 Hz).

EXAMPLE 169

A mixture of ethyl 3-[3-benzyloxy-1-[4-[2-(2-furyl)-5-methyl-4-oxazolylmethoxy]benzyl]-1H-pyrazol-4-yl]propionate (379 mg), 1 N aqueous sodium hydroxide solution (2 ml), tetrahydrofuran (4 ml), and ethanol (4 ml) was stirred at room temperature for 5 hours, diluted with 1 N hydrochloric acid (2 ml), and extracted with ethyl acetate. The ethyl acetate layer was washed with saturated aqueous sodium chloride solution, dried ($MgSO_4$), and concentrated. The obtained colorless crystals were collected by filtration, and 3-[3-benzyloxy-1-[4-[2-(2-furyl)-5-methyl-4-oxazolylmethoxy]benzyl]-1H-pyrazol-4-yl]propionic acid was obtained (299 mg, yield: 83%). This was recrystallized from ethanol-hexane. Melting point: 104–105° C.

EXAMPLE 170

To a mixture of ethyl 3-(3-ethoxy-1H-pyrazol-4-yl)propionate (1.59 g), 4-benzyloxy-3-methoxybenzyl chloride (1.97 g), and N,N-dimethylformamide (30 ml), sodium hydride (60%, oily, 0.30 g) was added at 0° C., and then the mixture was stirred at room temperature for 30 minutes. The reaction mixture was poured into water, which was extracted with ethyl acetate. The ethyl acetate layer was washed with water, then, with saturated aqueous sodium chloride solution, and dried ($MgSO_4$) and concentrated. The residue was subjected to silica gel column chromatography, and ethyl 3-[1-(4-benzyloxy-3-methoxybenzyl)-3-ethoxy-1H-pyrazol-4-yl]propionate (2.93 g, yield: 89%) was obtained as a colorless oily substance from the fractions eluted with ethyl acetate-hexane (1:2, volume ratio).

NMR($CDCl_3$) δ: 1.20 (3H, t, J=7.2 Hz), 1.36 (3H, t, J=7.0 Hz), 2.46–2.54 (2H, m), 2.60–2.68 (2H, m), 3.84 (3H, s), 4.08 (2H, q, J=7.2 Hz), 4.22 (2H, q, J=7.0 Hz), 4.97 (2H, s), 5.14 (2H, s), 6.66 (1H, dd, J=8.4, 2.0 Hz), 6.76 (1H, d, J=2.0 Hz), 6.81 (1H, d, J=8.4 Hz), 6.93 (1H, s), 7.28–7.44 (5H, m).

EXAMPLE 171

To a solution of ethyl 3-[(3-ethoxy-1-(4-hydroxy-3-methoxybenzyl)-1H-pyrazol-4-yl]propionate (505 mg) in N,N-dimethylformamide (10 ml), sodium hydride (60%, oily, 58.0 mg) was added at 0° C., and then the solution was stirred at room temperature for 30 minutes. 4-Chloromethyl-5-methyl-2-phenyloxazole (301 mg) was added to the reaction mixture, which was stirred at 60° C. for one hour. The reaction mixture was poured into water, which was extracted with ethyl acetate. The ethyl acetate layer was washed with water, then, with saturated aqueous sodium chloride solution, and dried ($MgSO_4$) and concentrated. The residue was subjected to silica gel column chromatography, and ethyl 3-[3-ethoxy-1-[3-methoxy-4-(5-methyl-2-phenyl-4-oxazolylmethoxy)benzyl]-1H-pyrazol-4-yl]propionate (661 mg, yield: 88%) was obtained as a colorless oily substance from the fraction eluted with ethyl acetate-hexane (1:1, volume ratio).

NMR($CDCl_3$) δ: 1.22 (3H, t, J=7.2 Hz), 1.37 (3H, t, J=7.2 Hz), 2.41 (3H, s), 2.47–2.55 (2H, m), 2.61–2.69 (2H, m), 3.82 (3H, s), 4.09 (2H, q, J=7.2 Hz), 4.23 (2H, q, J=7.2 Hz), 5.00 (2H, s), 5.04 (2H, s), 6.72 (1H, dd, J=8.2, 2.2 Hz), 6.76 (1H, d, J=2.2 Hz), 6.95 (1H, s), 7.00 (1H, d, J=8.2 Hz), 7.40–7.46 (3H, m), 7.98–8.03 (2H, m).

EXAMPLE 172

A mixture of ethyl 3-[3-ethoxy-1-[3-methoxy-4-(5-methyl-2-phenyl-4-oxazolylmethoxy)benzyl]-1H-pyrazol-4-yl]propionate (660 mg), 1 N aqueous sodium hydroxide solution (3 ml), tetrahydrofuran (6 ml), and ethanol (6 ml) was stirred at room temperature for 3 hours, diluted with 1 N hydrochloric acid (3 ml), and extracted with ethyl acetate. The ethyl acetate layer was washed with saturated aqueous sodium chloride solution, dried ($MgSO_4$), and concentrated. The obtained colorless crystals were collected by filtration, and 3-[3-ethoxy-1-[3-methoxy-4-(5-methyl-2-phenyl-4-oxazolylmethoxy)benzyl]-1H-pyrazol-4-yl]propionic acid (510 mg, yield: 82%) was obtained. This was recrystallized from ethanol-hexane. Melting point: 122–123° C.

EXAMPLE 173

To a solution of ethyl 3-[3-ethoxy-1-(4-hydroxy-3-methoxybenzyl)-1H-pyrazol-4-yl]propionate (505 mg) in N,N-dimethylformamide (10 ml), sodium hydride (60%, oily, 58.0 mg) was added at 0° C., and then the solution was stirred at room temperature for 30 minutes. 4-Chloromethyl-2-(2-furyl)-5-methyloxazole (573 mg) was added to the reaction mixture, which was stirred at room temperature for one hour. The reaction mixture was poured into water, which was extracted with ethyl acetate. The ethyl acetate layer was washed with water, then, with saturated aqueous sodium chloride solution, and dried ($MgSO_4$) and concentrated. The residue was subjected to silica gel column chromatography, and ethyl 3-[3-ethoxy-1-[4-[2-(2-furyl)-5-methyl-4-oxazolylmethoxy]-3-methoxybenzyl]-1H-pyrazol-4-yl]propionate (564 mg, yield: 76%) was obtained as a yellow oily substance from the fraction eluted with ethyl acetate-hexane (1:1, volume ratio).

NMR($CDCl_3$) δ: 1.21 (3H, t, J=7.2 Hz), 1.37 (3H, t, J=7.2 Hz), 2.40 (3H, s), 2.47–2.55 (2H, m), 2.61–2.69 (2H, m), 3.82 (3H, s), 4.09 (2H, q, J=7.2 Hz), 4.23 (2H, q, J=7.2 Hz), 4.99 (2H, s), 5.03 (2H, s), 6.52 (1H, dd, J=3.6, 1.8 Hz), 6.71 (1H, dd, J=8.2, 2.0 Hz), 6.75 (1H, d, J=2.0 Hz), 6.94 (1H, s), 6.96 (1H, d, J=8.2 Hz), 6.96 (1H, dd, J=3.6, 0.8 Hz), 7.53 (1H, dd, J=1.8, 0.8 Hz).

EXAMPLE 174

A mixture of ethyl 3-[3-ethoxy-1-[4-[2-(2-furyl)-5-methyl-4-oxazolylmethoxy]-3-methoxybenzyl]-1H-pyrazol-4-yl]propionate (561 mg), 1 N aqueous sodium hydroxide solution (2.5 ml), tetrahydrofuran (5 ml), and ethanol (5 ml) was stirred at room temperature for two hours, diluted with 1 N hydrochloric acid (2.5 ml), and extracted with ethyl acetate. The ethyl acetate layer was washed with saturated aqueous sodium chloride solution, dried ($MgSO_4$), and concentrated. The obtained colorless crystals were collected by filtration, and 3-[3-ethoxy-1-[4-[2-(2-furyl)-5-methyl-4-oxazolylmethoxy]-3-methoxybenzyl]-1H-pyrazol-4-yl]propionic acid (506 mg, yield: 96%) was obtained. This was recrystallized from ethanol-hexane. Melting point: 133–134° C.

EXAMPLE 175

To a solution of ethyl 3-[3-ethoxy-1-(4-hydroxy-3-methoxybenzyl]-1H-pyrazol-4-yl]propionate (505 mg) in N,N-dimethylformamide (10 ml), sodium hydride (60%, oily, 58.0 mg) was added at 0° C., and then the solution was stirred at room temperature for 30 minutes. 4-Chloromethyl-5-methyl-2-(2-thienyl)oxazole (310 mg) was added to the reaction mixture, which was stirred at room temperature for one hour. The reaction mixture was poured into water, which was extracted with ethyl acetate. The ethyl acetate layer was washed with water, then, with saturated aqueous sodium chloride solution, and dried ($MgSO_4$) and concentrated. The residue was subjected to silica gel column chromatography, and ethyl 3-[3-ethoxy-1-[3-methoxy-4-[5-methyl-2-(2-thienyl)-4-oxazolylmethoxy]benzyl]-1H-pyrazol-4-yl]propionate (500 mg, yield: 66%) was obtained as a colorless oily substance from the fraction eluted with ethyl acetate-hexane (1:1, volume ratio).

NMR(CDCl$_3$) δ: 1.21 (3H, t, J=7.2 Hz), 1.37 (3H, t, J=7.2 Hz), 2.39 (3H, s), 2.47–2.55 (2H, m), 2.61–2.69 (2H, m), 3.82 (3H, s), 4.09 (2H, q, J=7.2 Hz), 4.23 (2H, q, J=7.2 Hz), 4.99 (2H, s), 5.01 (2H, s), 6.71 (1H, dd, J=8.0, 2.2 Hz), 6.75 (1H, d, J=2.2 Hz), 6.94 (1H, s), 6.96 (1H, d, J=8.0 Hz), 7.09 (1H, dd, J=4.8, 3.6 Hz), 7.39 (1H, dd, J=4.8, 1.2 Hz), 7.62 (1H, dd, J=3.6, 1.2 Hz).

EXAMPLE 176

A mixture of ethyl 3-[3-ethoxy-1-[3-methoxy-4-[5-methyl-2-(2-thienyl)-4-oxazolylmethoxy]benzyl]-1H-pyrazol-4-yl]propionate (499 mg), 1 N aqueous sodium hydroxide solution (2 ml), tetrahydrofuran (4 ml), and ethanol (4 ml) was stirred at room temperature for 3 hours, diluted with 1 N hydrochloric acid (2 ml), and extracted with ethyl acetate. The ethyl acetate layer was washed with saturated aqueous sodium chloride solution, dried (MgSO$_4$), and concentrated. The obtained colorless crystals were collected by filtration, and 3-[3-ethoxy-1-[(3-methoxy-4-[5-methyl-2-(2-thienyl)-4-oxazolylmethoxy]benzyl]-1H-pyrazol-4-yl]propionic acid (392 mg, yield: 83%) was obtained. This was recrystallized from ethanol-hexane. Melting point: 123–124° C.

EXAMPLE 177

A mixture of ethyl 3-[3-ethoxy-1-(4-hydroxy-3-methoxybenzyl)-1H-pyrazol-4-yl]propionate (505 mg), 3-picolyl chloride hydrochloride (476 mg), potassium carbonate (601 mg), and N,N-dimethylformamide (10 ml) was stirred at room temperature overnight. The reaction mixture was poured into water, which was extracted with ethyl acetate. The ethyl acetate layer was washed with water, then, with saturated aqueous sodium chloride solution, and dried (MgSO$_4$) and concentrated. The residue was subjected to silica gel column chromatography, and ethyl 3-[3-ethoxy-1-[3-methoxy-4-(3-pyridylmethoxy)benzyl]-1H-pyrazol-4-yl]propionate (531 mg, yield: 83%) was obtained as a colorless oily substance from the fraction eluted with ethyl acetate.

NMR(CDCl$_3$) δ: 1.21 (3H, t, J=7.0 Hz), 1.37 (3H, t, J=7.0 Hz), 2.47–2.55 (2H, m), 2.61–2.69 (2H, m), 3.84 (3H, s), 4.09 (2H, q, J=7.0 Hz), 4.22 (2H, q, J=7.0 Hz), 4.99 (2H, s), 5.13 (2H, s), 6.68 (1H, dd, J=8.0, 2.2 Hz), 6.77 (1H, d, J=2.2 Hz), 6.84 (1H, d, J=8.0 Hz), 6.95 (1H, s), 7.31 (1H, dd, J=8.0, 4.8 Hz), 7.79 (1H, dt, J=8.0, 1.8 Hz), 8.57 (1H, d, J=4.8 Hz), 8.67 (1H, s).

EXAMPLE 178

A mixture of ethyl 3-[3-ethoxy-1-[3-methoxy-4-(3-pyridylmethoxy)benzyl]-1H-pyrazole-4-yl]propionate (527 mg), 1 N aqueous sodium hydroxide solution (2.5 ml), tetrahydrofuran (5 ml), and ethanol (5 ml) was stirred at room temperature for two hours, diluted with 1 N hydrochloric acid (2.5 ml), and extracted with ethyl acetate. The ethyl acetate layer was washed with saturated aqueous sodium chloride solution, dried (MgSO$_4$), and concentrated. The obtained colorless crystals were collected by filtration, and 3-[3-ethoxy-1-[3-methoxy-4-(3-pyridylmethoxy)benzyl]-1H-pyrazol-4-yl]propionic acid (381 mg, yield: 77%) was obtained. This was recrystallized from ethanol-hexane. Melting point: 124–125° C.

EXAMPLE 179

To a mixture of ethyl 3-[3-ethoxy-1H-pyrazol-4-yl]propionate (1.50 g), 4-benzyloxybenzyl chloride (1.81 g), and N,N-dimethylformamide (30 ml), sodium hydride (60%, oily, 0.35 g) was added at 0° C., and then the mixture was stirred at room temperature for one hour. The reaction mixture was poured into water, which was extracted with ethyl acetate. The ethyl acetate layer was washed with water, then, with saturated aqueous sodium chloride solution, and dried (MgSO$_4$) and concentrated. The residue was subjected to silica gel column chromatography, and ethyl 3-[1-(4-benzyloxybenzyl)-3-ethoxy-1H-pyrazol-4-yl]propionate (2.76 g, yield: 96%) was obtained as a colorless oily substance from the faction eluted with ethyl acetate-hexane (1:4, volume ratio).

NMR(CDCl$_3$) δ: 1.21 (3H, t, J=7.0 Hz), 1.37 (3H, t, J=7.0 Hz), 2.44–2.70 (4H, m), 4.09 (2H, q, J=7.0 Hz), 4.25 (2H, q, J=7.0 Hz), 5.03 (2H, s), 5.05 (2H, s), 6.88–6.98 (3H, m), 7.09–7.19 (2H, m), 7.30–7.48 (5H, m).

EXAMPLE 180

A mixture of ethyl 3-[1-(4-benzyloxybenzyl)-3-ethoxy-1H-pyrazol-4-yl]propionate (490 mg), 1 N aqueous sodium hydroxide solution (3 ml), tetrahydrofuran (5 ml), and ethanol (5 ml) was stirred at room temperature for two hours, diluted with 1 N hydrochloric acid (3 ml), and extracted with ethyl acetate. The ethyl acetate layer was washed with saturated aqueous sodium chloride solution, dried (MgSO$_4$), and concentrated. The obtained colorless crystals were collected by filtration, and 3-[1-(4-benzyloxybenzyl)-3-ethoxy-1H-pyrazol-4-yl]propionic acid (430 mg, yield: 94%) was obtained. This was recrystallized from acetone-hexane. Melting point: 115–116° C.

EXAMPLE 181

A mixture of ethyl 3-[3-ethoxy-1-(4-hydroxybenzyl)-1H-pyrazol-4-yl]propionate (1.50 g), 4-chloromethyl-2-phenylthiazole (1.05 g), potassium carbonate (1.30 g), and N,N-dimethylformamide (20 ml) was stirred at room temperature overnight. The reaction mixture was poured into water, which was extracted with ethyl acetate. The ethyl acetate layer was washed with water, then, with saturated aqueous sodium chloride solution, and dried (MgSO$_4$) and concentrated. The residue was subjected to silica gel column chromatography, and a colorless oily substance was obtained from the fraction eluted with ethyl acetate-hexane (1:2, volume ratio). A mixture of the obtained oily substance, 1 N aqueous sodium hydroxide solution (10 ml), tetrahydrofuran (10 ml), and ethanol (10 ml) was stirred at room temperature for two hours, diluted with 1 N hydrochloric acid (10 ml), and extracted with ethyl acetate. The ethyl acetate layer was washed with saturated aqueous sodium chloride solution, dried (MgSO$_4$), and concentrated. The obtained colorless crystals were collected by filtration and 3-[3-ethoxy-1-[4-(2-phenyl-4-thiazolylmethoxy)benzyl]-1H-pyrazol-4-yl]propionic acid (1.60 g, yield: 73%) was obtained. This was recrystallized from acetone-hexane. Melting point: 114–115° C.

EXAMPLE 182

A mixture of ethyl 3-[3-ethoxy-1-(4-hydroxybenzyl)-1H-pyrazol-4-yl]propionate (1.20 g), 4-chloromethyl-5-methyl-2-phenylthiazole (0.95 g), potassium carbonate (1.06 g), and N,N-dimethylformamide (20 ml) was stirred at room temperature overnight. The reaction mixture was poured into water, which was extracted with ethyl acetate. The ethyl acetate layer was washed with water, then, with saturated aqueous sodium chloride solution, and dried (MgSO$_4$) and concentrated. The residue was subjected to silica gel column chromatography, and a colorless oily substance was obtained from the fraction eluted with ethyl acetate-hexane (1:2, volume ratio). A mixture of the obtained oily substance, 1 N aqueous sodium hydroxide solution (10 ml), tetrahydrofuran (10 ml), and ethanol (10 ml) was stirred at room temperature for two hours, diluted with 1 N hydrochloric acid (10 ml), and extracted with ethyl acetate. The ethyl acetate layer was washed with saturated aqueous sodium chloride solution, dried (MgSO$_4$), and concentrated. The obtained colorless crystals were collected by filtration, and 3-[3-ethoxy-1-[4-(5-methyl-2-phenyl-4-thiazolylmethoxy) benzyl]-1H-pyrazol-4-yl]propionic acid (1.46 g, yield: 81%) was obtained. This was recrystallized from ethyl acetate-hexane. Melting point: 73–74%.

EXAMPLE 183

To a mixture of ethyl 3-[3-ethoxy-1H-pyrazol-4-yl]propionate (318 mg), 5-chloromethyl-2-(5-methyl-2-phenyl-4-oxazolylmethoxy)pyridine (472 mg), and N,N-dimethylformamide (10 ml), sodium hydride (60%, oily, 60.0 mg) was added at 0° C., and then the mixture was stirred at room temperature for 30 minutes. The reaction mixture was poured into water, which was extracted with ethyl acetate. The ethyl acetate layer was washed with water, then, with saturated aqueous sodium chloride solution, and dried (MgSO$_4$) and concentrated. The residue was subjected to silica gel column chromatography, and ethyl 3-[3-ethoxy-1-[2-(5-methyl-2-phenyl-4-oxazolylmethoxy)-5-pyridylmethyl]-1H-pyrazol-4-yl]propionate (651 mg, yield: 88%) was obtained as a colorless oily substance from the fraction eluted with ethyl acetate-hexane (1:1, volume ratio).

NMR(CDCl$_3$) δ: 1.21 (3H, t, J=7.2 Hz), 1.36 (3H, t, J=7.0 Hz), 2.47–2.55 (5H, m), 2.61–2.69 (2H, m), 4.09 (2H, q, J=7.2 Hz), 4.21 (2H, q, J=7.0 Hz), 4.98 (2H, s), 5.28 (2H, s), 6.77 (1H, d, J=8.4 Hz), 6.97 (1H, s), 7.39–7.46 (4H, m), 7.98–8.04 (3H, m).

EXAMPLE 184

A mixture of ethyl 3-[3-ethoxy-1-[2-(5-methyl-2-phenyl-4-oxazolylmethoxy)-5-pyridylmethyl]-1H-pyrazol-4-yl] propionate (638 mg), 1 N aqueous sodium hydroxide solution (2.5 ml), tetrahydrofuran (5 ml), and ethanol (5 ml) was stirred at room temperature for 3 hours, diluted with 1 N hydrochloric acid (2.5 ml), and extracted with ethyl acetate. The ethyl acetate layer was washed with saturated aqueous sodium chloride solution, dried (MgSO$_4$), and concentrated. The obtained colorless crystals were collected by filtration, and 3-[3-ethoxy-1-[2-(5-methyl-2-phenyl-4-oxazolylmethoxy)-5-pyridylmethyl]-1H-pyrazol-4-yl]propionic acid (495 mg, yield: 82%) was obtained. This was recrystallized from ethanol-hexane. Melting point: 143–144° C.

EXAMPLE 185

To a mixture of ethyl 3-[3-ethoxy-1H-pyrazol-4-yl]propionate (318 mg), 4-(4-chloromethylphenoxymethyl)-2-phenyloxazole (450 mg), and N,N-dimethylformamide (10 ml), sodium hydride (60%, oily, 60.0 mg) was added at 0° C., and then the mixture was stirred at room temperature for 30 minutes. The reaction mixture was poured into water, which was extracted with ethyl acetate. The ethyl acetate layer was washed with water, then, with saturated aqueous sodium chloride solution, and dried (MgSO$_4$) and concentrated. The obtained colorless crystals were collected by filtration, and ethyl 3-[3-ethoxy-1-[4-(2-phenyl-4-oxazolylmethoxy)benzyl]-1H-pyrazol-4-yl]propionate (616 mg, yield: 86%) was obtained. This was recrystallized from ethyl acetate-hexane. Melting point: 80–81° C.

EXAMPLE 186

A mixture of ethyl 3-[3-ethoxy-1-[4-(2-phenyl-4-oxazolylmethoxy)benzyl]-1H-pyrazol-4-yl]propionate (523 mg), 1 N aqueous sodium hydroxide solution (2.5 ml), tetrahydrofuran (5 ml), and ethanol (5 ml) was stirred at room temperature for 3 hours, diluted with 1 N hydrochloric acid (2.5 ml), and extracted with ethyl acetate. The ethyl acetate layer was washed with saturated aqueous sodium chloride solution, dried (MgSO$_4$), and concentrated. The obtained colorless crystals were collected by filtration, and 3-[3-ethoxy-1-[4-(2-phenyl-4-oxazolylmethoxy)benzyl]-1H-pyrazol-4-yl]propionic acid (456 mg, yield: 93%) was obtained. This was recrystallized from ethanol-hexane. Melting point: 135–136° C.

EXAMPLE 187

To a mixture of ethyl 3-(3-ethoxy-1H-pyrazol-4-yl]propionate (415 mg), 3-(4-chloromethylphenoxymethyl)pyridine (554 mg), and N,N-dimethylformamide (10 ml), sodium hydride (60%, oily, 80.0 mg) was added at 0° C., and then the mixture was stirred at room temperature for 30 minutes. The reaction mixture was poured into water, which was extracted with ethyl acetate. The ethyl acetate layer was washed with water, then, with saturated aqueous sodium chloride solution, dried (MgSO$_4$) and concentrated. The residue was subjected to silica gel column chromatography, and ethyl 3-[3-ethoxy-1-[4-(3-pyridylmethoxy)benzyl]-1H-pyrazol-4-yl]propionate (340 mg, yield: 55%) was obtained as a colorless oily substance from the fraction eluted with ethyl acetate-hexane (1:1, volume ratio).

NMR(CDCl$_3$) δ: 1.21 (3H, t, J=7.2 Hz), 1.36 (3H, t, J=7.0 Hz), 2.47–2.55 (2H, m), 2.61–2.69 (2H, m), 4.09 (2H, q, J=7.2 Hz), 4.22 (2H, q, J=7.0 Hz), 5.00 (2H, s), 5.07 (2H, s), 6.92 (2H, d, J=8.8 Hz), 6.93 (1H, s), 7.14 (2H, d, J=8.8 Hz), 7.32 (1H, dd, J=7.4, 4.8 Hz), 7.77 (1H, dt, J=7.4, 2.0 Hz), 8.59 (1H, dd, J=4.8, 2.0 Hz), 8.68 (1H, d, J=2.0 Hz).

EXAMPLE 188

A mixture of ethyl 3-[3-ethoxy-1-[4-(3-pyridylmethoxy)benzyl]-1H-pyrazol-4-yl]propionate (340 mg), 1 N aqueous sodium hydroxide solution (2 ml), tetrahydrofuran (4 ml), and ethanol (4 ml) was stirred at room temperature for two hours, diluted with 1 N hydrochloric acid (2 ml), and extracted with ethyl acetate. The ethyl acetate layer was washed with saturated aqueous sodium chloride solution, dried (MgSO$_4$), and concentrated. The obtained colorless crystals were collected by filtration, and 3-[3-ethoxy-1-[4-(3-pyridylmethoxy)benzyl]-1H-pyrazol-4-yl]propionic acid (260 mg, yield: 82%) was obtained. This was recrystallized from ethanol-hexane. Melting point: 120–121° C.

EXAMPLE 189

To a mixture of ethyl 3-(3-ethoxy-1H-pyrazole-4-yl]propionate (300 mg), 4-(4-chloromethylphenoxymethyl)-5-methyl-2-(2-thienyl)oxazole (450 mg), and N,N-dimethylformamide (5 ml), sodium hydride (60%, oily, 70.0 mg) was added at 0° C., and then the mixture was stirred at room temperature for 30 minutes. The reaction mixture was poured into water, which was extracted with ethyl acetate. The ethyl acetate layer was washed with water, then, with saturated aqueous sodium chloride solution, and dried (MgSO$_4$) and concentrated. The residue was subjected to silica gel column chromatography, and a colorless oily substance was obtained from the fraction eluted with ethyl acetate-hexane (1:2, volume ratio). A mixture of the obtained colorless oily substances, 1 N aqueous sodium hydroxide solution (5 ml), tetrahydrofuran (5 ml), and ethanol (5 ml) was stirred at room temperature overnight, diluted with 1 N hydrochloric acid (5 ml), and extracted with ethyl acetate. The ethyl acetate layer was washed with saturated aqueous sodium chloride solution, dried (MgSO$_4$), and concentrated. The obtained colorless crystals were collected by filtration, and 3-[3-ethoxy-1-[4-[5-methyl-2-(2-thienyl)-4-oxazolylmethoxy]benzyl]-1H-pyrazol-4-yl]propionic acid (460 mg, yield: 70%) was obtained. This was recrystallized from acetone-hexane. Melting point: 156–157° C.

EXAMPLE 190

To a mixture of ethyl 3-(3-ethoxy-1H-pyrazol-4-yl)propionate (415 mg), 2-[N-[2-(4-chloromethylphenoxy)ethyl]-N-methylamino]pyridine (554 mg), and N,N-dimethylformamide (10 ml), sodium hydride (60%, oily, 80.0 mg) was added at 0° C., and then the mixture was stirred at room temperature for 30 minutes. The reaction mixture was poured into water, which was extracted with ethyl acetate. The ethyl acetate layer was washed with water, then, with saturated aqueous sodium chloride solution, and dried (MgSO$_4$) and concentrated. The residue was subjected to silica gel column chromatography, and ethyl 3-[3-ethoxy-1-[4-[2-[N-methyl-N-(2-pyridyl)amino]ethoxy]benzyl]-1H-pyrazol-4-yl]propionate (771 mg, yield: 85%) was obtained as a colorless oily substance from the fraction eluted with ethyl acetate-hexane (1:1, volume ratio).

NMR(CDCl$_3$) δ: 1.20 (3H, t, J=7.2 Hz), 1.36 (3H, t, J=7.2 Hz), 2.47–2.54 (2H, m), 2.59–2.67 (2H, m), 3.14 (3H, s), 3.97 (2H, t, J=5.6 Hz), 4.08 (2H, q, J=7.2 Hz), 4.17 (2H, t, J=5.6 Hz), 4.21 (2H, q, J=7.2 Hz), 4.97 (2H, s), 6.49–6.58 (2H, m), 6.84 (2H, d, J=8.6 Hz), 6.89 (1H, s), 7.10 (2H, d, J=8.6 Hz), 7.45 (1H, ddd, J=8.6, 7.2, 1.8 Hz), 8.15 (1H, ddd, J=5.0, 1.8, 1.0 Hz).

EXAMPLE 191

A mixture of ethyl 3-[3-ethoxy-1-[4-[2-[N-methyl-N-(2-pyridyl)amino]ethoxy]benzyl]-1H-pyrazol-4-yl]propionate (769 mg), 1 N aqueous sodium hydroxide solution (4 ml), tetrahydrofuran (8 ml), and ethanol (8 ml) was stirred at room temperature for 3 hours, diluted with 1 N hydrochloric acid (4 ml), and extracted with ethyl acetate. The ethyl acetate layer was washed with saturated aqueous sodium chloride solution, dried (MgSO$_4$), and concentrated. The residue was subjected to silica gel column chromatography, and 3-[3-ethoxy-1-[4-[2-[N-methyl-N-(2-pyridyl)amino]ethoxy]benzyl]-1H-pyrazol-4-yl]propionic acid (402 mg, yield: 56%) was obtained as a colorless oily substance from the fraction eluted with ethyl acetate.

NMR(CDCl$_3$) δ: 1.34 (3H, t, J=7.0 Hz), 2.50–2.68 (4H, m), 3.12 (3H, s), 3.94 (2H, t, J=5.4 Hz), 4.15 (2H, t, J=5.4 Hz), 4.21 (2H, q, J=7.0 Hz), 4.97 (2H, s), 6.50–6.58 (2H, m), 6.82 (2H, d, J=8.8 Hz), 6.90 (1H, s), 7.08 (2H, d, J=8.8 Hz), 7.45 (1H, ddd, J=8.6, 7.2, 2.0 Hz), 8.15 (1H, ddd, J=7.2, 2.0, 1.0 Hz).

EXAMPLE 192

To a mixture of ethyl 3-(3-ethoxy-1H-pyrazol-4-yl)propionate (318 mg), 2-[4-(4-chloromethylphenoxy)piperidine-1-yl]pyridine (404 mg), and N,N-dimethylformamide (10 ml), sodium hydride (60%, oily, 60.0 mg) was added at 0° C., and then the mixture was stirred at room temperature for 30 minutes. The reaction mixture was poured into water, which was extracted with ethyl acetate. The ethyl acetate layer was washed with water, then, with saturated aqueous sodium chloride solution, and dried (MgSO$_4$) and concentrated. The residue was subjected to silica gel column chromatography, and ethyl 3-[3-ethoxy-1-[4-[1-(2-pyridyl)piperidine-4-yloxy]benzyl]-1H-pyrazol-4-yl]propionate (609 mg, yield: 85%) was obtained as a colorless oily substance from the fraction eluted with ethyl acetate-hexane (1:1, volume ratio).

NMR(CDCl$_3$) δ: 1.21 (3H, t, J=7.0 Hz), 1.37 (3H, t, J=7.0 Hz), 1.76–1.93 (2H, m), 1.98–2.12 (2H, m), 2.48–2.55 (2H, m), 2.61–2.69 (2H, m), 3.39–3.49 (2H, m), 3.85–3.97 (2H, m), 4.09 (2H, q, J=7.0 Hz), 4.23 (2H, q, J=7.0 Hz), 4.46–4.57 (1H, m), 4.99 (2H, s), 6.60 (1H, ddd, J=7.0, 5.0, 0.8 Hz), 6.69 (1H, dt, J=8.8, 0.8 Hz), 6.88 (2H, d, J=8.8 Hz), 6.93, (1H, s), 7.12 (2H, d, J=8.8 Hz), 7.47 (1H, ddd, J=8.8, 7.0, 1.8 Hz), 8.19 (1H, ddd, J=5.0, 1.8, 0.8 Hz).

EXAMPLE 193

A mixture of ethyl 3-[3-ethoxy-1-[4-[1-(2-pyridyl)piperidine-4-yloxy]benzyl]-1H-pyrazole-4-yl]propionate (598 mg), 1 N aqueous sodium hydroxide solution (2.5 ml), tetrahydrofuran (5 ml), and ethanol (5 ml) was stirred at room temperature for 3 hours, diluted with 1 N hydrochloric acid (2.5 ml), and extracted with ethyl acetate. The ethyl acetate layer was washed with saturated aqueous sodium chloride solution, dried (MgSO$_4$), and concentrated. The obtained crystals were collected by filtration, and 3-[3-ethoxy-1-[4-[1-(2-pyridyl)piperidine-4-yloxy]benzyl]-1H-pyrazol-4-yl]propionic acid (408 mg, yield: 72%) was obtained. This was recrystallized from ethanol-hexane. Melting point: 142–143° C.

EXAMPLE 194

To a mixture of ethyl 3-(3-ethoxy-1H-pyrazol-4-yl)propionate (318 mg), 2-[2-(4-chloromethylphenoxy)ethyl]-5-ethylpyridine (414 mg), and N,N-dimethylformamide (10 ml), sodium hydride (60%, oily, 60.0 mg) was added at 0° C., and then the mixture was stirred at room temperature for 30 minutes. The reaction mixture was poured into water, which was extracted with ethyl acetate. The ethyl acetate layer was washed with water, then, with saturated aqueous sodium chloride solution, and dried (MgSO$_4$) and concentrated. The residue was subjected to silica gel column chromatography, and ethyl 3-[3-ethoxy-1-[4-[2-(5-ethyl-2-pyridyl)ethoxy]benzyl]-1H-pyrazol-4-yl]propionate (520 mg, yield: 77%) was obtained as a colorless oily substance from the fraction eluted with ethyl acetate-hexane (1:1, volume ratio).

NMR(CDCl$_3$) δ: 1.20 (3H, t, J=7.0 Hz), 1.24 (3H, t, J=7.6 Hz), 1.36 (3H, t, J=7.0 Hz), 2.46–2.54 (2H, m), 2.57–2.68 (4H, m), 3.22 (2H, t, J=6.6 Hz), 4.08 (2H, q, J=7.0 Hz), 4.12 (2H, q, J=7.0 Hz), 4.33 (2H, t, J=6.6 Hz), 4.97 (2H, s), 6.85 (2H, d, J=8.6 Hz), 6.90 (1H, s), 7.11 (2H, d, J=8.6 Hz), 7.18 (1H, d, J=7.8 Hz), 7.45 (1H, dd, J=7.8, 2.0 Hz), 8.39 (1H, d, J=2.0 Hz).

EXAMPLE 195

A mixture of ethyl 3-[3-ethoxy-1-[4-[2-(5-ethyl-2-pyridyl)ethoxy]benzyl]-1H-pyrazol-4-yl]propionate (519 mg), 1 N aqueous sodium hydroxide solution (2.5 ml), tetrahydrofuran (5 ml), and ethanol (5 ml) was stirred at room temperature for 3 hours, diluted with 1 N hydrochloric acid (2.5 ml), and extracted with ethyl acetate. The ethyl acetate layer was washed with saturated aqueous sodium chloride solution, dried ($MgSO_4$), and concentrated. The obtained colorless crystals were collected by filtration, and 3-[3-ethoxy-1-[4-[2-(5-ethyl-2-pyridyl)ethoxy]benzyl]-1H-pyrazol-4-yl]propionic acid (228 mg, yield: 47%) was obtained. This was recrystallized from ethanol-hexane. Melting point: 89–90° C.

EXAMPLE 196

To a mixture of ethyl 3-(3-ethoxy-1H-pyrazol-4-yl)propionate (690 mg), 4-[2-(4-chloromethylphenoxy)ethyl)]-5-methyl-2-phenyloxazole (1.05 g), and N,N-dimethylformamide (20 ml), sodium hydride (60%, oily, 130 mg) was added at 0° C., and then the mixture was stirred at room temperature for 30 minutes. The reaction mixture was poured into water, which was extracted with ethyl acetate. The ethyl acetate layer was washed with water, then, with saturated aqueous sodium chloride solution, and dried ($MgSO_4$) and concentrated. The residue was subjected to silica gel column chromatography, and a colorless oily substance was obtained from the fraction eluted with ethyl acetate-hexane (1:2, volume ratio). A mixture of the obtained colorless oily substance, 1N aqueous sodium hydroxide solution (6 ml), tetrahydrofuran (6 ml), and ethanol (6 ml) was stirred at room temperature for two hours, diluted with 1 N hydrochloric acid (6 ml), and extracted with ethyl acetate. The ethyl acetate layer was washed with saturated sodium chloride solution, dried ($MgSO_4$), and concentrated. The obtained colorless crystals were collected by filtration, and 3-[3-ethoxy-1-[4-[2-(5-methyl-2-phenyl-4-oxazolyl)ethoxy]benzyl]-1H-pyrazol-4-yl]propionic acid (1.09 g, yield: 72%) was obtained. This was recrystallized from acetone-hexane. Melting point: 142–143° C.

EXAMPLE 197

To a solution of ethyl 3-(3-ethoxy-1H-pyrazol-4-yl)propionate (780 mg) in N,N-dimethylformamide (50 ml), sodium hydride (60%, oily, 180 mg) was added at 0° C., and then the solution was stirred at room temperature for 30 minutes. 2-[4-(5-Methyl-2-phenyl-4-oxazolyl)methoxy]phenyl]ethyl methanesulfonate (2.17 g) was added to the reaction mixture at 0° C., and then the mixture was stirred at 90° C. for one hour. The reaction mixture was poured into water, which was extracted with ethyl acetate. The ethyl acetate layer was washed with water, then, with saturated aqueous sodium chloride solution, and dried ($MgSO_4$) and concentrated. The residue was subjected to silica gel column chromatography, and ethyl 3-[3-ethoxy-1-[2-[4-(5-methyl-2-phenyl-4-oxazolylmethoxy)phenyl]ethyl]-1H-pyrazol-4-yl]propionate (1.08 g, yield: 58%) was obtained as a colorless oily substance from the fraction eluted with ethyl acetate-hexane (1:4, volume ratio).

NMR($CDCl_3$) δ: 1.23 (3H, t, J=7.0 Hz), 1.38 (3H, t, J=7.0 Hz), 2.43 (3H, s), 2.49–2.65 (4H, m), 3.00 (2H, t, J=7.0 Hz), 4.04 (2H, t, J=7.0 Hz), 4.11 (2H, q, J=7.0 Hz), 4.24 (2H, q, J=7.0 Hz), 4.97 (2H, s), 6.78 (1H, s), 6.89–7.01 (4H, m), 7.42–7.46 (3H, m), 7.99–8.04 (2H, m).

EXAMPLE 198

A mixture of ethyl 3-[3-ethoxy-1-[2-[4-(5-methyl-2-phenyl-4-oxazolylmethoxy)phenyl]ethyl]-1H-pyrazol-4-yl]propionate (1.08 g), 1 N aqueous sodium hydroxide solution (4.2 ml), tetrahydrofuran (3 ml), and ethanol (3 ml) was stirred at room temperature for two hours, diluted with 1 N hydrochloric acid (5 ml), and extracted with ethyl acetate. The ethyl acetate layer was washed with saturated aqueous sodium chloride solution, dried ($MgSO_4$), and concentrated. The obtained crystals were collected by filtration, and 3-[3-ethoxy-1-[2-[4-(5-methyl-2-phenyl-4-oxazolylmethoxy)phenyl]ethyl]-1H-pyrazol-4-yl]propionic acid (880 mg, yield: 88%) was obtained. This was recrystallized from ethyl acetate-hexane. Melting point: 110–111° C.

EXAMPLE 199

To a mixture of ethyl 3-(3-ethoxy-1H-pyrazol-4-yl)propionate (509 mg), 4-(2-chloromethylphenoxymethyl)-5-methyl-2-phenyloxazole (753 mg), and N,N-dimethylformamide (10 ml), sodium hydride (60%, oily, 96.0 mg) was added at 0° C., and then the mixture was stirred at room temperature for 30 minutes. The reaction mixture was poured into water, which was extracted with ethyl acetate. The ethyl acetate layer was washed with water, then, with saturated aqueous sodium chloride solution, and dried ($MgSO_4$) and concentrated. The residue was subjected to silica gel column chromatography, and ethyl 3-[3-ethoxy-1-[2-(5-methyl-2-phenyl-4-oxazolylmethoxy)benzyl]-1H-pyrazol-4-yl]propionate (1.09 g, yield: 93%) was obtained as a colorless oily substance from the fraction eluted with ethyl acetate-hexane (1:2, volume ratio).

NMR($CDCl_3$) δ: 1.20 (3H, t, J=7.2 Hz), 1.34 (3H, t, J=7.2 Hz), 2.39 (3H, s), 2.46–2.54 (2H, m), 2.60–2.68 (2H, m), 4.08 (2H, q, J=7.2 Hz), 4.20 (2H, q, J=7.2 Hz), 5.03 (2H, s), 5.11 (2H, s), 6.91–6.93 (2H, m), 7.01–7.06 (2H, m), 7.22–7.31 (1H, m), 7.41–7.48 (3H, m), 7.98–8.05 (2H, m).

EXAMPLE 200

A mixture of ethyl 3-[3-ethoxy-1-[2-(5-methyl-2-phenyl-4-oxazolylmethoxy)benzyl]-1H-pyrazol-4-yl]propionate (1.09 g), 1N aqueous sodium hydroxide solution (5 ml), tetrahydrofuran (10 ml), and ethanol (10 ml) was stirred at room temperature for two hours, diluted with 1 N hydrochloric acid (5 ml), and extracted with ethyl acetate. The ethyl acetate layer was washed with saturated aqueous sodium chloride solution, dried ($MgSO_4$), and concentrated. The obtained colorless crystals were collected by filtration, and 3-[3-ethoxy-1-[2-(5-methyl-2-phenyl-4-oxazolylmethoxy)benzyl]-1H-pyrazol-4-yl]propionic acid (834 mg, yield: 82%) was obtained. This was recrystallized from ethanol-hexane. Melting point: 127–128° C.

EXAMPLE 201

To a mixture of ethyl 3-(3-ethoxy-1H-pyrazol-4-yl)propionate (509 mg), 4-(3-chloromethylphenoxymethyl)-5-methyl-2-phenyloxazole (753 mg), and N,N-dimethylformamide (10 ml), sodium hydride (60%, oily, 96.0 mg) was added at 0° C., and then the mixture was stirred at room temperature for 30 minutes. The reaction mixture was poured into water, which was extracted with ethyl acetate.

The ethyl acetate layer was washed with water, then, with saturated aqueous sodium chloride solution, dried (MgSO$_4$) and concentrated. The residue was subjected to silica gel column chromatography, and ethyl 3-[3-ethoxy-1-[3-(5-methyl-2-phenyl-4-oxazolylmethoxy)benzyl]-1H-pyrazol-4-yl]propionate (809 mg, yield: 69%) was obtained as a colorless oily substance from the fraction eluted with ethyl acetate-hexane (1:3, volume ratio).

NMR(CDCl$_3$) δ: 1.21 (3H, t, J=7.2 Hz), 1.36 (3H, t, J=7.2 Hz), 2.42 (3H, s), 2.48–2.55 (2H, m), 2.61–2.69 (2H, m), 4.09 (2H, q, J=7.2 Hz), 4.22 (2H, q, J=7.2 Hz), 4.95 (2H, s), 5.04 (2H, s), 6.74–6.83 (2H, m), 6.91–6.97 (2H, m), 7.25 (1H, t, J=7.8 Hz), 7.42–7.45 (3H, m), 7.99–8.04 (2H, m).

EXAMPLE 202

A mixture of ethyl 3-[3-ethoxy-1-[3-(5-methyl-2-phenyl-4-oxazolylmethoxy)benzyl]-1H-pyrazol-4-yl]propionate (808 mg), 1N aqueous sodium hydroxide solution (4 ml), tetrahydrofuran (8 ml), and ethanol (8 ml) was stirred at room temperature for 3 hours, diluted with 1 N hydrochloric acid (4 ml), and extracted with ethyl acetate. The ethyl acetate layer was washed with saturated aqueous sodium chloride solution, dried (MgSO$_4$), and concentrated. The residue was subjected to silica gel column chromatography, and 3-[3-ethoxy-1-[3-(5-methyl-2-phenyl-4-oxazolylmethoxy)benzyl]-1H-pyrazol-4-yl]propionic acid (709 mg, yield: 93%) was obtained as a colorless oily substance from the fraction eluted with ethyl acetate-methanol (5:1, volume ratio).

NMR(CDCl$_3$) δ: 1.35 (3H, t, J=7.0 Hz), 2.48 (3H, s), 2.67 (4H, s), 4.21 (2H, q, J=7.0 Hz), 4.96 (2H, s), 5.11 (2H, s), 6.42 (1H, s), 6.84–6.91 (2H, m), 7.19 (1H, s), 7.26 (1H, d, J=8.0 Hz), 7.43–7.47 (3H, m), 7.94–7.99 (2H, m).

EXAMPLE 203

A mixture of ethyl 1-[4-(5-methyl-2-phenyl-4-oxazolylmethoxy)benzyl]-3-[4-(5-methyl-2-phenyl-4-oxazolylmethoxy)benzyloxy]-1H-pyrazol-4-carboxylate (2.84 g), 5% palladium-carbon (5.00 g), ethanol (25 ml), and tetrahydrofuran (25 ml) was stirred under a hydrogen atmosphere at room temperature for 4 hours. After removal oh the catalyst by filtration, the filtrate was concentrated. The obtained crystals were collected by filtration, and ethyl 3-hydroxy-1-[4-(5-methyl-2-phenyl-4-oxazolylmethoxy)benzyl]-1H-pyrazol-4-carboxylate (968 mg, yield: 56%) was obtained. This was recrystallized from tetrahydrofuran-hexane. Melting point: 152–153° C.

EXAMPLE 204

A mixture of ethyl 3-hydroxy-1H-pyrazol-4-carboxylate (10.30 g), 4-benzyloxybenzyl chloride (18.60 g), potassium carbonate (16.60 g), and N,N-dimethylformamide (200 ml) was stirred at 100° C. overnight. The reaction mixture was poured into water, which was extracted with ethyl acetate. The ethyl acetate layer was washed with dilute hydrochloric acid, then, with saturated aqueous sodium chloride solution, and dried (MgSO$_4$) and concentrated. The residue was subjected to silica gel column chromatography, and ethyl 1-(4-benzyloxybenzyl)-3-(4-benzyloxybenzyloxy)-1H-pyrazol-4-carboxylate (11.90 g, yield: 54%) was obtained as colorless crystals from the fraction eluted with ethyl acetate. This was recrystallized from ethyl acetate-hexane. Melting point: 124–125° C.

EXAMPLE 205

To a solution of ethyl diethylphosphonoacetate (2.74 ml) in tetrahydrofuran (50 ml), sodium hydride (60%, oily, 552 mg) was added at 0° C., and then the solution was stirred at room temperature for 30 minutes. To the reaction mixture, a solution of 1-(4-benzyloxybenzyl)-3-(4-benzyloxybenzyloxy)-1H-pyrazol-4-carbaldehyde (6.31 g) in tetrahydrofuran (100 ml) was added slowly, and the solution was stirred at room temperature for 15 minutes. The reaction mixture was poured into water, which was extracted with ethyl acetate. The ethyl acetate layer was washed with dilute hydrochloric acid, then, with saturated aqueous sodium chloride solution, and dried (MgSO$_4$) and concentrated. The obtained crystals were collected by filtration, and ethyl 3-[1-(4-benzyloxybenzyl)-3-(4-benzyloxybenzyloxy)-1H-pyrazol-4-yl]propionate (6.79 g, yield: 95%) was obtained. This was recrystallized from ethyl acetate-hexane. Melting point: 98–99° C.

EXAMPLE 206

To a solution of ethyl 3-[3-hydroxy-1-(4-hydroxybenzyl)-1H-pyrazol-4-yl]propionate (435 mg) in N,N-dimethylformamide (10 ml), sodium hydride (60%, oily, 120 mg) was added at 0° C., and then the solution was stirred at room temperature for 30 minutes. 3-Picolyl chloride (574 mg) was added to the reaction mixture, which was stirred at room temperature for one hour. The reaction mixture was poured into water, which was extracted with ethyl acetate. The ethyl acetate layer was washed with dilute hydrochloric acid, then, with saturated aqueous sodium chloride solution, and dried (MgSO$_4$) and concentrated. The residue was subjected to silica gel column chromatography, and ethyl 3-[3-(3-pyridylmethoxy)-1-[4-(3-pyridylmethoxy)benzyl]-1H-pyrazol-4-yl]propionate (533 mg, yield: 75%) was obtained as a colorless oily substance from the fraction eluted with ethyl acetate.

NMR(CDCl$_3$) δ: 1.19 (3H, t, J=7.2 Hz), 2.46–2.54 (2H, m), 2.62–2.70 (2H, m), 4.07 (2H, q, J=7.2 Hz), 5.01 (2H, s), 5.07 (2H, s), 5.25 (2H, s), 6.93 (2H, d, J=8.8 Hz), 7.14 (2H, d, J=8.8 Hz), 7.26–7.36 (2H, m), 7.74–7.80 (2H, m), 8.55–8.60 (2H, m), 8.69 (2H, s).

EXAMPLE 207

A mixture of ethyl 3-[3-(3-pyridylmethoxy)-1-[4-(3-pyridylmethoxy)benzyl]-1H-pyrazol-4-yl]propionate (529 mg), 1 N aqueous sodium hydroxide solution (3 ml), tetrahydrofuran (6 ml), and ethanol (6 ml) was stirred at room temperature for one hour, diluted with 1 N hydrochloric acid (3 ml), and extracted with ethyl acetate. The ethyl acetate layer was washed with saturated aqueous sodium chloride solution, dried (MgSO$_4$), and concentrated. The obtained colorless crystals were collected by filtration, and 3-[3-(3-pyridylmethoxy)-1-[4-(3-pyridylmethoxy)benzyl]-1H-pyrazol-4-yl]propionic acid (427 mg, yield: 86%) was obtained. This was recrystallized from ethanol-hexane. Melting point: 116–117° C.

EXAMPLE 208

A mixture of ethyl 3-[1-(4-benzyloxy-3-methoxybenzyl)-3-ethoxy-1H-pyrazol-4-yl]propionate (2.92 g), 5% palladium-carbon (6.00 g), ethanol (20 ml), and tetrahydrofuran (20 ml) was stirred at room temperature for one hour under a hydrogen atmosphere. After removal of the catalyst by filtration, the filtrate was concentrated. The residue was subjected to silica gel column chromatography, and ethyl 3-[3-ethoxy-1-(4-hydroxy-3-methoxybenzyl)-1H-pyrazol-4-yl]propionate (2.04 g, yield: 89%) was obtained as a colorless oily substance from the fraction eluted with ethyl acetate-hexane (1:1, volume ratio).

NMR(CDCl$_3$) δ: 1.21(3H, t, J=7.0 Hz), 1.37(3H, t, J=7.0 Hz), 2.47–2.55 (2H, m), 2.61–2.69 (2H, m), 3.85 (3H, s), 4.08 (2H, q, J=7.0 Hz), 4.23 (2H, q, J=7.0 Hz), 4.97 (2H, s), 5.65 (1H, br.s), 6.71 (1H, d, J=8.0 Hz), 6.73 (1H, s), 6.86 (1H, d, J=8.0 Hz), 6.93 (1H, s).

EXAMPLE 209

A mixture of ethyl 3-[3-ethoxy-1-(4-hydroxybenzyl)-1H-pyrazol-4-yl]propionate (360 mg), 2-chloromethylquinoline hydrochloride (270 mg), potassium carbonate (300 mg) and N,N-dimethylformamide (10 ml) was stirred at 80° C. for 5 hours. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain a colorless oily substance from the fraction eluted with ethyl acetate-hexane (1:1, volume ratio). After a mixture of the resulting oily substance, 1N aqueous sodium hydroxide solution (5 ml), tetrahydrofuran (5 ml) and ethanol (5 ml) was stirred at room temperature for 2 hours, 1N hydrochloric acid (5 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[4-(2-quinolylmethoxy)benzyl]-1H-pyrazol-4-yl]propionic acid (420 mg, yield: 86%). This was recrystallized from acetone-hexane. Melting point: 140–141° C.

EXAMPLE 210

Sodium hydride (60%, oily, 60.0 mg) was added to a solution of ethyl 3-(3-ethoxy-1H-pyrazol-4-yl)propionate (318 mg) and 4-chloromethyl-2-(5-methyl-2-phenyl-4-oxazolylmethoxy)pyridine (472 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-ethoxy-1-[2-(5-methyl-2-phenyl-4-oxazolylmethoxy)-4-pyridylmethyl]-1H-pyrazol-4-yl]propionate (640 mg, yield: 87%) as a colorless oily substance from the fraction eluted with ethyl acetate-hexane (1:1, volume ratio).

NMR(CDCl$_3$) δ: 1.21(3H, t, J=7.0 Hz), 1.35(3H, t, J=7.0 Hz), 2.46(3H, s), 2.49–2.57(2H, m), 2.62–2.70(2H, m), 4.10(2H, q, J=7.0 Hz), 4.19(2H, q, J=7.0 Hz), 5.01(2H, s), 5.27(2H, s), 6.46(1H, s), 6.63(1H, d, J=5.2 Hz), 7.03(1H, s), 7.39–7.46(3H, m), 7.97–8.04(2H, m), 8.09(1H, d, J=5.2 Hz).

EXAMPLE 211

After a mixture of ethyl 3-[3-ethoxy-1-[2-(5-methyl-2-phenyl-4-oxazolylmethoxy)-4-pyridylmethyl]-1H-pyrazol-4-yl]propionate (638 mg), 1N aqueous sodium hydroxide solution (3 ml), tetrahydrofuran (6 ml) and ethanol (6 ml) was stirred at room temperature for 3 hours, 1N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[2-(5-methyl-2-phenyl-4-oxazolylmethoxy)-4-pyridylmethyl]-1H-pyrazol-4-yl]propionic acid (495 mg, yield: 82%). This was recrystallized from ethanol-hexane. Melting point: 114–115° C.

EXAMPLE 212

Sodium hydride (60%, oily, 60.0 mg) was added to a solution of ethyl 3-(3-ethoxy-1H-pyrazol-4-yl)propionate (318 mg) and 3-chloromethyl-5-(5-methyl-2-phenyl-4-oxazolylmethoxy)pyridine (472 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-ethoxy-1-[5-(5-methyl-2-phenyl-4-oxazolylmethoxy)-3-pyridylmethyl]-1H-pyrazol-4-yl]propionate (616 mg, yield: 84%) as a colorless oily substance from the fraction eluted with ethyl acetate.

NMR(CDCl$_3$) δ: 1.21(3H, t, J=7.0 Hz), 1.36(3H, t, J=7.0 Hz), 2.43(3H, s), 2.47–2.55(2H, m), 2.61–2.69(2H, m), 4.10(2H, q, J=7.0 Hz), 4.21(2H, q, J=7.0 Hz), 5.00(2H, s), 5.07(2H, s), 7.02(1H, s), 7.14(1H, dd, J=1.4, 3.0 Hz), 7.41–7.47(3H, m), 7.97–8.03(2H, m), 8.10(1H, d, J=1.4 Hz), 8.34(1H, d, J=3.0 Hz).

EXAMPLE 213

After a mixture of ethyl 3-[3-ethoxy-1-[5-(5-methyl-2-phenyl-4-oxazolylmethoxy)-3-pyridylmethyl]-1H-pyrazol-4-yl]propionate (613 mg), 1N aqueous sodium hydroxide solution (3 ml), tetrahydrofuran (6 ml) and ethanol (6 ml) was stirred at room temperature for 3 hours, 1N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[5-(5-methyl-2-phenyl-4-oxazolylmethoxy)-3-pyridylmethyl]-1H-pyrazol-4-yl]propionic acid (532 mg, yield: 92%). This was recrystallized from ethanol-hexane. Melting point: 133–134° C.

EXAMPLE 214

Sodium hydride (60%, oily, 60.0 mg) was added to a solution of ethyl 3-(3-ethoxy-1H-pyrazol-4-yl)propionate (318 mg) and 4-(5-chloromethyl-2-methoxyphenoxymethyl)-5-methyl-2-phenyloxazole (516 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-ethoxy-1-[4-methoxy-3-(5-methyl-2-phenyl-4-oxazolylmethoxy)benzyl]-1H-pyrazol-4-yl]propionate (647 mg, yield: 83%) as colorless crystals from the fraction eluted with ethyl acetate-hexane (1:1, volume ratio). This was recrystallized from ethyl acetate-hexane. Melting point: 109–110° C.

EXAMPLE 215

After a mixture of ethyl 3-[3-ethoxy-1-[4-methoxy-3-(5-methyl-2-phenyl-4-oxazolylmethoxy)benzyl]-1H-pyrazol-4-yl]propionate (572 mg), 1N aqueous sodium hydroxide solution (3 ml), tetrahydrofuran (6 ml) and ethanol (6 ml) was stirred at room temperature for 3 hours, 1N hydrochloric acid (3 ml) was added to the mixture, and then the mixture was extracted with ethyl acetate. The ethyl acetate layer was washed with saturated aqueous sodium chloride solution, dried ($MgSO_4$) and concentrated. The resulting colorless crystals were collected by filtration to obtain 3-[3-ethoxy-1-[4-methoxy-3-(5-methyl-2-phenyl-4-oxazolylmethoxy)benzyl]-1H-pyrazol-4-yl]propionic acid (498 mg, yield: 92%). This was recrystallized from ethanol-hexane. Melting point: 136–137° C.

EXAMPLE 216

Sodium hydride (60%, oily, 50.0 mg) was added to a solution of ethyl 3-(3-ethoxy-1H-pyrazol-4-yl)propionate (265 mg) and 4-(4-chloromethyl-2-ethoxyphenoxymethyl)-5-methyl-2-phenyloxazole (447 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried ($MgSO_4$), and concentrated. The residue was subjected to silica gel column chromatography to obtain ethyl 3-[3-ethoxy-1-[3-ethoxy-4-(5-methyl-2-phenyl-4-oxazolylmethoxy)benzyl]-1H-pyrazol-4-yl]propionate (548 mg, yield: 82%) as a colorless oily substance from the fraction eluted with ethyl acetate-hexane (1:1, volume ratio).
NMR($CDCl_3$) δ: 1.21(3H, t, J=7.0 Hz), 1.37(3H, t, J=7.0 Hz), 1.42(3H, t, J=7.0 Hz), 2.43(3H, s), 2.47–2.55(2H, m), 2.61–2.69(2H, m), 4.05(2H, q, J=7.0 Hz), 4.09(2H, q, J=7.0 Hz), 4.23(2H, q, J=7.0 Hz), 4.98(2H, s), 5.06(2H, s), 6.70 (1H, dd, J=1.8, 8.0 Hz), 6.75(1H, d, J=1.8 Hz), 6.94(1H, s), 6.98(1H, d, J=8.0 Hz), 7.40–7.49(3H, m), 7.96–8.03(2H, m).

EXAMPLE 217

After a mixture of ethyl 3-[3-ethoxy-1-[3-ethoxy-4-(5-methyl-2-phenyl-4-oxazolylmethoxy)benzyl]-1H-pyrazol-4-yl]propionate (544 mg), 1N aqueous sodium hydroxide solution (3 ml), tetrahydrofuran (6 ml) and ethanol (6 ml) was stirred at room temperature for 3 hours, 1N hydrochloric acid (3 ml) was added to the mixture, and then the mixture was extracted with ethyl acetate. The ethyl acetate layer was washed with saturated aqueous sodium chloride solution, dried ($MgSO_4$) and concentrated. The resulting colorless crystals were collected by filtration to obtain 3-[3-ethoxy-1-[3-ethoxy-4-(5-methyl-2-phenyl-4-oxazolylmethoxy)benzyl]-1H-pyrazol-4-yl]propionic acid (466 mg, yield: 90%) This was recrystallized from ethanol-hexane. Melting point: 105–106° C.

EXAMPLE 218

Sodium hydride (60%, oily, 60.0 mg) was added to a solution of ethyl 3-(3-ethoxy-1H-pyrazol-4-yl)propionate (318 mg) and 5-chloromethyl-3-(5-methyl-2-phenyl-4-oxazolylmethoxy)isoxazole (457 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried ($MgSO_4$), and concentrated. The residue was subjected to silica gel column chromatography to obtain ethyl 3-[3-ethoxy-1-[3-(5-methyl-2-phenyl-4-oxazolylmethoxy)-5-isoxazolylmethyl]-1H-pyrazol-4-yl]propionate (653 mg, yield: 91%) as colorless crystals from the fraction eluted with ethyl acetate-hexane (1:1, volume ratio). This was recrystallized from ethyl acetate-hexane. Melting point: 82–83° C.

EXAMPLE 219

After a mixture of ethyl 3-[3-ethoxy-1-[3-(5-methyl-2-phenyl-4-oxazolylmethoxy)-5-isoxazolylmethyl]-1H-pyrazol-4-yl]propionate (519 mg), 1N aqueous sodium hydroxide solution (3 ml), tetrahydrofuran (6 ml) and ethanol (6 ml) was stirred at room temperature for 3 hours, 1N hydrochloric acid (3 ml) was added to the mixture, and then the mixture was extracted with ethyl acetate. The ethyl acetate layer was washed with saturated aqueous sodium chloride solution, dried ($MgSO_4$) and concentrated. The resulting colorless crystals were collected by filtration to obtain 3-[3-ethoxy-1-[3-(5-methyl-2-phenyl-4-oxazolylmethoxy)-5-isoxazolylmethyl]-1H-pyrazol-4-yl]propionic acid (459 mg, yield: 94%). This was recrystallized from ethanol-hexane. Melting point: 142–143° C.

EXAMPLE 220

Sodium hydride (60%, oily, 90.3 mg) was added to a solution of ethyl 3-(3-ethoxy-1H-pyrazol-4-yl)propionate (400 mg) and 2-[2-(4-chloromethylphenoxy)ethyl]-[(2H)-phthalazinone (650 mg) in N,N-dimethylformamide (10 ml) at 0° C., and the mixture was stirred at room temperature overnight. The reaction mixture was poured into dilute hydrochloric acid, and extracted with ethyl acetate. The ethyl acetate layer was washed successively with water and saturated aqueous sodium chloride solution, dried ($MgSO_4$), and concentrated. The residue was subjected to silica gel column chromatography to obtain a colorless oily substance from the fraction eluted with ethyl acetate-hexane (1:1, volume ratio). After a mixture of the colorless oily substance, 1N aqueous sodium hydroxide solution (5 ml), tetrahydrofuran (5 ml) and ethanol (5 ml) was stirred at room temperature for 2 hours, 1N hydrochloric acid (5 ml) was added to the mixture, and then the mixture was extracted with ethyl acetate. The ethyl acetate layer was washed with saturated aqueous sodium chloride solution, dried ($MgSO_4$) and concentrated. The resulting colorless crystals were collected by filtration to obtain 3-[3-ethoxy-1-[4-[2-[1-oxophthalazin-2(1H)-yl]ethoxy]benzyl]-1H-pyrazol-4-yl]propionic acid (730 mg, yield: 84%). This was recrystallized from acetone-hexane. Melting point: 152–153° C.

EXAMPLE 221

Sodium hydride (60%, oily, 90.3 mg) was added to a solution of ethyl 3-(3-ethoxy-1H-pyrazol-4-yl)propionate (400 mg) and 2-[2-(3-chloromethylphenoxy)ethyl]-[(2H)-phthalazinone (650 mg) in N,N-dimethylformamide (10 ml) at 0° C., and the mixture was stirred at room temperature overnight. The reaction mixture was poured into dilute hydrochloric acid, and extracted with ethyl acetate. The ethyl acetate layer was washed successively with water and saturated aqueous sodium chloride solution, dried (MgSO$_4$), and concentrated. The residue was subjected to silica gel column chromatography to obtain a colorless oily substance from the fraction eluted with ethyl acetate-hexane (1:1, volume ratio). After a mixture of the resulting colorless oily substance, 1N aqueous sodium hydroxide solution (5 ml), tetrahydrofuran (5 ml) and ethanol (5 ml) was stirred at room temperature for 2 hours, 1N hydrochloric acid (5 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[3-[2-[1-oxophthalazin-2(1H)-yl]ethoxy]benzyl]-1H-pyrazol-4-yl]propionic acid (690 mg, yield: 79%). This was recrystallized from acetone-hexane. Melting point: 146–147° C.

EXAMPLE 222

Sodium hydride (60%, oily, 60.0 mg) was added to a solution of ethyl 3-(3-ethoxy-1H-pyrazol-4-yl)propionate (318 mg) and 2-chloromethyl-6-(5-methyl-2-phenyl-4-oxazolylmethoxy)pyridine (472 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-ethoxy-1-[6-(5-methyl-2-phenyl-4-oxazolylmethoxy)-2-pyridylmethyl]-1H-pyrazol-4-yl]propionate (656 mg, yield: 89%) as a colorless oily substance from the fraction eluted with ethyl acetate-hexane (1:1, volume ratio).

NMR(CDCl$_3$) δ: 1.22(3H, t, J=7.0 Hz), 1.37(3H, t, J=7.0 Hz), 2.47(3H, s), 2.51–2.59(2H, m), 2.66–2.74(2H, m), 4.11(2H, q, J=7.0 Hz), 4.23(2H, q, J=7.0 Hz), 5.11(2H, s), 5.28(2H, s), 6.46(1H, d, J=7.2 Hz), 6.70(1H, d, J=8.0 Hz), 7.13(1H, s), 7.41–7.46(3H, m), 7.48(1H, dd, J=7.2, 8.0 Hz), 7.99–8.05(2H, m).

EXAMPLE 223

After a mixture of ethyl 3-[3-ethoxy-1-[6-(5-methyl-2-phenyl-4-oxazolylmethoxy)-2-pyridylmethyl]-1H-pyrazol-4-yl]propionate (652 mg), 1N aqueous sodium hydroxide solution (3 ml), tetrahydrofuran (6 ml) and ethanol (6 ml) was stirred at room temperature for 3 hours, 1N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[6-(5-methyl-2-phenyl-4-oxazolylmethoxy)-2-pyridylmethyl]-1H-pyrazol-4-yl]propionic acid (522 mg, yield: 85%). This was recrystallized from ethanol-hexane. Melting point: 144–145° C.

EXAMPLE 224

Sodium hydride (60%, oily, 60.0 mg) was added to a solution of ethyl 3-[3-ethoxy-1-(4-hydroxybenzyl)-H-pyrazol-4-yl]propionate (302 mg) and 5-chloro-2-chloromethylimidazo[1,2-a]pyridine (302 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[1-[4-(5-chloroimidazo[1,2-a]pyridin-2-ylmethoxy)benzyl]-3-ethoxy-1H-pyrazol-4-yl]propionate (625 mg, yield: 86%) as colorless crystals from the fraction eluted with ethyl acetate. This was recrystallized from ethyl acetate-hexane. Melting point: 69–70° C.

EXAMPLE 225

After a mixture of ethyl 3-[1-[4-(5-chloroimidazo[1,2-a]pyridin-2-ylmethoxy)benzyl]-3-ethoxy-1H-pyrazol-4-yl]propionate (507 mg), 1N aqueous sodium hydroxide solution (2 ml), tetrahydrofuran (4 ml) and ethanol (4 ml) was stirred at room temperature for 3 hours, 1N hydrochloric acid (2 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[1-[4-(5-chloroimidazo[1,2-a]pyridin-2-ylmethoxy)benzyl]-3-ethoxy-1H-pyrazol-4-yl]propionic acid (448 mg, yield 94%). This was recrystallized from ethanol. Melting point: 153–154° C.

EXAMPLE 226

Sodium hydride (60%, oily, 60.0 mg) was added to a solution of ethyl 3-[3-ethoxy-1-(4-hydroxybenzyl)-1H-pyrazol-4-yl]propionate (478 mg) and 2-chloromethyl-5-ethoxyimidazo[1,2-a]pyridine (316 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-ethoxy-1-[4-(5-ethoxyimidazo[1,2-a]pyridin-2-ylmethoxy)benzyl]-1H-pyrazol-4-yl]propionate (442 mg, yield: 60%) as a colorless oily substance from the fraction eluted with ethyl acetate.

NMR(CDCl$_3$) δ: 1.20(3H, t, J=7.0 Hz), 1.36(3H, t, J=7.0 Hz), 1.55(3H, t, J=7.0 Hz), 2.47–2.54(2H, m), 2.61–2.68(2H, m), 4.08(2H, q, J=7.0 Hz), 4.22(2H, q, J=7.0 Hz), 4.29(2H, q, J=7.0 Hz), 4.99(2H, s), 5.25(2H, s), 6.02(1H, dd, J=2.0, 6.2 Hz), 6.92(1H, s), 7.00(2H, d, J=8.8 Hz), 7.13(2H, d, J=8.8 Hz), 7.18–7.25(2H, m), 7.71(1H, s).

EXAMPLE 227

After a mixture of ethyl 3-[3-ethoxy-1-[4-(5-ethoxyimidazo[1,2-a]pyridin-2-ylmethoxy)benzyl]-1H-pyrazol-4-yl]propionate (441 mg), 1N aqueous sodium hydroxide solution (2 ml), tetrahydrofuran (4 ml) and ethanol (4 ml) was stirred at room temperature for 3 hours, 1N hydrochloric acid (2 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[4-(5-ethoxyimidazo[1,2-a]pyridin-2-ylmethoxy)benzyl]-1H-pyrazol-4-yl]propionic acid (335 mg, yield: 81%). This was recrystallized from ethanol-hexane. Melting point: 197–198° C.

EXAMPLE 228

Sodium hydride (60%, oily, 60.0 mg) was added to a solution of ethyl 3-[3-ethoxy-1-(4-hydroxybenzyl)-1H-pyrazol-4-yl]propionate (478 mg) and 1-chloromethyl-1H-benzotriazole (251 mg) in N,N-dimethylformamide (10 ml) at, 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[1-[4-(1H-benzotriazol-1-ylmethoxy)benzyl]-3-ethoxy-1H-pyrazol-4-yl]propionate (652 mg, yield: 97%) as a colorless oily substance from the fraction eluted with ethyl acetate-hexane (1:1, volume ratio).

NMR(CDCl$_3$) δ: 1.19(3H, t, J=7.2 Hz), 1.35(3H, t, J=7.0 Hz), 2.45–2.53(2H, m), 2.59–2.67(2H, m), 4.08(2H, q, J=7.2 Hz), 4.20(2H, q, J=7.0 Hz), 4.96(2H, s), 6.53(2H, s), 6.90(1H, s), 7.01–7.11(4H, m), 7.40(1H, ddd, J=1.2, 7.0, 8.4 Hz), 7.53(1H, ddd, J=1.2, 7.0, 8.4 Hz), 7.69(1H, dd, J=1.2, 8.4 Hz), 8.07(1H, dd, J=1.2, 8.4 Hz).

EXAMPLE 229

After a mixture of ethyl 3-[1-[4-(1H-benzotriazol-1-ylmethoxy)benzyl]-3-ethoxy-1H-pyrazol-4-yl]propionate (652 mg), 1N aqueous sodium hydroxide solution (3 ml), tetrahydrofuran (6 ml) and ethanol (6 ml) was stirred at room temperature for 3 hours, 1N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[1-[4-(1H-benzotriazol-1-ylmethoxy)benzyl]-3-ethoxy-1H-pyrazol-4-yl]propionic acid (576 mg, yield: 94%). This was recrystallized from ethanol-hexane. Melting point: 136–137° C.

EXAMPLE 230

A mixture of ethyl 3-[3-ethoxy-1-(4-hydroxybenzyl)-1H-pyrazol-4-yl]propionate (690 mg), 5-chloromethyl-2-phenylpyridine (470 mg), potassium carbonate (450 mg) and N,N-dimethylformamide (10 ml) was stirred at 80° C. for 5 hours. The reaction mixture was poured into water, and extracted with ethyl acetate. The ethyl acetate layer was washed with saturated aqueous sodium chloride solution, dried (MgSO$_4$), and concentrated. The residue was subjected to silica gel chromatography to obtain a colorless oily substance from the fraction eluted with ethyl acetate-hexane (1:1, volume ratio). After a mixture of the resulting colorless oily substance, 1N aqueous sodium hydroxide solution (5 ml), tetrahydrofuran (5 ml) and ethanol (5 ml) was stirred at room temperature for 2 hours, 1 N hydrochloric acid (5 ml) was added, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[4-(6-phenyl-3-pyridylmethoxy)benzyl]-1H-pyrazol-4-yl]propionic acid (900 mg, yield: 91%). This was recrystallized from acetone-hexane. Melting point: 140–141° C.

EXAMPLE 231

A mixture of ethyl 3-[1-[4-(5-chloroimidazo[1,2-a]pyridin-2-ylmethoxy)benzyl]-3-ethoxy-1H-pyrazol-4-yl]propionate (676 mg), phenylboronic acid (195 mg), tetrakis(triphenylphosphine)palladium (40.4 mg), sodium carbonate (339 mg), ethanol (3 ml), water (3 ml) and toluene (15 ml) was refluxed overnight under an argon atmosphere. The reaction mixture was poured into water and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-ethoxy-1-[4-(5-phenylimidazo[1,2-a]pyridin-2-ylmethoxy)benzyl]-1H-pyrazol-4-yl]propionate (707 mg, yield: 96%) as colorless crystals from the fraction eluted with ethyl acetate. This was recrystallized from ethyl acetate-hexane. Melting point: 104–105° C.

EXAMPLE 232

After a mixture of ethyl 3-[3-ethoxy-1-[4-(5-phenylimidazo[1,2-a]pyridin-2-ylmethoxy)benzyl]-1H-pyrazol-4-yl]propionate (551 mg), 1N aqueous sodium hydroxide solution (3 ml), tetrahydrofuran (6 ml) and ethanol (6 ml) was stirred at room temperature for 3 hours, 1 N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[4-(5-phenylimidazo[1,2-a]pyridin-2-ylmethoxy)benzyl]-1H-pyrazol-4-yl]propionic acid (469 mg, yield: 90%). This was recrystallized from ethanol-hexane. Melting point: 160–161° C.

EXAMPLE 233

Sodium hydride (60%, oily, 60.0 mg) was added to a solution of ethyl 3-(3-ethoxy-1H-pyrazol-4-yl)propionate (318 mg) and 4-chloromethyl-2-[2-(2-furyl)-5-methyl-4-oxazolylmethoxy]pyridine (457 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-ethoxy-1-[2-[2-(2-furyl)-5-methyl-4-oxazolylmethoxy]-4-pyridylmethyl]-1H-pyrazol-4-yl]propionate (643 mg, yield: 89%) as a colorless oily substance from the fraction eluted with ethyl acetate-hexane (1:1, volume ratio).

NMR(CDCl$_3$) δ: 1.22(3H, t, J=7.2 Hz), 1.36(3H, t, J=7.0 Hz), 2.46(3H, s), 2.49–2.57(2H, m), 2.63–2.71(2H, m), 4.10(2H, q, J=7.2 Hz), 4.20(2H, q, J=7.0 Hz), 5.01(2H, s), 5.25(2H, s), 6.44(1H, dd, J=0.8, 1.8 Hz), 6.51(1H, dd, J=1.8, 3.4 Hz), 6.63(1H, dd, J=1.8, 5.4 Hz), 6.97(1H, dd, J=0.8, 3.4 Hz), 7.03(1H, s), 7.52(1H, dd, J=0.6, 1.8 Hz), 8.08(1H, dd, J=0.6, 5.4 Hz).

EXAMPLE 234

After a mixture of ethyl 3-[3-ethoxy-1-[2-[2-(2-furyl)-5-methyl-4-oxazolylmethoxy]-4-pyridylmethyl]-1H-pyrazol-4-yl]propionate (639 mg), 1N aqueous sodium hydroxide solution (3 ml), tetrahydrofuran (6 ml) and ethanol (6 ml) was stirred at room temperature for 3 hours, 1 N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[2-[2-(2-furyl)-5-methyl-4-oxazolyl-methoxy]-4-pyridylmethyl]-1H-pyrazol-4-yl]propionic acid (569 mg, yield: 94%). This was recrystallized from ethanol-hexane. Melting point: 138–139° C.

EXAMPLE 235

Sodium hydride (60%, oily, 160 mg) was added to a solution of ethyl 3-(3-ethoxy-1H-pyrazol-4-yl)propionate (849 mg) and 5-chloro-2-(4-chloromethyl-2-pyridyloxymethyl)imidazo[1,2-a]pyridine (1230 mg) in N,N-dimethylformamide (20 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[1-[2-(5-chloroimidazo[1,2-a]pyridin-2-ylmethoxy)-4-pyridylmethyl]-3-ethoxy-1H-pyrazol-4-yl]propionate (1570 mg, yield: 81%) as a colorless oily substance from the fraction eluted with ethyl acetate.

NMR(CDCl$_3$) δ: 1.22(3H, t, J=7.2 Hz), 1.36(3H, t, J=7.2 Hz), 2.50–2.58(2H, m), 2.63–2.71(2H, m), 4.11(2H, q, J=7.2 Hz), 4.20(2H, q, J=7.2 Hz), 5.04(2H, s), 5.56(2H, d, J=0.8 Hz), 6.50(1H, d, J=0.6 Hz), 6.65(1H, dd, J=1.4, 5.2 Hz), 6.89(1H, dd, J=0.8, 7.2 Hz), 7.05(1H, s), 7.18(1H, dd, J=7.2, 9.2 Hz), 7.55–7.60(1H, m), 7.84(1H, d, J=0.8 Hz), 8.12(1H, dd, J=0.6, 5.2 Hz).

EXAMPLE 236

After a mixture of ethyl 3-[1-[2-(5-chloroimidazo[1,2-a]pyridin-2-ylmethoxy)-4-pyridylmethyl]-3-ethoxy-1H-pyrazol-4-yl]propionate (605 mg), 1N aqueous sodium hydroxide solution (3 ml), tetrahydrofuran (6 ml) and ethanol (6 ml) was stirred at room temperature for 3 hours, 1 N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[1-[2-(5-chloroimidazo[1,2-a]pyridin-2-ylmethoxy)-4-pyridylmethyl]-3-ethoxy-1H-pyrazol-4-yl]propionic acid (534 mg, yield: 94%). This was recrystallized from ethanol-hexane. Melting point: 160–161° C.

EXAMPLE 237

A mixture of ethyl 3-[1-[2-(5-chloroimidazo[1,2-a]pyridin-2-ylmethoxy)-4-pyridylmethyl]-3-ethoxy-1H-pyrazol-4-yl]propionate (968 mg), phenylboronic acid (280 mg), tetrakis(triphenylphosphine)palladium (57.8 mg), sodium carbonate (488 mg), ethanol (3 ml), water (3 ml) and toluene (15 ml) was refluxed overnight under an argon atmosphere. The reaction mixture was poured into water and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-ethoxy-1-[2-(5-phenylimidazo[1,2-a]pyridin-2-ylmethoxy)-4-pyridylmethyl]-1H-pyrazol-4-yl]propionate (1040 mg, yield: 99%) as a colorless oily substance from the fraction eluted with ethyl acetate.

NMR(CDCl$_3$) δ: 1.21(3H, t, J=7.0 Hz), 1.35(3H, t, J=7.0 Hz), 2.49–2.56(2H, m), 2.62–2.70(2H, m), 4.10(2H, q, J=7.0 Hz), 4.19(2H, q, J=7.0 Hz), 5.01(2H, s), 5.49(2H, s), 6.47 (1H, s), 6.61(1H, d, J=5.2 Hz), 6.74(1H, d, J=7.0 Hz), 7.02(1H, s), 7.27(1H, dd, J=7.0, 9.2 Hz), 7.42–7.72(7H, m), 8.08(1H, d, J=5.2 Hz).

EXAMPLE 238

After a mixture of ethyl 3-[3-ethoxy-1-[2-(5-phenylimidazo[1,2-a]pyridin-2-ylmethoxy)-4-pyridylmethyl]-1H-pyrazol-4-yl]propionate (1030 mg), 1N aqueous sodium hydroxide solution (4 ml), tetrahydrofuran (8 ml) and ethanol (8 ml) was stirred at room temperature for 3 hours, 1 N hydrochloric acid (4 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[2-(5-phenylimidazo[1,2-a]pyridin-2-ylmethoxy)-4-pyridylmethyl]-1H-pyrazol-4-yl]propionic acid (922 mg, yield: 95%). This was recrystallized from ethanol-hexane. Melting point: 177–178° C.

EXAMPLE 239

A mixture of ethyl 3-[3-ethoxy-1-(4-hydroxybenzyl)-1H-pyrazol-4-yl]propionate (700 mg), 3-chloromethyl-5-phenylpyridine (500 mg), potassium carbonate (500 mg) and N,N-dimethylformamide (10 ml) was stirred at 80° C. for 5 hours. The reaction mixture was poured into water and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-ethoxy-1-[4-(5-phenyl-3-pyridylmethoxy)benzyl]-1H-pyrazol-4-yl]propionate (720 mg, yield: 67%) as a colorless oily substance from the fraction eluted with ethyl acetate-hexane (1:1, volume ratio).

NMR(CDCl$_3$) δ: 1.21(3H, t, J=7.0 Hz), 1.36(3H, t, J=7.0 Hz), 2.45–2.70(4H, m), 4.09(2H, q, J=7.0 Hz), 4.22(2H, q, J=7.0 Hz), 5.01(2H, s), 5.13(2H, s), 6.88–7.02(2H, m), 7.10–7.22(2H, m), 7.40–7.64(5H, m), 7.96(1H, t, J=2.2 Hz), 8.65(1H, d, J=2.2 Hz), 8.82(1H, d, J=2.2 Hz).

EXAMPLE 240

After a mixture of ethyl 3-[3-ethoxy-1-[4-(5-phenyl-3-pyridylmethoxy)benzyl]-1H-pyrazol-4-yl]propionate (700 mg), 1N aqueous sodium hydroxide solution (3 ml), tetrahydrofuran (5 ml), and ethanol (5 ml) was stirred at room temperature for 2 hours, 1 N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[4-(5-phenyl-3-pyridylmethoxy)benzyl]-1H-pyrazol-4-yl]propionic acid (560 mg, yield: 85%). This was recrystallized from acetone-hexane. Melting point: 92–93° C.

EXAMPLE 241

Sodium hydride (60%, oily, 70.0 mg) was added to a solution of ethyl 3-(3-ethoxy-1H-pyrazol-4-yl)propionate (371 mg) and 2-(5-chloromethyl-3-isoxazolylmethyl)quinoline (481 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain-ethyl 3-[3-ethoxy-1-[3-(2-quinolylmethoxy)-5-isoxazolylmethyl]-1H-pyrazol-4-yl] propionate (722 mg, yield: 92%) as a colorless oily substance from the fraction eluted with ethyl acetate-hexane (1:1, volume ratio).

NMR(CDCl$_3$) δ: 1.23(3H, t, J=7.0 Hz), 1.36(3H, t, J=7.0 Hz), 2.49–2.57(2H, m), 2.62–2.70(2H, m), 4.11(2H, q, J=7.0 Hz), 4.20(2H, q, J=7.0 Hz), 5.06(2H, s), 5.54(2H, s), 5.86 (1H, s), 7.09(1H, s), 7.51–7.60(2H, m), 7.73(1H, ddd, J=1.6, 7.0, 8.6 Hz), 7.83(1H, dd, J=1.6, 8.0 Hz), 8.06–8.12(1H, m), 8.20(1H, d, J=8.6 Hz).

EXAMPLE 242

After a mixture of ethyl 3-[3-ethoxy-1-[3-(2-quinolyl-methoxy)-5-isoxazolylmethyl]-1H-pyrazol-4-yl]propionate (721 mg), 1N aqueous sodium hydroxide solution (3 ml), tetrahydrofuran (6 ml) and ethanol (6 ml) was stirred at room temperature for 3 hours, 1 N hydrochloric acid (3 ml) was added to the mixture, and then the mixture was extracted with ethyl acetate. The ethyl acetate layer was washed with a saturated aqueous sodium chloride solution, dried (MgSO$_4$) and concentrated. The resulting colorless crystals were collected by filtration to obtain 3-[3-ethoxy-1-[3-(2-quinolylmethoxy)-5-isoxazolylmethyl]-1H-pyrazol-4-yl] propionic acid (608 mg, yield: 90%). This was recrystallized from ethanol-hexane. Melting point: 123–124° C.

EXAMPLE 243

Sodium hydride (60%, oily, 60.0 mg) was added to a solution of ethyl 3-[3-ethoxy-1-(4-hydroxybenzyl)-1H-pyrazol-4-yl]propionate (478 mg) and 3-chloro-2-chloromethyl-6-phenylpyridine (357 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[1-[4-(3-chloro-6-phenyl-2-pyridylmethoxy)benzyl]-3-ethoxy-1H-pyrazol-4-yl]propionate (740 mg, yield: 95%) as a colorless oily substance from the fraction eluted with ethyl acetate-hexane (1:3, volume ratio).

NMR(CDCl$_3$) δ: 1.20(3H, t, J=7.2 Hz), 1.36(3H, t, J=7.2 Hz), 2.46–2.54(2H, m), 2.60–2.68(2H, m), 4.09(2H, q, J=7.2 Hz), 4.22(2H, q, J=7.2 Hz), 5.00(2H, s), 5.34(2H, s), 6.92 (1H, s), 7.03(2H, d, J=8.8 Hz), 7.15(2H, d, J=8.8 Hz), 7.37–7.51(3H, m), 7.67(1H, d, J=8.4 Hz), 7.78(1H, d, J=8.4 Hz), 7.91–7.98(2H, m).

EXAMPLE 244

After a mixture of ethyl 3-[1-[4-(3-chloro-6-phenyl-2-pyridylmethoxy)benzyl]-3-ethoxy-1H-pyrazol-4-yl]propionate (738 mg), 1N aqueous sodium hydroxide solution (3 ml), tetrahydrofuran (6 ml) and ethanol (6 ml) was stirred at room temperature for 3 hours, 1 N hydrochloric acid (3 ml) was added to the mixture, and then the mixture was extracted with ethyl acetate. The ethyl acetate layer was washed with a saturated aqueous sodium chloride solution, dried (MgSO$_4$) and concentrated. The resulting colorless crystals were collected by filtration to obtain 3-[1-[4-(3-chloro-6-phenyl-2-pyridylmethoxy)benzyl]-3-ethoxy-1H-pyrazol-4-yl]propionic acid (669 mg, yield: 96%). This was recrystallized from ethyl acetate-hexane. Melting point: 120–121° C.

EXAMPLE 245

Sodium hydride (60%, oily, 60.0 mg) was added to a solution of ethyl 3-[3-ethoxy-1-(4-hydroxybenzyl)-1H-pyrazol-4-yl]propionate (478 mg) and 2-chloromethyl-6-phenylpyridine (306 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-ethoxy-1-[4-(6-phenyl-2-pyridylmethoxy)benzyl]-1H-pyrazol-4-yl]propionate (689 mg, yield: 95%) as a colorless oily substance from the fraction eluted with ethyl acetate-hexane (1:2, volume ratio).

NMR(CDCl$_3$) δ: 1.20(3H, t, J=7.2 Hz), 1.36(3H, t, J=7.2 Hz), 2.46–2.55(2H, m), 2.60–2.68(2H, m), 4.12(2H, q, J=7.2 Hz), 4.22(2H, q, J=7.2 Hz), 5.00(2H, s), 5.28(2H, s), 6.93 (1H, s), 6.97(2H, d, J=8.8 Hz), 7.13(2H, d, J=8.8 Hz), 7.38–7.53(4H, m), 7.64(1H, dd, J=0.8, 7.6 Hz), 7.71(1H, t, J=7.6 Hz), 7.97–8.03(2H, m).

EXAMPLE 246

After a mixture of ethyl 3-[3-ethoxy-1-[4-(6-phenyl-2-pyridylmethoxy)benzyl]-1H-pyrazol-4-yl]propionate (685 mg), 1N aqueous sodium hydroxide solution (3 ml), tetrahydrofuran (6 ml) and ethanol (6 ml) was stirred at room temperature for 3 hours, 1 N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[4-(6-phenyl-2-pyridylmethoxy)benzyl]-1H-pyrazol-4-yl]propionic acid (482 mg, yield: 75%). This was recrystallized from ethanol-hexane. Melting point: 95–96° C.

EXAMPLE 247

A mixture of ethyl 3-[3-ethoxy-1-(4-hydroxybenzyl)-1H-pyrazol-4-yl]propionate (600 mg), 2-chloromethyl-1-methyl-1H-benzimidazole (360 mg), potassium carbonate (550 mg) and N,N-dimethylformamide (10 ml) was stirred at 80° C. for 5 hours. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-ethoxy-1-[4-(1-methyl-1H-benzimidazol-2-ylmethoxy)benzyl]-1H-pyrazol-4-yl]propionate (730 mg, yield: 84%) as a colorless oily substance from the fraction eluted with ethyl acetate-hexane (1:1, volume ratio).

NMR(CDCl$_3$) δ: 1.20(3H, t, J=7.0 Hz), 1.35(3H, t, J=7.0 Hz), 2.44–2.68(4H, m), 3.88(3H, s), 4.08(2H, q, J=7.0 Hz), 4.21(2H, q, J=7.0 Hz), 4.98(2H, s), 5.38(2H, s), 6.91(1H, s), 6.98–7.17(4H, m), 7.23–7.41(3H, m), 7.72–7.82(1H, m).

EXAMPLE 248

After a mixture of ethyl 3-[3-ethoxy-1-[4-(1-methyl-1H-benzimidazol-2-ylmethoxy)benzyl]-1H-pyrazol-4-yl]propionate (700 mg), 1N aqueous sodium hydroxide solution (3 ml), tetrahydrofuran (5 ml) and ethanol (5 ml) was stirred at room temperature for 2 hours, 1 N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[4-(1-methyl-1H-benzimidazol-2-ylmethoxy)benzyl]-1H-pyrazol-4-yl]propionic acid (520 mg, yield: 79%). This was recrystallized from ethanol-water. Melting point: 177–178° C.

EXAMPLE 249

A mixture of 5-phenyl-2-pyridylmethanol (300 mg), thionyl chloride (0.25 ml) and toluene (10 ml) was stirred at 80° C. for 1 hour. After the reaction mixture was concentrated under reduced pressure, the resulting crystals were filtered, and washed with hexane. A mixture of the resulting crystals, ethyl 3-[3-ethoxy-1-(4-hydroxybenzyl)-1H-pyrazol-4-yl]propionate (500 mg), potassium carbonate (420 mg) and N,N-dimethylformamide (10 ml) was stirred at 70° C. overnight. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-ethoxy-1-[4-(5-phenyl-2-pyridylmethoxy)benzyl]-1H-pyrazol-4-yl]propionate (730 mg, yield: 96%) as a colorless oily substance from the fraction eluted with ethyl acetate-hexane (1:2, volume ratio).

NMR(CDCl$_3$) δ: 1.20(3H, t, J=7.0 Hz), 1.36(3H, t, J=7.0 Hz), 2.44–2.70(4H, m), 4.09(2H, q, J=7.0 Hz), 4.22(2H, q, J=7.0 Hz), 5.00(2H, s), 5.24(2H, s), 6.90–7.02(3H, m), 7.07–7.19(2H, m), 7.34–7.68(6H, m), 7.91(1H, dd, J=2.2, 8.0 Hz), 8.82(1H, d, J=2.2 Hz).

EXAMPLE 250

After a mixture of ethyl 3-[3-ethoxy-1-[4-(5-phenyl-2-pyridylmethoxy)benzyl]-1H-pyrazol-4-yl]propionate (700 mg), 1N aqueous sodium hydroxide solution (3 ml), tetrahydrofuran (5 ml) and ethanol (5 ml) was stirred at room temperature for 2 hours, 1 N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[4-(5-phenyl-2-pyridylmethoxy)benzyl]-1H-pyrazol-4-yl]propionic acid (620 mg, yield: 94%). This was recrystallized from acetone-hexane. Melting point: 127–128° C.

EXAMPLE 251

Sodium hydride (60%, oily, 70.0 mg) was added to a solution of 2-(5-chloromethyl-2-pyridyloxymethyl)quinoline (498 mg), ethyl 3-(3-ethoxy-1H-pyrazol-4-yl)propionate (371 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-ethoxy-1-[6-(2-quinolylmethoxy)-3-pyridylmethyl]-1H-pyrazol-4-yl]propionate (733 mg, yield: 91%) as a colorless oily substance from the fraction eluted with ethyl acetate-hexane (1:1, volume ratio).

NMR(CDCl$_3$) δ: 1.20(3H, t, J=7.0 Hz), 1.36(3H, t, J=7.0 Hz), 2.47–2.55(2H, m), 2.60–2.68(2H,m), 4.09(2H, q, J=7.0 Hz), 4.21(2H, q, J=7.0 Hz), 4.98(2H, s), 5.67(2H, s), 6.87(1H, dd, J=0.8, 8.4 Hz), 6.97(1H, s), 7.48(1H, dd, J=2.6, 8.4 Hz), 7.53(1H, ddd, J=1.4, 7.0, 8.4 Hz), 7.57(1H, d, J=8.6 Hz), 7.72(1H, ddd, J=1.4, 7.0, 8.4 Hz), 7.81(1H, dd, J=1.4, 8.4 Hz), 8.00(1H, dd, J=0.8, 2.6 Hz), 8.07–8.13(1H, m), 8.15(1H, d, J=8.6 Hz).

EXAMPLE 252

After a mixture of ethyl 3-[3-ethoxy-1-[6-(2-quinolylmethoxy)-3-pyridylmethyl]-1H-pyrazol-4-yl]propionate (732 mg), 1N aqueous sodium hydroxide solution (3 ml), tetrahydrofuran (6 ml) and ethanol (6 ml) was stirred at room temperature for 2 hours, 1 N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[6-(2-quinolylmethoxy)-3-pyridylmethyl]-1H-pyrazol-4-yl]propionic acid (629 mg, yield: 91%). This was recrystallized from ethanol-hexane. Melting point: 133–134° C.

EXAMPLE 253

Sodium hydride (60%, oily, 60.0 mg) was added to a solution of 5-chloromethyl-2-(2-phenyl-4-thiazolylmethoxy)pyridine (475 mg), ethyl 3-(3-ethoxy-1H-pyrazol-4-yl)propionate (318 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-ethoxy-1-[6-(2-phenyl-4-thiazolylmethoxy)-3-pyridylmethyl]-1H-pyrazol-4-yl]propionate (657 mg, yield: 89%) as a colorless oily substance from the fraction eluted with ethyl acetate-hexane (2:3, volume ratio).

NMR(CDCl$_3$) δ: 1.21(3H, t, J=7.0 Hz), 1.36(3H, t, J=7.0 Hz), 2.47–2.56(2H, m), 2.61–2.69(2H,m), 4.10(2H, q, J=7.0 Hz), 4.22(2H, q, J=77.0 Hz), 5.00(2H, s), 5.54(2H, d, J=0.8 Hz), 6.81(1H, d, J=8.4 Hz), 7.31(1H, t, J=0.8 Hz), 7.40–7.49 (4H, m), 7.92–8.01(2H, m), 8.04(1H, d, J=2.6 Hz).

EXAMPLE 254

After a mixture of ethyl 3-[3-ethoxy-1-[6-(2-phenyl-4-thiazolylmethoxy)-3-pyridylmethyl]-1H-pyrazol-4-yl]propionate (655 mg), 1N aqueous sodium hydroxide solution (3 ml), tetrahydrofuran (6 ml) and ethanol (6 ml) was stirred at room temperature for 2 hours, 1 N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[6-(2-phenyl-4-thiazolylmethoxy)-3-pyridylmethyl]-1H-pyrazol-4-yl]propionic acid (569 mg, yield: 92%). This was recrystallized from ethanol-hexane. Melting point: 121–122° C.

EXAMPLE 255

A mixture of 2-(4-chloromethyl-3-methyl-1H-pyrazol-1-yl)pyridine (350 mg), ethyl 3-[3-ethoxy-1-(4-hydroxybenzyl)-1H-pyrazol-4-yl]propionate (500 mg), potassium carbonate (500 mg) and N,N-dimethylformamide (10 ml) was stirred at 80° C. for 5 hours. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-ethoxy-1-[4-[3-methyl-1-(2-pyridyl)-1H-pyrazol-4-ylmethoxy]benzyl]-1H-pyrazol-4-yl]propionate (700 mg, yield: 91%) as a colorless oily substance from the fraction eluted with ethyl acetate-hexane (1:2, volume ratio).

NMR(CDCl$_3$) δ: 1.21(3H, t, J=7.0 Hz), 1.36(3H, t, J=7.0 Hz), 2.38(3H, s), 2.44–2.71(4H, m), 4.09(2H, q, J=7.0 Hz), 4.22(2H, q, J=7.0 Hz), 4.96(2H, s), 5.00(2H, s), 6.88–6.98 (3H, m), 7.08–7.20(3H, m), 7.72–7.82(1H, m), 7.86–7.94 (1H, m), 8.35–8.40(1H, m), 8.53(1H, s).

EXAMPLE 256

After a mixture of ethyl 3-[3-ethoxy-1-[4-[3-methyl-1-(2-pyridyl)-1H-pyrazol-4-ylmethoxy]benzyl]-1H-pyrazol-4-yl]propionate (680 mg), 1N aqueous sodium hydroxide solution (3 ml), tetrahydrofuran (5 ml) and ethanol (5 ml) was stirred at room temperature for 2 hours, 1 N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[4-(3-methyl-1-(2-pyridyl)-1H-pyrazol-4-ylmethoxy]benzyl]-1H-pyrazol-4-yl]propionic acid (620 mg, yield: 97%). This was recrystallized from acetone-hexane. Melting point: 126–127° C.

EXAMPLE 257

A mixture of 5-(5-methyl-2-phenyl-4-oxazolylmethoxy)-2-pyridylmethanol (550 mg) and thionyl chloride (10 ml) was stirred at 0° C. for 2 hours, and the reaction mixture was concentrated under reduced pressure. The residue was dissolved into ethyl acetate, washed successively with saturated aqueous sodium bicarbonate solution and saturated aqueous sodium chloride solution, dried (MgSO$_4$) and concentrated. A mixture of the resulting residue, ethyl 3-(3-ethoxy-1H-pyrazol-4-yl)propionate (400 mg), potassium carbonate (510 mg) and N,N-dimethylformamide (15 ml) was stirred at 80° C. overnight. The reaction mixture was poured into water, and extracted with ethyl acetate. The ethyl acetate layer was washed with saturated aqueous sodium chloride solution, dried (MgSO$_4$) and concentrated. The residue was subjected to silica gel column chromatography to obtain ethyl 3-[3-ethoxy-1-[5-(5-methyl-2-phenyl-4-oxazolylmethoxy)-2-pyridylmethyl]-1H-pyrazol-4-yl]propionate (730 mg, yield: 80%) as a colorless oily substance from the fraction eluted with ethyl acetate-hexane (2:1, volume ratio).

NMR(CDCl$_3$) δ: 1.22(3H, t, J=7.2 Hz), 1.36(3H, t, J=7.0 Hz), 2.44(3H, s), 2.47–2.75(4H, m), 4.03–4.28(4H, m), 5.02(2H, s), 5.15(2H, s), 6.93(1H, d, J=8.8 Hz), 7.09(1H, s), 7.28(1H, dd, J=3.0, 8.8 Hz), 7.38–7.50(3H, m), 7.94–8.06 (2H, m), 8.35(1H, d, J=3.0 Hz).

EXAMPLE 258

After a mixture of ethyl 3-[3-ethoxy-1-[5-(5-methyl-2-phenyl-4-oxazolylmethoxy)-2-pyridylmethyl]-1H-pyrazol-4-yl]propionate (730 mg), 1N aqueous sodium hydroxide solution (3 ml), tetrahydrofuran (5 ml) and ethanol (5 ml) was stirred at room temperature for 2 hours, 1 N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-ethoxy-1-[5-(5-methyl-2-phenyl-4-oxazolylmethoxy)-2-pyridylmethyl]-1H-pyrazol-4-yl]propionic acid (650 mg, yield: 95%). This was recrystallized from acetone-hexane. Melting point: 133–134° C.

EXAMPLE 259

Sodium hydride (60%, oily, 70.0 mg) was added to a solution of 4-(4-chloromethylphenoxymethyl)-5-methyl-2-phenyloxazole (549 mg), ethyl 3-ethoxy-1H-pyrazol-4-ylacetate (347 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-ethoxy-1-[4-(5-methyl-2-phenyl-4-oxazolylmethoxy)benzyl]-1H-pyrazol-4-ylacetate (618 mg, yield: 74%) as a colorless oily substance from the fraction eluted with ethyl acetate-hexane (1:1, volume ratio).

NMR(CDCl$_3$) δ: 1.25(3H, t, J=7.0 Hz), 1.34(3H, t, J=7.0 Hz), 2.43(3H, s), 3.36(2H, s), 4.14(2H, q, J=7.0 Hz), 4.23 (2H, q, J=7.0 Hz), 4.98(2H, s), 5.04(2H, s), 6.98(1H, d, J=8.8 Hz), 7.13(1H, s), 7.17(1H, d, J=8.8 Hz), 7.40–7.50 (3H, m), 7.97–8.04(2H, m).

EXAMPLE 260

After a mixture of ethyl 3-ethoxy-1-[4-(5-methyl-2-phenyl-4-oxazolylmethoxy)benzyl]-1H-pyrazol-4-ylacetate (618 mg), 1N aqueous sodium hydroxide solution (3 ml), tetrahydrofuran (6 ml) and ethanol (6 ml) was stirred at room temperature for 2 hours, 1 N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-ethoxy-1-[4-(5-methyl-2-phenyl-4-oxazolylmethoxy)benzyl]-1H-pyrazol-4-ylacetic acid (502 mg, yield: 86%). This was, recrystallized from ethanol-hexane. Melting point: 125–126° C.

EXAMPLE 261

Sodium hydride (60%, oily, 70.0 mg) was added to a solution of 5-chloromethyl-2-(5-methyl-2-phenyl-4-oxazolylmethoxy)pyridine (551 mg), ethyl 3-ethoxy-1H-pyrazol-4-ylacetate (347 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-ethoxy-1-[6-(5-methyl-2-phenyl-4-oxazolylmethoxy)-3-pyridylmethyl]-1H-pyrazol-4-ylacetate (608 mg, yield: 73%) as a colorless oily substance from the fraction eluted with ethyl acetate-hexane (1:1, volume ratio).

NMR(CDCl$_3$) δ: 1.25(3H, t, J=7.2 Hz), 1.35(3H, t, J=7.0 Hz), 2.47(3H, s), 3.36(2H, s), 4.15(2H, q, J=7.2 Hz), 4.22 (2H, q, J=7.0 Hz), 5.02(2H, s), 5.29(2H, s), 6.78(1H, d, J=8.4 Hz), 7.19(1H, s), 7.39–7.49(4H, m), 7.98–8.07(3H, m).

EXAMPLE 262

After a mixture of ethyl 3-ethoxy-1-[6-(5-methyl-2-phenyl-4-oxazolylmethoxy)-3-pyridylmethyl]-1H-pyrazol-4-ylacetate (605 mg), 1N aqueous sodium hydroxide solution (3 ml), tetrahydrofuran (6 ml) and ethanol (6 ml) was stirred at room temperature for 2 hours, 1 N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-ethoxy-1-[6-(5-methyl-2-phenyl-4-oxazolylmethoxy)-3-pyridylmethyl]-1H-pyrazol-4-ylacetic acid (518 mg, yield: 91%). This was recrystallized from ethanol-hexane. Melting point: 126–127° C.

EXAMPLE 263

Sodium hydride (60%, oily, 39.4 mg) was added to a solution of 5-chloromethyl-2-[2-(2-furyl)-5-methyl-4-oxazolylmethoxy]pyridine (300 mg), ethyl 3-ethoxy-1H-pyrazol-4-ylacetate (195 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-ethoxy-1-[6-[2-(2-furyl)-5-methyl-4-oxazolylmethoxy]-3-pyridylmethyl]-1H-pyrazol-4-ylacetate (364 mg, yield 79%) as a colorless oily substance from the fraction eluted with ethyl acetate-hexane (1:1, volume ratio).

NMR(CDCl$_3$) δ: 1.25(3H, t, J=7.2 Hz), 1.35(3H, t, J=7.0 Hz), 2.46(3H, s), 3.66(2H, s), 4.14(2H, q, J=7.2 Hz), 4.22 (2H, q, J=7.0 Hz), 5.02(2H, s), 5.26(2H, s), 6.52(1H, dd, J=1.8, 3.2 Hz), 6.76(1H, d, J=8.6 Hz), 6.98(1H, dd, J=0.8, 3.2 Hz), 7.19(1H, s), 7.46(1H, dd, J=2.4, 8.6 Hz), 7.52(1H, dd, J=0.8, 1.8 Hz), 8.05(1H, d, J=2.4 Hz).

EXAMPLE 264

After a mixture of ethyl 3-ethoxy-1-[6-[2-(2-furyl)-5-methyl-4-oxazolylmethoxy]-3-pyridylmethyl]-1H-pyrazol-4-ylacetate (364 mg), 1N aqueous sodium hydroxide solution (2 ml), tetrahydrofuran (4 ml) and ethanol (4 ml) was stirred at room temperature for 2 hours, 1 N hydrochloric acid (2 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-ethoxy-1-[6-[2-(2-furyl)-5-methyl-4-oxazolylmethoxy]-3-pyridylmethyl]-1H-pyrazol-4-ylacetic acid (308 mg, yield: 90%). This was recrystallized from ethanol-hexane. Melting point: 155–156° C.

EXAMPLE 265

Sodium hydride (601, oily, 0.30 g) was added to a solution of ethyl 3-[1-(3,5-dihydroxybenzyl)-4-phenyl-3-pyrrolyl]propionate (1.83 g) in N,N-dimethylformamide (20 ml) at 0° C., and the mixture was stirred at room temperature for 15 minutes. 4-Chloromethyl-2-phenylthiazole (1.05 g) was added to the mixture and the mixture was stirred at room temperature for 30 minutes. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[1-[3,5-bis(2-phenyl-4-thiazolylmethoxy)benzyl]-4-phenyl-3-pyrrolyl]propionate (513 mg, yield: 14%) as a colorless oily substance from the fraction eluted with ethyl acetate-hexane (1:2, volume ratio).

NMR(CDCl$_3$) δ: 1.19(3H, t, J=7.2 Hz), 2.52(2H, t, J=7.8 Hz), 2.95(2H, t, J=7.8 Hz), 4.08(2H, q, J=7.2 Hz), 4.95(2H, s), 5.21(4H, s), 6.47(2H, d, J=2.2 Hz), 6.52(1H, d, J=2.4 Hz), 6.66(1H, t, J=2.2 Hz), 6.72 (H, d, J=2.4 Hz), 7.16–7.46 (13H, m), 7.90–7.97(4H, m).

EXAMPLE 266

After a mixture of ethyl 3-[1-[3,5-bis(2-phenyl-4-thiazolylmethoxy)benzyl]-4-phenyl-3-pyrrolyl]propionate (498 mg), 1N aqueous sodium hydroxide solution (2 ml), tetrahydrofuran (5 ml) and ethanol (5 ml) was stirred at room temperature for 2 hours, 1 N hydrochloric acid (2 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[1-[3,5-bis(2-phenyl-4-thiazolylmethoxy)benzyl]-4-phenyl-3-pyrrolyl]propionic acid (378 mg, yield: 79%). This was recrystallized from ethyl acetate-hexane. Melting point: 78–79° C.

EXAMPLE 267

Sodium hydride (60%, oily, 190 mg) was added to a solution of 1-[6-(5-methyl-2-phenyl-4-oxazolylmethoxy)-3-pyridylmethyl]-4-phenyl-3-pyrrolecarbaldehyde (1.05 g) and ethyl diethylphosphonoacetate (1.05 g) in N,N-dimethylformamide (50 ml) at 0° C., and the mixture was stirred at 0° C. for 2 hours. The reaction mixture was poured into water, and the precipitated crystals were collected by filtration to obtain ethyl(E)-3-[1-[6-(5-methyl-2-phenyl-4-oxazolylmethoxy)-3-pyridylmethyl]-4-phenyl-3-pyrrolyl]propenoate. The crystals were dissolved in ethanol (80 ml), and hydrogenated on 5% palladium-carbon (800 mg) at room temperature under a normal pressure. The catalyst was filtered, and the filtrate was concentrated. The residue was subjected to silica gel column chromatography to obtain ethyl 3-[1-[6-(5-methyl-2-phenyl-4-oxazolylmethoxy)-3-pyridylmethyl]-4-phenyl-3-pyrrolyl]propionate (1.05 g, yield: 86%) as a colorless oily substance from the fraction eluted with ethyl acetate-hexane (1:2, volume 5 ratio).

EXAMPLE 268

A mixture of ethyl 3-[1-[6-(5-methyl-2-phenyl-4-oxazolylmethoxy)-3-pyridylmethyl]-4-phenyl-3-pyrrolyl]propionate (1.03 g), 1N aqueous sodium hydroxide solution (8 ml), ethanol (10 ml) and tetrahydrofuran (10 ml) was stirred at room temperature. The reaction mixture was poured into water, neutralized with 1N hydrochloric acid, and extracted with ethyl acetate. The ethyl acetate layer was washed with water, dried (MgSO$_4$) and concentrated. The residue was subjected to silica gel column chromatography to obtain crystals of 3-[1-[6-(5-methyl-2-phenyl-4-oxazolylmethoxy)-3-pyridylmethyl]-4-phenyl-3-pyrrolyl]propionic acid from the fraction eluted with acetone-hexane (1:1, volume ratio). This was recrystallized from ethyl acetate-hexane to obtain colorless prisms (740 mg, yield: 74%). Melting point: 123–124° C.

EXAMPLE 269

Sodium hydride (60%, oily, 0.56 g) was added to a solution of ethyl 3-[1-(3,5-dihydroxybenzyl)-4-phenyl-3-pyrrolyl]propionate (5.12 g) in N,N-dimethylformamide (50 ml) at 0° C., and the mixture was stirred at room temperature for 15 minutes. Ethyl iodide (1.12 ml) was added to the mixture, and the mixture was stirred at room temperature for 30 minutes. The reaction mixture was poured into water, and extracted with ethyl acetate. The ethyl acetate layer was washed with saturated aqueous sodium chloride solution, dried ($MgSO_4$), and concentrated. The residue was subjected to silica gel column chromatography to obtain ethyl 3-[1-(3,5-diethoxybenzyl)-4-phenyl-3-pyrrolyl]propionate (1040 mg, yield: 24%) as a colorless oily substance from the fraction eluted with ethyl acetate-hexane (1:2, volume ratio).

NMR($CDCl_3$) δ: 1.20(3H, t, J=7.0 Hz), 1.38(6H, t, J=7.0 Hz), 2.48–2.56(2H, m), 2.91–2.99(2H, m), 3.97(2H, q, J=7.0 Hz), 4.08(4H, q, J=7.0 Hz), 4.91(2H, s), 6.29(2H, d, J=2.2 Hz), 6.36(1H, t, J=2.2 Hz), 6.51(1H, d, J=2.4 Hz), 6.72(1H, d, J=2.4 Hz), 7.15–7.25(1H, m), 7.29–7.42(4H, m).

EXAMPLE 270

In silica gel column chromatography described in Example 269, ethyl 3-[1-(3-ethoxy-5-hydroxybenzyl)-4-phenyl-3-pyrrolyl]propionate (2040 mg, yield: 37%) was obtained as a colorless oily substance from the fraction which eluted next to the compound described in Example 269.

NMR($CDCl_3$) δ: 1.17(3H, t, J=7.0 Hz), 1.37(3H, t, J=7.0 Hz), 2.47–2.55(2H, m), 2.92–3.00(2H, m), 3.96(2H, q, J=7.0 Hz), 4.09(2H, q, J=7.0 Hz), 4.89(2H, s), 5.67(1H, s), 6.06(1H, s), 6.29–6.32(2H, m), 6.50(1H, d, J=2.4 Hz), 6.71(1H, d, J=2.4 Hz), 7.15–7.41(5H, m).

EXAMPLE 271

Sodium hydride (60%, oily, 50.0 mg) was added to a solution of ethyl 3-[1-(3-ethoxy-5-hydroxybenzyl)-4-phenyl-3-pyrrolyl]propionate (492 mg) in N,N-dimethylformamide (10 ml) at 0° C., and the mixture was stirred at room temperature for 15 minutes. 4-Chloromethyl-5-methyl-2-phenyloxazole (260 mg) was added to the mixture, and the mixture was stirred at room temperature for 30 minutes. The reaction mixture was poured into water, and extracted with ethyl acetate. The ethyl acetate layer was washed with saturated aqueous sodium chloride solution, dried ($MgSO_4$), and concentrated. The residue was subjected to silica gel column chromatography to obtain ethyl 3-[1-[3-ethoxy-5-(5-methyl-2-phenyl-4-oxazolylmethoxy)benzyl]-4-phenyl-3-pyrrolyl]propionate (622 mg, yield: 88%) as a colorless oily substance from the fraction eluted with ethyl acetate-hexane (1:3, volume ratio).

NMR($CDCl_3$) δ: 1.20(3H, t, J=7.0 Hz), 1.38(3H, t, J=7.0 Hz), 2.41(3H, s), 2.47–2.55(2H, m), 2.91–2.99(2H, m), 3.98(2H, q, J=7.0 Hz), 4.08(2H, q, J=7.0 Hz), 4.93(4H, s), 6.34(1H, s), 6.43(1H, s), 6.51(1H, s), 6.52(1H, d, J=2.4 Hz), 6.72(1H, d, J=2.4 Hz), 7.16–7.45(8H, m), 7.98–8.03(2H, m).

EXAMPLE 272

After a mixture of ethyl 3-[1-[3-ethoxy-5-(5-methyl-2-phenyl-4-oxazolylmethoxy)benzyl]-4-phenyl-3-pyrrolyl]propionate (621 mg), 1N aqueous sodium hydroxide solution (2.5 ml), tetrahydrofuran (5 ml) and ethanol (5 ml) was stirred at room temperature for 2 hours, 1 N hydrochloric acid (2.5 ml) was added to the mixture, and then the mixture was extracted with ethyl acetate. The ethyl acetate layer was washed with saturated aqueous sodium chloride solution, dried ($MgSO_4$) and concentrated. The resulting colorless crystals were collected by filtration to obtain 3-[1-[3-ethoxy-5-(5-methyl-2-phenyl-4-oxazolylmethoxy)benzyl]-4-phenyl-3-pyrrolyl]propionic acid (439 mg, yield: 74%). This was recrystallized from ethanol-hexane. Melting point: 126–127° C.

EXAMPLE 273

Sodium hydride (60%, oily, 50.0 mg) was added to a solution of ethyl 3-[1-(3-ethoxy-5-hydroxybenzyl)-4-phenyl-3-pyrrolyl]propionate (492 mg) in N,N-dimethylformamide (10 ml) at 0° C., and the mixture was stirred at room temperature for 15 minutes. 4-Chloromethyl-2-phenylthiazole (262 mg) was added to the mixture, and the mixture was stirred at room temperature for 30 minutes. The reaction mixture was poured into water, and extracted with ethyl acetate. The ethyl acetate layer was washed with saturated aqueous sodium chloride solution, dried ($MgSO_4$), and concentrated. The residue was subjected to silica gel column chromatography to obtain ethyl 3-[1-[3-ethoxy-5-(2-phenyl-4-thiazolylmethoxy)benzyl]-4-phenyl-3-pyrrolyl]propionate (601 mg, yield: 85%) as a colorless oily substance from the fraction eluted with ethyl acetate-hexane (1:3, volume ratio).

NMR($CDCl_3$) δ: 1.20(3H, t, J=7.0 Hz), 1.38(3H, t, J=7.0 Hz), 2.48–2.56(2H, m), 2.91–2.99(2H, m), 3.97(2H, q, J=7.0 Hz), 4.08(2H, q, J=7.0 Hz), 4.93(2H, s), 5.20(2H, s), 6.34(1H, s), 6.42(1H, s), 6.50(1H, d, J=2.4 Hz), 6.52(1H, s), 6.72(1H, d, J=2.4 Hz), 7.15–7.46(9H, m), 7.92–7.96(2H, m).

EXAMPLE 274

After a mixture of ethyl 3-[1-[3-ethoxy-5-(2-phenyl-4-thiazolylmethoxy)benzyl]-4-phenyl-3-pyrrolyl]propionate (595 mg), 1N aqueous sodium hydroxide solution (2.5 ml), tetrahydrofuran (5 ml) and ethanol (5 ml) was stirred at room temperature for 2 hours, 1 N hydrochloric acid (2.5 ml) was added to the mixture, and then the mixture was extracted with ethyl acetate. The ethyl acetate layer was washed with saturated aqueous sodium chloride solution, dried ($MgSO_4$) and concentrated. The resulting colorless crystals were collected by filtration to obtain 3-[1-[3-ethoxy-5-(2-phenyl-4-thiazolylmethoxy)benzyl]-4-phenyl-3-pyrrolyl]propionic acid (538 mg, yield: 95%). This was recrystallized from ethanol-hexane. Melting point: 109–110° C.

EXAMPLE 275

Sodium hydride (60%, oily, 50.0 mg) was added to a solution of ethyl 3-[1-(3-ethoxy-5-hydroxybenzyl)-4-phenyl-3-pyrrolyl]propionate (492 mg) in N,N-dimethylformamide (10 ml) at 0° C., and the mixture was stirred at room temperature for 15 minutes. 4-Chloromethyl-2-(2-thienyl)thiazole (270 mg) was added to the mixture, and the mixture was stirred at room temperature for 30 minutes. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[1-[3-ethoxy-5-[2-(2-thienyl)-4-thiazolylmethoxy)benzyl]-4-phenyl-3-pyrrolyl]propionate (657 mg, yield: 92%) as a colorless oily substance from the fraction eluted with ethyl acetate-hexane (1:3, volume ratio).

NMR(CDCl$_3$) δ: 1.20(3H, t, J=7.0 Hz), 1.38(3H, t, J=7.0 Hz), 2.48–2.56(2H, m), 2.91–2.99(2H, m), 3.97(2H, q, J=7.0 Hz), 4.08(2H, q, J=7.0 Hz), 4.92(2H, s), 5.16(2H, s), 6.33 (1H, s), 6.41(1H, s), 6.48(1H, t, J=2.2 Hz), 6.51(1H, d, J=2.4 Hz), 6.72(1H, d, J=2.4 Hz), 7.06(1H, dd, J=3.6, 5.2 Hz), 7.19–7.25(2H, m), 7.29–7.40(5H, m), 7.50(1H, dd, J=1.2, 3.6 Hz).

EXAMPLE 276

After a mixture of ethyl 3-[1-[3-ethoxy-5-[2-(2-thienyl)-4-thiazolylmethoxy)benzyl]-4-phenyl-3-pyrrolyl]propionate (653 mg), 1N aqueous sodium hydroxide solution (2.5 ml), tetrahydrofuran (5 ml) and ethanol (5 ml) was stirred at room temperature for 2 hours, 1 N hydrochloric acid (2.5 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[1-[3-ethoxy-5-[2-(2-thienyl)-4-thiazolylmethoxy)benzyl]-4-phenyl-3-pyrrolyl]propionic acid (545 mg, yield: 88%). This was recrystallized from ethanol-hexane. Melting point: 104–105° C.

EXAMPLE 277

A mixture of ethyl 3-[1-(4-hydroxybenzyl)-4-phenyl-3-pyrrolyl]propionate (600 mg), 5-chloromethyl-2-phenylpyridine (370 mg), potassium carbonate (450 mg) and N,N-dimethylformamide (10 ml) was stirred at 80° C. for 5 hours. The reaction mixture was poured into water, and extracted with ethyl acetate. The ethyl acetate layer was washed with saturated aqueous sodium chloride solution, dried (MgSO$_4$) and concentrated. The residue was subjected to silica gel column chromatography to obtain a colorless oily substance from the fraction eluted with ethyl acetate-hexane (1:1, volume ratio). After a mixture of the resulting colorless oily substance, 1N aqueous sodium hydroxide solution (5 ml), tetrahydrofuran (5 ml) and ethanol (5 ml) was stirred at room temperature for 2 hours, 1N hydrochloric acid (5 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[4-phenyl-1-[4-(6-phenyl-3-pyridylmethoxy)benzyl]-3-pyrrolyl]propionic acid (820 mg, yield: 98%). This was recrystallized from acetone-hexane. Melting point: 185–186° C.

EXAMPLE 278

A mixture of 5-phenyl-2-pyridinemethanol (390 mg), thionyl chloride (0.3 ml) and toluene (10 ml) was stirred at 80° C. for 1 hour. After the reaction mixture was concentrated under reduced pressure, the resulting crystals were filtered and washed with hexane. A mixture of the resulting crystals, ethyl 3-[1-(4-hydroxybenzyl)-4-phenyl-3-pyrrolyl] propionate (790 mg), potassium carbonate (700 mg) and N,N-dimethylformamide (15 ml) was stirred at 70° C. overnight. The reaction mixture was poured into water, and extracted with ethyl acetate. The ethyl acetate layer was washed with a saturated aqueous sodium chloride solution, dried (MgSO$_4$) and concentrated. The residue was subjected to silica gel column chromatography to obtain ethyl 3-[1-[4-(5-phenyl-2-pyridylmethoxy)benzyl]-4-phenyl-3-pyrrolyl]propionate (1050 mg, yield: 96%) as a colorless oily substance from the fraction eluted with ethyl acetate-hexane (1:2, volume ratio).

NMR(CDCl$_3$) δ: 1.20(3H, t, J=7.0 Hz), 2.46–2.58(2H, m), 2.88–3.00(2H, m), 4.08(2H, q, J=7.0 Hz), 4.95(2H, s), 5.25(2H, s), 6.51(1H, d, J=2.6 Hz), 6.71(1H, d, J=2.6 Hz), 6.94–7.04(2H, m), 7.08–7.64(13H, m), 7.91(1H, dd, J=2.2, 8.0 Hz), 8.82(1H, d, J=2.2 Hz).

EXAMPLE 279

After a mixture of ethyl 3-[1-[4-(5-phenyl-2-pyridylmethoxy)benzyl]-4-phenyl-3-pyrrolyl]propionate (1020 mg), 1N aqueous sodium hydroxide solution (4 ml), tetrahydrofuran (5 ml) and ethanol (5 ml) was stirred at room temperature for 2 hours, 1 N hydrochloric acid (4 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[1-[4-(5-phenyl-2-pyridylmethoxy)benzyl]-4-phenyl-3-pyrrolyl]propionic acid (930 mg, yield: 97%). This was recrystallized from acetone-hexane. Melting point: 169–170° C.

EXAMPLE 280

A mixture of 4-benzyloxybenzyl chloride (11.60 g), ethyl 3-(4-fluorophenyl)-1H-pyrazole-4-carboxylate (11.70 g), potassium carbonate (13.80 g) and N,N-dimethylformamide (150 ml) was stirred at room temperature for 5 hours. The reaction mixture was poured into water, and extracted with ethyl acetate. The ethyl acetate layer was washed with saturated aqueous sodium chloride solution, dried (MgSO$_4$) and concentrated. The resulting colorless crystals were collected by filtration to obtain ethyl 1-(4-benzyloxybenzyl)-3-(4-fluorophenyl)-1H-pyrazole-4-carboxylate (16.90 g, yield: 79%). This was recrystallized from ethyl acetate-hexane. Melting point: 103–104° C.

EXAMPLE 281

Sodium hydride (60%, oily, 1.10 g) was added to a solution of 1-(4-benzyloxybenzyl)-3-(4-fluorophenyl)-1H-pyrazole-4-carbaldehyde (9.66 g) and ethyl diethylphosphonoacetate (5.46 ml) in N,N-dimethylformamide (150 ml) at 0° C., and the mixture was stirred at room temperature for 2 hours. Ice water was poured into the reaction mixture, and the resulting crystals were collected by filtration. After drying, recrystallization from ethyl acetate-hexane gave ethyl (E)-3-[1-(4-benzyloxybenzyl)-3-(4-fluorophenyl)-1H-pyrazol-4-yl]propenoate (10.60 g, yield: 93%). Melting point: 113–114° C.

EXAMPLE 282

Sodium hydride (60%, oily, 140 mg) was added to a solution of 1-[6-(5-methyl-2-phenyl-4-oxazolylmethoxy)-3-pyridylmethyl]-3-phenyl-1H-pyrazole-4-carbaldehyde (1.20 g) and ethyl diethylphosphonoacetate (780 mg) in N,N- dimethylformamide (30 ml) at 0° C., and the mixture was stirred at 0° C. for 2 hours. The reaction mixture was poured into water, and the precipitated crystals were collected by filtration to obtain ethyl(E)-3-[1-[6-(5-methyl-2-phenyl-4-oxazolylmethoxy)-3-pyridylmethyl]-3-phenyl-1H-pyrazol-4-yl]propionate. The crystals were dissolved into ethanol (100 ml), and hydrogenated on 5% palladium-carbon (1.0 g) at room temperature under a normal pressure. The catalyst was removed by filtration, and the filtrate was concentrated. The residue was subjected to silica gel column chromatography to obtain ethyl 3-[1-[6-(5-methyl-2-phenyl-4-oxazolylmethoxy)-3-pyridylmethyl]-3-phenyl-1H-pyrazol-4-yl]propionate (1.20 g, yield: 86%) as a colorless oily substance.

NMR(CDCl$_3$) δ: 1.19(3H, t, J=7 Hz), 2.47(3H, s), 2.52 (2H, t, J=7.5 Hz), 2.94(2H, t, J=7, 5 Hz), 4.08(2H, q, J=7 Hz), 5.23(2H, s), 5.29(2H, s), 6.80(1H, d, J=8.5 Hz), 7.2–7.65(10H, m), 7.95–8.15(3H, m).

EXAMPLE 283

A mixture of ethyl 3-[1-[2-(5-methyl-2-phenyl-4-oxazolylmethoxy)-5-pyridylmethyl]-3-phenyl-1H-pyrazol-4-yl]propionate (1.20 g), a 1N aqueous sodium hydroxide solution (10 ml) and ethanol (20 ml) was stirred at room temperature for 2 hours. After the reaction mixture was poured into water and neutralized with 1N hydrochloric acid, the precipitated crystals of 3-[1-[2-(5-methyl-2-phenyl-4-oxazolylmethoxy)-5-pyridylmethyl]-3-phenyl-1H-pyrazol-4-yl]propionic acid were collected by filtration. This was recrystallized from ethyl acetate to obtain colorless prism crystals (810 mg, yield: 71%). Melting point: 172–173° C.

EXAMPLE 284

A mixture of 1-(4-benzyloxybenzyl)-3-phenyl-1H-pyrazol-4-ylmethanol (26.39 g), activated manganese dioxide (70.26 g) and tetrahydrofuran (300 ml) was stirred at room temperature overnight. After the manganese dioxide was removed by filtration, the filtrate was concentrated. The residue was subjected to silica gel column chromatography to obtain a colorless oily substance from the fraction eluted with ethyl acetate-hexane (1:2, volume ratio). Sodium hydride (60%, oily, 3.20 g) was added to a solution of the resulting colorless oily substance and ethyl diethylphosphonoacetate (18.19 g) in N,N-dimethylformamide (100 ml) at 0° C., and the mixture was stirred at room temperature for 2 hours. Ice water was poured into the reaction mixture, and the resulting crystals were collected by filtration. After drying, recrystallization from ethyl acetate-hexane gave ethyl (E)-3-[1-(4-benzyloxybenzyl)-3-phenyl-1H-pyrazol-4-yl]propenoate (26.71 g, yield: 86%). Melting point: 94–95° C.

EXAMPLE 285

A mixture of ethyl 3-[1-(4-hydroxybenzyl)-3-phenyl-1H-pyrazol-4-yl]propionate (600 mg), 2-chloromethylquinoline hydrochloride (380 mg), potassium carbonate (360 mg) and N,N-dimethylformamide (10 ml) was stirred at 80° C. for 5 hours. The reaction mixture was poured into water, and extracted with ethyl acetate. The ethyl acetate layer was washed with saturated aqueous sodium chloride solution, dried (MgSO$_4$) and concentrated. The residue was subjected to silica gel column chromatography to obtain a colorless oily substance from the fraction eluted with ethyl acetate-hexane (1:1, volume ratio). After a mixture of the resulting colorless oily substance, 1N aqueous sodium hydroxide solution (5 ml), tetrahydrofuran (5 ml) and ethanol (5 ml) was stirred at room temperature for 2 hours, 1N hydrochloric acid was added to the mixture, and then the mixture was extracted with ethyl acetate. The ethyl acetate layer was washed with a saturated aqueous sodium chloride solution, dried (MgSO$_4$), and concentrated. The resulting colorless crystals were collected by filtration to obtain 3-[3-phenyl-1-[4-(2-quinolylmethoxy)benzyl]-1H-pyrazol-4-yl]propionic acid (660 mg, yield: 83%). This was recrystallized from acetone-hexane. Melting point: 147–148° C.

EXAMPLE 286

A mixture of ethyl 3-[1-[4-(2-bromoethoxy)benzyl]-3-phenyl-1H-pyrazol-4-yl]propionate (1050 mg), 1(2H)-phthalazinone (530 mg), potassium carbonate (1000 mg) and N,N-dimethylformamide (15 ml) was stirred at 90° C. for 5 hours. The reaction mixture was poured into water, and extracted with ethyl acetate. The ethyl acetate layer was washed successively with dilute hydrochloric acid and saturated aqueous sodium chloride solution, dried (MgSO$_4$) and concentrated. The residue was subjected to silica gel column chromatography to obtain a colorless oily substance from the fraction eluted with ethyl acetate-hexane (1:1, volume ratio). After a mixture of the resulting colorless oily substance, 1N aqueous sodium hydroxide solution (5 ml), tetrahydrofuran (5 ml) and ethanol (5 ml) was stirred at room temperature for 3 hours, 1N hydrochloric acid (5 ml) was added to the mixture, and then the mixture was extracted with ethyl acetate. The ethyl acetate layer was washed with a saturated aqueous sodium chloride solution, dried (MgSO$_4$), and concentrated. The resulting colorless crystals were collected by filtration to obtain 3-[1-[4-[2-[1-oxophthalazin-2(1H)-yl]ethoxy]benzyl]-3-phenyl-1H-pyrazol-4-yl]propionic acid (1460 mg, yield 90%). This was recrystallized from acetone-hexane. Melting point: 155–156° C.

EXAMPLE 287

A mixture of ethyl 3-[1-[4-(2-bromoethoxy)benzyl]-3-phenyl-1H-pyrazol-4-yl]propionate (883 mg), 2H-1,4-benzothiazin-3(4H)-one (320 mg), potassium carbonate (530 mg) and N,N-dimethylformamide (10 ml) was stirred at 80° C. for 8 hours. The reaction mixture was poured into water, and extracted with ethyl acetate. The ethyl acetate layer was washed successively with dilute hydrochloric acid and saturated aqueous sodium chloride solution, dried (MgSO$_4$) and concentrated. The residue was subjected to silica gel column chromatography to obtain a colorless oily substance from the fraction eluted with ethyl acetate-hexane (1:2, volume ratio). After a mixture of the resulting colorless oily substance, 1N aqueous sodium hydroxide solution (5 ml), tetrahydrofuran (5 ml) and ethanol (5 ml) was stirred at room temperature for 3 hours, 1N hydrochloric acid (5 ml) was added to the mixture, and then the mixture was extracted with ethyl acetate. The ethyl acetate layer was washed with a saturated aqueous sodium chloride solution, dried (MgSO$_4$), and concentrated to obtain 3-[1-[4-[2-(3-oxo-2,3-dihydro-4H-1,4-benzothiazin-4-yl)ethoxy]benzyl]-3-phenyl-1H-pyrazol-4-yl]propionic acid (680 mg, yield: 69%) as a colorless amorphous substance.

EXAMPLE 288

A mixture of ethyl 3-[1-(4-hydroxybenzyl)-3-phenyl-1H-pyrazol-4-yl]propionate (600 mg), 5-chloromethyl-2-phenylpyridine (350 mg), potassium carbonate (460 mg) and N,N-dimethylformamide (10 ml) was stirred at 80° C. for 5 hours. The reaction mixture was poured into water, and extracted with ethyl acetate. The ethyl acetate layer was washed with saturated aqueous sodium chloride solution, dried (MgSO$_4$) and concentrated. The residue was subjected to silica gel column chromatography to obtain a colorless oily substance from the fraction eluted with ethyl acetate-hexane (1:1, volume ratio). After a mixture of the resulting colorless oily substance, 1N aqueous sodium hydroxide solution (3 ml), tetrahydrofuran (5 ml) and ethanol (5 ml) was stirred at room temperature for 2 hours, 1N hydrochloric acid (3 ml) was added to the mixture, and then the mixture was extracted with ethyl acetate. The ethyl acetate layer was washed with saturated aqueous sodium chloride solution, dried (MgSO$_4$), and concentrated. The resulting colorless crystals were collected by filtration to obtain 3-[3-phenyl-1-[4-(6-phenyl-3-pyridylmethoxy)benzyl]-1H-pyrazol-4-yl] propionic acid (710 mg, yield: 85%). This was recrystallized from acetone-hexane. Melting point: 155–156° C.

EXAMPLE 289

A mixture of ethyl 3-[1-(4-hydroxybenzyl)-3-phenyl-1H-pyrazol-4-yl]propionate (840 mg), 3-chloromethyl-5-phenylpyridine (550 mg), potassium carbonate (500 mg) and N,N-dimethylformamide (10 ml) was stirred at 80° C. for 5 hours. The reaction mixture was poured into water, and extracted with ethyl acetate. The ethyl acetate layer was washed with saturated aqueous sodium chloride solution, dried (MgSO$_4$) and concentrated. The residue was subjected to silica gel column chromatography to obtain ethyl 3-[3-phenyl-1-[4-(5-phenyl-3-pyridylmethoxy)benzyl]-1H-pyrazol-4-yl]propionate (1010 mg, yield: 81%) as a colorless oily substance from the fraction eluted with ethyl acetate-hexane (1:1, volume ratio).

NMR(CDCl$_3$) δ: 1.19(3H, t, J=7.0 Hz), 2.46–2.56(2H, m), 2.88–3.00(2H, m), 4.12(2H, q, J=7.0 Hz), 5.15(2H, s), 5.25(2H, s), 6.92–7.04(2H, m), 7.16–7.67(13H, m), 7.94–7.99(1H, m), 8.65(1H, d, J=2.2 Hz), 8.82(1H, d, J=2.2 Hz).

EXAMPLE 290

After a mixture of ethyl 3-[3-phenyl-1-[4-(5-phenyl-3-pyridylmethoxy)benzyl]-1H-pyrazol-4-yl]propionate (980 mg), 1N aqueous sodium hydroxide solution (4 ml), tetrahydrofuran (10 ml) and ethanol (10 ml) was stirred at room temperature for 2 hours, 1 N hydrochloric acid (4 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-phenyl-1-[4-(5-phenyl-3-pyridylmethoxy)benzyl]-1H-pyrazol-4-yl]propionic acid (760 mg, yield: 82%). This was recrystallized from acetone-hexane. Melting point: 161–162° C.

EXAMPLE 291

A mixture of ethyl 3-[1-(4-hydroxybenzyl)-3-phenyl-1H-pyrazol-4-yl]propionate (460 mg), 2-chloromethyl-1-methyl-1H-benzimidazole (250 mg), potassium carbonate (360 mg) and N,N-dimethylformamide (15 ml) was stirred at 80° C. for 5 hours. The reaction mixture was poured into water, and extracted with ethyl acetate. The ethyl acetate layer was washed with saturated aqueous sodium chloride solution, dried (MgSO$_4$) and concentrated. The residue was subjected to silica gel column chromatography to obtain ethyl 3-[1-[4-(1-methyl-1H-benzimidazol-2-ylmethoxy)benzyl]-3-phenyl-1H-pyrazol-4-yl]propionate (550 mg, yield: 85%) as a colorless oily substance from the fraction eluted with ethyl acetate-hexane (2:1, volume ratio).

NMR(CDCl$_3$) δ: 1.17(3H, t, J=7.0 Hz), 2.45–2.56(2H, m), 2.86–2.98(2H, m), 3.89(3H, s), 4.06(2H, q, J=7.0 Hz), 5.22(2H, s), 5.39(2H, s), 7.01–7.10(2H, m), 7.16–7.47(9H, m), 7.58–7.66(2H, m), 7.73–7.82(1H, m).

EXAMPLE 292

After a mixture of ethyl 3-[1-[4-(1-methyl-1H-benzimidazol-2-ylmethoxy)benzyl]-3-phenyl-1H-pyrazol-4-yl]propionate (520 mg), 1N aqueous sodium hydroxide solution (2 ml), tetrahydrofuran (5 ml) and ethanol (5 ml) was stirred at room temperature for 2 hours, 1 N hydrochloric acid (2 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[1-[4-(1-methyl-1H-benzimidazol-2-ylmethoxy)benzyl]-3-phenyl-1H-pyrazol-4-yl]propionic acid (420 mg, yield: 86%). This was recrystallized from ethanol-hexane. Melting point: 225–226° C.

EXAMPLE 293

A mixture of ethyl 3-[3-(4-fluorophenyl)-1-(4-hydroxybenzyl)-1H-pyrazol-4-yl]propionate (950 mg), 2-chloromethylquinoline hydrochloride (600 mg), potassium carbonate (700 mg) and N,N-dimethylformamide (15 ml) was stirred at 60° C. for 5 hours. The reaction mixture was poured into water, and extracted with ethyl acetate. The ethyl acetate layer was washed with saturated aqueous sodium chloride solution, dried (MgSO$_4$) and concentrated. The residue was subjected to silica gel column chromatography to obtain ethyl 3-[3-(4-fluorophenyl)-1-[4-(2-quinolylmethoxy)benzyl]-1H-pyrazol-4-yl]propionate (1210 mg, yield: 92%) as a colorless oily substance from the fraction eluted with ethyl acetate-hexane (1:2, volume ratio).

NMR(CDCl$_3$) δ: 1.18(3H, t, J=7.0 Hz), 2.45–2.56(2H, m), 2.83–2.96(2H, m), 4.07(2H, q, J=7.0 Hz), 5.21(2H, s), 5.38(2H, s), 6.94–7.26(7H, m), 7.50–7.88(6H, m), 8.04–8.13(1H, m), 8.16–8.24(1H, m).

EXAMPLE 294

After a mixture of ethyl 3-[3-(4-fluorophenyl)-1-[4-(2-quinolylmethoxy)benzyl]-1H-pyrazol-4-yl]propionate (1150 mg), 1N aqueous sodium hydroxide solution (5 ml), tetrahydrofuran (10 ml) and ethanol (10 ml) was stirred at room temperature for 2 hours, 1 N hydrochloric acid (5 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-(4-fluorophenyl)-1-[4-(2-quinolylmethoxy)benzyl]-1H-pyrazol-4-yl]propionic acid (1010 mg, yield: 93%). This was recrystallized from tetrahydrofuran-hexane. Melting point: 178–179° C.

EXAMPLE 295

A mixture of 5-phenyl-2-pyridinemethanol (330 mg), thionyl chloride (0.3 ml) and toluene (10 ml) was stirred at 80° C. for 1 hour. After the reaction mixture was concentrated under reduced pressure, the resulting crystals were filtered and washed with hexane. A mixture of the resulting crystals, ethyl 3-[3-(4-fluorophenyl)-1-(4-hydroxybenzyl)-1H-pyrazol-4-yl]propionate (650 mg), potassium carbonate (550 mg) and N,N-dimethylformamide (10 ml) was stirred at 70° C. overnight. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-(4-fluorophenyl)-1-[(4-(5-phenyl-2-pyridyl-methoxy)benzyl]-1H-pyrazol-4-yl]propionate (850 mg, yield: 90%) as a colorless oily substance from the fraction eluted with ethyl acetate-hexane (1:2, volume ratio).

NMR(CDCl$_3$) δ: 1.18(3H, t, J=7.0 Hz), 2.44–2.56(2H, m), 2.85–2.97(2H, m), 4.07(2H, q, J=7.0 Hz), 5.22(2H, s), 5.25(2H, s), 6.94–7.26(8H, m), 7.34–7.68(7H, m), 7.91(1H, dd, J=2.2, 8.4 Hz), 8.82(1H, d, J=2.2 Hz).

EXAMPLE 296

After a mixture of ethyl 3-[3-(4-fluorophenyl)-1-[4-(5-phenyl-2-pyridylmethoxy)benzyl]-1H-pyrazol-4-yl]propionate (800 mg), 1N aqueous sodium hydroxide solution (3 ml), tetrahydrofuran (3 ml) and ethanol (3 ml) was stirred at room temperature for 5 hours, 1 N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-(4-fluorophenyl)-1-[4-(5-phenyl-2-pyridylmethoxy)benzyl]-1H-pyrazol-4-yl]propionic acid (700 mg, yield: 93%). This was recrystallized from ethanol-water. Melting point: 162–163° C.

EXAMPLE 297

Sodium hydride (60%, oily, 70.0 mg) was added to a solution of 2-(5-chloromethyl-2-pyridyloxymethyl)quinoline (498 mg), ethyl 3-(3-phenyl-1H-pyrazol-4-yl)propionate (428 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-phenyl-1-[6-(2-quinolylmethoxy)-3-pyridylmethyl]-1H-pyrazol-4-yl]propionate (651 mg, yield: 76%) as a colorless oily substance from the fraction eluted with ethyl acetate-hexane (1:1, volume ratio).

NMR(CDCl$_3$) δ: 1.18(3H, t, J=7.2 Hz), 2.48–2.56(2H, m), 2.90–2.98(2H, m), 4.07(2H, q, J=7.2 Hz), 5.22(2H, s), 5.68(2H, s), 6.89(1H, d, J=8.8 Hz), 7.23(1H, s), 7.29–7.65 (8H, m), 7.53(1H, ddd, J=1.4, 7.0, 8.4 Hz), 7.72(1H, ddd, J=1.8, 6.8, 8.4 Hz), 7.81(1H, dd, J=1.8, 8.2 Hz), 8.08–8.18 (3H, m).

EXAMPLE 298

After a mixture of ethyl 3-[3-phenyl-1-[6-(2-quinolylmethoxy)-3-pyridylmethyl]-1H-pyrazol-4-yl]propionate (650 mg), 1N aqueous sodium hydroxide solution (3 ml), tetrahydrofuran (6 ml) and ethanol (6 ml) was stirred at room temperature for 2 hours, 1 N hydrochloric acid (3 ml) was added to the mixture, and then the mixture was extracted with ethyl acetate. The ethyl acetate layer was washed with saturated aqueous sodium chloride solution, dried (MgSO$_4$) and concentrated. The resulting colorless crystals were collected by filtration to obtain 3-[3-phenyl-1-(6-(2-quinolylmethoxy)-3-pyridylmethyl]-1H-pyrazol-4-yl]propionic acid (489 mg, yield: 80%). This was recrystallized from acetone-hexane. Melting point: 166–167° C.

EXAMPLE 299

Sodium hydride (60%, oily, 70.0 mg) was added to a solution of 5-chloromethyl-2-(2-phenyl-4-thiazolylmethoxy)pyridine (554 mg), ethyl 3-(3-phenyl-1H-pyrazol-4-yl)propionate (428 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$) and concentrated. The residue was subjected to silica gel column chromatography to obtain ethyl 3-[3-phenyl-1-[2-(2-phenyl-4-thiazolylmethoxy)-3-pyridylmethyl]-1H-pyrazol-4-yl]propionate (678 mg, yield: 74%) as colorless crystals from the fraction eluted with ethyl acetate-hexane (2:3, volume ratio). This was recrystallized from ethyl acetate-hexane. Melting point: 88–89° C.

EXAMPLE 300

After a mixture of ethyl 3-[3-phenyl-1-[2-(2-phenyl-4-thiazolylmethoxy)-5-pyridylmethyl]-1H-pyrazol-4-yl]propionate (603 mg), 1N sodium hydroxide solution (3 ml), tetrahydrofuran (6 ml), and ethanol (6 ml) was stirred at room temperature for 2 hours, 1N hydrochloric acid (3 ml) was added to the mixture, and the mixture was extracted with ethyl acetate. The ethyl acetate layer was washed with saturated aqueous sodium chloride solution, dried (MgSO$_4$), and concentrated. The resulting colorless crystals were collected by filtration to obtain 3-[3-phenyl-1-[6-(2-phenyl-4-thiazolylmethoxy)-3-pyridylmethyl]-1H-pyrazol-4-yl]propionic acid (500 mg, yield: 88%). This was recrystallized from acetone-hexane. Melting point: 107–108° C.

EXAMPLE 301

A mixture of 4-(5-phenyl-2-pyridylmethoxy)benzyl alcohol (600 mg), thionyl chloride (0.35 ml), and toluene (30 ml) was stirred at 80° C. for 2 hours. The reaction mixture was concentrated under reduced pressure, and dissolved in ethyl acetate. The solution was washed successively with saturated aqueous solution of sodium bicarbonate and saturated aqueous sodium chloride solution, dried (MgSO$_4$), and concentrated. Sodium hydride (60%, oily, 92.0 mg) was added to a solution of the residual oily substance and ethyl 3-(3-phenyl-1H-pyrazol-4-yl)propionate (510 mg) in N,N-dimethylformamide (15 ml) at 0° C., and the mixture was stirred at room temperature for 2 hours. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-phenyl]-[4-(5-phenyl-2-pyridylmethoxy)benzyl]-1H-pyrazol-4-yl]propionate (970 mg, yield: 91%) as a colorless oily substance from the fraction eluted with ethyl acetate-hexane (1:2, volume ratio).

NMR(CDCl$_3$) δ: 1.18(3H, t, J=7.4 Hz), 2.47–2.57(2H, m), 2.90–3.00(2H, m), 4.07(2H, q, J=7.4 Hz), 5.24(2H, s), 5.26(2H, s), 7.00(2H, d, J=8.8 Hz), 7.19–7.68(14H, m), 7.91(1H, dd, J=2.2, 8.0 Hz), 8.83(1H, d, J=2.2 Hz).

EXAMPLE 302

After a mixture of ethyl 3-[3-phenyl-1-[4-(5-phenyl-2-pyridylmethoxy)benzyl]-1H-pyrazol-4-yl]propionate (970 mg), 1N sodium hydroxide solution (5 ml), tetrahydrofuran (5 ml), and ethanol (5 ml) was stirred at room temperature for 2 hours, 1N hydrochloric acid (5 ml) was added to the mixture, and then the mixture was extracted with ethyl acetate. The ethyl acetate layer was washed with saturated aqueous sodium chloride solution, dried (MgSO$_4$), and concentrated. The resulting colorless crystals were collected by filtration to obtain 3-[3-phenyl-1-[4-(5-phenyl-2-pyridylmethoxy)benzyl]-1H-pyrazol-4-yl]propionic acid (820 mg, yield: 90%). This was recrystallized from acetone-hexane. Melting point: 149–150° C.

EXAMPLE 303

Sodium hydride (60%, oily, 110 mg) was added to a solution of 4-(4-chloromethylphenoxymethyl)-2-phenylthiazole (760 mg) and ethyl 3-(3-phenyl-1H-pyrazol-4-yl)propionate (580 mg) in N,N-dimethylformamide (10 ml) at 0° C., and the mixture was stirred at room temperature for 2 hours. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[3-phenyl-1-[4-(2-phenyl-4-thiazolylmethoxy)benzyl]-1H-pyrazol-4-yl]propionate (1110 mg, yield: 89%) as a colorless oily substance from the fraction eluted with ethyl acetate-hexane (1:2, volume ratio).

NMR(CDCl$_3$) δ: 1.19(3H, t, J=7.0 Hz), 2.47–2.57(2H, m), 2.89–3.00(2H, m), 4.07(2H, q, J=7.0 Hz), 5.24(2H, s), 5.27(2H, s), 6.96–7.05(2H, m), 7.18–7.49(10H, m), 7.59–7.68(2H, m), 7.90–7.99(2H, m).

EXAMPLE 304

After a mixture of ethyl 3-[3-phenyl-1-[4-(2-phenyl-4-thiazolylmethoxy)benzyl]-1H-pyrazol-4-yl]propionate (1110 mg), 1N sodium hydroxide solution (5 ml), tetrahydrofuran (5 ml), and ethanol (5 ml) was stirred at room temperature for 2 hours, 1 N hydrochloric acid (5 ml) was added to the mixture, and then the mixture was extracted with ethyl acetate. The ethyl acetate layer was washed with saturated aqueous sodium chloride solution, dried (MgSO$_4$), and concentrated. The resulting colorless crystals were collected by filtration to obtain 3-[3-phenyl-1-[4-(2-phenyl-4-thiazolylmethoxy)benzyl]-1H-pyrazol-4-yl]propionic acid (630 mg, yield: 60%). This was recrystallized from acetone-hexane. Melting point: 132–133° C.

EXAMPLE 305

A mixture of 5-(5-methyl-2-phenyl-4-oxazolylmethoxy)-2-pyridinemethanol (630 mg) and thionyl chloride (10 ml) was stirred at 0° C. for 2 hours, and the reaction mixture was concentrated under reduced pressure. The residue was dissolved in ethyl acetate, washed successively with saturated aqueous sodium bicarbonate solution and saturated aqueous sodium chloride solution, dried (MgSO$_4$), and concentrated. A mixture of the resulting crystals, ethyl 3-(3-phenyl-1H-pyrazol-4-yl)propionate (520 mg), potassium carbonate (590 mg) and N,N-dimethylformamide (15 ml) was stirred at 80° C. overnight. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 3-[1-[5-(5-methyl-2-phenyl-4-oxazolylmethoxy)-2-pyridylmethyl]-3-phenyl-1H-pyrazol-4-yl]propionate (950 mg, yield: 85%) as a colorless oily substance from the fraction eluted with ethyl acetate-hexane (2:1, volume ratio).

NMR(CDCl$_3$) δ: 1.20(3H, t, J=7.0 Hz), 2.44(3H, s), 2.48–2.58(2H, m), 2.92–3.03(2H, m), 4.09(2H, q, J=7.0 Hz), 5.02(2H, s), 5.38(2H, s), 7.08(1H, d, J=8.4 Hz), 7.20–7.54 (8H, m), 7.60–7.68(2H, m), 7.95–8.08(2H, m), 8.38(1H, d, J=2.6 Hz).

EXAMPLE 306

After a mixture of ethyl 3-[1-[5-(5-methyl-2-phenyl-4-oxazolylmethoxy)-2-pyridylmethyl]-3-phenyl-1H-pyrazol-4-yl]propionate (930 mg), 1N sodium hydroxide solution (3 ml), tetrahydrofuran (5 ml), and ethanol (5 ml) was stirred at room temperature for 2 hours, 1N hydrochloric acid (3 ml) was added to the mixture, and the mixture was extracted with ethyl acetate. The ethyl acetate layer was washed with saturated aqueous sodium chloride solution, dried (MgSO$_4$), and concentrated. The resulting colorless crystals were collected by filtration to obtain 3-[1-[5-(5-methyl-2-phenyl-4-oxazolylmethoxy)-2-pyridylmethyl]-3-phenyl-1H-pyrazol-4-yl]propionic acid (830 mg, yield: 94%). This was recrystallized from acetone-hexane. Melting point: 175–176° C.

EXAMPLE 307

Sodium hydride (60%, oily, 70.0 mg) was added to a solution of 5-chloromethyl-2-(5-methyl-2-phenyl-4-oxazolylmethoxy)pyridine (551 mg) and ethyl(3-phenyl-1H-pyrazol-4-yl)acetate (403 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl [1-[6-(5-methyl-2-phenyl-4-oxazolylmethoxy)-3-pyridylmethyl]-3-phenyl-1H-pyrazol-4-yl]acetate (513 mg, yield: 58%) as a colorless oily substance from the fraction eluted with ethyl acetate-hexane (2:3, volume ratio).

NMR(CDCl$_3$) δ: 1.21(3H, t, J=7.0 Hz), 2.48(3H, s), 3.60(2H, s), 4.13(2H, q, J=7.0 Hz), 5.26(2H, s), 5.30(2H, s), 6.81(1H, d, J=8.8 Hz), 7.30–7.47(7H, m), 7.53–7.62(3H, m), 7.98–8.05(2H, m), 8.16(1H, d, J=2.2 Hz).

EXAMPLE 308

After a mixture of ethyl [1-[6-(5-methyl-2-phenyl-4-oxazolylmethoxy)-3-pyridylmethyl]-3-phenyl-1H-pyrazol-4-yl]acetate (509 mg), 1N sodium hydroxide solution (2 ml), tetrahydrofuran (4 ml), and ethanol (4 ml) was stirred at room temperature for 2 hours, 1N hydrochloric acid (2 ml) was added to the mixture, and the mixture was extracted with ethyl acetate. The ethyl acetate layer was washed with saturated aqueous sodium chloride solution, dried (MgSO$_4$), and concentrated. The resulting colorless crystals were collected by filtration to obtain [1-[6-(5-methyl-2-phenyl-4- oxazolylmethoxy)-3-pyridylmethyl]-3-phenyl-1H-pyrazol-4-yl]acetic acid (408 mg, yield: 85%). This was recrystallized from acetone-hexane. Melting point: 144–145° C.

EXAMPLE 309

Sodium hydride (60%, oily, 70.0 mg) was added to a solution of 5-chloromethyl-2-(2-phenyl-4-thiazolylmethoxy)pyridine (554 mg) and ethyl(3-phenyl-1H-pyrazol-4-yl)acetate (403 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried ($MgSO_4$), and concentrated. The residue was subjected to silica gel column chromatography to obtain ethyl(3-phenyl-1-[6-(2-phenyl-4-thiazolylmethoxy)-3-pyridylmethyl]-1H-pyrazol-4-yl]acetate (594 mg, yield: 66%) as colorless crystals from the fraction eluted with ethyl acetate-hexane (1:1, volume ratio). This was recrystallized from ethyl acetate-hexane. Melting point: 75–76° C.

EXAMPLE 310

After a mixture of ethyl [3-phenyl-1-(6-(2-phenyl-4-thiazolylmethoxy)-3-pyridylmethyl]-1H-pyrazol-4-yl]acetate (536 mg), 1N sodium hydroxide solution (2 ml), tetrahydrofuran (4 ml), and ethanol (4 ml) was stirred at room temperature for 2 hours, 1N hydrochloric acid (2 ml) was added to the mixture, and the mixture was extracted with ethyl acetate. The ethyl acetate layer was washed with saturated aqueous sodium chloride solution, dried ($MgSO_4$), and concentrated. The resulting colorless crystals were collected by filtration to obtain [3-phenyl-1-[6-(2-phenyl-4-thiazolylmethoxy)-3-pyridylmethyl]-1H-pyrazol-4-yl]acetic acid (459 mg, yield: 91%). This was recrystallized from ethanol-hexane. Melting point: 118–119° C.

EXAMPLE 311

Sodium hydride (60%, oily, 70.0 mg) was added to a solution of 5-chloromethyl-2-(5-methyl-2-phenyl-4-thiazolylmethoxy)pyridine (579 mg) and ethyl(3-phenyl-1H-pyrazol-4-yl)acetate (403 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried ($MgSO_4$), and concentrated. The residue was subjected to silica gel column chromatography to obtain ethyl [1-[6-(5-methyl-2-phenyl-4-thiazolylmethoxy)-3-pyridylmethyl]-3-phenyl-1H-pyrazol-4-yl]acetate (476 mg, yield: 52%) as a colorless oily substance from the fraction eluted with ethyl acetate-hexane (2:3, volume ratio).

NMR($CDCl_3$) δ: 1.21(3H, t, J=7.2 Hz), 2.56(3H, s), 3.60(2H, s), 4.13(2H, q, J=7.2 Hz), 5.26(2H, s), 5.44(2H, s), 6.82(1H, d, J=8.0 Hz), 7.29–7.47(7H, m), 7.53–7.62(3H, m), 7.86–7.92(2H, m), 8.17(1H, d, J=2.2 Hz).

EXAMPLE 312

After a mixture of ethyl [1-[6-(5-methyl-2-phenyl-4-thiazolylmethoxy)-3-pyridylmethyl]-3-phenyl-1H-pyrazol-4-yl]acetate (475 mg), 1N sodium hydroxide solution (2 ml), tetrahydrofuran (4 ml), and ethanol (4 ml) was stirred at room temperature for 2 hours, 1N hydrochloric acid (2 ml) was added to the mixture, and the mixture was extracted with ethyl acetate. The ethyl acetate layer was washed with saturated aqueous sodium chloride solution, dried ($MgSO_4$), and concentrated. The resulting colorless crystals were collected by filtration to obtain [1-[6-(5-methyl-2-phenyl-4-thiazolylmethoxy)-3-pyridylmethyl]-3-phenyl-1H-pyrazol-4-yl]acetic acid (402 mg, yield: 89%). This was recrystallized from ethanol-hexane. Melting point: 140–141° C.

EXAMPLE 313

Sodium hydride (60%, oily, 70.0 mg) was added to a solution of 5-chloromethyl-2-[2-(5-methyl-2-phenyl-4-oxazolyl)ethoxy]pyridine (575 mg) and ethyl(3-phenyl-1H-pyrazol-4-yl)acetate (403 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried ($MgSO_4$), and concentrated. The residue was subjected to silica gel column chromatography to obtain ethyl [1-[6-[2-(5-methyl-2-phenyl-4-oxazolyl)ethoxy]-3-pyridylmethyl]-3-phenyl-1H-pyrazol-4-yl]acetate (575 mg, yield: 63%) as a colorless oily substance from the fraction eluted with ethyl acetate-hexane (1:1, volume ratio).

NMR($CDCl_3$) δ: 1.21(3H, t, J=7.0 Hz), 2.34(3H, s), 2.98(2H, t, J=6.8 Hz), 3.59(2H, s), 4.12(2H, q, J=77.0 Hz), 4.56(2H, t, J=6.8 Hz), 5.24(2H, s), 6.71(1H, d, J=8.4 Hz), 7.29–7.47(7H, m), 7.51–7.61(3H, m), 7.94–8.01(2H, m), 8.12(1H, d, J=2.6 Hz).

EXAMPLE 314

After a mixture of ethyl [1-[6-[2-(5-methyl-2-phenyl-4-oxazolyl)ethoxy]-3-pyridylmethyl]-3-phenyl-1H-pyrazol-4-yl]acetate (575 mg), 1N sodium hydroxide solution (3 ml), tetrahydrofuran (6 ml), and ethanol (6 ml) was stirred at room temperature for 2 hours, 1N hydrochloric acid (3 ml) was added to the mixture, and the mixture was extracted with ethyl acetate. The ethyl acetate layer was washed with saturated aqueous sodium chloride solution, dried ($MgSO_4$), and concentrated. The resulting colorless crystals were collected by filtration to obtain [1-[6-[2-(5-methyl-2-phenyl-4-oxazolyl)ethoxy]-3-pyridylmethyl]-3-phenyl-1H-pyrazol-4-yl]acetic acid (466 mg, yield: 86%). This was recrystallized from ethanol-hexane. Melting point: 148–149° C.

EXAMPLE 315

Sodium hydride (60%, oily, 70.0 mg) was added to a solution of 5-chloromethyl-2-[2-(2-furyl)-5-methyl-4-oxazolylmethoxy]pyridine (533 mg) and ethyl(3-phenyl-1H-pyrazol-4-yl)acetate (403 mg) in N,N-dimethylformamide (10 ml) at 0° C., and the mixture was stirred at room temperature for 1 hour. The reaction mixture was poured into water, and extracted with ethyl acetate. The ethyl acetate layer was washed with saturated aqueous sodium chloride solution, dried ($MgSO_4$), and concentrated. The residue was subjected to silica gel column chromatography to obtain ethyl [1-[6-[2-(2-furyl)-5-methyl-4-oxazolylmethoxy]-3-pyridylmethyl]-3-phenyl-1H-pyrazol-4-yl]acetate (581 mg, yield: 67%) as a colorless oily substance from the fraction eluted with ethyl acetate-hexane (1:1, volume ratio).

NMR(CDCl$_3$) δ: 1.21(3H, t, J=7.0 Hz), 2.46(3H, s), 3.60(2H, s), 4.13(2H, q, J=7.0 Hz), 5.26(2H, s), 5.28(2H, s), 6.51(1H, dd, J=1.8, 3.6 Hz), 6.79(1H, d, J=8.4 Hz), 6.98(1H, dd, J=0.6, 3.6 Hz), 7.30–7.46(4H, m), 7.52–7.61(4H, m), 8.14(1H, d, J=2.2 Hz).

EXAMPLE 316

After a mixture of ethyl [1-[6-[2-(2-furyl)-5-methyl-4-oxazolylmethoxy]-3-pyridylmethyl]-3-phenyl-1H-pyrazol-4-yl]acetate (578 mg), 1N sodium hydroxide solution (3 ml), tetrahydrofuran (6 ml), and ethanol (6 ml) was stirred at room temperature for 2 hours, 1N hydrochloric acid (3 ml) was added to the mixture, and the mixture was extracted with ethyl acetate. The ethyl acetate layer was washed with saturated aqueous sodium chloride solution, dried (MgSO$_4$), and concentrated. The resulting colorless crystals were collected by filtration to obtain [1-[6-[2-(2-furyl)-5-methyl-4-oxazolylmethoxy]-3-pyridylmethyl]-3-phenyl-1H-pyrazol-4-yl]acetic acid (467 mg, yield: 86%). This was recrystallized from acetone-hexane. Melting point: 135–136° C.

EXAMPLE 317

A mixture of [1-(4-benzyloxybenzyl)-3-(4-fluorophenyl)-1H-pyrazol-4-yl]acetonitrile (4.37 g), 4N sodium hydroxide solution (20 ml), tetrahydrofuran (20 ml), and ethanol (20 ml) was refluxed for 2 days. After cooling, the mixture was neutralized with dilute hydrochloric acid and extracted with ethyl acetate. The ethyl acetate layer was washed with saturated aqueous sodium chloride solution, dried (MgSO$_4$), and concentrated to obtain [1-(4-benzyloxybenzyl)-3-(4-fluorophenyl)-1H-pyrazol-4-yl]acetic acid (4.37 g, yield: 95%). This was recrystallized from tetrahydrofuran-hexane. Melting point: 194–195° C.

EXAMPLE 318

A mixture of [1-(4-benzyloxybenzyl)-3-(4-fluorophenyl)-1H-pyrazol-4-yl]acetic acid (4.16 g), methyl iodide (0.95 ml), potassium carbonate (2.76 g), and N,N-dimethylformamide (50 ml) was stirred at room temperature for 3 hours. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain methyl [1-(4-benzyloxybenzyl)-3-(4-fluorophenyl)-1H-pyrazol-4-yl]acetate (4.21 g, yield 98%) as colorless crystals from the fraction eluted with ethyl acetate-hexane (1:2, volume ratio). This was recrystallized from ethyl acetate-hexane. Melting point: 58–59° C.

EXAMPLE 319

A mixture of ethyl 3-hydroxy-1H-pyrazole-4-carboxylate (8.95 g), 4-phenoxybenzyl chloride (25.35 g), potassium carbonate (31.88 g), and N,N-dimethylformamide (200 ml) was stirred at 90° C. for 8 hours. The reaction mixture was poured into water, and extracted with ethyl acetate. The ethyl acetate layer was washed successively with dilute hydrochloric acid and aqueous sodium chloride solution, dried (MgSO$_4$), and concentrated. The residue was subjected to silica gel column chromatography to obtain ethyl 1-(4-phenoxybenzyl)-3-(4-phenoxybenzyloxy)-1H-pyrazole-4-carboxylate (22.71 g, yield: 76%) as a colorless oily substance from the fraction eluted with ethyl acetate-hexane (1:4, volume ratio).

NMR(CDCl$_3$) δ: 1.31(3H, t, J=7.4 Hz), 4.25(2H, q, J=7.4 Hz), 5.09(2H, s), 5.31(2H, s), 6.93–7.50(18H, m), 7.67(1H, s).

EXAMPLE 320

After a mixture of ethyl 1-(4-phenoxybenzyl)-3-(4-phenoxybenzyloxy)-1H-pyrazole-4-carboxylate (500 mg), 1N sodium hydroxide solution (2 ml), tetrahydrofuran (5 ml), and ethanol (5 ml) was stirred at room temperature for 2 hours, 1N hydrochloric acid (3 ml) was added to the mixture, and the mixture was extracted with ethyl acetate. The ethyl acetate layer was washed with saturated aqueous sodium chloride solution, dried (MgSO$_4$), and concentrated. The resulting colorless crystals were collected by filtration to obtain 1-(4-phenoxybenzyl)-3-(4-phenoxybenzyloxy)-1H-pyrazole-4-carboxylic acid (450 mg, yield: 95%). This was recrystallized from acetone-hexane. Melting point: 141–142° C.

EXAMPLE 321

A mixture of ethyl 3-hydroxy-1-(4-phenoxybenzyl)-1H-pyrazole-4-carboxylate (3.00 g), 4-(4-chloromethyl-2-methoxyphenoxymethyl)-2-(2-furyl)-5-methyloxazole (3.00 g), potassium carbonate (2.52 g), and N,N-dimethylformamide (30 ml) was stirred at 80° C. for 8 hours. The reaction mixture was poured into water, and extracted with ethyl acetate. The ethyl acetate layer was washed successively with dilute hydrochloric acid and aqueous sodium chloride solution, dried (MgSO$_4$), and concentrated. The residue was subjected to silica gel column chromatography to obtain ethyl 3-[4-[2-(2-furyl)-5-methyl-4-oxazolylmethoxy]-3-methoxybenzyloxy]-1-(4-phenoxybenzyl)-1H-pyrazole-4-carboxylate (5.30 g, yield: 94%) as colorless crystals from the fraction eluted with ethyl acetate-hexane (1:2, volume ratio). This was recrystallized from ethyl acetate-hexane. Melting point: 98–99° C.

EXAMPLE 322

After a mixture of ethyl 3-[4-[2-(2-furyl)-5-methyl-4-oxazolylmethoxy]-3-methoxybenzyloxy]-1-(4-phenoxybenzyl)-1H-pyrazole-4-carboxylate (1500 mg), 1N sodium hydroxide solution (5 ml), tetrahydrofuran (10 ml), and ethanol (10 ml) was stirred at room temperature for 2 hours, 1N hydrochloric acid (5 ml) was added to the mixture, and the mixture was extracted with ethyl acetate. The ethyl acetate layer was washed with saturated aqueous sodium chloride solution, dried (MgSO$_4$), and concentrated. The resulting colorless crystals were collected by filtration to obtain 3-[4-[2-(2-furyl)-5-methyl-4-oxazolylmethoxy]-3-methoxybenzyloxy]-1-(4-phenoxybenzyl)-1H-pyrazole-4-carboxylic acid (1330 mg, yield: 93%). This was recrystallized from acetone-hexane. Melting point: 153–154° C.

EXAMPLE 323

A mixture of 3-[4-[2-(2-furyl)-5-methyl-4-oxazolylmethoxy]-3-methoxybenzyloxy]-1-(4-phenoxybenzyl)-1H-pyrazole-4-carboxylic acid (0.80 g), 1H-1,2,3-benzotriazol-1-ol ammonia complex (0.22 g), 1-ethyl-3-(3-dimethylaminopropyl)carbodiimide hydrochloride (0.28 g), and N,N-dimethylformamide (10 ml) was stirred at room temperature overnight. The reaction mixture was poured into water, and extracted with ethyl acetate. The ethyl acetate layer was washed successively with dilute hydrochloric acid and aqueous sodium chloride solution, dried (MgSO$_4$), and concentrated. The residue was subjected to silica gel column chromatography to obtain 3-[4-[2-(2-furyl)-5-methyl-4-oxazolylmethoxy]-3-methoxybenzyloxy]-1-(4-phenoxybenzyl)-1H-pyrazole-4-carbamide (0.75 g, yield 94%) as colorless crystals from the fraction eluted with ethyl acetate-hexane (1:2, volume ratio). This was recrystallized from acetone-hexane. Melting point: 105–106° C.

EXAMPLE 324

A mixture of ethyl 3-hydroxy-1-(4-phenoxybenzyl)-1H-pyrazole-4-carboxylate (3.00 g), 4-(4-chloromethyl-2-methoxyphenoxymethyl)-5-methyl-2-phenyloxazole (3.06 g), potassium carbonate (2.50 g), and N,N-dimethylformamide (30 ml) was stirred at 80° C. for 8 hours. The reaction mixture was poured into water, and extracted with ethyl acetate. The ethyl acetate layer was washed successively with dilute hydrochloric acid and aqueous sodium chloride solution, dried (MgSO$_4$), and concentrated. The residue was subjected to silica gel column chromatography to obtain ethyl 3-[3-methoxy-4-(5-methyl-2-phenyl-4-oxazolylmethoxy)benzyloxy]-1-(4-phenoxybenzyl)-1H-pyrazole-4-carboxylate (5.43 g, yield: 95%) as colorless crystals from the fraction eluted with ethyl acetate-hexane (1:2, volume ratio). This was recrystallized from acetone-hexane. Melting point: 127–128° C.

EXAMPLE 325

After a mixture of ethyl 3-[3-methoxy-4-(5-methyl-2-phenyl-4-oxazolylmethoxy)benzyloxy]-1-(4-phenoxybenzyl)-1H-pyrazole-4-carboxylate (750 mg), 1N sodium hydroxide solution (2 ml), tetrahydrofuran (5 ml), and ethanol (5 ml) was stirred at room temperature for 2 hours, 1N hydrochloric acid (2 ml) was added to the mixture, and the mixture was extracted with ethyl acetate. The ethyl acetate layer was washed with saturated aqueous sodium chloride solution, dried (MgSO$_4$), and concentrated. The resulting colorless crystals were collected by filtration to obtain 3-[3-methoxy-4-(5-methyl-2-phenyl-4-oxazlyl-methoxy)benzyloxy]-1-(4-phenoxybenzyl)-1H-pyrazole-4-carboxylic acid (680 mg, yield: 95%). This was recrystallized from tetrahydrofuran-hexane. Melting point: 176–177° C.

EXAMPLE 326

After a mixture of ethyl 1-[4-[2-(2-furyl)-5-methyl-4-oxazolylmethoxy]benzyl]-3-[4-[2-(2-furyl)-5-methyl-4-oxazolylmethoxy]benzyloxy]-1H-pyrazole-4-carboxylate (250 mg), 1N sodium hydroxide solution (1 ml), tetrahydrofuran (5 ml), and ethanol (5 ml) was stirred at room temperature for 2 hours, 1N hydrochloric acid (1 ml) was added to the mixture, and the mixture was extracted with ethyl acetate. The ethyl acetate layer was washed with saturated aqueous sodium chloride solution, dried (MgSO$_4$), and concentrated. The resulting colorless crystals were collected by filtration to obtain 1-[4-[2-(2-furyl)-5-methyl-4-oxazolylmethoxy]benzyl]-3-[4-[2-(2-furyl)-5-methyl-4-oxazolylmethoxy]benzyloxy]-1H-pyrazole-4-carboxylic acid (230 mg, yield: 93%). This was recrystallized from acetone-hexane. Melting point: 144–145° C.

EXAMPLE 327

Sodium hydride (60%, oily, 310 mg) was added to a mixture of methyl 4-phenyl-3-pyrrolcarboxylate (1.20 g), 5-chloromethyl-2-(5-methyl-2-phenyl-4-oxazolylmethoxy) pyridine (1.88 g), and N,N-dimethylformamide (50 ml) at room temperature, and the mixture was stirred for 15 hours. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain methyl 1-[6-(5-methyl-2-phenyl-4-oxazolylmethoxy)-3-pyridylmethyl]-4-phenyl-1H-pyrrol-3-carboxylate (2.74 g, yield: 96%) as a colorless oily substance from the fraction eluted with ethyl acetate-hexane (1:2, volume ratio).

NMR(CDCl$_3$) δ: 2.48(3H, s), 3.72(2H, s), 5.00(2H, s), 5.30(2H, s), 6.66(1H, d, J=1.5 Hz), 6.82(1H, d, J=8.5 Hz), 7.2–7.5(10H, m), 7.95–8.15(3H, m).

EXAMPLE 328

Sodium hydride (60%, oily, 270 mg) was added to a mixture of ethyl 3-phenyl-1H-pyrazole-4-carboxylate (1.20 g), 5-chloromethyl-2-(5-methyl-2-phenyl-4-oxazolyl-methoxy)pyridine (1.75 g), and N,N-dimethylformamide (50 ml) at 0° C., and the mixture was stirred at room temperature for 8 hours. The reaction mixture was poured into water, and extracted with ethyl acetate. The ethyl acetate layer was washed with water, dried (MgSO$_4$), and concentrated. The residue was subjected to silica gel column chromatography to obtain ethyl 1-[6-(5-methyl-2-phenyl-4-oxazolylmethoxy)-3-pyridylmethyl]-3-phenyl-1H-pyrazole-4-carboxylate (1.56 g, yield: 57%) as a colorless oily substance from the fraction eluted with diethyl ether-hexane (2:3, volume ratio).

NMR(CDCl$_3$) δ: 1.14(3H, t, J=7 Hz), 2.45(3H, s), 4.13 (2H, q, J=7 Hz), 5.10(2H, s), 5.25(2H, s), 6.72(1H, d, J=8.5 Hz), 7.2–7.5(9H, m), 7.80(1H, d, J=2 Hz), 7.95–8.05(3H, m).

EXAMPLE 329

A mixture of ethyl 3-hydroxy-1-(4-phenoxybenzyl)-1H-pyrazole-4-carboxylate (4.07 g), 4-chloromethyl-5-methyl-2-phenyloxazole (2.58 g), potassium carbonate (1.73 g) and N,N-dimethylformamide (30 ml) was stirred at 80° C. for 8 hours. The reaction mixture was poured into water, and extracted with ethyl acetate. The ethyl acetate layer was washed successively with dilute hydrochloric acid and saturated aqueous sodium chloride solution, dried (MgSO$_4$), and concentrated. The residue was subjected to silica gel column chromatography to obtain ethyl 3-(5-methyl-2-phenyl-4-oxazolylmethoxy)-1-(4-phenoxybenzyl)-1H-pyrazole-4-carboxylate (5.86 g, yield: 96%) as colorless crystals from the fraction eluted with ethyl acetate-hexane (1:2, volume ratio). This was recrystallized from ethyl acetate-hexane. Melting point: 96–97° C.

EXAMPLE 330

After a mixture of ethyl 3-(5-methyl-2-phenyl-4-oxazolylmethoxy)-1-(4-phenoxybenzyl)-1H-pyrazole-4-carboxylate (1600 mg), 1N sodium hydroxide solution (5 ml), tetrahydrofuran (10 ml), and ethanol (10 ml) was stirred at room temperature for 2 hours, 1N hydrochloric acid (5 ml) was added to the mixture, and the mixture was extracted with ethyl acetate. The ethyl acetate layer was washed with saturated aqueous sodium chloride solution, dried (MgSO$_4$), and concentrated. The resulting colorless crystals were collected by filtration to obtain 3-(5-methyl-2-phenyl-4-oxazolylmethoxy)-1-(4-phenoxybenzyl)-1H-pyrazole-4-carboxylic acid (1470 mg, yield: 97%). This was recrystallized from tetrahydrofuran-hexane. Melting point: 222–223° C.

EXAMPLE 331

A mixture of 3-(5-methyl-2-phenyl-4-oxazolylmethoxy)-1-(4-phenoxybenzyl)-1H-pyrazole-4-carboxylic acid (0.75 g), 1H-1,2,3-benzotriazol-1-ol ammonia complex (0.26 g), 1-ethyl-3-(3-dimethylaminopropyl)carbodiimide hydrochloride (0.33 g), and N,N-dimethylformamide (10 ml) was stirred at room temperature overnight. The reaction mixture was poured into water, and extracted with ethyl acetate. The ethyl acetate layer was washed successively with dilute hydrochloric acid and saturated aqueous sodium chloride solution, dried (MgSO$_4$), and concentrated. The residue was subjected to silica gel column chromatography to obtain 3-(5-methyl-2-phenyl-4-oxazolylmethoxy)-1-(4-phenoxybenzyl)-1H-pyrazole-4-carbamide (0.70 g, yield 94%) as colorless crystals from the fraction eluted with ethyl acetate-hexane (1:2, volume ratio). This was recrystallized from acetone-hexane. Melting point: 158–159° C.

EXAMPLE 332

Sodium hydride (60%, oily, 220 mg) was added to a solution of 3-(5-methyl-2-phenyl-4-oxazolylmethoxy)-1-(4-phenoxy)-1H-pyrazole-4-carbaldehyde (2.00 g) and ethyl diethylphosphonoacetate (1.06 g) in N,N-dimethylformamide (25 ml) at 0° C., and the mixture was stirred at room temperature for 2 hours. The reaction mixture was poured into water, and extracted with ethyl acetate. The ethyl acetate layer was washed successively with dilute hydrochloric acid and saturated aqueous sodium chloride solution, dried (MgSO$_4$), and concentrated. The residue was subjected to silica gel column chromatography to obtain ethyl(E)-3-[3-(5-methyl-2-phenyl-4-oxazolylmethoxy)-1-(4-phenoxybenzyl)-1H-pyrazol-4-yl]propenoate (2.19 g, yield: 95%) as colorless crystals from the fraction eluted with ethyl acetate-hexane (1:2, volume ratio). This was recrystallized from acetone-hexane. Melting point: 93–94° C.

EXAMPLE 333

After a mixture of ethyl(E)-3-[3-(5-methyl-2-phenyl-4-oxazolylmethoxy)-1-(4-phenoxybenzyl)-1H-pyrazol-4-yl]propenoate (450 mg), 1N sodium hydroxide solution (1.5 ml), tetrahydrofuran (5 ml), and ethanol (5 ml) was stirred at 50° C. for 2 hours, 1N hydrochloric acid (1.5 ml) was added to the mixture, and the mixture was extracted with ethyl acetate. The ethyl acetate layer was washed with saturated aqueous sodium chloride solution, dried (MgSO$_4$), and concentrated. The resulting colorless crystals were collected by filtration to obtain (E)-3-[3-(5-methyl-2-phenyl-4-oxazolylmethoxy)-1-(4-phenoxybenzyl)-1H-pyrazol-4-yl]propenoic acid (410 mg, yield: 96%). This was recrystallized from acetone-hexane. Melting point: 210–211° C.

EXAMPLE 334

A mixture of ethyl(E)-3-[3-(5-methyl-2-phenyl-4-oxazolylmethoxy)-1-(4-phenoxybenzyl)-1H-pyrazol-4-yl]propenoate (1100 mg), 5% palladium-carbon (390 mg), and tetrahydrofuran (30 ml) was stirred at room temperature for 5 hours under a hydrogen atmosphere. After the palladium-carbon was removed by filtration, the filtrate was concentrated. The residue was subjected to silica gel column chromatography to obtain ethyl 3-[3-(5-methyl-2-phenyl-4-oxazolylmethxy)-1-(4-phenoxybenzyl)-1H-pyrazol-4-yl]propionate (980 mg, yield: 95%) as a colorless oily substance from the fraction eluted with ethyl acetate-hexane (1:1, volume ratio).

NMR(CDCl$_3$) δ: 1.17(3H, t, J=7.0 Hz), 2.39(3H, s), 2.45–2.72(4H, m), 4.06(2H, q, J=7.0 Hz), 5.05(2H, s), 5.15(2H, s), 6.90–7.46(13H, m), 7.94–8.06(2H, m).

EXAMPLE 335

After a mixture of ethyl 3-[3-(5-methyl-2-phenyl-4-oxazolylmethoxy)-1-(4-phenoxybenzyl)-1H-pyrazol-4-yl]propionate (800 mg), 1N sodium hydroxide solution (3 ml), tetrahydrofuran (5 ml), and ethanol (5 ml) was stirred at room temperature for 2 hours, 1N hydrochloric acid (3 ml) was added to the mixture, and the mixture was extracted with ethyl acetate. The ethyl acetate layer was washed with saturated aqueous sodium chloride solution, dried (MgSO$_4$), and concentrated. The resulting colorless crystals were collected by filtration to obtain 3-[3-(5-methyl-2-phenyl-4-oxazolylmethoxy)-1-(4-phenoxybenzyl)-1H-pyrazol-4-yl]propionic acid (740 mg, yield: 97%). This was recrystallized from acetone-hexane. Melting point: 120–121° C.

EXAMPLE 336

A mixture of ethyl 3-(2-thienyl)-1H-pyrazole-4-caboxylate (10.23 g), 4-(4-chloromethylphenoxy)methyl-5-methyl-2-phenyloxazole (14.66 g), potassium carbonate (13.09 g), and N,N-dimethylformamide (100 ml) was stirred at 80° C. for 8 hours. The reaction mixture was poured into water, and extracted with ethyl acetate. The ethyl acetate layer was washed with saturated aqueous sodium chloride solution, dried (MgSO$_4$), and concentrated. The residue was subjected to silica gel column chromatography to obtain ethyl 1-[4-(5-methyl-2-phenyl-4-oxazolylmethoxy)benzyl]-3-(2-thienyl)-1H-pyrazole-4-carboxylate as colorless crystals (19.88 g, yield: 87%) from the fraction eluted with ethyl acetate-hexane (1:2, volume ratio). This was recrystallized from ethyl acetate-hexane. Melting point: 113~114° C.

EXAMPLE 337

A mixture of ethyl 1-[4-(5-methyl-2-phenyl-4-oxazolylmethoxy)benzyl]-3-(2-thienyl)-1H-pyrazole-4-carboxylate (900 mg), 1N sodium hydroxide solution (3 ml), tetrahydrofuran (5 ml), and ethanol (5 ml) was stirred at 80° C. for 5 hours. After cooling, 1N hydrochloric acid (3 ml) was added to the mixture, and the mixture was extracted with ethyl acetate. The ethyl acetate layer was washed with saturated aqueous sodium chloride solution, dried (MgSO$_4$), and concentrated. The resulting colorless crystals were collected by filtration to obtain 1-[4-(5-methyl-2-phenyl-4-oxazolylmethoxy)benzyl]-3-(2-thienyl)-1H-pyrazole-4-carboxylic acid (750 mg, yield: 88%). This was recrystallized from acetone-hexane. Melting point: 204~205° C.

EXAMPLE 338

A mixture of [1-[4-(5-methyl-2-phenyl-4-oxazolylmethoxy)benzyl]-3-(2-thienyl)-1H-pyrazol-4-yl]acetonitrile (1.69 g), 4N sodium hydroxide solution (10 ml), and ethanol (10 ml) was refluxed overnight. After cooling, 1N hydrochloric acid (40 ml) was added to the mixture, and the mixture was extracted with ethyl acetate. The ethyl acetate layer was washed with saturated aqueous sodium chloride solution, dried (MgSO₄), and concentrated. The resulting colorless crystals were collected by filtration to obtain [1-[4-(5-methyl-2-phenyl-4-oxazolylmethoxy)benzyl]-3-(2-thienyl)-1H-pyrazol-4-yl]acetic acid (1.13 g, yield: 64%). This was recrystallized from acetone-hexane. Melting point: 98~99° C.

EXAMPLE 339

A mixture of diethyl [1-[4-(5-methyl-2-phenyl-4-oxazolylmethoxy)benzyl]-3-(2-thienyl)-1H-pyrazol-4-yl]methylmalonate (6.08 g), 4N sodium hydroxide solution (10 ml), and ethanol (10 ml) was refluxed for 1 hour. After cooling, 1N hydrochloric acid (40 ml) was added to the mixture, and the mixture was extracted with ethyl acetate. The ethyl acetate layer was washed with saturated aqueous sodium chloride solution, dried (MgSO₄), and concentrated. The resulting colorless oily substance was dissolved in pyridine (50 ml), and stirred at 110° C. for 2 hours. After pyridine was removed under reduced pressure, ethyl acetate was added to the residue. The resulting solution was washed successively with dilute hydrochloric acid and saturated aqueous sodium chloride solution, dried (MgSO₄), and concentrated. The resulting colorless crystals were collected by filtration to obtain 3-[1-[4-(5-methyl-2-phenyl-4-oxazolylmethoxy)benzyl]-3-(2-thienyl)-1H-pyrazol-4-yl]propionic acid (4.02 g, yield: 80%). This was recrystallized from acetone-hexane. Melting point: 172~173° C.

EXAMPLE 340

Sodium hydride (60%, oily, 150 mg) was added to a solution of 1-[4-(2-phenyl-4-thiazolylmethoxy)benzyl]-3-(2-thienyl)-1H-pyrazole-4-carbaldehyde (1.54 g) and ethyl diethylphosphonoacetate (0.82 g) in N,N-dimethylformamide (15 ml) at 0° C., and the mixture was stirred at room temperature for 2 hours. The reaction mixture was poured into water, and extracted with ethyl acetate. The ethyl acetate layer was washed successively with dilute hydrochloric acid and saturated aqueous sodium chloride solution, dried (MgSO₄), and concentrated. The residue was subjected to silica gel column chromatography to obtain ethyl(E)-3-[1-[4-(2-phenyl-4-thiazolylmethoxy)benzyl]-3-(2-thienyl)-1H-pyrazol-4-yl]propenoate (1.65 g, yield: 93%) as colorless crystals from the fraction eluted with ethyl acetate-hexane (1: 2, volume ratio). This was recrystallized from ethyl acetate-hexane. Melting point: 104~105° C.

EXAMPLE 341

After a mixture of ethyl(E)-3-[1-[4-(2-phenyl-4-thiazolylmethoxy)benzyl]-3-(2-thienyl)-1H-pyrazol-4-yl]propenoate (1.25 g), 1N aqueous sodium hydroxide solution (5 ml), tetrahydrofuran (5 ml), and ethanol (5 ml) was stirred at 50° C. for 2 hours, 1N hydrochloric acid (5 ml) was added to the mixture, and then the mixture was extracted with ethyl acetate. The ethyl acetate layer was washed with saturated aqueous sodium chloride solution, dried (MgSO₄), and concentrated. The resulting colorless crystals were collected by filtration to obtain (E)-3-[1-[4-(2-phenyl-4-thiazolylmethoxy)benzyl]-3-(2-thienyl)-1H-pyrazol-4-yl]propenoic acid (970 mg, yield 82%). This was recrystallized from ethyl acetate-hexane. Melting point: 137~138° C.

EXAMPLE 342

A mixture of diethyl [1-[4-(2-phenyl-4-thiazolylmethoxy)benzyl]-3-(2-thienyl)-1H-pyrazol-4-yl]methylmalonate (4.09 g), 1N aqueous sodium hydroxide solution (30 ml), tetrahydrofuran (30 ml), and ethanol (30 ml) was refluxed for 1 hour. After cooling, 1N hydrochloric acid (30 ml) was added to the mixture, and the mixture was extracted with ethyl acetate. The ethyl acetate layer was washed with saturated aqueous sodium chloride solution, dried (MgSO₄), and concentrated. The resulting colorless oily substance was dissolved in pyridine (50 ml), and the mixture was stirred at 110° C. for 2 hours. After removing pyridine under reduced pressure, ethyl acetate was added to the residue. The resulting solution was washed successively with dilute hydrochloric acid and saturated aqueous sodium chloride solution, dried (MgSO₄), and concentrated. The resulting colorless crystals were collected by filtration to obtain 3-[1-[4-(2-phenyl-4-thiazolylmethoxy)benzyl]-3-(2-thienyl)-1H-pyrazol-4-yl]propionic acid (3.25 g, yield: 95%). This was recrystallized from ethyl acetate-hexane. Melting point: 133~134° C.

EXAMPLE 343

A mixture of ethyl 3-(2-thienyl)-1H-pyrazole-4-caboxylate (1.43 g), 4-(4-chloromethylphenoxy)methyl-2-phenyloxazole (1.88 g), potassium carbonate (1.30 g), and N,N-dimethylformamide (30 ml) was stirred at 80° C. for 8 hours. The reaction mixture was poured into water, and extracted with ethyl acetate. The ethyl acetate layer was washed with saturated aqueous sodium chloride solution, dried (MgSO₄), and concentrated. The residue was subjected to silica gel column chromatography to obtain ethyl 1-[4-(2-phenyl-4-oxazolylmethoxy)benzyl]-3-(2-thienyl)-1H-pyrazole-4-carboxylate as colorless crystals (2.81 g, yield: 92%) from the fraction eluted with ethyl acetate-hexane (1:2, volume ratio). This was recrystallized from ethyl acetate-hexane. Melting point: 114~115° C.

EXAMPLE 344

A mixture of diethyl [1-[4-(2-phenyl-4-oxazolylmethoxy)benzyl]-3-(2-thienyl)-1H-pyrazol-4-yl]methylmalonate (1.75 g), 2N sodium hydroxide solution (10 ml), and ethanol (10 ml) was refluxed for 2 hour. After cooling, 1N hydrochloric acid (20 ml) was added to the mixture, and the mixture was extracted with ethyl acetate. The ethyl acetate layer was washed with saturated aqueous sodium chloride solution, dried (MgSO₄), and concentrated. The resulting colorless oily substance was dissolved in pyridine (30 ml), and stirred at 110° C. for 2 hours. After pyridine was removed under reduced pressure, ethyl acetate was added to the residue. The resulting solution was washed successively with dilute hydrochloric acid and saturated aqueous sodium chloride solution, dried (MgSO₄), and concentrated. The resulting colorless crystals were collected by filtration to obtain 3-[1-[4-(2-phenyl-4-oxazolylmethoxy)benzyl]-3-(2-thienyl)-1H-pyrazol-4-yl]propionic acid (1.24 g, yield: 85%). This was recrystallized from ethyl acetate-hexane. Melting point: 145~146° C.

EXAMPLE 345

A mixture of ethyl 3-(2-thienyl)-1H-pyrazole-4-carboxylate (5.60 g), 4-(4-chloromethylphenoxy)methyl-2-phenylthiazole (7.96 g), potassium carbonate (6.98 g), and N,N-dimethylformamide (75 ml) was stirred at 80° C. for 8 hours. The reaction mixture was poured into water, and extracted with ethyl acetate. The ethyl acetate layer was washed with saturated aqueous sodium chloride solution, dried (MgSO₄), and concentrated. The residue was subjected to silica gel column chromatography to obtain ethyl 1-[4-(2-phenyl-4-thiazolylmethoxy)benzyl]-3-(2-thienyl)-1H- pyrazole-4-carboxylate as colorless crystals (10.93 g, yield: 87%) from the fraction eluted with ethyl acetate-hexane (1:2, volume ratio). This was recrystallized from ethyl acetate-hexane. Melting point: 94~95° C.

EXAMPLE 346

A mixture of ethyl 1-[4-(2-phenyl-4-thiazolylmethoxy)benzyl]-3-(2-thienyl)-1H-pyrazole-4-carboxylate (750 mg), 1N aqueous sodium hydroxide solution (3 ml), tetrahydrofuran (5 ml), and ethanol (5 ml) was stirred at 80° C. for 5 hours. After cooling, 1N hydrochloric acid (3 ml) was added to the mixture and the mixture was extracted with ethyl acetate. The ethyl acetate layer was washed with saturated aqueous sodium chloride solution, dried (MgSO$_4$), and concentrated. The resulting colorless crystals were collected by filtration to obtain 1-[4-(2-phenyl-4-thiazolylmethoxy)benzyl]-3-(2-thienyl)-1H-pyrazole-4-carboxylic acid (640 mg, yield: 90%). This was recrystallized from acetone-hexane. Melting point: 187~188° C.

| Preparation Example 1 (Production of capsules) | |
| --- | --- |
| 1) Compound of Example 4 | 30 mg |
| 2) Finely divided cellulose | 10 mg |
| 3) Lactose | 19 mg |
| 4) Magnesium stearate | 1 mg |
| Total | 60 mg |

1), 2), 3) and 4) are admixed and filled into a gelatin capsule.

| Preparation Example 2 (Production of tablets) | |
| --- | --- |
| 1) Compound of Example 4 | 30 g |
| 2) Lactose | 50 g |
| 3) Corn starch | 15 g |
| 4) Carboxymethylcellulose calcium | 44 g |
| 5) Magnesium stearate | 1 g |
| 1000 tablets | 140 g |

The whole amounts of 1), 2) and 3) and 30 g of 4) are kneaded together with water and the mixture, after vacuum drying, is granulated. The granular mixture is admixed with 14 g of 4) and 1 g of 5) and the resulting mixture is tableted using a tableting machine, to give 1000 tablets each containing 30 mg of compound of Example 4.

INDUSTRIAL APPLICABILITY

The compound of the present invention and the pharmaceutical composition of the present invention are of low toxicity and can be used as an agent for preventing or treating diabetes (e.g., type 1 diabetes mellitus, type 2 diabetes mellitus, gestational diabetes mellitus); an agent for preventing or treating hyperlipidemia (e.g., hypertriglycemia, hypercholesterolemia, hypo-high-density-lipoproteinemia, postprandial hyperlipemia); an agent for enhancing insulin sensitivity; an agent for improving insulin resistance; an agent for preventing or treating impaired glucose tolerance (IGT); and an agent for preventing progress from impaired glucose tolerance to diabetes mellitus.

The compound of the present invention and the pharmaceutical composition of the present invention can be used also as an agent for preventing or treating diabetic complications (e.g., neuropathy, nephropathy, retinopathy, cataract, macroangiopathy, osteopenia, diabetic hyperosmolar coma, infectious diseases (e.g., respiratory infection, urinary tract infection, gastrointestinal tract infection, dermal soft tissue infection, inferior limb infection), diabetic gangrene, xerostomia, lowered sense of hearing, cerebrovascular disease, peripheral circulatory disturbance, etc.), obesity, osteoporosis, cachexia (e.g., carcinomatous cachexia, tuberculous cachexia, diabetic cachexia, hemopathic cachexia, endocrinopathic cachexia, infectious cachexia, cachexia induced by acquired immunodeficiency syndrome), fatty liver, hypertension, polycystic ovary syndrome, renal diseases (e.g., diabetic nephropathy, glomerular nephritis, glomerulosclerosis, nephrotic syndrome, hypertensive nephrosclerosis, terminal renal disorder), muscular dystrophy, myocardiac infarction, angina pectoris, cerebrovascular disease (e.g., cerebral infarction, cerebral apoplexy), insulin resistant syndrome, syndrome X, hyperinsulinemia, hyperinsulinemia-induced sensory disorder, tumor (e.g., leukemia, breast cancer, prostate cancer, skin cancer), irritable intestinum syndrome, acute or chronic diarrhea, inflammatory diseases (e.g., chronic rheumatoid arthritis, spondylitis deformans, osteoarthritis, lumbago, gout, postoperative or traumatic inflammation, remission of swelling, neuralgia, pharyngolaryngitis, cystitis, hepatitis (including steatohepatitis such as non-alcoholic steatohepatitis), pneumonia, pancreatitis, inflammatory colitis, ulcerative colitis), visceral obesity syndrome, arteriosclerosis (e.g., atherosclerosis), etc.

Also, the compound of the present invention and the pharmaceutical composition of the present invention can be used for ameliorating bellyache, nausea, vomiting, or dysphoria in epigastrium, each of which is accompanied by gastrointestinal ulcer, acute or chronic gastritis, biliary dyskinesia, or cholecystitis.

Further, the compound of the present invention and the pharmaceutical composition of the present invention can control (enhance or inhibit) appetite and food intake, and therefore, can be used as an agent for treating leanness and cibophobia (the weight increase in administration subjects suffering from leanness or cibophobia) or an agent for treating obesity.

The invention claimed is:

1. A compound of the formula:

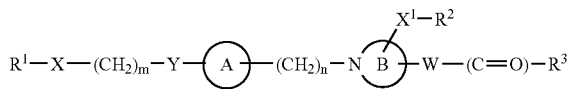
(I)

wherein $R^1$ represents a hydrocarbon group which is optionally substituted or a heterocyclic group which is optionally substituted;

X represents a bond, an oxygen atom, a sulfur atom, or a group of the formula: —CO—, —CS—, —CR$^4$(OR$^5$)— or —NR$^6$— wherein each of $R^4$ and $R^6$ represents a hydrogen atom or a hydrocarbon group which is optionally substituted, $R^5$ represents a hydrogen atom or a protective group for a hydroxyl group;

m represents an integer of 0 to 3;

Y represents an oxygen atom, a sulfur atom, or a group of the formula: —SO—, —SO$_2$—, —NR$^7$—, —CONR$^7$— or —NR$^7$CO— wherein $R^7$ represents a hydrogen atom or a hydrocarbon group which is optionally substituted;

ring A represents benzene, naphthalene or pyridine, each of which optionally has 1 to 3 substituents;

n represents an integer of 1 to 8;

ring B represents pyrrole or pyrazole, each of which is optionally substituted by an alkyl group;

$X^1$ represents a bond, an oxygen atom, a sulfur atom, or a group of the formula: —SO—, —SO$_2$—, —O—SO$_2$— or —NR$^{16}$— wherein $R^{16}$ represents a hydrogen atom or a hydrocarbon group which is optionally substituted;

$R^2$ represents a hydrogen atom, a hydrocarbon group which is optionally substituted or a heterocyclic group which is optionally substituted;

W represents a bond or a divalent hydrocarbon group having 1 to 20 carbon atoms;

$R^3$ represents a group of the formula: —OR$^8$ ($R^8$ represents a hydrogen atom or a hydrocarbon group which is optionally substituted) or —NR$^9$R$^{10}$ (each of $R^9$ and $R^{10}$, whether identical or not, represents a hydrogen atom, a hydrocarbon group which is optionally substituted, a heterocyclic group which is optionally substituted, or an acyl group which is optionally substituted; or $R^9$ and $R^{10}$ may bind together to form a 5- to 7-membered cyclic amino group);

provided that $R^1$ is a heterocyclic group which is optionally substituted or $R^2$ is an aromatic hydrocarbon group which is optionally substituted or a heterocyclic group which is optionally substituted, when ring A is benzene which is optionally substituted, and Y is an oxygen atom, a sulfur atom, —NH— or —CONH—; or a salt thereof.

2. A compound according to claim 1, wherein $X^1$ is a bond.

3. A compound according to claim 1, wherein $R^1$ is a heterocyclic group which is optionally substituted or a cyclic hydrocarbon group which is optionally substituted.

4. A compound according to claim 1, wherein $R^1$ is a heterocyclic group which is optionally substituted.

5. A compound according to claim 1, wherein X is a bond.

6. A compound according to claim 1, wherein m is 1 or 2.

7. A compound according to claim 1, wherein Y is an oxygen atom.

8. A compound according to claim 1, wherein ring A is benzene or pyridine, each of which optionally has 1 to 3 substituents.

9. A compound according to claim 1, wherein n is an integer of 1 to 3.

10. A compound according to claim 1, wherein $X^1$ is a bond or an oxygen atom.

11. A compound according to claim 1, wherein W is a divalent hydrocarbon group having 1 to 8 carbon atoms.

12. A compound according to claim 1, wherein $R^3$ is a group of the formula: —OR$^8$ ($R^8$ represents a hydrogen atom or a hydrocarbon group which is optionally substituted).

13. A compound according to claim 1, which is

3-[3-ethoxy-1-[4-(2-phenyl-4-thiazolylmethoxy)benzyl]-1H-pyrazol-4-yl]propionic acid, 3-[3-ethoxy-1-[4-(2-phenyl-4-oxazolylmethoxy)benzyl]-1H-pyrazol-4-yl]propionic acid, 3-[3-ethoxy-1-[4-[3-methyl-1-(2-pyridyl)-1H-pyrazol-4-ylmethoxy]benzyl]-1H-pyrazol-4-yl]propionic acid, 3-[1-[4-(5-methyl-2-phenyl-4-oxazolylmethoxy)benzyl]-3-(2-thienyl)-1H-pyrazol-4-yl]propionic acid, 3-[1-[4-(2-phenyl-4-thiazolylmethoxy)benzyl]-3-(2-thienyl)-1H-pyrazol-4-yl]propionic acid, or 3-[1-[4-(2-phenyl-4-oxazolylmethoxy)benzyl]-3-(2-thienyl)-1H-pyrazol-4-yl]propionic acid.

14. A prodrug of a compound of the formula:

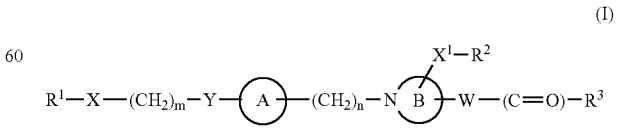
(I)

wherein $R^1$ represents a hydrocarbon group which is optionally substituted or a heterocyclic group which is optionally substituted;

X represents a bond, an oxygen atom, a sulfur atom, or a group of the formula: —CO—, —CS—, —CR$^4$(OR$^5$)— or —NR$^6$— wherein each of R$^4$ and R$^6$ represents a hydrogen atom or a hydrocarbon group which is optionally substituted, R$^5$ represents a hydrogen atom or a protective group for a hydroxyl group;

m represents an integer of 0 to 3;

Y represents an oxygen atom, a sulfur atom, or a group of the formula: —SO—, —SO$_2$—, —NR$^7$—, —CONR$^7$— or —NR$^7$CO— wherein R$^7$ represents a hydrogen atom or a hydrocarbon group which is optionally substituted;

ring A represents benzene, naphthalene or pyridine, each of which optionally has 1 to 3 substituents;

n represents an integer of 1 to 8;

ring B represents pyrrole or pyrazole, each of which is optionally substituted by an alkyl group;

X$^1$ represents a bond, an oxygen atom, a sulfur atom, or a group of the formula: —SO—, —SO$_2$—, —O—SO$_2$— or —NR$^{16}$— wherein R$^{16}$ represents a hydrogen atom or a hydrocarbon group which is optionally substituted;

R$^2$ represents a hydrogen atom, a hydrocarbon group which is optionally substituted or a heterocyclic group which is optionally substituted;

W represents a bond or a divalent hydrocarbon group having 1 to 20 carbon atoms;

R$^3$ represents a group of the formula: —OR$^8$ (R$^8$ represents a hydrogen atom or a hydrocarbon group which is optionally substituted) or —NR$^9$R$^{10}$ (each of R$^9$ and R$^{10}$, whether identical or not, represents a hydrogen atom, a hydrocarbon group which is optionally substituted, a heterocyclic group which is optionally substituted, or an acyl group which is optionally substituted; or R$^9$ and R$^{10}$ may bind together to form a 5- to 7-membered cyclic amino group);

provided that R$^1$ is a heterocyclic group which is optionally substituted or R$^2$ is an aromatic hydrocarbon group which is optionally substituted or a heterocyclic group which is optionally substituted, when ring A is benzene which is optionally substituted, and Y is an oxygen atom, a sulfur atom, —NH— or —CONH—; or a salt thereof.

15. A pharmaceutical composition comprising a compound of the formula:

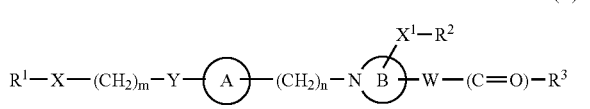

(II)

wherein R$^1$ represents a hydrocarbon group which is optionally substituted or a heterocyclic group which is optionally substituted;

X represents a bond, an oxygen atom, a sulfur atom, or a group of the formula: —CO—, —CS—, —CR$^4$(OR$^5$)— or —NR$^6$— wherein each of R$^4$ and R$^6$ represents a hydrogen atom or a hydrocarbon group which is optionally substituted, R$^5$ represents a hydrogen atom or a protective group for a hydroxyl group;

m represents an integer of 0 to 3;

Y represents an oxygen atom, a sulfur atom, or a group of the formula: —SO—, —SO$_2$—, —NR$^7$—, —CONR$^7$— or —NR$^7$CO— wherein R$^7$ represents a hydrogen atom or a hydrocarbon group which is optionally substituted;

ring A represents benzene, naphthalene or pyridine, each of which optionally has 1 to 3 substituents;

n represents an integer of 1 to 8;

ring B represents pyrrole or pyrazole, each of which is optionally substituted by an alkyl group;

X$^1$ represents a bond, an oxygen atom, a sulfur atom, or a group of the formula: —SO—, —SO$_2$—, —O—SO$_2$— or —NR$^{16}$— wherein R$^{16}$ represents a hydrogen atom or a hydrocarbon group which is optionally substituted;

R$^2$ represents a hydrogen atom, a hydrocarbon group which is optionally substituted or a heterocyclic group which is optionally substituted;

W represents a bond or a divalent hydrocarbon group having 1 to 20 carbon atoms;

R$^3$ represents a group of the formula: —R$^8$ (R$^8$ represents a hydrogen atom or a hydrocarbon group which is optionally substituted) or —NR$^9$R$^{10}$ (each of R$^9$ and R$^{10}$, whether identical or not, represents a hydrogen atom, a hydrocarbon group which is optionally substituted, a heterocyclic group which is optionally substituted, or an acyl group which is optionally substituted; or R$^9$ and R$^{10}$ may bind together to form a 5- to 7-membered cyclic amino group); or a salt thereof or a prodrug thereof, and a pharmaceutically acceptable carrier.

16. A composition according to claim 15, wherein X$^1$ is a bond.

17. A method for treating diabetes mellitus in a mammal in need thereof, which comprises administering to said mammal an effective amount of a compound of the formula:

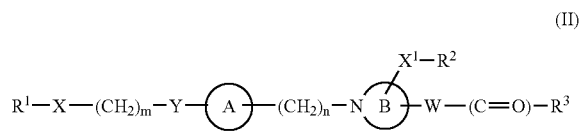

(II)

wherein R$^1$ represents a hydrocarbon group which is optionally substituted or a heterocyclic group which is optionally substituted;

X represents a bond, an oxygen atom, a sulfur atom, or a group of the formula: —CO—, —CS—, —CR$^4$(OR$^5$)— or —NR$^6$— wherein each of R$^4$ and R$^6$ represents a hydrogen atom or a hydrocarbon group which is optionally substituted, R$^5$ represents a hydrogen atom or a protective group for a hydroxyl group;

m represents an integer of 0 to 3;

Y represents an oxygen atom, a sulfur atom, or a group of the formula: —SO—, —SO$_2$—, —NR$^7$—, —CONR$^7$— or —NR$^7$CO— wherein R$^7$ represents a hydrogen atom or a hydrocarbon group which is optionally substituted;

ring A represents benzene, naphthalene or pyridine, each of which optionally has 1 to 3 substituents;

n represents an integer of 1 to 8;

ring B represents pyrrole or pyrazole, each of which is optionally substituted by an alkyl group;

X$^1$ represents a bond, an oxygen atom, a sulfur atom, or a group of the formula: —SO—, —SO$_2$—, —O—SO$_2$— or —NR$^{16}$— wherein R$^{16}$ represents a hydrogen atom or a hydrocarbon group which is optionally substituted;

R$^2$ represents a hydrogen atom, a hydrocarbon group which is optionally substituted or a heterocyclic group which is optionally substituted;

W represents a bond or a divalent hydrocarbon group having 1 to 20 carbon atoms;

R$^3$ represents a group of the formula: —OR$^8$ (R$^8$ represents a hydrogen atom or a hydrocarbon group which is optionally substituted) or —NR$^9$R$^{10}$ (each of R$^9$ and R$^{10}$, whether identical or not, represents a hydrogen atom, a hydrocarbon group which is optionally substituted, a heterocyclic group which is optionally substituted, or an acyl group which is optionally substituted; or R$^9$ and R$^{10}$ may bind together to form a 5- to 7-membered cyclic amino group); or a salt thereof or a prodrug thereof.

* * * * *